US006949363B2

(12) United States Patent
Feder et al.

(10) Patent No.: US 6,949,363 B2
(45) Date of Patent: Sep. 27, 2005

(54) POLYNUCLEOTIDES ENCODING NOVEL HUMAN LEUCINE-RICH REPEAT CONTAINING PROTEIN EXPRESSED PREDOMINATELY IN BONE MARROW, HLRRBM1

(75) Inventors: John N. Feder, Belle Mead, NJ (US); Chandra S. Ramanathan, Wallingford, CT (US); Gabriel A. Mintier, Hightstown, NJ (US)

(73) Assignee: Brilstol-Myers Squibb, Princeton, NJ (US)

( * ) Notice: Subject to any disclaimer, the term of this patent is extended or adjusted under 35 U.S.C. 154(b) by 244 days.

(21) Appl. No.: 10/183,770

(22) Filed: Jun. 27, 2002

(65) Prior Publication Data

US 2003/0180812 A1 Sep. 25, 2003

Related U.S. Application Data

(63) Continuation-in-part of application No. 10/028,374, filed on Dec. 20, 2001, now abandoned.

(60) Provisional application No. 60/257,773, filed on Dec. 22, 2000.

(51) Int. Cl.[7] .......................... C12N 15/12; C12N 5/10; C12P 21/02; C07K 14/47

(52) U.S. Cl. .................. 435/69.1; 435/71.1; 435/320.1; 435/471; 435/325; 536/23.5; 530/350

(58) Field of Search .............................. 435/69.1, 71.1, 435/320.1, 471, 325; 536/23.5; 530/350

(56) References Cited

U.S. PATENT DOCUMENTS 5,849,902 A 12/1998 Arrow et al. .............. 536/24.5

FOREIGN PATENT DOCUMENTS

| WO | WO 01/75067 | 10/2001 |
|---|---|---|
| WO | WO 02/40668 | 5/2002 |
| WO | WO 02/061049 | 8/2002 |

OTHER PUBLICATIONS

Inohara et al. (1999) J. of Biological Chemistry 274:14560–14567.

NCBI Entrez Accession No. AAA40132 (gi:201045), Dickinson, D.P. et al., Apr. 27, 1993.

NCBI Entrez Accession No. AAC39910 (gi:3341996), Mao, M. et al., May 22, 2001.

NCBI Entrez Accession No. AAG15254 (gi:10198209), Bertin, J. et al., Feb. 19, 2002.

NCBI Entrez Accession No. AAH28069 (gi:20380400), Strausberg, R.L. et al., Jun. 29, 2004.

NCBI Entrez Accession No. AAL12497 (gi:17027237), Hoffman, H.M. et al., Nov. 21, 2001.

NCBI Entrez Accession No. AAM18227 (gi:21314907), Wang, L. et al., Aug. 12, 2002.

NCBI Entrez Accession No. AAM75142 (gi:21711821), Williams, K.L. et al., May 21, 2003.

NCBI Entrez Accession No. AAM75143 (gi:21711823), Williams, K.L. et al., May 21, 2003.

NCBI Entrez Accession No. AAM75144 (gi:21711825), Williams, K.L. et a., May 21, 2003.

NCBI Entrez Accession No. AAM75145 (gi:21711827), Williams, K.L. et al., May 21, 2003.

NCBI Entrez Accession No. AAO18163 (gi:28436378), Tschopp, J. et al., Feb. 20, 2003.

NCBI Entrez Accession No. AF231021 (gi:13182796), Shami, P.J. et al., Apr. 30, 2004.

NCBI Entrez Accession No. AY095146 (gi:21314906), Wang, L. et al., Aug. 12, 2002.

NCBI Entrez Accession No. BC028069 (gi:20380399), Strausberg, R.L. et al., Jun. 29, 2004.

NCBI Entrez Accession No. CAD35284 (gi:21449785), Reed, J.C. et al., Jun. 14, 2002.

NCBI Entrez Accession No. NP_006083 (gi:5174617), Kim, J.G. et al., Oct. 28, 2004.

NCBI Entrez Accession No. NP_055737 (gi:7662386), Tschopp, J. et al., Oct. 28, 2004.

NCBI Entrez Accession No. NP_653286 (gi:21955154), Williams, K.L. et al., Oct. 27, 2004.

NCBI Entrez Accession No. P59046 (gi:24212103), Wang, L. et al., Sep. 15, 2003.

Altschul, S.F. et al., "Gapped BLAST and PSI–BLAST: a new generation of protein database search programs", Nucleic Acids Research, vol. 25, No. 17, pp. 3389–3402 (1997).

Bause, E., "Structural requirements of N–glycosylation of proteins: Studies with proline peptides as conformational probes", Biochem. J., vol. 209, pp. 331–336 (1983).

Bengtsson, E. et al., "The Primary Structure of a Basic Leucine–rich Repeat Protein, PRELP, Found in Connective Tissues", The Journal of Biological Chemistry, vol. 270, No. 43, pp. 25639–25644 (1995).

Bertin, J. et al., "Human CARD4 Protein Is a Novel CED–4/Apaf–1 Cell Death Family Member That Activates NF–κB", The Journal of Biological Chemistry, vol. 274, No. 19, pp. 12955–12958 (1999).

(Continued)

*Primary Examiner*—Janet Andres
*Assistant Examiner*—Fozia Hamud
(74) *Attorney, Agent, or Firm*—Stephen C. D'Amico

(57) ABSTRACT

The present invention provides novel polynucleotides encoding HLRRBM1 polypeptides, fragments and homologues thereof. Also provided are vectors, host cells, antibodies, and recombinant and synthetic methods for producing said polypeptides. The invention further relates to diagnostic and therapeutic methods for applying these novel HLRRBM1 polypeptides to the diagnosis, treatment, and/or prevention of various diseases and/or disorders related to these polypeptides, particularly immune diseases and/or disorders. The invention further relates to screening methods for identifying agonists and antagonists of the polynucleotides and polypeptides of the present invention.

20 Claims, 12 Drawing Sheets

OTHER PUBLICATIONS

Figure 3:
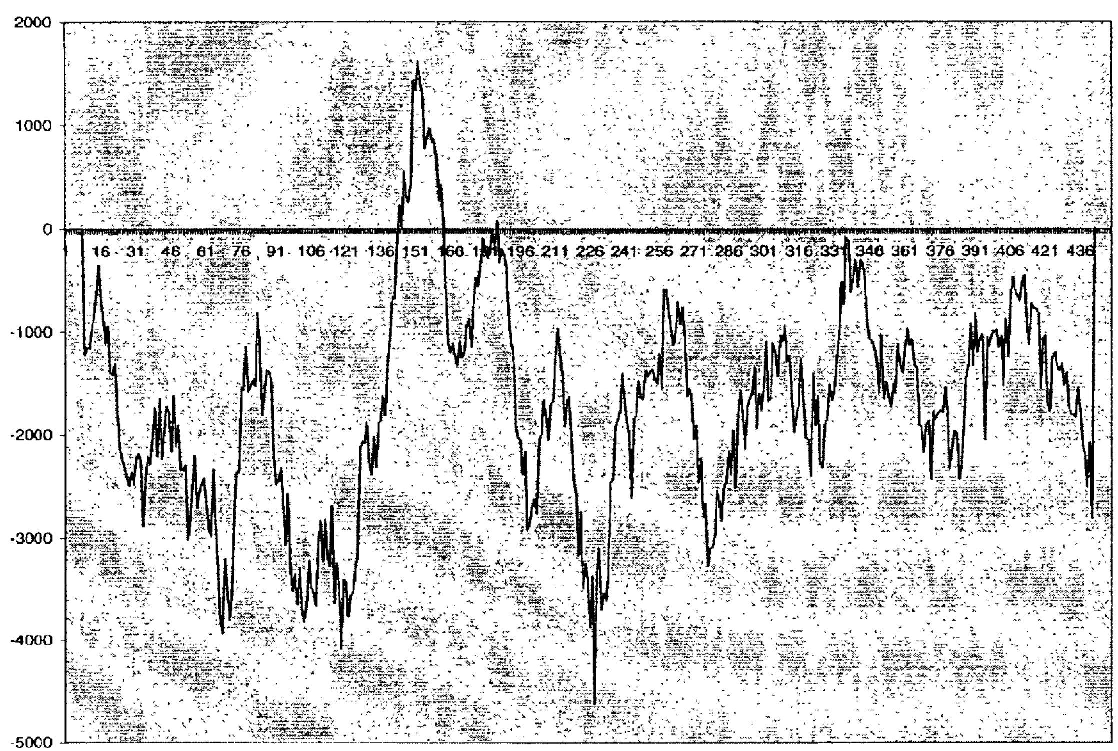

Bertin, J. et al., "The PYRIN domain: a novel motif found in apoptosis and inflammation proteins", Cell Death and Differentiation, vol. 7, pp. 1273–1274 (2000).

Buchanan, S.G.S.C. et al., "Structural and Functional Diversity in the Leucine–Rich Repeat Family of Proteins", Prog. Biophys. Molec. Biol., vol. 65, No. 1/2, pp. 1–44 (1996).

Bunz, F. et al., "Requirement for p53 and p21 to Sustain $G_2$ Arrest DNA Damage", Science, vol. 282, pp. 1497–1501 (1998).

Cheng, T. et al., "Hematopoietic Stem Cell Quiescence Maintained by $p21^{cip1/waf1}$", Science, vol. 287, pp. 1804–1808 (2000).

Collins, N. et al., "Molecular Characterization of the Maize Rp1–D Rust Resistance Haplotype and Its Mutants", The Plant Cell, vol. 11, pp. 1365–1376 (1999).

Dixon, J. et al., "Increased levels of apoptosis in the prefusion neural folds underlie the craniofacial disorder, Treacher Collins syndrome", Human Molecular Genetics, vol. 9, No. 10, pp. 1473–1480 (2000).

Dixon, M.S. et al., "Genetic complexity of pathogen perception by plants: The example of Rcr3, a tomato gene required specifically by Cf–2", Proc. Natl. Acad. Sci., vol. 97, No. 16, pp. 8807–8814 (2000).

Dixon, M.S. et al., "The Tomato Cf–5 Disease Resistance Gene and Six Homologs Show Pronounced Alleic Variation in Leucine–Rich Repeat Copy Number", The Plant Cell, vol. 10, pp. 1915–1925 (1998).

Draetta, G.F., "Mammalian $G_1$ cyclins", Current Opinion in Cell Biology, vol. 6, pp. 842–846 (1994).

Eldon, E. et al., "The *Drosophila 18 wheeler* is required for morphogenesis and has striking similarities to *Toll*", Development, vol. 120, pp. 885–899 (1994).

Ellis, J. et al., "Structure and function of proteins controlling strain–specific pathogen resistance in plants", Current Opinion in Plant Biology, vol. 1, pp. 288–293 (1998).

Gavel, Y. et al., "Sequence differences between glycosylated and non–glycosylated Asn–X–Thr/Ser acceptor sites: implications for protein engineering", Protein Engineering, vol. 3, No. 5, pp. 433–442 (1990).

Gavrieli, Y. et al., "Identification of Programmed Cell Death In Situ via Specific Labeling of Nuclear DNA Fragmentation", The Journal of Cell Biology, vol. 119, No. 3, pp. 493–501 (1992).

Graham, M.A. et al., "Expression and genome organization of resistance gene analogs in soybean", Genome, vol. 43, pp. 86–93 (2000).

Halfon, M.S. et al., "The *Drosophila Toll* Gene Functions Zygotically and Is Necessary for Proper Motoneuron and Muscle Development", Developmental Biology, vol. 169, pp. 151–167 (1995).

Harton, J.A. et al., "Class II Transactivator: Mastering the Art of Major Histocompatibility Complex Expression", Molecular and Cellular Biology, vol. 20, No. 17, pp. 6185–6194 (2000).

Hayashi, T. et al., "Molecular Pathogenesis of Bernard–Soulier Syndrome", Seminars in Thrombosis and Hemostasis, vol. 26, No. 1, pp. 53–59 (2000).

He, Z. et al., "Perception of Brassinosteroids by the Extracellular Domain of the Receptor Kinase BRI1", Science, vol. 288, pp. 2360–2363 (2000).

Hofmann, K. et al., MF C–35: "A Database of Membrane Spanning Protein Segments", Biol. Chem. Hoppe–Seyler, vol. 374, p. 166 (1993).

Imai, Y. et al., "The CED–4–homologous protein FLASH is involved in Fas–mediated activation of capase–8 during apoptosis", Nature, vol. 398, pp. 777–785 (1999).

Inohara, N. et al., "An Induced Proximity Model for NF–κB Activation in the Nod1/RICK and RIP Signaling Pathways", The Journal of Biological Chemistry, vol. 275, No. 36, pp. 27823–27831 (2000).

Inohara, N. et al., "Genes with homology to DFF/CIDEs found in *Drosophila melanogaster*", Cell Death and Differentiation, vol. 6, pp. 823–824 (1999).

Inohara, N. et al., "Genes with homology to mammalian apoptosis regulators identified in zebrafish", Cell Death and Differentiation, vol. 7, pp. 509–510 (2000).

Iozzo, R.V., "Matrix Proteoglycans: From Molecular Design to Cellular Function", Annu. Rev. Biochem., vol. 67, pp. 609–652 (1998).

Jacobs, J.R.,. "Perturbed Glial Scaffold Formation Precedes Axon Tract Malformation in *Drosophila* Mutants", Journal of Neurobiology, vol. 24, No. 5, pp. 611–626 (1993).

Jacobs, J.R. et al., "Embryonic Development of Axon Pathways in the *Drosophila* CNS. I. A Glial Scafford Appears Before the First Growth Cones", The Journal of Neuroscience, vol. 9, No. 7, pp. 2402–2411 (1989).

Jones, D.A. et al., "A Two–Step Adhesion Cascade for T Cell/Endothelial Cell Interactions under Flow Conditions", J. Clin. Invest., vol. 94, pp. 2443–2450 (1994).

Kajava, A.V., "Structural Diversity of Leucine–rich Repeat Proteins", J. Mol. Biol., vol. 277, pp. 519–527 (1998).

Kim, D. et al., "A cDNA encoding a putative 37 kDa leucine–rich repeat (LRR) protein, p37NB, isolated from S–type neuroblastoma cell has a differential tissue distribution", Biochimica et Biophysica Acta, vol. 1309, pp. 183–188 (1996).

Kishimoto, A. et al., "Studies on the Phosphorylation of Myelin Basic Protein by Protein Kinase C and Adenosine 3':5'–Monophosphate–dependent Protein Kinase", The Journal of Biological Chemistry, vol. 260, No. 23, pp. 12492–12499 (1985).

Koarada, S., et al., "B Cells Lacking RP105, a Novel B Cell Antigen, in Systemic Lupus Erythematosus", Arthritis & Rheumatism, vol. 42, No. 12, pp. 2593–2600 (1999).

Kobe, B. et al., "Proteins with leucine–rich repeats", Current Opinion in Structural Biology, vol. 5, pp. 409–416 (1995).

Kobe, B. et al., "The leucine–rich repeat: a versatile binding motif", Trends in Biochemical Sciences, vol. 19, pp. 415–421 (1994).

Lee, E. et al., "Reversal of Human Neutrophil Survival by Leukotriene $B_4$ Receptor Blockade and 5–Lipoxygenase and 5–Lipoxygenase Activating Protein Inhibitors", American Journal of Respiratory and Critical Care Medicine, vol. 160, pp. 2079–2085 (1999).

Liang, Y. et al., "Mammalian Homologues of the *Drosophila* Slit Protein Are Ligands of the Heparan Sulfate Proteoglycan Glypican–1 in Brain", The Journal of Biological Chemistry, vol. 274, No. 25, pp. 17885–17892 (1999).

Marshall, R.D., "Glycoproteins", Annu. Rev. Biochem., pp. 673–702 (1972).

Meltzer, E.O., "Role for cysteinyl leukotriene receptor antagonist therapy in asthma and their potential role in allergic rhinitis based on the concept of 'one linked airway disease'", Annals of Allergy, Asthma & Immunology, vol. 84, pp. 176–187 (2000).

Miletich, J.P. et al., "β Protein C Is Not Glycosylated at Asparagine 329", The Journal of Biological Chemistry, vol. 265, No. 19, pp. 11397–11404 (1990).
Nicholson, D.W., "Caspase structure, proteolytic substrates, and function during apoptotic cell death", Cell Death and Differentiation, vol. 6, pp. 1028–1042 (1999).
Pless, D.D. et al., "Enzymatic conversion of proteins to glycoproteins", Proc. Natl. Acad. Sci. USA, Vo. 74, No. 1, pp. 134–138 (1977).
Richter, T.E. et al., "The evolution of disease resistance genes", Plant Molecular Biology, vol. 42, pp. 195–204 (2000).
Schafer, K.A., "The Cell Cycle: A Review", Vet. Pathol., vol. 35, No. 6, pp. 461–478 (1998).
Schneider, D.S. et al., "Dominant and recessive mutations define functional domains of *Toll*, a transmembrane protein required for dorsal–ventral polarity in the *Drosophila* embryo", Genes & Development, vol. 5, pp. 797–807 (1991).
Schuster, J.M. et al., "Toll receptors: an expanding role in our understanding of human disease", Journal of Leukocyte Biology, vol. 67, pp. 767–773 (2000).
Srinivasula, S.M. et al., "CLAP, a Novel Caspase Recruitment Domain–containing Protein in the Tumor Necrosis Factor Receptor Pathway, Regulates NF–κB Activation and Apoptosis", The Journal of Biological Chemistry, vol. 274, No. 25, pp. 17946–17954 (1999).
Tong, Z.B. et al., "A Mouse Gene Encoding an Oocyte Antigen Associated with Autoimmune Premature Ovarian Failure", Endocrinology, vol. 140, No. 8, pp. 3720–3726 (1999).
Tschopp, J. et al., "NALPs: A Novel Protein Family Involved in Inflammation", Nature Reviews: Molecular Cell Biology, vol. 4, pp. 95–104 (2003).
van der Voort, R. et al., "Regulation of Cytokine Signaling by B Cell Antigen Receptor and CD40–controlled Expression of Heparan Sulfate Proteoglycans", J. Exp. Med., vol. 1992, No. 8, pp. 1115–1124 (2000).
van der Voort, R. et al., "The Hepatocyte Growth Factor/Met Pathway in Development, Tumorigenesis, and B–Cell Differentiation", Advances in Cancer Research, pp. 39–90 (2000).
Verbeek, M.M. et al., "Agrin Is a Major Heparan Sulfate Proteoglycan Accumulating in Alzheimer's Disease Brain", American Journal of Pathology, vol. 155, No. 6, pp. 2115–2125 (1999).
Wang, L. et al., "PYPAF7, a Novel PYRIN–containing Apaf1–like Protein That Regulates Activation of NF–κB and Caspase–1–dependent Cytokine Processing", The Journal of Biological Chemistry, vol. 277, No. 33, pp. 29874–29880 (2002).
Wang, Z.–X. et al., "The *Pib* gene for rice blast resistance belongs to the nucleotide binding and leucine–rich repeat class of plant disease resistance genes", The Plant Journal, vol. 19, No. 1, pp. 54–64 (1999).
Woodgett, J.R. et al., "Substrate specificity of protein kinase C: Use of synthetic peptides corresponding to physiological sites as probes for substrates recognition requirements", Eur. J. Biochem., vol. 161, pp. 177–184 (1986).
Yoshida, S. et al., "Efficacy of leukotriene receptor antagonist in bronchial hyperresponsiveness and hypersensitivity to analgesic in aspirin–intolerant asthma", Clinical and Experimental Allergy, vol. 30, pp. 64–70 (2000).

Figure 1A

```
   1  CCACGCGTCCGAACATGGGCTGAGAGCCCCCCCAAGAGCATCTCTAAGACCGGAGTGGGC    60
  61  AGGGACCCGGGCCTCTGAGGGGCTCAGGCTCCAGGCCGGAAACTGCACGCGGTGCTGGCG   120
 121  TCAGGCCCGAGGCCCAGCTACGCCTCCCACGGCCTCCCTAATCGCCATTCGGGGCTTGCG   180
 181  GGAGCACCTGGGAGGCTCCACCCGGAGCCAGACACTGCCTGCCCCCACGCCCCTCCAGGA   240
 241  CCCTCGAAGGAGAAGGAAATCGGGACTGGCCCAGCGTCCCGTGCTCTAGAACGCGGGCTA   300
 301  CTGCCCCGTCCCAAGCAGGGGAGGAGGACGAGCGAGGGCGTCACTCATTCTGTCCCCCGC   360
 361  GGAAGGATGAGGAAGCTCTGTTTACCTAAATGAAAAGCTTTCTAGGAGGAACTCCTAAGT   420
 421  GAACAATGATGCATGAGGATGCAATCTTACAGACACAGGGGTCTCCCTATGTTGTTCAAG   480
 481  CTGGTCTCGAACTCCTGGCCTCAAGTGATCCTCCTGCCTCGACCTCTCAAAGCTCTGCTA   540
 541  TTATAGGCAAGGAGCCCAGTGATAACAAATGGCTGTAGATGCTTTTCCTCCATCAAGCTT   600
 601  CCAGGAGGAGATGAGATGGAGCCCATCGCTGAGCCAAGAATTCTAATTTCATCCCTTTGG   660
 661  TCTTTGTTCATGCTGTGTTCTGCCTGGAATATTCTCCATCTTCTTTGCCTGGAAAAGTAT   720
 721  TACTTACTGAAACCTTGAAGCCACTACCTTCTCTAAACATTGACAATGCATAACCATTTG   780
 781  CCGAGCGTTCTTCCCCGGACTGCATCCGTTTAGTCTACTGAGAGGCAGCTCAGCGTTCCC   840
 841  AAGGAGACAGATGTCTAGCTTTGCTCTTTCTGTCTGTGTGATGCTGGAGAATCGATATGC   900
 901  CCCTGGGCCTCCATCTCCATCTGTAAAACAAGGGCATCAGATACCCCACCTGGTGGCCCG   960
 961  TCCTCACTTGGGAACCAGTCAACATGCCTTCTGGAAGTCTCTCTTGTCACTCCAAGAAAA  1020
1021  GATCCCCAGGAAACCTACAGGGACTATGTCCGCAGGAAATTCCGGCTCATGGAAGACCGC  1080
1081  AATGCGCGCCTAGGGGAATGTGTCAACCTCAGCCACCGGTACACCCGGCTCCTGCTGGTG  1140
1141  AAGGAGCACTCAAACCCCATGCAGGTCCAGCAGCAGCTTCTGGACACAGGCCGGGGACAC  1200
```

Figure 1B

```
1201 GCGAGGACCGTGGGACACCAGGCTAGCCCCATCAAGATAGAGACCCTCTTTGAGCCAGAC 1260

1261 GACGAGCGCCCCGAGCCACCGCGCACCGTGGTCATGCAAGGCGCGGCAGGGATAGGGAGA 1320
   1                                                            M 1

1321 TGAACCAGAGTGCCACGGAATGCAGCATGCAAGACCTCATCTTCAGCTGCTGGCCTGAGC 1380
   2  N  Q  S  A  T  E  C  S  M  Q  D  L  I  F  S  C  W  P  E  P 21

1381 CCAGCGCGCCTCTCCAGGAGCTCATCCGAGTTCCCGAGCGCCTCCTTTTCATCATCGACG 1440
  22  S  A  P  L  Q  E  L  I  R  V  P  E  R  L  L  F  I  I  D  G 41

1441 GCTTCGATGAGCTCAAGCCTTCTTTCCACGATCCTCAGGGACCCTGGTGCCTCTGCTGGG 1500
  42  F  D  E  L  K  P  S  F  H  D  P  Q  G  P  W  C  L  C  W  E 61

1501 AGGAGAAACGGCCCACGGAGCTGCTTCTTAACAGCTTAATTCGGAAGAAGCTGCTCCCTG 1560
  62  E  K  R  P  T  E  L  L  L  N  S  L  I  R  K  K  L  L  P  E 81

1561 AGCTATCTTTGCTCATCACCACACGGCCCACGGCTTTGGAGAAGCTCCACCGTCTGCTGG 1620
  82  L  S  L  L  I  T  T  R  P  T  A  L  E  K  L  H  R  L  L  E 101

1621 AGCACCCCAGGCATGTGGAGATCCTGGGCTTCTCTGAGGCAGAAAGGAAGGAATACTTCT 1680
 102  H  P  R  H  V  E  I  L  G  F  S  E  A  E  R  K  E  Y  F  Y 121

1681 ACAAGTATTTCCACAATGCAGAGCAGGCGGGCCAAGTCTTCAATTACGTGAGGGACAACG 1740
 122  K  Y  F  H  N  A  E  Q  A  G  Q  V  F  N  Y  V  R  D  N  E 141

1741 AGCCTCTCTTCACCATGTGCTTCGTCCCCCTGGTGTGCTGGGTGGTGTGTACCTCCCTCC 1800
 142  P  L  F  T  M  C  F  V  P  L  V  C  W  V  V  C  T  C  L  Q 161

1801 AGCAGCAGCTGGAGGGTGGGGGGCTGTTGAGACAGACGTCCAGGACCACCACTGCAGTGT 1860
 162  Q  Q  L  E  G  G  G  L  L  R  Q  T  S  R  T  T  T  A  V  Y 181

1861 ACATGCTCTACCTGCTGAGTCTGATGCAACCCAAGCCGGGGGCCCCGCGCCTCCAGCCCC 1920
 182  M  L  Y  L  L  S  L  M  Q  P  K  P  G  A  P  R  L  Q  P  P 201

1921 CACCCAACCAGAGAGGGTTGTGCTCCTTGGCGGCAGATGGGCTCTGGAATCAGAAAATCC 1980
 202  P  N  Q  R  G  L  C  S  L  A  A  D  G  L  W  N  Q  K  I  L 221

1981 TATTTGAGGAGCAGGACCTCCGGAAGCACGGCCTAGACGGGGAAGACGTCTCTGCCTTCC 2040
 222  F  E  E  Q  D  L  R  K  H  G  L  D  G  E  D  V  S  A  F  L 241

2041 TCAACATGAACATCTTCCAGAAGGACATCAACTGTGAGAGGAGCTTCCTGGCACTCACCA 2100
 242  N  M  N  I  F  Q  K  D  I  N  C  E  R  S  F  L  A  L  T  S 261
```

Figure 1C

```
2101 GCCGCTTCCTGTTTGGACTCCTGAACGAGGAGACCAGGACCCACCTGGAGAAGAGTCTCT 2160
262   R  F  L  F  G  L  L  N  E  E  T  R  S  H  L  E  K  S  L  C  281

2161 GCTGGAAGGTCTCGCCGCACATCAAGATGGACCTGTTGCAGTGGATCCAAAGCAAAGCTC 2220
282   W  K  V  S  P  H  I  K  M  D  L  L  Q  W  I  Q  S  K  A  Q  301

2221 AGAGCGACGGCTCCACCCTGCAGCAGGGCTCCTTGGAGTTCTTCAGCTGCTTGTACGAGA 2280
302   S  D  G  S  T  L  Q  Q  G  S  L  E  F  F  S  C  L  Y  E  I  321

2281 TCCAGGAGGAGGAGTTTATCCAGCAGGCCCTGAGCCACTTCCAGGTGATCGTGGTCAGCA 2340
322   Q  E  E  E  F  I  Q  Q  A  L  S  H  F  Q  V  I  V  V  S  N  341

2341 ACATTGCCTCCAAGATGGAGCACATGGTCTCCTCGTTCTGTCTGAAGCGCTGCAGGAGCG 2400
342   I  A  S  K  M  E  H  M  V  S  S  F  C  L  K  R  C  R  S  A  361

2401 CCCAGGTGCTGCACTTGTATGGCGCCACCTACAGCGCGGACGGGGAAGACCGCGCGAGGT 2460
362   Q  V  L  H  L  Y  G  A  T  Y  S  A  D  G  E  D  R  A  R  C  381

2461 GCTCCGCAGGAGCGCACACGCTGTTGGTGCAGCTACCAGAGAGGACCGTTCTGCTGGACG 2520
382   S  A  G  A  H  T  L  L  V  Q  L  P  E  R  T  V  L  L  D  A  401

2521 CCTACAGTGAACATCTGGCAGCGGCCCTGTGCACCAATCCAAACCTGATAGAGCTGTCTC 2580
402   Y  S  E  H  L  A  A  A  L  C  T  N  P  N  L  I  E  L  S  L  421

2581 TGTACCGAAATGCCCTGGGCAGCCGGGGGGTGAAGCTGCTCTGTCAAGGACTCAGACACC 2640
422   Y  R  N  A  L  G  S  R  G  V  K  L  L  C  Q  G  L  R  H  P  441

2641 CCAACTGCAAACTTCAGAACCTGAGGTAAAATTTATCATATATAACATGATATTTTGAAA 2700
442   N  C  K  L  Q  N  L  R  *                                   449

2701 TAAATATATTGGCCAGGTATGATGGCTCACGCCTGTAATTCCAGCACTTTGGGAGGCCCA 2760

2761 GATGGGGAGGATCACTTGACCCAGGAGTTCAAGACCAGCCTGGCCAACATGGTGAAACCC 2820

2821 CATCTCTACTAAAAATACCAAAATGAGCCAGGCATGGTCGCACACGTCTGTAAGCCCAGC 2880

2881 TACTCAGGAGGCCAAGGCAGGAGGATTGCTTCAACCCAGGAGGCAGAGGTTGTGGCTGAA 2940

2941 GAGGTGCCGCATCTCCAGCTCAGCCTGCGAGGACCTCTCTGCACCTCTCATAGCCAATAA 3000

3001 GAATTTGACAAGGATGGATCTCAGTGGCAACGGCGTTGCATTCCCAGGCATGATGCTGCT 3060

3061 TTGCGAGGGCCTGCGGCATCCCCAATGCAGGCTGCAGATGATTCAGTTGAGGAAGTGTCA 3120
```

Figure 1D

3121 GCTGGAGTCCGGGGCTTGTCAGGAGATGGCTTCTGTGCTTGGCACCAACCCACATCTGGT 3180

3181 TGAGTTGGACCTGACAGGAAATGCACTGGAGGATTTGGGCCTGAGGTTACTATGCCAGGG 3240

3241 ACTGAGGCACCCAGTCTGCAGACTACGGACTTTGTGGCTGAAGATCTGCCGCCTCACTGC 3300

3301 TGCTGCCTGTGACGAGCTGGCCTCAACTCTCAGTGTGAACCAGAGCCTGAGAGAGCTGGA 3360

3361 CCTGAGCCTGAATGAGCTGGGGGACCTCGGGGTGCTGCTGCTGTGTGAGGGCCTCAGGCA 3420

3421 TCCCACGTGCAAGCTCCAGACCCTGCGGTGAGTCCCGTTTTGCTCACCACGCTAGGAGTC 3480

3481 CCAATCCATGAACGCAGCCCTCTCACCTGGGACCACGGAGGCCAGGTTCTCTCTGCTCCT 3540

3541 AAACTCTAGCTACTACATCAGCCCTTTTTTTTTTTTTTTTGAGACTCCCAAGTAGCTGAG 3600

3601 ATTACAGGCGCCCGCCACCAAGCCCAGCTAATTTTTGTATTTTTAGTAGAGACAGGGTT 3660

3661 TCATCATGTTAGCAGGATGGTCTCGATCTACTGACCTCATGATCTGCCTGCCTTGGCCTC 3720

3721 CCAAAGTGCTGGGATTACAGGCTTGAGCCACTGCACCCAGCCTACATCAGCCTTTTTAAA 3780

3781 AGGATTTTTCTGGCCGGGCATGGTGGCTGACACCTTAATTCCAGCACTTTTGGGAGGCCG 3840

3841 AGGTGGGAGGATCACCTGAGGTGGGGAATTCGAGACCAGCCTGACCAACATGTAGAAACA 3900

3901 CCCCATCTGTACTAAAAATACAAAAGTAGCCAGGCATGGTGGTGCATGCCTATAATGCCA 3960

3961 GCTACTCGCGAGGCTGAGGCAGGAGAATCCGTTGAACCCGGGAGGTGGAAGTTGCTGTGA 4020

4021 GCTGAGATGGAGCCATTGCACTCCAGTCTGCCCAACAAGAGCGAAACTCCGTCTCAAAAA 4080

4081 AAAAAAAGGGCGGGGTTTTCTGACGCACGGCCCTTTGCACAAGCAATTCTTATTCCCTGG 4140

4141 CATGCCTTCTGCTCTCTGTCCCCTCTTTGCCTGCAGAAGTTCAATTTTTCTTCTGAACAC 4200

4201 TCTTTACTTTGTATTTTGAGACAGGGTCTTGCTCTGTCACCAGTGCTGGAGTGGAGTGGT 4260

4261 GTGATCATAGCCCGACATCCTGGGCTGAAGCCATCCTCCCAACTCAGCCTCCTGAGTAGC 4320

Figure 1E

```
4321  TGGGACTGCAAGCGCATGCCACCACAGATGGCTAATTTTTACTTTTTTTTTGAGATTTTG  4380

4381  CCACTGCACTCCAGCCTGGATGACAGAGCGAGATTCCATCTCAAAAAAAAAAAAGAAAAA  4440

4441  TTTGTAATTTGTGTATATGTGTGTGTGGTGGCATTCCACAAGCATAGGAGCTATGCCAAC  4500

4501  TGTATCTCCTAGTGACTAGTATAAGACGTGGGTAGAAGTGCTCAAAAAACACACTTTGTG  4560

4561  TATTTTTTTTATCAAGGCACCAGCAAAAAACAAAAAACAAAAAATCACACACGCGGCTGG  4620

4621  GCGCGGTGGCTCATGCCTGTAAACCCAGCACTTTGGGAGGCTGAGGCGGGTGGATCACGA  4680

4681  GGTCAAGAGATGGAGACCATCCTGGCCAACTGGTGAAACCCCGTCTCTACTAAAAATACA  4740

4741  AAAATTAGCTGGGCGTGGTGGTGTGCACCTGTAGTCACAGCTACTCAGGAGGCTGAGGCA  4800

4801  GAAGAATCACTTGAACCCAGGAGGCGGAGGTTGCAGTGAGCCGAGATCGCGCCACTGCAC  4860

4861  TCCAGCCTGGGCGACAGAGTGGGACTCCATCTCAAAAAAAAAAAAAAAAAAAAAAAAAAA  4920

4921  AAAAAAAAAAA  4931
```

Figure 2A

```
                                 1                                                50
                HNTTBMY1   (1)   --------------------------------------------------
caspase_recruitment_protein (1)  MAGGAWGRLACYLEFLKKEELKEFQLLLANKAHSRSSSGETPAQPEKTSC
               cryopyrin   (1)   -MASTRCKLARYLEDLEDVDLKKFKMHLEDYPPQKGCIPLPRGQTEKADH
                    NOD1   (1)   ---------------MEEQGHSEMEIIPSESHPHIQLLKSNR--ELLVTH

                                 51                                              100
                HNTTBMY1   (1)   --------------------------------------------------
caspase_recruitment_protein (51) MEVASYLVAQYGEQRAWDLALHTWEQMGLRSLCAQAQEGAGHSPSFPYSP
               cryopyrin  (50)   VDLATLMIDFNGEEKAWAMAVWIFAAINRRDLYEKAKRDEPKWGSDNARV
                    NOD1  (34)   IRNTQCLVDN-------LLKNDYFSAEDAEIVCACPTQPDKVRKILDLVQ

                                 101                                             150
                HNTTBMY1   (1)   --------------------------------------------------
caspase_recruitment_protein (101) SEPHLGSPSQPTSTAVLMPWLHELPAKCTQGSEERVLRQLEDTSGRRWRE
               cryopyrin (100)   SN---------PDVICQEDSIEEEWMGLLEYLSRISICKMKKDYRKKYRK
                    NOD1  (77)   SK-------------GEE--VSEFFLYLLQQLADAYVDLRPWLLEIGFSP

                                 151                                             200
                HNTTBMY1   (1)   --------------------------------------------------
caspase_recruitment_protein (151) ISASHLYQALPSSPDHESPSQESPNAPTSTAVLGSWGSPPQPSLAPREQE
               cryopyrin (141)   YVRSRFQCIEDRNARLG---------------------------------
                    NOD1 (112)   SLLTQSKVVVNTDPVSRYTQQLR---------------------------

                                 201                                             250
                HNTTBMY1   (1)   --------------------------------------------------
caspase_recruitment_protein (201) APGTQWPLDETSGIYYTEIREREREKSEKGRPPWAAVVGTPPQAHSSLQP
               cryopyrin (158)   --------------------------------------------------
                    NOD1 (135)   --------------------------------------------------

                                 251                                             300
                HNTTBMY1   (1)   --------------------------------------MPKNSKVTQREH
caspase_recruitment_protein (251) HHHPWEPSVRESLCSTWPWKNEDFNQKFTQLLLLQRPHPRSQ-DPLVKRS
               cryopyrin (158)   -------------------ESVSLNKRYTRLRLIKEHRSQQEREQELLAI
                    NOD1 (135)   -------------------HHLGRDSKFVLCYAQKEELLLEEIYMDTTME

                                 301                                             350
                HNTTBMY1  (13)   SSEHVTESVADLLALEEPVEYKQSVLNVAG--------EAG GKQKAVEE
caspase_recruitment_protein (300) WPDYVEENRCHLLIEIRDLFGPGLDTQEPR--IVILQGAAGIGKSTLARQV
               cryopyrin (189)   GKTKTCESPVSPIKMEILFDPDDEHSEPVH-TVVFQGAAGIGKTILARKM
                    NOD1 (166)   LVGESNESLGSLNSLACLLDHTTGILNEQGETIFILGDAGVGKSMLLQRL

                                 351                                             400
                HNTTBMY1  (54)   ELLTEDRPAWNSKLQYILAQIGFSVGLGNIWR---EPYLCQKNGGAYLV
caspase_recruitment_protein (348) KEAWGRCQLYGDRFQHVFYFSCRELAQSKVVS---LAELIGKDGTATPAE
               cryopyrin (238)   MLDWASGTLYQDRFDYLFYIHCREVSLVTQRS---LGDLIMSCCPDPNPP
                    NOD1 (216)   QSLWAIGRLDAG-VKEFFHHRCRMFSCFKESDRLCLQDILFKHYCYPERD

                                 401                                             450
                HNTTBMY1 (101)   EYLVLLIIIGIPLFFLELAVGQRIRRGSIGVWHYICPRLGGIGFSSCIVC
caspase_recruitment_protein (395) ----IRQILSRPLRLLFILDGVDEPGWVLQEPSSELCLHWSQ-PQPADAL
               cryopyrin (285)   ----THKFVRKPSRILFLMDGFDELQGAFDEHICPLCTDWQK-AERGDIL
                    NOD1 (265)   PEEVFAFLLRFPHVALFTFDGLDELHSDLDLSRVPDSSCPWE-PAHPLVL

                                 451                                             500
                HNTTBMY1 (151)   LFVCLYYNVIIGWSIFYFFKSFQYPLPWSECPVVRNGSVAVVEAECEKSS
caspase_recruitment_protein (440) LGSLLGKTILPEASFLITARTTALQNLIPSLEQARWVEVLGFSESSRKEY
               cryopyrin (330)   LSSLIRKKLLPEASLLITTRPVALEKLQHLLDHPRHVEILGFSEAKRKEY
                    NOD1 (314)   LANLLSGKLLKGASKLLTARTGIEVPRQFLR---KKVLLRGFSPSHLRAY

                                 501                                             550
                HNTTBMY1 (201)   ATTYFWYREALEISDSISESGGLNWKMTLCLEVAWSEVGMAVVKGIQSS-
caspase_recruitment_protein (490) FYRYFTDERQAIRAFRLVKSNKELWALCLVPWVSWLACTCLMQQMKRKE-
               cryopyrin (380)   FFKYFSDEAQARAAFSLIQENEVLFTMCFIPLVCWIVCTGLKQQMESGK-
                    NOD1 (361)   ARRMEPERALQDRLLSQLEANPNLCSLCSVPLFCWIIFRCEQHFRAAFEG

                                 551                                             600
                HNTTBMY1 (250)   -----GKVMYFSSLFPYVVLACFLVRG----------------LLLRGAV
caspase_recruitment_protein (539) --KLTLFSKTTTTLCLHYLAQALQAQP-----------------LGPQL
               cryopyrin (429)   --SLAQTSKTTTAVYVFFLSSLLQPRGGS------------QEHGLCAHL
                    NOD1 (411)   SPQLPDCTMTLLDVELIVTEVILNRMQPSSLVQRNTRSPVETLHAGRDTL
```

Figure 2B

```
                                      601                                                650
                     HNTTBMY1  (279)  DGILHMFTPKLDKMLDPQVWREAATQVHFALGLGFGGVIAFSSYNKQDNN
 caspase_recruitment_protein  (569)  RDLCSLAAEGIWQKKTLFSPDDLRKHGLDGAIISTFLKMGILQEHP--IP
                    cryopyrin  (465)  WGLCSLAADGIWNQKILFEESDLRNHGLQKADVSAFLRMNLFQKEVD-CE
                         NOD1  (461)  CSLGQVAHRGMEKSLFVFTQEEVQASGLQERDMQLGRLRAMPELGPGGDQ

                                      651                                                700
                     HNTTBMY1  (329)  CHFTAALVSFTINFFTSVLATLVVFAVLGFKANIMNEKCVVENAEKILGYL
 caspase_recruitment_protein  (617)  LSYSFIHLCFQEFFAAMSYVLEDEKGR------GKHSNCITDLEKTLEAY
                    cryopyrin  (514)  KFYSFIHMTFQEFFAAMYYLLEEEKECRTNVPGSRLKLPSRDVTVLLENY
                         NOD1  (511)  QSYEFFHLTLQAFFTAFFIVLDDRVGTQELLRFFQEWMPPAGAATSCYP

                                      701                                                750
                     HNTTBMY1  (379)  NTNVLSRDLIPPHVNFSHLTTKDYMEMYNVIMTVKEDQF----------
 caspase_recruitment_protein  (661)  G-IHCLFCASTTRFLLLGLLSDEGEREMENIFHCRLSQGR----N--LMQW
                    cryopyrin  (564)  GKFEKGYLIFVVRFLFGLVNQERTSYLEKKLSCKISQQIRLELLKWIEVK
                         NOD1  (561)  PFLPFQCLQGSGPAREDLLFKNKDHFQLTNLFLCGLLSKA----------K

                                      751                                                800
                     HNTTBMY1  (418)  SALGLDPCLLEDELDKSVQGTGLALIALTEAMTHFEASPFWSVMFHLMLT
 caspase_recruitment_protein  (704)  VPSLQLLLQPHSLESIHCLYETRNKTFLTQVMAHFEEMGMCVETDMELLV
                    cryopyrin  (614)  AKAKKLQIQPSQLELFYCLYEMQEEDFVQRAMDYFPKIEINLSTRMDHMV
                         NOD1  (601)  QKLLRHEVPAAALRRKRKALWAHLFSSLRGYLKSLPRVQVESFNQVQAMP

                                      801                                                850
                     HNTTBMY1  (468)  N-------------------------------------------------
 caspase_recruitment_protein  (754)  CTFCIKFRRHVKKLQLIEGRQHR-------------------STWSPS
                    cryopyrin  (664)  SSFCIENCHRVESLSLGFLHNMPKEEEEEEKEGRHLDMVQCVLPSSSHAA
                         NOD1  (651)  TFIWMLRCIKETQSQKVCQLAAR-----------------------GICA

                                      851                                                900
                     HNTTBMY1  (469)  ---------------LGLGSMIGTMAGTRTPITDTFKVPKEMFTVGQCVF
 caspase_recruitment_protein  (783)  MVVLFRWVPVTDAYWQILFSVLKVTRNLKELDLSGNSLSHSAVKSLCKAL
                    cryopyrin  (714)  CSHGLVNSHLTSSFCRGLFSVLSTSQSLTELDLSDNSLGDPGMRVLCETL
                         NOD1  (678)  NYLKKTYCNACSADLSAISFVIHHFPKRLALDLDNNNLNDYGVRELQPCF

                                      901                                                950
                     HNTTBMY1  (504)  AFLVGLLFVQRSENYFVLMFLDYSAILPLTLIVILENLAVAWIYGIKKFM
 caspase_recruitment_protein  (833)  RRPRCLLETLRLAGCGLTAEDCKDLAFGLRANQTLTELDLSFNVLMDAGA
                    cryopyrin  (764)  QHPGCNIRRLWLGRCGLSHECCFDISLVLSSNQKLVELDLSDNALGDFGI
                         NOD1  (728)  SR----LTVLRLSVNQITDGGVKVLSEELTKYKIVTYLGLYNNQITDVGA

                                      951                                               1000
                     HNTTBMY1  (554)  QELTEMLG--FRPYRFYFYMWKFVSPLCMAVLTTASIIQLGVTPPGYSAW
 caspase_recruitment_protein  (883)  KHLCQRLRQPSCKLQRLQLVSCGLTSDCCQDLASVLSASPSLKELDLQQN
                    cryopyrin  (814)  RLLCVGLKHLLCNLKKLWLVSCCLTSACCQDLASVLSTSHSLTRLYVGEN
                         NOD1  (774)  RYVTKILD-ECKGLTHLKLGKNKITSEGGKYLALAVKNSKSISEVGMWGN

                                      1001                                              1050
                     HNTTBMY1  (602)  IKEEAAERYLYFPNWAMALLIALIVVATLPTPVVFVLRHFHLLSDG
 caspase_recruitment_protein  (933)  NLDDVGVRLLCEGLRHPACKLIRLGLDQTTLSDEMRQELRALEQEKPQLL
                    cryopyrin  (864)  ALGDSGVAILCEKAKNPQCNLQKLGLVNSGLTSVCCSALSSVLSTNQNLT
                         NOD1  (823)  QVCDEGAKAFAEALRN-HPSLTTLSLASNGTSTFGGKSLARALQQN----

                                      1051                                              1100
                     HNTTBMY1  (648)  ------------------------SN--TLSVSYK--K--GRMMKLISNLE
 caspase_recruitment_protein  (983)  IFSRRKPSVMTPIEGLDTGEMSNSTSSLKRQRLGSERAASHVAQANLKLL
                    cryopyrin  (914)  HLYLRGNTLGDKGIKLLCEGLLHPDCKLQVLELDNCNLTSHCCWDLSTLL
                         NOD1  (868)  -------------------------TSLEIEWLTQNELNDEVAESLAEML

                                      1101                                              1150
                     HNTTBMY1  (669)  ENDETRFLLSKVPS---------EAPSLMPTHRSYLGPGSTSPLETSGNP
 caspase_recruitment_protein  (1033)  DVSKIFPIAEIAEESSPEVVPVELLCVESPASQGDLHTKPLGTDDDFWGP
                    cryopyrin  (964)  TSSQSLRKLSLGNN---DLGDLGVMMFCEVLKQQSCLLQNLGLSEMYFNY
                         NOD1  (893)  KVNQTLKHLWLIQN---------QITAKGTAQLADALQSNTGLTELCLNG

                                      1151                                              1200
                     HNTTBMY1  (710)  NGRYGSGYLLASTPESEL--------------------------------
 caspase_recruitment_protein  (1083)  TGPVATEVVDKEKNLYRVHFPVAGSYRWPNTGLCFVVREAVTVEIEFCVW
                    cryopyrin  (1011)  ETKSALETLQEEKPELTVVFEPSW--------------------------
                         NOD1  (934)  NLIKPEEAKVYEDEKRILCS------------------------------
                    Consensus  (1151)  NGK ASF LL EKPE   V F   A
```

Figure 2C

```
                                    1201                                               1250
                  HNTTBMY1   (728)  --------------------------------------------------
caspase_recruitment_protein (1133)  DQFLGEINPQHSWMVAGPLLDIKAEPGAVEAVHLPHFVALQGGHVDTSLF
                  cryopyrin (1035)  --------------------------------------------------
                       NOD1  (954)  --------------------------------------------------

                                    1251                                               1300
                  HNTTBMY1   (728)  --------------------------------------------------
caspase_recruitment_protein (1183)  QVAHFKEEGMLLEKPARVELHHIVLENPSFSPLGVLLKMIHNALRFIPVT
                  cryopyrin (1035)  --------------------------------------------------
                       NOD1  (954)  --------------------------------------------------

                                    1301                                               1350
                  HNTTBMY1   (728)  --------------------------------------------------
caspase_recruitment_protein (1233)  SVVLLYHRLHPEEVTFHLYLIPSDCSIRKELELCYRSPGEDQLFSEFYVC
                  cryopyrin (1035)  --------------------------------------------------
                       NOD1  (954)  --------------------------------------------------

                                    1351                                               1400
                  HNTTBMY1   (728)  --------------------------------------------------
caspase_recruitment_protein (1283)  HLGSGIRLQVKDKKDETLVWEALVKFGDLMPATTLIPPACIAVPSPLDAP
                  cryopyrin (1035)  --------------------------------------------------
                       NOD1  (954)  --------------------------------------------------

                                    1401                                               1450
                  HNTTBMY1   (728)  --------------------------------------------------
caspase_recruitment_protein (1333)  QLLHFVDQYREQLIARVTSVEVVLDKLHGQVLSQEQYERVLAENTRPSQM
                  cryopyrin (1035)  --------------------------------------------------
                       NOD1  (954)  --------------------------------------------------

                                    1451                                          1497
                  HNTTBMY1   (728)  -----------------------------------------------
caspase_recruitment_protein (1383)  RKLFSLSQSWDRKCKDGLYQALKETHPHLIMELWEKGSKKGLLPLSS
                  cryopyrin (1035)  -----------------------------------------------
                       NOD1  (954)  -----------------------------------------------
```

Figure 5.

| Protein | Genbank ID | Percent Identity | Percent Similarity |
|---|---|---|---|
| human caspase recruitment protein 7 | gi\|10198209 | 35% | 48% |
| human NOD caspase recruitment protein 4 | gi\|5174617 | 25% | 38% |
| human cryopyrin protein | gi\|17027237 | 51.7% | 64.0% |

```
                              SEQUENCE LISTING

<160> NUMBER OF SEQ ID NOS: 35

<210> SEQ ID NO 1
<211> LENGTH: 4931
<212> TYPE: DNA
<213> ORGANISM: homo sapiens
<220> FEATURE:
<221> NAME/KEY: CDS
<222> LOCATION: (1320)..(2666)

<400> SEQUENCE: 1

ccacgcgtcc gaacatgggc tgagagcccc cccaagagca tctctaagac cggagtgggc      60

agggacccgg gcctctgagg ggctcaggct ccaggccgga aactgcacgc ggtgctggcg     120

tcaggcccga ggcccagcta cgcctcccac ggcctcccta atcgccattc ggggcttgcg     180

ggagcacctg ggaggctcca cccggagcca gacactgcct gcccccacgc ccctccagga     240

ccctcgaagg agaaggaaat cgggactggc ccagcgtccc gtgctctaga aggcgggcta     300

ctgccccgtc ccaagcaggg gaggaggacg agcgagggcg tcactcattc tgtcccccgc     360

ggaaggatga ggaagctctg tttacctaaa tgaaaagctt tctaggagga agtcctaagt     420

gaacaatgat gcatgaggat gcaatcttac agacacaggg gtctccctat gttgttcaag     480

ctggtctcga actcctggcc tcaagtgatc ctcctgcctc gacctctcaa agctctggta     540

ttataggcaa ggagcccagt gataacaaat ggctgtagat gcttttcctc catcaagctt     600

ccaggaggag atgagatgga gcccatcgct gagccaagaa ttctaatttc atccctttgg     660

tctttgttca tgctgtgttc tgcctggaat attctccatc ttctttgcct ggaaaagtat     720

tacttactga aaccttgaag ccactacctt ctctaaacat tgacaatgca taaccatttg     780

ccgagcgttc ttccccggac tgcatccgtt tagtctactg agaggcagct cagcgttccc     840

aaggagacag atgtctagct ttgctctttc tgtctgtgtg atgctggaga atcgatatgc     900

ccctgggcct ccatctccat ctgtaaaaca agggcatcag ataccccacc tggtggcccg     960

tcctcacttg ggaaccagtc aacatgcctt ctggaagtct ctcttgtcac tccaagaaaa    1020

gatccccagg aaacctacag ggactatgtc cgcaggaaat tccggctcat ggaagaccgc    1080

aatgcgcgcc taggggaatg tgtcaacctc agccaccggt acacccggct cctgctggtg    1140

aaggagcact caaaccccat gcaggtccag cagcagcttc tggacacagg ccggggacac    1200

gcgaggaccg tgggacacca ggctagcccc atcaagatag agaccctctt tgagccagac    1260

gaggagcgcc ccgagccacc gcgcaccgtg gtcatgcaag gcgcggcagg gatagggag     1319
```

-continued

```
atg aac cag agt gcc acg gaa tgc agc atg caa gac ctc atc ttc agc      1367
Met Asn Gln Ser Ala Thr Glu Cys Ser Met Gln Asp Leu Ile Phe Ser
1               5                   10                  15

tgc tgg cct gag ccc agc gcg cct ctc cag gag ctc atc cga gtt ccc      1415
Cys Trp Pro Glu Pro Ser Ala Pro Leu Gln Glu Leu Ile Arg Val Pro
            20                  25                  30

gag cgc ctc ctt ttc atc atc gac ggc ttc gat gag ctc aag cct tct      1463
Glu Arg Leu Leu Phe Ile Ile Asp Gly Phe Asp Glu Leu Lys Pro Ser
        35                  40                  45

ttc cac gat cct cag gga ccc tgg tgc ctc tgc tgg gag gag aaa cgg      1511
Phe His Asp Pro Gln Gly Pro Trp Cys Leu Cys Trp Glu Glu Lys Arg
    50                  55                  60

ccc acg gag ctg ctt ctt aac agc tta att cgg aag aag ctg ctc cct      1559
Pro Thr Glu Leu Leu Leu Asn Ser Leu Ile Arg Lys Lys Leu Leu Pro
65                  70                  75                  80

gag cta tct ttg ctc atc acc aca cgg ccc acg gct ttg gag aag ctc      1607
Glu Leu Ser Leu Leu Ile Thr Thr Arg Pro Thr Ala Leu Glu Lys Leu
                85                  90                  95

cac cgt ctg ctg gag cac ccc agg cat gtg gag atc ctg ggc ttc tct      1655
His Arg Leu Leu Glu His Pro Arg His Val Glu Ile Leu Gly Phe Ser
            100                 105                 110

gag gca gaa agg aag gaa tac ttc tac aag tat ttc cac aat gca gag      1703
Glu Ala Glu Arg Lys Glu Tyr Phe Tyr Lys Tyr Phe His Asn Ala Glu
        115                 120                 125

cag gcg ggc caa gtc ttc aat tac gtg agg gac aac gag cct ctc ttc      1751
Gln Ala Gly Gln Val Phe Asn Tyr Val Arg Asp Asn Glu Pro Leu Phe
    130                 135                 140

acc atg tgc ttc gtc ccc ctg gtg tgc tgg gtg gtg tgt acc tgc ctc      1799
Thr Met Cys Phe Val Pro Leu Val Cys Trp Val Val Cys Thr Cys Leu
145                 150                 155                 160

cag cag cag ctg gag ggt ggg ggc ctg ttg aga cag acg tcc agg acc      1847
Gln Gln Gln Leu Glu Gly Gly Gly Leu Leu Arg Gln Thr Ser Arg Thr
                165                 170                 175

acc act gca gtg tac atg ctc tac ctg ctg agt ctg atg caa ccc aag      1895
Thr Thr Ala Val Tyr Met Leu Tyr Leu Leu Ser Leu Met Gln Pro Lys
            180                 185                 190

ccg ggg gcc ccg cgc ctc cag ccc cca ccc aac cag aga ggg ttg tgc      1943
Pro Gly Ala Pro Arg Leu Gln Pro Pro Pro Asn Gln Arg Gly Leu Cys
        195                 200                 205

tcc ttg gcg gca gat ggg ctc tgg aat cag aaa atc cta ttt gag gag      1991
Ser Leu Ala Ala Asp Gly Leu Trp Asn Gln Lys Ile Leu Phe Glu Glu
    210                 215                 220

cag gac ctc cgg aag cac ggc cta gac ggg gaa gac gtc tct gcc ttc      2039
Gln Asp Leu Arg Lys His Gly Leu Asp Gly Glu Asp Val Ser Ala Phe
225                 230                 235                 240

ctc aac atg aac atc ttc cag aag gac atc aac tgt gag agg agc ttc      2087
Leu Asn Met Asn Ile Phe Gln Lys Asp Ile Asn Cys Glu Arg Ser Phe
                245                 250                 255

ctg gca ctc acc agc cgc ttc ctg ttt gga ctc ctg aac gag gag acc      2135
Leu Ala Leu Thr Ser Arg Phe Leu Phe Gly Leu Leu Asn Glu Glu Thr
            260                 265                 270

agg agc cac ctg gag aag agt ctc tgc tgg aag gtc tcg ccg cac atc      2183
Arg Ser His Leu Glu Lys Ser Leu Cys Trp Lys Val Ser Pro His Ile
        275                 280                 285

aag atg gac ctg ttg cag tgg atc caa agc aaa gct cag agc gac ggc      2231
Lys Met Asp Leu Leu Gln Trp Ile Gln Ser Lys Ala Gln Ser Asp Gly
    290                 295                 300

tcc acc ctg cag cag ggc tcc ttg gag ttc ttc agc tgc ttg tac gag      2279
Ser Thr Leu Gln Gln Gly Ser Leu Glu Phe Phe Ser Cys Leu Tyr Glu
305                 310                 315                 320
```

-continued

```
atc cag gag gag gag ttt atc cag cag gcc ctg agc cac ttc cag gtg     2327
Ile Gln Glu Glu Glu Phe Ile Gln Gln Ala Leu Ser His Phe Gln Val
                325                 330                 335

atc gtg gtc agc aac att gcc tcc aag atg gag cac atg gtc tcc tcg     2375
Ile Val Val Ser Asn Ile Ala Ser Lys Met Glu His Met Val Ser Ser
            340                 345                 350

ttc tgt ctg aag cgc tgc agg agc gcc cag gtg ctg cac ttg tat ggc     2423
Phe Cys Leu Lys Arg Cys Arg Ser Ala Gln Val Leu His Leu Tyr Gly
        355                 360                 365

gcc acc tac agc gcg gac ggg gaa gac cgc gcg agg tgc tcc gca gga     2471
Ala Thr Tyr Ser Ala Asp Gly Glu Asp Arg Ala Arg Cys Ser Ala Gly
    370                 375                 380

gcg cac acg ctg ttg gtg cag cta cca gag agg acc gtt ctg ctg gac     2519
Ala His Thr Leu Leu Val Gln Leu Pro Glu Arg Thr Val Leu Leu Asp
385                 390                 395                 400

gcc tac agt gaa cat ctg gca gcg gcc ctg tgc acc aat cca aac ctg     2567
Ala Tyr Ser Glu His Leu Ala Ala Ala Leu Cys Thr Asn Pro Asn Leu
                405                 410                 415

ata gag ctg tct ctg tac cga aat gcc ctg ggc agc cgg ggg gtg aag     2615
Ile Glu Leu Ser Leu Tyr Arg Asn Ala Leu Gly Ser Arg Gly Val Lys
            420                 425                 430

ctg ctc tgt caa gga ctc aga cac ccc aac tgc aaa ctt cag aac ctg     2663
Leu Leu Cys Gln Gly Leu Arg His Pro Asn Cys Lys Leu Gln Asn Leu
        435                 440                 445

agg taaaatttat catatataac atgatatttt gaaataaata tattggccag          2716
Arg

gtatgatggc tcacgcctgt aattccagca ctttgggagg cccagatggg gaggatcact   2776

tgacccagga gttcaagacc agcctggcca acatggtgaa accccatctc tactaaaaat   2836

accaaaatga gccaggcatg gtggcacacg tctgtaagcc cagctactca ggaggccaag   2896

gcaggaggat tgcttcaacc caggaggcag aggttgtggc tgaagaggtg ccgcatctcc   2956

agctcagcct gcgaggacct ctctgcagct ctcatagcca ataagaattt gacaaggatg   3016

gatctcagtg gcaacggcgt tggattccca ggcatgatgc tgctttgcga gggcctgcgg   3076

catccccaat gcaggctgca gatgattcag ttgaggaagt gtcagctgga gtccggggct   3136

tgtcaggaga tggcttctgt gcttggcacc aacccacatc tggttgagtt ggacctgaca   3196

ggaaatgcac tggaggattt gggcctgagg ttactatgcc agggactgag gcacccagtc   3256

tgcagactac ggactttgtg gctgaagatc tgccgcctca ctgctgctgc ctgtgacgag   3316

ctggcctcaa ctctcagtgt gaaccagagc ctgagagagc tggacctgag cctgaatgag   3376

ctgggggacc tcggggtgct gctgctgtgt gagggcctca ggcatcccac gtgcaagctc   3436

cagaccctgc ggtgagtccc gttttgctca ccacgctagg agtcccaatc catgaacgca   3496

gccctctcac ctgggaccac ggaggccagg ttgtctctgc tcctaaactc tagctactac   3556

atcagccctt tttttttttt ttttgagact cccaagtagc tgagattaca ggcgcccgcc   3616

accaagccca gctaattttt tgtattttta gtagagacag ggtttcatca tgttagcagg   3676

atggtctcga tctactgacc tcatgatctg cctgccttgg cctcccaaag tgctgggatt   3736

acaggcttga gccactgcac ccagcctaca tcagcctttt taaaaggatt tttctggccg   3796

ggcatggtgg ctgacacctt aattccagca cttttgggag gccgaggtgg gaggatcacc   3856

tgaggtgggg aattcgagac cagcctgacc aacatgtaga aacaccccat ctgtactaaa   3916

aatacaaaag tagccaggca tggtggtgca tgcctataat gccagctact cgcgaggctg   3976

aggcaggaga atccgttgaa cccgggaggt ggaagttgct gtgagctgag atggagccat   4036
```

```
tgcactccag tctgggcaac aagagcgaaa ctccgtctca aaaaaaaaaa aggggggggt   4096

tttctgacgc acggcccttt gcacaagcaa ttcttattcc ctggcatgcc ttctgctctc   4156

tgtcccctct ttgcctggag aagttcaatt tttcttctga acactcttta ctttgtattt   4216

tgagacaggg tcttgctctg tcaccagtgc tggagtggag tggtgtgatc atagcccgac   4276

atcctgggct gaagccatcc tcccaactca gcctcctgag tagctgggac tgcaagcgca   4336

tgccaccaca gatggctaat ttttactttt tttttgagat tttgccactg cactccagcc   4396

tggatgacag agcgagattc catctcaaaa aaaaaaaaga aaaatttgta atttgtgtat   4456

atgtgtgtgt ggtggcattc cacaagcata ggagctatgc caactgtatc tcctagtgac   4516

tagtataaga cgtgggtaga agtgctcaaa aaacacactt tgtgtatttt ttttatcaag   4576

gcaccagcaa aaaacaaaaa acaaaaaatc acacacgcgg ctgggcgcgg tggctcatgc   4636

ctgtaaaccc agcactttgg gaggctgagg cgggtggatc acgaggtcaa gagatggaga   4696

ccatcctggc caactggtga aaccccgtct ctactaaaaa tacaaaaatt agctgggcgt   4756

ggtggtgtgc acctgtagtc acagctactc aggaggctga ggcagaagaa tcacttgaac   4816

ccaggaggcg gaggttgcag tgagccgaga tcgcgccact gcactccagc ctgggcgaca   4876

gagtgggact ccatctcaaa aaaaaaaaaa aaaaaaaaaa aaaaaaaaaa aaaaa        4931
```

```
<210> SEQ ID NO 2
<211> LENGTH: 449
<212> TYPE: PRT
<213> ORGANISM: homo sapiens

<400> SEQUENCE: 2

Met Asn Gln Ser Ala Thr Glu Cys Ser Met Gln Asp Leu Ile Phe Ser
1               5                   10                  15

Cys Trp Pro Glu Pro Ser Ala Pro Leu Gln Glu Leu Ile Arg Val Pro
            20                  25                  30

Glu Arg Leu Leu Phe Ile Ile Asp Gly Phe Asp Glu Leu Lys Pro Ser
        35                  40                  45

Phe His Asp Pro Gln Gly Pro Trp Cys Leu Cys Trp Glu Glu Lys Arg
    50                  55                  60

Pro Thr Glu Leu Leu Leu Asn Ser Leu Ile Arg Lys Lys Leu Leu Pro
65                  70                  75                  80

Glu Leu Ser Leu Leu Ile Thr Thr Arg Pro Thr Ala Leu Glu Lys Leu
                85                  90                  95

His Arg Leu Leu Glu His Pro Arg His Val Glu Ile Leu Gly Phe Ser
            100                 105                 110

Glu Ala Glu Arg Lys Glu Tyr Phe Tyr Lys Tyr Phe His Asn Ala Glu
        115                 120                 125

Gln Ala Gly Gln Val Phe Asn Tyr Val Arg Asp Asn Glu Pro Leu Phe
    130                 135                 140

Thr Met Cys Phe Val Pro Leu Val Cys Trp Val Val Cys Thr Cys Leu
145                 150                 155                 160

Gln Gln Gln Leu Glu Gly Gly Gly Leu Leu Arg Gln Thr Ser Arg Thr
                165                 170                 175

Thr Thr Ala Val Tyr Met Leu Tyr Leu Leu Ser Leu Met Gln Pro Lys
            180                 185                 190

Pro Gly Ala Pro Arg Leu Gln Pro Pro Pro Asn Gln Arg Gly Leu Cys
        195                 200                 205
```

```
Ser Leu Ala Ala Asp Gly Leu Trp Asn Gln Lys Ile Leu Phe Glu Glu
    210                 215                 220

Gln Asp Leu Arg Lys His Gly Leu Asp Gly Glu Asp Val Ser Ala Phe
225                 230                 235                 240

Leu Asn Met Asn Ile Phe Gln Lys Asp Ile Asn Cys Glu Arg Ser Phe
                245                 250                 255

Leu Ala Leu Thr Ser Arg Phe Leu Phe Gly Leu Leu Asn Glu Glu Thr
            260                 265                 270

Arg Ser His Leu Glu Lys Ser Leu Cys Trp Lys Val Ser Pro His Ile
        275                 280                 285

Lys Met Asp Leu Leu Gln Trp Ile Gln Ser Lys Ala Gln Ser Asp Gly
    290                 295                 300

Ser Thr Leu Gln Gln Gly Ser Leu Glu Phe Phe Ser Cys Leu Tyr Glu
305                 310                 315                 320

Ile Gln Glu Glu Glu Phe Ile Gln Gln Ala Leu Ser His Phe Gln Val
                325                 330                 335

Ile Val Val Ser Asn Ile Ala Ser Lys Met Glu His Met Val Ser Ser
            340                 345                 350

Phe Cys Leu Lys Arg Cys Arg Ser Ala Gln Val Leu His Leu Tyr Gly
        355                 360                 365

Ala Thr Tyr Ser Ala Asp Gly Glu Asp Arg Ala Arg Cys Ser Ala Gly
    370                 375                 380

Ala His Thr Leu Leu Val Gln Leu Pro Glu Arg Thr Val Leu Leu Asp
385                 390                 395                 400

Ala Tyr Ser Glu His Leu Ala Ala Ala Leu Cys Thr Asn Pro Asn Leu
                405                 410                 415

Ile Glu Leu Ser Leu Tyr Arg Asn Ala Leu Gly Ser Arg Gly Val Lys
            420                 425                 430

Leu Leu Cys Gln Gly Leu Arg His Pro Asn Cys Lys Leu Gln Asn Leu
        435                 440                 445

Arg


<210> SEQ ID NO 3
<211> LENGTH: 1429
<212> TYPE: PRT
<213> ORGANISM: homo sapiens

<400> SEQUENCE: 3

Met Ala Gly Gly Ala Trp Gly Arg Leu Ala Cys Tyr Leu Glu Phe Leu
1               5                   10                  15

Lys Lys Glu Glu Leu Lys Glu Phe Gln Leu Leu Leu Ala Asn Lys Ala
            20                  25                  30

His Ser Arg Ser Ser Ser Gly Glu Thr Pro Ala Gln Pro Glu Lys Thr
        35                  40                  45

Ser Gly Met Glu Val Ala Ser Tyr Leu Val Ala Gln Tyr Gly Glu Gln
    50                  55                  60

Arg Ala Trp Asp Leu Ala Leu His Thr Trp Glu Gln Met Gly Leu Arg
65                  70                  75                  80

Ser Leu Cys Ala Gln Ala Gln Glu Gly Ala Gly His Ser Pro Ser Phe
                85                  90                  95

Pro Tyr Ser Pro Ser Glu Pro His Leu Gly Ser Pro Ser Gln Pro Thr
            100                 105                 110

Ser Thr Ala Val Leu Met Pro Trp Ile His Glu Leu Pro Ala Gly Cys
        115                 120                 125
```

-continued

```
Thr Gln Gly Ser Glu Arg Arg Val Leu Arg Gln Leu Pro Asp Thr Ser
    130                 135                 140

Gly Arg Arg Trp Arg Glu Ile Ser Ala Ser His Leu Tyr Gln Ala Leu
145                 150                 155                 160

Pro Ser Ser Pro Asp His Glu Ser Pro Ser Gln Glu Ser Pro Asn Ala
                165                 170                 175

Pro Thr Ser Thr Ala Val Leu Gly Ser Trp Gly Ser Pro Pro Gln Pro
            180                 185                 190

Ser Leu Ala Pro Arg Glu Gln Glu Ala Pro Gly Thr Gln Trp Pro Leu
        195                 200                 205

Asp Glu Thr Ser Gly Ile Tyr Tyr Thr Glu Ile Arg Glu Arg Glu Arg
    210                 215                 220

Glu Lys Ser Glu Lys Gly Arg Pro Pro Trp Ala Ala Val Val Gly Thr
225                 230                 235                 240

Pro Pro Gln Ala His Ser Ser Leu Gln Pro His His His Pro Trp Glu
                245                 250                 255

Pro Ser Val Arg Glu Ser Leu Cys Ser Thr Trp Pro Trp Lys Asn Glu
            260                 265                 270

Asp Phe Asn Gln Lys Phe Thr Gln Leu Leu Leu Leu Gln Arg Pro His
        275                 280                 285

Pro Arg Ser Gln Asp Pro Leu Val Lys Arg Ser Trp Pro Asp Tyr Val
    290                 295                 300

Glu Glu Asn Arg Gly His Leu Ile Glu Ile Arg Asp Leu Phe Gly Pro
305                 310                 315                 320

Gly Leu Asp Thr Gln Glu Pro Arg Ile Val Ile Leu Gln Gly Ala Ala
                325                 330                 335

Gly Ile Gly Lys Ser Thr Leu Ala Arg Gln Val Lys Glu Ala Trp Gly
            340                 345                 350

Arg Gly Gln Leu Tyr Gly Asp Arg Phe Gln His Val Phe Tyr Phe Ser
        355                 360                 365

Cys Arg Glu Leu Ala Gln Ser Lys Val Val Ser Leu Ala Glu Leu Ile
    370                 375                 380

Gly Lys Asp Gly Thr Ala Thr Pro Ala Pro Ile Arg Gln Ile Leu Ser
385                 390                 395                 400

Arg Pro Glu Arg Leu Leu Phe Ile Leu Asp Gly Val Asp Glu Pro Gly
                405                 410                 415

Trp Val Leu Gln Glu Pro Ser Ser Glu Leu Cys Leu His Trp Ser Gln
            420                 425                 430

Pro Gln Pro Ala Asp Ala Leu Leu Gly Ser Leu Leu Gly Lys Thr Ile
        435                 440                 445

Leu Pro Glu Ala Ser Phe Leu Ile Thr Ala Arg Thr Thr Ala Leu Gln
    450                 455                 460

Asn Leu Ile Pro Ser Leu Glu Gln Ala Arg Trp Val Glu Val Leu Gly
465                 470                 475                 480

Phe Ser Glu Ser Ser Arg Lys Glu Tyr Phe Tyr Arg Tyr Phe Thr Asp
                485                 490                 495

Glu Arg Gln Ala Ile Arg Ala Phe Arg Leu Val Lys Ser Asn Lys Glu
            500                 505                 510

Leu Trp Ala Leu Cys Leu Val Pro Trp Val Ser Trp Leu Ala Cys Thr
        515                 520                 525

Cys Leu Met Gln Gln Met Lys Arg Lys Glu Lys Leu Thr Leu Thr Ser
    530                 535                 540
```

-continued

```
Lys Thr Thr Thr Thr Leu Cys Leu His Tyr Leu Ala Gln Ala Leu Gln
545                 550                 555                 560

Ala Gln Pro Leu Gly Pro Gln Leu Arg Asp Leu Cys Ser Leu Ala Ala
                565                 570                 575

Glu Gly Ile Trp Gln Lys Lys Thr Leu Phe Ser Pro Asp Asp Leu Arg
            580                 585                 590

Lys His Gly Leu Asp Gly Ala Ile Ile Ser Thr Phe Leu Lys Met Gly
        595                 600                 605

Ile Leu Gln Glu His Pro Ile Pro Leu Ser Tyr Ser Phe Ile His Leu
    610                 615                 620

Cys Phe Gln Glu Phe Phe Ala Ala Met Ser Tyr Val Leu Glu Asp Glu
625                 630                 635                 640

Lys Gly Arg Gly Lys His Ser Asn Cys Ile Ile Asp Leu Glu Lys Thr
                645                 650                 655

Leu Glu Ala Tyr Gly Ile His Gly Leu Phe Gly Ala Ser Thr Thr Arg
            660                 665                 670

Phe Leu Leu Gly Leu Leu Ser Asp Glu Gly Glu Arg Glu Met Glu Asn
        675                 680                 685

Ile Phe His Cys Arg Leu Ser Gln Gly Arg Asn Leu Met Gln Trp Val
    690                 695                 700

Pro Ser Leu Gln Leu Leu Leu Gln Pro His Ser Leu Glu Ser Leu His
705                 710                 715                 720

Cys Leu Tyr Glu Thr Arg Asn Lys Thr Phe Leu Thr Gln Val Met Ala
                725                 730                 735

His Phe Glu Glu Met Gly Met Cys Val Glu Thr Asp Met Glu Leu Leu
            740                 745                 750

Val Cys Thr Phe Cys Ile Lys Phe Ser Arg His Val Lys Lys Leu Gln
        755                 760                 765

Leu Ile Glu Gly Arg Gln His Arg Ser Thr Trp Ser Pro Ser Met Val
    770                 775                 780

Val Leu Phe Arg Trp Val Pro Val Thr Asp Ala Tyr Trp Gln Ile Leu
785                 790                 795                 800

Phe Ser Val Leu Lys Val Thr Arg Asn Leu Lys Glu Leu Asp Leu Ser
                805                 810                 815

Gly Asn Ser Leu Ser His Ser Ala Val Lys Ser Leu Cys Lys Thr Leu
            820                 825                 830

Arg Arg Pro Arg Cys Leu Leu Glu Thr Leu Arg Leu Ala Gly Cys Gly
        835                 840                 845

Leu Thr Ala Glu Asp Cys Lys Asp Leu Ala Phe Gly Leu Arg Ala Asn
    850                 855                 860

Gln Thr Leu Thr Glu Leu Asp Leu Ser Phe Asn Val Leu Met Asp Ala
865                 870                 875                 880

Gly Ala Lys His Leu Cys Gln Arg Leu Arg Gln Pro Ser Cys Lys Leu
                885                 890                 895

Gln Arg Leu Gln Leu Val Ser Cys Gly Leu Thr Ser Asp Cys Cys Gln
            900                 905                 910

Asp Leu Ala Ser Val Leu Ser Ala Ser Pro Ser Leu Lys Glu Leu Asp
        915                 920                 925

Leu Gln Gln Asn Asn Leu Asp Asp Val Gly Val Arg Leu Leu Cys Glu
    930                 935                 940

Gly Leu Arg His Pro Ala Cys Lys Leu Ile Arg Leu Gly Leu Asp Gln
945                 950                 955                 960
```

-continued

```
Thr Thr Leu Ser Asp Glu Met Arg Gln Glu Leu Arg Ala Leu Glu Gln
                965                 970                 975

Glu Lys Pro Gln Leu Leu Ile Phe Ser Arg Arg Lys Pro Ser Val Met
            980                 985                 990

Thr Pro Ile Glu Gly Leu Asp Thr  Gly Glu Met Ser Asn  Ser Thr Ser
        995                 1000                 1005

Ser Leu  Lys Arg Gln Arg Leu  Gly Ser Glu Arg Ala  Ala Ser His
    1010                 1015                 1020

Val Ala  Gln Ala Asn Leu Lys  Leu Leu Asp Val Ser  Lys Ile Phe
    1025                 1030                 1035

Pro Ile  Ala Glu Ile Ala Glu  Glu Ser Ser Pro Glu  Val Val Pro
    1040                 1045                 1050

Val Glu  Leu Leu Cys Val Pro  Ser Pro Ala Ser Gln  Gly Asp Leu
    1055                 1060                 1065

His Thr  Lys Pro Leu Gly Thr  Asp Asp Asp Phe Trp  Gly Pro Thr
    1070                 1075                 1080

Gly Pro  Val Ala Thr Glu Val  Val Asp Lys Glu Lys  Asn Leu Tyr
    1085                 1090                 1095

Arg Val  His Phe Pro Val Ala  Gly Ser Tyr Arg Trp  Pro Asn Thr
    1100                 1105                 1110

Gly Leu  Cys Phe Val Val Arg  Glu Ala Val Thr Val  Glu Ile Glu
    1115                 1120                 1125

Phe Cys  Val Trp Asp Gln Phe  Leu Gly Glu Ile Asn  Pro Gln His
    1130                 1135                 1140

Ser Trp  Met Val Ala Gly Pro  Leu Leu Asp Ile Lys  Ala Glu Pro
    1145                 1150                 1155

Gly Ala  Val Glu Ala Val His  Leu Pro His Phe Val  Ala Leu Gln
    1160                 1165                 1170

Gly Gly  His Val Asp Thr Ser  Leu Phe Gln Val Ala  His Phe Lys
    1175                 1180                 1185

Glu Glu  Gly Met Leu Leu Glu  Lys Pro Ala Arg Val  Glu Leu His
    1190                 1195                 1200

His Ile  Val Leu Glu Asn Pro  Ser Phe Ser Pro Leu  Gly Val Leu
    1205                 1210                 1215

Leu Lys  Met Ile His Asn Ala  Leu Arg Phe Ile Pro  Val Thr Ser
    1220                 1225                 1230

Val Val  Leu Leu Tyr His Arg  Leu His Pro Glu Glu  Val Thr Phe
    1235                 1240                 1245

His Leu  Tyr Leu Ile Pro Ser  Asp Cys Ser Ile Arg  Lys Glu Leu
    1250                 1255                 1260

Glu Leu  Cys Tyr Arg Ser Pro  Gly Glu Asp Gln Leu  Phe Ser Glu
    1265                 1270                 1275

Phe Tyr  Val Gly His Leu Gly  Ser Gly Ile Arg Leu  Gln Val Lys
    1280                 1285                 1290

Asp Lys  Lys Asp Glu Thr Leu  Val Trp Glu Ala Leu  Val Lys Pro
    1295                 1300                 1305

Gly Asp  Leu Met Pro Ala Thr  Thr Leu Ile Pro Pro  Ala Cys Ile
    1310                 1315                 1320

Ala Val  Pro Ser Pro Leu Asp  Ala Pro Gln Leu Leu  His Phe Val
    1325                 1330                 1335

Asp Gln  Tyr Arg Glu Gln Leu  Ile Ala Arg Val Thr  Ser Val Glu
    1340                 1345                 1350
```

-continued

```
Val Val  Leu Asp Lys Leu His  Gly Gln Val Leu Ser  Gln Glu Gln
    1355                 1360                 1365

Tyr Glu  Arg Val Leu Ala Glu  Asn Thr Arg Pro Ser  Gln Met Arg
    1370                 1375                 1380

Lys Leu  Phe Ser Leu Ser Gln  Ser Trp Asp Arg Lys  Cys Lys Asp
    1385                 1390                 1395

Gly Leu  Tyr Gln Ala Leu Lys  Glu Thr His Pro His  Leu Ile Met
    1400                 1405                 1410

Glu Leu  Trp Glu Lys Gly Ser  Lys Lys Gly Leu Leu  Pro Leu Ser
    1415                 1420                 1425

Ser


<210> SEQ ID NO 4
<211> LENGTH: 953
<212> TYPE: PRT
<213> ORGANISM: Homo sapiens

<400> SEQUENCE: 4

Met Glu Glu Gln Gly His Ser Glu Met Glu Ile Ile Pro Ser Glu Ser
1               5                   10                  15

His Pro His Ile Gln Leu Leu Lys Ser Asn Arg Glu Leu Leu Val Thr
            20                  25                  30

His Ile Arg Asn Thr Gln Cys Leu Val Asp Asn Leu Leu Lys Asn Asp
        35                  40                  45

Tyr Phe Ser Ala Glu Asp Ala Glu Ile Val Cys Ala Cys Pro Thr Gln
    50                  55                  60

Pro Asp Lys Val Arg Lys Ile Leu Asp Leu Val Gln Ser Lys Gly Glu
65                  70                  75                  80

Glu Val Ser Glu Phe Phe Leu Tyr Leu Leu Gln Gln Leu Ala Asp Ala
                85                  90                  95

Tyr Val Asp Leu Arg Pro Trp Leu Leu Glu Ile Gly Phe Ser Pro Ser
            100                 105                 110

Leu Leu Thr Gln Ser Lys Val Val Val Asn Thr Asp Pro Val Ser Arg
        115                 120                 125

Tyr Thr Gln Gln Leu Arg His His Leu Gly Arg Asp Ser Lys Phe Val
    130                 135                 140

Leu Cys Tyr Ala Gln Lys Glu Glu Leu Leu Leu Glu Glu Ile Tyr Met
145                 150                 155                 160

Asp Thr Ile Met Glu Leu Val Gly Phe Ser Asn Glu Ser Leu Gly Ser
                165                 170                 175

Leu Asn Ser Leu Ala Cys Leu Leu Asp His Thr Thr Gly Ile Leu Asn
            180                 185                 190

Glu Gln Gly Glu Thr Ile Phe Ile Leu Gly Asp Ala Gly Val Gly Lys
        195                 200                 205

Ser Met Leu Leu Gln Arg Leu Gln Ser Leu Trp Ala Thr Gly Arg Leu
    210                 215                 220

Asp Ala Gly Val Lys Phe Phe Phe His Phe Arg Cys Arg Met Phe Ser
225                 230                 235                 240

Cys Phe Lys Glu Ser Asp Arg Leu Cys Leu Gln Asp Leu Leu Phe Lys
                245                 250                 255

His Tyr Cys Tyr Pro Glu Arg Asp Pro Glu Glu Val Phe Ala Phe Leu
            260                 265                 270

Leu Arg Phe Pro His Val Ala Leu Phe Thr Phe Asp Gly Leu Asp Glu
        275                 280                 285
```

-continued

```
Leu His Ser Asp Leu Asp Leu Ser Arg Val Pro Asp Ser Ser Cys Pro
    290                 295                 300

Trp Glu Pro Ala His Pro Leu Val Leu Leu Ala Asn Leu Leu Ser Gly
305                 310                 315                 320

Lys Leu Leu Lys Gly Ala Ser Lys Leu Leu Thr Ala Arg Thr Gly Ile
                325                 330                 335

Glu Val Pro Arg Gln Phe Leu Arg Lys Lys Val Leu Leu Arg Gly Phe
            340                 345                 350

Ser Pro Ser His Leu Arg Ala Tyr Ala Arg Arg Met Phe Pro Glu Arg
        355                 360                 365

Ala Leu Gln Asp Arg Leu Leu Ser Gln Leu Glu Ala Asn Pro Asn Leu
    370                 375                 380

Cys Ser Leu Cys Ser Val Pro Leu Phe Cys Trp Ile Ile Phe Arg Cys
385                 390                 395                 400

Phe Gln His Phe Arg Ala Ala Phe Glu Gly Ser Pro Gln Leu Pro Asp
                405                 410                 415

Cys Thr Met Thr Leu Thr Asp Val Phe Leu Leu Val Thr Glu Val His
            420                 425                 430

Leu Asn Arg Met Gln Pro Ser Ser Leu Val Gln Arg Asn Thr Arg Ser
        435                 440                 445

Pro Val Glu Thr Leu His Ala Gly Arg Asp Thr Leu Cys Ser Leu Gly
    450                 455                 460

Gln Val Ala His Arg Gly Met Glu Lys Ser Leu Phe Val Phe Thr Gln
465                 470                 475                 480

Glu Glu Val Gln Ala Ser Gly Leu Gln Glu Arg Asp Met Gln Leu Gly
                485                 490                 495

Phe Leu Arg Ala Leu Pro Glu Leu Gly Pro Gly Gly Asp Gln Gln Ser
            500                 505                 510

Tyr Glu Phe Phe His Leu Thr Leu Gln Ala Phe Phe Thr Ala Phe Phe
        515                 520                 525

Leu Val Leu Asp Asp Arg Val Gly Thr Gln Glu Leu Leu Arg Phe Phe
    530                 535                 540

Gln Glu Trp Met Pro Pro Ala Gly Ala Ala Thr Thr Ser Cys Tyr Pro
545                 550                 555                 560

Pro Phe Leu Pro Phe Gln Cys Leu Gln Gly Ser Gly Pro Ala Arg Glu
                565                 570                 575

Asp Leu Phe Lys Asn Lys Asp His Phe Gln Phe Thr Asn Leu Phe Leu
            580                 585                 590

Cys Gly Leu Leu Ser Lys Ala Lys Gln Lys Leu Leu Arg His Leu Val
        595                 600                 605

Pro Ala Ala Ala Leu Arg Arg Lys Arg Lys Ala Leu Trp Ala His Leu
    610                 615                 620

Phe Ser Ser Leu Arg Gly Tyr Leu Lys Ser Leu Pro Arg Val Gln Val
625                 630                 635                 640

Glu Ser Phe Asn Gln Val Gln Ala Met Pro Thr Phe Ile Trp Met Leu
                645                 650                 655

Arg Cys Ile Tyr Glu Thr Gln Ser Gln Lys Val Gly Gln Leu Ala Ala
            660                 665                 670

Arg Gly Ile Cys Ala Asn Tyr Leu Lys Leu Thr Tyr Cys Asn Ala Cys
        675                 680                 685

Ser Ala Asp Cys Ser Ala Leu Ser Phe Val Leu His His Phe Pro Lys
    690                 695                 700
```

```
Arg Leu Ala Leu Asp Leu Asp Asn Asn Asn Leu Asn Asp Tyr Gly Val
705                 710                 715                 720

Arg Glu Leu Gln Pro Cys Phe Ser Arg Leu Thr Val Leu Arg Leu Ser
                725                 730                 735

Val Asn Gln Ile Thr Asp Gly Gly Val Lys Val Leu Ser Glu Glu Leu
            740                 745                 750

Thr Lys Tyr Lys Ile Val Thr Tyr Leu Gly Leu Tyr Asn Asn Gln Ile
        755                 760                 765

Thr Asp Val Gly Ala Arg Tyr Val Thr Lys Ile Leu Asp Glu Cys Lys
    770                 775                 780

Gly Leu Thr His Leu Lys Leu Gly Lys Asn Lys Ile Thr Ser Glu Gly
785                 790                 795                 800

Gly Lys Tyr Leu Ala Leu Ala Val Lys Asn Ser Lys Ser Ile Ser Glu
                805                 810                 815

Val Gly Met Trp Gly Asn Gln Val Gly Asp Glu Gly Ala Lys Ala Phe
            820                 825                 830

Ala Glu Ala Leu Arg Asn His Pro Ser Leu Thr Thr Leu Ser Leu Ala
        835                 840                 845

Ser Asn Gly Ile Ser Thr Glu Gly Gly Lys Ser Leu Ala Arg Ala Leu
    850                 855                 860

Gln Gln Asn Thr Ser Leu Glu Ile Leu Trp Leu Thr Gln Asn Glu Leu
865                 870                 875                 880

Asn Asp Glu Val Ala Glu Ser Leu Ala Glu Met Leu Lys Val Asn Gln
                885                 890                 895

Thr Leu Lys His Leu Trp Leu Ile Gln Asn Gln Ile Thr Ala Lys Gly
            900                 905                 910

Thr Ala Gln Leu Ala Asp Ala Leu Gln Ser Asn Thr Gly Ile Thr Glu
        915                 920                 925

Ile Cys Leu Asn Gly Asn Leu Ile Lys Pro Glu Glu Ala Lys Val Tyr
    930                 935                 940

Glu Asp Glu Lys Arg Ile Ile Cys Phe
945                 950
```

<210> SEQ ID NO 5
<211> LENGTH: 308
<212> TYPE: DNA
<213> ORGANISM: homo sapiens

<400> SEQUENCE: 5

```
ccacctggag aagagtctct gctggaaggt ctcgccgcac atcaagatgg acctgttgca     60

gtggatccaa agcaaagctc agagcgacgg ctccaccctg cagcagggct cctttgagtt    120

cttcagttgc ttgtacgaga tccaggagga ggagtttatc cagcaggccc tgagccactt    180

ccaggtgatc gtggtcagca acattgcctc caagatggag cacatggtct cctcgttctg    240

tctgatgcgc tgcaggagcg cccaggtggt gcacttgtat ggcgccacct acagcgcgga    300

cggggaag                                                             308
```

<210> SEQ ID NO 6
<211> LENGTH: 16
<212> TYPE: PRT
<213> ORGANISM: homo sapiens

<400> SEQUENCE: 6

```
Phe Thr Met Cys Phe Val Pro Leu Val Cys Trp Val Val Cys Thr Cys
1               5                   10                  15
```

<210> SEQ ID NO 7
<211> LENGTH: 21
<212> TYPE: DNA
<213> ORGANISM: homo sapiens

<400> SEQUENCE: 7
gatggacctg ttgcagtgga t 21

<210> SEQ ID NO 8
<211> LENGTH: 21
<212> TYPE: DNA
<213> ORGANISM: homo sapiens

<400> SEQUENCE: 8
gaccacgatc acctggaagt g 21

<210> SEQ ID NO 9
<211> LENGTH: 80
<212> TYPE: DNA
<213> ORGANISM: homo sapiens

<400> SEQUENCE: 9
tgaagaactc aaaggagccc tgctgcaggg tggagccgtc gctctgagct ttgctttgga 60
tccactgcaa caggtccatc 80

<210> SEQ ID NO 10
<211> LENGTH: 13
<212> TYPE: PRT
<213> ORGANISM: homo sapiens

<400> SEQUENCE: 10

Leu Ser Leu Leu Ile Thr Thr Arg Pro Thr Ala Leu Glu
1 5 10

<210> SEQ ID NO 11
<211> LENGTH: 13
<212> TYPE: PRT
<213> ORGANISM: homo sapiens

<400> SEQUENCE: 11

Gly Leu Leu Arg Gln Thr Ser Arg Thr Thr Thr Ala Val
1 5 10

<210> SEQ ID NO 12
<211> LENGTH: 13
<212> TYPE: PRT
<213> ORGANISM: homo sapiens

<400> SEQUENCE: 12

Ser Phe Leu Ala Leu Thr Ser Arg Phe Leu Phe Gly Leu
1 5 10

<210> SEQ ID NO 13
<211> LENGTH: 10
<212> TYPE: PRT
<213> ORGANISM: homo sapiens

<400> SEQUENCE: 13

Met Asn Gln Ser Ala Thr Glu Cys Ser Met
1 5 10

<210> SEQ ID NO 14
<211> LENGTH: 514
<212> TYPE: PRT
<213> ORGANISM: homo sapiens

<400> SEQUENCE: 14

```
Met Cys Phe Ile Pro Leu Val Cys Trp Ile Val Cys Thr Gly Leu Lys
1               5                   10                  15

Gln Gln Met Glu Ser Gly Lys Ser Leu Ala Gln Thr Ser Lys Thr Ser
            20                  25                  30

Thr Ala Val Tyr Val Phe Phe Leu Ser Ser Leu Leu Gln Pro Arg Gly
        35                  40                  45

Gly Ser Gln Glu His Gly Leu Cys Ala His Leu Trp Gly Leu Cys Ser
    50                  55                  60

Leu Ala Ala Asp Gly Ile Trp Asn Gln Lys Ile Leu Phe Glu Glu Ser
65                  70                  75                  80

Asp Leu Arg Asn His Gly Leu Gln Lys Ala Asp Val Ser Ala Phe Leu
                85                  90                  95

Arg Met Asn Leu Phe Gln Lys Glu Val Asp Cys Glu Lys Phe Tyr Ser
            100                 105                 110

Phe Ile His Met Thr Phe Gln Glu Phe Phe Ala Ala Met Tyr Tyr Leu
        115                 120                 125

Leu Glu Glu Glu Lys Glu Gly Arg Thr Asn Val Pro Gly Ser Arg Leu
    130                 135                 140

Lys Leu Pro Ser Arg Asp Val Thr Val Leu Leu Glu Asn Tyr Gly Lys
145                 150                 155                 160

Phe Glu Lys Gly Tyr Leu Ile Phe Val Val Arg Phe Leu Phe Gly Leu
                165                 170                 175

Val Asn Gln Glu Arg Thr Ser Tyr Leu Glu Lys Lys Leu Ser Cys Met
            180                 185                 190

Ile Ser Gln Gln Ile Arg Leu Glu Leu Leu Lys Trp Ile Glu Val Lys
        195                 200                 205

Ala Lys Ala Lys Lys Leu His Asp Gln Pro Ser Gln Leu Glu Leu Phe
    210                 215                 220

Tyr Cys Leu Tyr Glu Met Gln Glu Glu Asp Phe Val Gln Arg Ala Met
225                 230                 235                 240

Asp Tyr Phe Pro Lys Ile Glu Ile Asn Leu Ser Thr Arg Met Asp His
                245                 250                 255

Met Val Ser Ser Phe Cys Ile Glu Asn Cys His Arg Val Glu Ser Leu
            260                 265                 270

Ser Leu Gly Phe Leu His Asn Met Pro Lys Glu Glu Glu Glu Glu Glu
        275                 280                 285

Lys Glu Gly Arg His Leu Asp Met Val Gln Cys Val Leu Pro Ser Ser
    290                 295                 300

Ser His Ala Ala Cys Ser His Gly Leu Gly Arg Cys Gly Leu Ser His
305                 310                 315                 320

Glu Cys Cys Phe Asp Ile Ser Leu Val Leu Ser Ser Asn Gln Lys Leu
                325                 330                 335

Val Glu Leu Asp Leu Ser Asp Asn Ala Leu Gly Asp Phe Gly Ile Arg
            340                 345                 350

Leu Leu Cys Val Gly Leu Lys His Leu Leu Cys Asn Leu Lys Lys Leu
        355                 360                 365
```

```
Trp Leu Val Asn Ser Ala Leu Arg Gln Ser Val Val Gln Leu Cys Pro
    370                 375                 380

Arg Tyr Ser Ala Leu Ile Arg Ile Ser Arg Thr Phe Thr Ala Arg Gln
385                 390                 395                 400

His Ser Arg Arg Gln Gly Ile Lys Leu Leu Cys Glu Gly Leu Leu His
                405                 410                 415

Pro Asp Cys Lys Leu Gln Val Leu Glu Leu Asp Asn Cys Asn Leu Thr
            420                 425                 430

Ser His Cys Cys Trp Asp Leu Ser Thr Leu Leu Thr Ser Ser Gln Ser
        435                 440                 445

Leu Arg Lys Leu Ser Leu Gly Asn Asn Asp Leu Gly Asp Leu Gly Val
    450                 455                 460

Met Met Phe Cys Glu Val Leu Lys Gln Gln Ser Cys Leu Leu Gln Asn
465                 470                 475                 480

Leu Gly Leu Ser Glu Met Tyr Phe Asn Tyr Glu Thr Lys Ser Ala Leu
                485                 490                 495

Glu Thr Leu Gln Glu Glu Lys Pro Glu Leu Thr Val Val Phe Glu Pro
            500                 505                 510

Ser Trp

<210> SEQ ID NO 15
<211> LENGTH: 1429
<212> TYPE: PRT
<213> ORGANISM: homo sapiens

<400> SEQUENCE: 15

Met Ala Gly Gly Ala Trp Gly Arg Leu Ala Cys Tyr Leu Glu Phe Leu
1               5                   10                  15

Lys Lys Glu Glu Leu Lys Glu Phe Gln Leu Leu Leu Ala Asn Lys Ala
            20                  25                  30

His Ser Arg Ser Ser Ser Gly Glu Thr Pro Ala Gln Pro Glu Lys Thr
        35                  40                  45

Ser Gly Met Glu Val Ala Ser Tyr Leu Val Ala Gln Tyr Gly Glu Gln
    50                  55                  60

Arg Ala Trp Asp Leu Ala Leu His Thr Trp Glu Gln Met Gly Leu Arg
65                  70                  75                  80

Ser Leu Cys Ala Gln Ala Gln Glu Gly Ala Gly His Ser Pro Ser Phe
                85                  90                  95

Pro Tyr Ser Pro Ser Glu Pro His Leu Gly Ser Pro Ser Gln Pro Thr
            100                 105                 110

Ser Thr Ala Val Leu Met Pro Trp Ile His Glu Leu Pro Ala Gly Cys
        115                 120                 125

Thr Gln Gly Ser Glu Arg Arg Val Leu Arg Gln Leu Pro Asp Thr Ser
    130                 135                 140

Gly Arg Arg Trp Arg Glu Ile Ser Ala Ser Leu Leu Tyr Gln Ala Leu
145                 150                 155                 160

Pro Ser Ser Pro Asp His Glu Ser Pro Ser Gln Glu Ser Pro Asn Ala
                165                 170                 175

Pro Thr Ser Thr Ala Val Leu Gly Ser Trp Gly Ser Pro Pro Gln Pro
            180                 185                 190

Ser Leu Ala Pro Arg Glu Gln Glu Ala Pro Gly Thr Gln Trp Pro Leu
        195                 200                 205

Asp Glu Thr Ser Gly Ile Tyr Tyr Thr Glu Ile Arg Glu Arg Glu Arg
    210                 215                 220
```

```
Glu Lys Ser Glu Lys Gly Arg Pro Pro Trp Ala Ala Val Val Gly Thr
225                 230                 235                 240

Pro Pro Gln Ala His Thr Ser Leu Gln Pro His His His Pro Trp Glu
                245                 250                 255

Pro Ser Val Arg Glu Ser Leu Cys Ser Thr Trp Pro Trp Lys Asn Glu
            260                 265                 270

Asp Phe Asn Gln Lys Phe Thr Gln Leu Leu Leu Leu Gln Arg Pro His
        275                 280                 285

Pro Arg Ser Gln Asp Pro Leu Val Lys Arg Ser Trp Pro Asp Tyr Val
    290                 295                 300

Glu Glu Asn Arg Gly His Leu Ile Glu Ile Arg Asp Leu Phe Gly Pro
305                 310                 315                 320

Gly Leu Asp Thr Gln Glu Pro Arg Ile Val Ile Leu Gln Gly Ala Ala
                325                 330                 335

Gly Ile Gly Lys Ser Thr Leu Ala Arg Gln Val Lys Glu Ala Trp Gly
            340                 345                 350

Arg Gly Gln Leu Tyr Gly Asp Arg Phe Gln His Val Phe Tyr Phe Ser
        355                 360                 365

Cys Arg Glu Leu Ala Gln Ser Lys Val Val Ser Leu Ala Glu Leu Ile
    370                 375                 380

Gly Lys Asp Gly Thr Ala Thr Pro Ala Pro Ile Arg Gln Ile Leu Ser
385                 390                 395                 400

Arg Pro Glu Arg Leu Leu Phe Ile Leu Asp Gly Val Asp Glu Pro Gly
                405                 410                 415

Trp Val Leu Gln Glu Pro Ser Ser Glu Leu Cys Leu His Trp Ser Gln
            420                 425                 430

Pro Gln Pro Ala Asp Ala Leu Leu Gly Ser Leu Leu Gly Lys Thr Ile
        435                 440                 445

Leu Pro Glu Ala Ser Phe Leu Ile Thr Ala Arg Thr Thr Ala Leu Gln
    450                 455                 460

Asn Leu Ile Pro Ser Leu Glu Gln Ala Arg Trp Val Glu Val Leu Gly
465                 470                 475                 480

Phe Ser Glu Ser Ser Arg Lys Glu Tyr Phe Tyr Arg Tyr Phe Thr Asp
                485                 490                 495

Glu Arg Gln Ala Ile Arg Ala Phe Arg Leu Val Lys Ser Asn Lys Glu
            500                 505                 510

Leu Trp Ala Leu Cys Leu Val Pro Trp Val Ser Trp Leu Ala Cys Thr
        515                 520                 525

Cys Leu Met Gln Gln Met Lys Arg Lys Glu Lys Leu Thr Leu Thr Ser
    530                 535                 540

Lys Thr Thr Thr Thr Leu Cys Leu His Tyr Leu Ala Gln Ala Leu Gln
545                 550                 555                 560

Ala Gln Pro Leu Gly Pro Gln Leu Arg Asp Leu Cys Ser Leu Ala Ala
                565                 570                 575

Glu Gly Ile Trp Gln Lys Lys Thr Leu Phe Ser Pro Asp Asp Leu Arg
            580                 585                 590

Lys His Gly Leu Asp Gly Ala Ile Ile Ser Thr Phe Leu Lys Met Gly
        595                 600                 605

Ile Leu Gln Glu His Pro Ile Pro Leu Ser Tyr Ser Phe Ile His Leu
    610                 615                 620

Cys Phe Gln Glu Phe Phe Ala Ala Met Ser Tyr Val Leu Glu Asp Glu
625                 630                 635                 640
```

-continued

```
Lys Gly Arg Gly Lys His Ser Asn Cys Ile Ile Asp Leu Glu Lys Thr
                645                 650                 655

Leu Glu Ala Tyr Gly Ile His Gly Leu Phe Gly Ala Ser Thr Thr Arg
            660                 665                 670

Phe Leu Leu Gly Leu Leu Ser Asp Glu Gly Glu Arg Glu Met Glu Asn
        675                 680                 685

Ile Phe His Cys Arg Leu Ser Gln Gly Arg Asn Leu Met Gln Trp Val
    690                 695                 700

Pro Ser Leu Gln Leu Leu Leu Gln Pro His Ser Leu Glu Ser Leu His
705                 710                 715                 720

Cys Leu Tyr Glu Thr Arg Asn Lys Thr Phe Leu Thr Gln Val Met Ala
                725                 730                 735

His Phe Glu Glu Met Gly Met Cys Val Glu Thr Asp Met Glu Leu Leu
            740                 745                 750

Val Cys Thr Phe Cys Ile Lys Phe Ser Arg His Val Lys Lys Leu Gln
        755                 760                 765

Leu Ile Glu Gly Arg Gln His Arg Ser Thr Trp Ser Pro Thr Met Val
    770                 775                 780

Val Leu Phe Arg Trp Val Pro Val Thr Asp Ala Tyr Trp Gln Ile Leu
785                 790                 795                 800

Phe Ser Val Leu Lys Val Thr Arg Asn Leu Lys Glu Leu Asp Leu Ser
                805                 810                 815

Gly Asn Ser Leu Ser His Ser Ala Val Lys Ser Leu Cys Lys Thr Leu
            820                 825                 830

Arg Arg Pro Arg Cys Leu Leu Glu Thr Leu Arg Leu Ala Gly Cys Gly
        835                 840                 845

Leu Thr Ala Glu Asp Cys Lys Asp Leu Ala Phe Gly Leu Arg Ala Asn
    850                 855                 860

Gln Thr Leu Thr Glu Leu Asp Leu Ser Phe Asn Val Leu Thr Asp Ala
865                 870                 875                 880

Gly Ala Lys His Leu Cys Gln Arg Leu Arg Gln Pro Ser Cys Lys Leu
                885                 890                 895

Gln Arg Leu Gln Leu Val Ser Cys Gly Leu Thr Ser Asp Cys Cys Gln
            900                 905                 910

Asp Leu Ala Ser Val Leu Ser Ala Ser Pro Ser Leu Lys Glu Leu Asp
        915                 920                 925

Leu Gln Gln Asn Asn Leu Asp Asp Val Gly Val Arg Leu Leu Cys Glu
    930                 935                 940

Gly Leu Arg His Pro Ala Cys Lys Leu Ile Arg Leu Gly Leu Asp Gln
945                 950                 955                 960

Thr Thr Leu Ser Asp Glu Met Arg Gln Glu Leu Arg Ala Leu Glu Gln
                965                 970                 975

Glu Lys Pro Gln Leu Leu Ile Phe Ser Arg Arg Lys Pro Ser Val Met
            980                 985                 990

Thr Pro Thr Glu Gly Leu Asp Thr  Gly Glu Met Ser Asn  Ser Thr Ser
        995                 1000                1005

Ser Leu  Lys Arg Gln Arg Leu  Gly Ser Glu Arg Ala  Ala Ser His
    1010                 1015                 1020

Val Ala  Gln Ala Asn Leu Lys  Leu Leu Asp Val Ser  Lys Ile Phe
    1025                 1030                 1035

Pro Ile  Ala Glu Ile Ala Glu  Glu Ser Ser Pro Glu  Val Val Pro
    1040                 1045                 1050
```

```
Val Glu Leu Leu Cys Val Pro Ser Pro Ala Ser Gln Gly Asp Leu
    1055                1060                1065

His Thr Lys Pro Leu Gly Thr Asp Asp Asp Phe Trp Gly Pro Thr
    1070                1075                1080

Gly Pro Val Ala Thr Glu Val Val Asp Lys Glu Lys Asn Leu Tyr
    1085                1090                1095

Arg Val His Phe Pro Val Ala Gly Ser Tyr Arg Trp Pro Asn Thr
    1100                1105                1110

Gly Leu Cys Phe Val Met Arg Glu Ala Val Thr Val Glu Ile Glu
    1115                1120                1125

Phe Cys Val Trp Asp Gln Phe Leu Gly Glu Ile Asn Pro Gln His
    1130                1135                1140

Ser Trp Met Val Ala Gly Pro Leu Leu Asp Ile Lys Ala Glu Pro
    1145                1150                1155

Gly Ala Val Glu Ala Val His Leu Pro His Phe Val Ala Leu Gln
    1160                1165                1170

Gly Gly His Val Asp Thr Ser Leu Phe Gln Met Ala His Phe Lys
    1175                1180                1185

Glu Glu Gly Met Leu Leu Glu Lys Pro Ala Arg Val Glu Leu His
    1190                1195                1200

His Ile Val Leu Glu Asn Pro Ser Phe Ser Pro Leu Gly Val Leu
    1205                1210                1215

Leu Lys Met Ile His Asn Ala Leu Arg Phe Ile Pro Val Thr Ser
    1220                1225                1230

Val Val Leu Leu Tyr His Arg Val His Pro Glu Glu Val Thr Phe
    1235                1240                1245

His Leu Tyr Leu Ile Pro Ser Asp Cys Ser Ile Arg Lys Glu Leu
    1250                1255                1260

Glu Leu Cys Tyr Arg Ser Pro Gly Glu Asp Gln Leu Phe Ser Glu
    1265                1270                1275

Phe Tyr Val Gly His Leu Gly Ser Gly Ile Arg Leu Gln Val Lys
    1280                1285                1290

Asp Lys Lys Asp Glu Thr Leu Val Trp Glu Ala Leu Val Lys Pro
    1295                1300                1305

Gly Asp Leu Met Pro Ala Thr Thr Leu Ile Pro Pro Ala Arg Ile
    1310                1315                1320

Ala Val Pro Ser Pro Leu Asp Ala Pro Gln Leu Leu His Phe Val
    1325                1330                1335

Asp Gln Tyr Arg Glu Gln Leu Ile Ala Arg Val Thr Ser Val Glu
    1340                1345                1350

Val Val Leu Asp Lys Leu His Gly Gln Val Leu Ser Gln Glu Gln
    1355                1360                1365

Tyr Glu Arg Val Leu Ala Glu Asn Thr Arg Pro Ser Gln Met Arg
    1370                1375                1380

Lys Leu Phe Ser Leu Ser Gln Ser Trp Asp Arg Lys Cys Lys Asp
    1385                1390                1395

Gly Leu Tyr Gln Ala Leu Lys Glu Thr His Pro His Leu Ile Met
    1400                1405                1410

Glu Leu Trp Glu Lys Gly Ser Lys Lys Gly Leu Leu Pro Leu Ser
    1415                1420                1425

Ser
```

<210> SEQ ID NO 16
<211> LENGTH: 8
<212> TYPE: PRT
<213> ORGANISM: bacteriophage T7

<400> SEQUENCE: 16

```
Asp Tyr Lys Asp Asp Asp Asp Lys
1               5
```

<210> SEQ ID NO 17
<211> LENGTH: 733
<212> TYPE: DNA
<213> ORGANISM: homo sapiens

<400> SEQUENCE: 17

```
gggatccgga gcccaaatct tctgacaaaa ctcacacatg cccaccgtgc ccagcacctg     60

aattcgaggg tgcaccgtca gtcttcctct tcccccaaaa acccaaggac accctcatga    120

tctcccggac tcctgaggtc acatgcgtgg tggtggacgt aagccacgaa gaccctgagg    180

tcaagttcaa ctggtacgtg gacggcgtgg aggtgcataa tgccaagaca aagccgcggg    240

aggagcagta caacagcacg taccgtgtgg tcagcgtcct caccgtcctg caccaggact    300

ggctgaatgg caaggagtac aagtgcaagg tctccaacaa agccctccca acccccatcg    360

agaaaaccat ctccaaagcc aaagggcagc cccgagaacc acaggtgtac accctgcccc    420

catcccggga tgagctgacc aagaaccagg tcagcctgac ctgcctggtc aaaggcttct    480

atccaagcga catcgccgtg gagtgggaga gcaatgggca gccggagaac aactacaaga    540

ccacgcctcc cgtgctggac tccgacggct ccttcttcct ctacagcaag ctcaccgtgg    600

acaagagcag gtggcagcag gggaacgtct tctcatgctc cgtgatgcat gaggctctgc    660

acaaccacta cacgcagaag agcctctccc tgtctccggg taaatgagtg cgacggccgc    720

gactctagag gat                                                       733
```

<210> SEQ ID NO 18
<211> LENGTH: 1034
<212> TYPE: PRT
<213> ORGANISM: Homo sapiens

<400> SEQUENCE: 18

```
Met Ala Ser Thr Arg Cys Lys Leu Ala Arg Tyr Leu Glu Asp Leu Glu
1               5                   10                  15

Asp Val Asp Leu Lys Lys Phe Lys Met His Leu Glu Asp Tyr Pro Pro
            20                  25                  30

Gln Lys Gly Cys Ile Pro Leu Pro Arg Gly Gln Thr Glu Lys Ala Asp
        35                  40                  45

His Val Asp Leu Ala Thr Leu Met Ile Asp Phe Asn Gly Glu Glu Lys
    50                  55                  60

Ala Trp Ala Met Ala Val Trp Ile Phe Ala Ala Ile Asn Arg Arg Asp
65                  70                  75                  80

Leu Tyr Glu Lys Ala Lys Arg Asp Glu Pro Lys Trp Gly Ser Asp Asn
                85                  90                  95

Ala Arg Val Ser Asn Pro Thr Val Ile Cys Gln Glu Asp Ser Ile Glu
            100                 105                 110

Glu Glu Trp Met Gly Leu Leu Glu Tyr Leu Ser Arg Ile Ser Ile Cys
        115                 120                 125

Lys Met Lys Lys Asp Tyr Arg Lys Lys Tyr Arg Lys Tyr Val Arg Ser
    130                 135                 140
```

```
Arg Phe Gln Cys Ile Glu Asp Arg Asn Ala Arg Leu Gly Glu Ser Val
145                 150                 155                 160

Ser Leu Asn Lys Arg Tyr Thr Arg Leu Arg Leu Ile Lys Glu His Arg
                165                 170                 175

Ser Gln Gln Glu Arg Glu Gln Glu Leu Leu Ala Ile Gly Lys Thr Lys
            180                 185                 190

Thr Cys Glu Ser Pro Val Ser Pro Ile Lys Met Glu Leu Leu Phe Asp
        195                 200                 205

Pro Asp Asp Glu His Ser Glu Pro Val His Thr Val Val Phe Gln Gly
    210                 215                 220

Ala Ala Gly Ile Gly Lys Thr Ile Leu Ala Arg Lys Met Met Leu Asp
225                 230                 235                 240

Trp Ala Ser Gly Thr Leu Tyr Gln Asp Arg Phe Asp Tyr Leu Phe Tyr
                245                 250                 255

Ile His Cys Arg Glu Val Ser Leu Val Thr Gln Arg Ser Leu Gly Asp
            260                 265                 270

Leu Ile Met Ser Cys Cys Pro Asp Pro Asn Pro Pro Ile His Lys Ile
        275                 280                 285

Val Arg Lys Pro Ser Arg Ile Leu Phe Leu Met Asp Gly Phe Asp Glu
    290                 295                 300

Leu Gln Gly Ala Phe Asp Glu His Ile Gly Pro Leu Cys Thr Asp Trp
305                 310                 315                 320

Gln Lys Ala Glu Arg Gly Asp Ile Leu Leu Ser Ser Leu Ile Arg Lys
                325                 330                 335

Lys Leu Leu Pro Glu Ala Ser Leu Leu Ile Thr Thr Arg Pro Val Ala
            340                 345                 350

Leu Glu Lys Leu Gln His Leu Leu Asp His Pro Arg His Val Glu Ile
        355                 360                 365

Leu Gly Phe Ser Glu Ala Lys Arg Lys Glu Tyr Phe Phe Lys Tyr Phe
    370                 375                 380

Ser Asp Glu Ala Gln Ala Arg Ala Ala Phe Ser Leu Ile Gln Glu Asn
385                 390                 395                 400

Glu Val Leu Phe Thr Met Cys Phe Ile Pro Leu Val Cys Trp Ile Val
                405                 410                 415

Cys Thr Gly Leu Lys Gln Gln Met Glu Ser Gly Lys Ser Leu Ala Gln
            420                 425                 430

Thr Ser Lys Thr Thr Thr Ala Val Tyr Val Phe Phe Leu Ser Ser Leu
        435                 440                 445

Leu Gln Pro Arg Gly Gly Ser Gln Glu His Gly Leu Cys Ala His Leu
    450                 455                 460

Trp Gly Leu Cys Ser Leu Ala Ala Asp Gly Ile Trp Asn Gln Lys Ile
465                 470                 475                 480

Leu Phe Glu Glu Ser Asp Leu Arg Asn His Gly Leu Gln Lys Ala Asp
                485                 490                 495

Val Ser Ala Phe Leu Arg Met Asn Leu Phe Gln Lys Glu Val Asp Cys
            500                 505                 510

Glu Lys Phe Tyr Ser Phe Ile His Met Thr Phe Gln Glu Phe Phe Ala
        515                 520                 525

Ala Met Tyr Tyr Leu Leu Glu Glu Glu Lys Glu Gly Arg Thr Asn Val
    530                 535                 540

Pro Gly Ser Arg Leu Lys Leu Pro Ser Arg Asp Val Thr Val Leu Leu
545                 550                 555                 560
```

-continued

```
Glu Asn Tyr Gly Lys Phe Glu Lys Gly Tyr Leu Ile Phe Val Val Arg
                565                 570                 575

Phe Leu Phe Gly Leu Val Asn Gln Glu Arg Thr Ser Tyr Leu Glu Lys
            580                 585                 590

Lys Leu Ser Cys Lys Ile Ser Gln Gln Ile Arg Leu Glu Leu Leu Lys
        595                 600                 605

Trp Ile Glu Val Lys Ala Lys Ala Lys Lys Leu Gln Ile Gln Pro Ser
    610                 615                 620

Gln Leu Glu Leu Phe Tyr Cys Leu Tyr Glu Met Gln Glu Glu Asp Phe
625                 630                 635                 640

Val Gln Arg Ala Met Asp Tyr Phe Pro Lys Ile Glu Ile Asn Leu Ser
                645                 650                 655

Thr Arg Met Asp His Met Val Ser Ser Phe Cys Ile Glu Asn Cys His
            660                 665                 670

Arg Val Glu Ser Leu Ser Leu Gly Phe Leu His Asn Met Pro Lys Glu
        675                 680                 685

Glu Glu Glu Glu Glu Lys Glu Gly Arg His Leu Asp Met Val Gln Cys
    690                 695                 700

Val Leu Pro Ser Ser Ser His Ala Ala Cys Ser His Gly Leu Val Asn
705                 710                 715                 720

Ser His Leu Thr Ser Ser Phe Cys Arg Gly Leu Phe Ser Val Leu Ser
                725                 730                 735

Thr Ser Gln Ser Leu Thr Glu Leu Asp Leu Ser Asp Asn Ser Leu Gly
            740                 745                 750

Asp Pro Gly Met Arg Val Leu Cys Glu Thr Leu Gln His Pro Gly Cys
        755                 760                 765

Asn Ile Arg Arg Leu Trp Leu Gly Arg Cys Gly Leu Ser His Glu Cys
    770                 775                 780

Cys Phe Asp Ile Ser Leu Val Leu Ser Ser Asn Gln Lys Leu Val Glu
785                 790                 795                 800

Leu Asp Leu Ser Asp Asn Ala Leu Gly Asp Phe Gly Ile Arg Leu Leu
                805                 810                 815

Cys Val Gly Leu Lys His Leu Leu Cys Asn Leu Lys Lys Leu Trp Leu
            820                 825                 830

Val Ser Cys Cys Leu Thr Ser Ala Cys Cys Gln Asp Leu Ala Ser Val
        835                 840                 845

Leu Ser Thr Ser His Ser Leu Thr Arg Leu Tyr Val Gly Glu Asn Ala
    850                 855                 860

Leu Gly Asp Ser Gly Val Ala Ile Leu Cys Glu Lys Ala Lys Asn Pro
865                 870                 875                 880

Gln Cys Asn Leu Gln Lys Leu Gly Leu Val Asn Ser Gly Leu Thr Ser
                885                 890                 895

Val Cys Cys Ser Ala Leu Ser Ser Val Leu Ser Thr Asn Gln Asn Leu
            900                 905                 910

Thr His Leu Tyr Leu Arg Gly Asn Thr Leu Gly Asp Lys Gly Ile Lys
        915                 920                 925

Leu Leu Cys Glu Gly Leu Leu His Pro Asp Cys Lys Leu Gln Val Leu
    930                 935                 940

Glu Leu Asp Asn Cys Asn Leu Thr Ser His Cys Cys Trp Asp Leu Ser
945                 950                 955                 960

Thr Leu Leu Thr Ser Ser Gln Ser Leu Arg Lys Leu Ser Leu Gly Asn
                965                 970                 975
```

```
Asn Asp Leu Gly Asp Leu Gly Val Met Met Phe Cys Glu Val Leu Lys
            980                 985                 990

Gln Gln Ser Cys Leu Leu Gln Asn  Leu Gly Leu Ser Glu  Met Tyr Phe
        995                 1000                1005

Asn Tyr  Glu Thr Lys Ser Ala  Leu Glu Thr Leu Gln  Glu Glu Lys
    1010                1015                1020

Pro Glu  Leu Thr Val Val Phe  Glu Pro Ser Trp
    1025                1030


<210> SEQ ID NO 19
<211> LENGTH: 39
<212> TYPE: DNA
<213> ORGANISM: Homo sapiens

<400> SEQUENCE: 19

gcagcagcgg ccgctacaag tatttccaca atgcagagc                            39


<210> SEQ ID NO 20
<211> LENGTH: 37
<212> TYPE: DNA
<213> ORGANISM: Homo sapiens

<400> SEQUENCE: 20

gcagcagtcg accctcaggt tctgaagttt gcagttg                              37


<210> SEQ ID NO 21
<211> LENGTH: 38
<212> TYPE: DNA
<213> ORGANISM: Homo sapiens

<400> SEQUENCE: 21

gcagcagcgg ccgcatgaac cagagtgcca cggaatgc                             38


<210> SEQ ID NO 22
<211> LENGTH: 37
<212> TYPE: DNA
<213> ORGANISM: Homo sapiens

<400> SEQUENCE: 22

gcagcagtcg accatgtaca ctgcagtggt ggtcctg                              37


<210> SEQ ID NO 23
<211> LENGTH: 25
<212> TYPE: DNA
<213> ORGANISM: Artificial Sequence
<220> FEATURE:
<223> OTHER INFORMATION: Synthesized Oligonucleotide.

<400> SEQUENCE: 23

gcccactccg gucuuagaga ugcuc                                           25


<210> SEQ ID NO 24
<211> LENGTH: 25
<212> TYPE: DNA
<213> ORGANISM: Artificial Sequence
<220> FEATURE:
<223> OTHER INFORMATION: Synthesized Oligonucleotide.

<400> SEQUENCE: 24

gctgcctctc aguagacuaa acgga                                           25


<210> SEQ ID NO 25
```

-continued

<211> LENGTH: 25
<212> TYPE: DNA
<213> ORGANISM: Artificial Sequence
<220> FEATURE:
<223> OTHER INFORMATION: Synthesized Oligonucleotide.

<400> SEQUENCE: 25
ttgactggtu cccaagugag gacgg 25

<210> SEQ ID NO 26
<211> LENGTH: 25
<212> TYPE: DNA
<213> ORGANISM: Artificial Sequence
<220> FEATURE:
<223> OTHER INFORMATION: Synthesized Oligonucleotide.

<400> SEQUENCE: 26
ataccagagc uuugagaggu cgagg 25

<210> SEQ ID NO 27
<211> LENGTH: 25
<212> TYPE: DNA
<213> ORGANISM: Artificial Sequence
<220> FEATURE:
<223> OTHER INFORMATION: Synthesized Oligonucleotide.

<400> SEQUENCE: 27
ttacagatgg agauggaggc ccagg 25

<210> SEQ ID NO 28
<211> LENGTH: 17
<212> TYPE: DNA
<213> ORGANISM: Homo sapiens

<400> SEQUENCE: 28
agccgagcca catcgct 17

<210> SEQ ID NO 29
<211> LENGTH: 19
<212> TYPE: DNA
<213> ORGANISM: Homo sapiens

<400> SEQUENCE: 29
gtgaccaggc gcccaatac 19

<210> SEQ ID NO 30
<211> LENGTH: 28
<212> TYPE: DNA
<213> ORGANISM: Homo sapiens

<400> SEQUENCE: 30
caaatccgtt gactccgacc ttcacctt 28

<210> SEQ ID NO 31
<211> LENGTH: 21
<212> TYPE: DNA
<213> ORGANISM: Homo sapiens

<400> SEQUENCE: 31
ctggagactc tcagggtcga a 21

<210> SEQ ID NO 32
<211> LENGTH: 17
<212> TYPE: DNA
<213> ORGANISM: Homo sapiens

<400> SEQUENCE: 32
gcgcttccag gactgca 17

<210> SEQ ID NO 33
<211> LENGTH: 27
<212> TYPE: DNA
<213> ORGANISM: Homo sapiens

<400> SEQUENCE: 33
acagatttct accactccaa acgccgg 27

<210> SEQ ID NO 34
<211> LENGTH: 20
<212> TYPE: PRT
<213> ORGANISM: Artificial Sequence
<220> FEATURE:
<223> OTHER INFORMATION: Leucine Rich Repeat Protein Consensus Sequence
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: MISC_FEATURE
<222> LOCATION: (12)..(12)
<223> OTHER INFORMATION: wherein “Xaa” equals an aliphatic amino acid.
<220> FEATURE:
<221> NAME/KEY: misc_feature
<222> LOCATION: (13)..(15)
<223> OTHER INFORMATION: Xaa can be any naturally occurring amino acid
<220> FEATURE:
<221> NAME/KEY: MISC_FEATURE
<222> LOCATION: (16)..(16)
<223> OTHER INFORMATION: wherein “Xaa” equals an aliphatic amino acid.
<220> FEATURE:
<221> NAME/KEY: misc_feature
<222> LOCATION: (17)..(18)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid

<400> SEQUENCE: 34

Xaa Leu Xaa Xaa Leu Xaa Leu Xaa Xaa Asn Xaa Xaa Xaa Xaa Xaa Xaa
1 5 10 15

Xaa Xaa Leu Xaa
20

<210> SEQ ID NO 35
<211> LENGTH: 24
<212> TYPE: PRT
<213> ORGANISM: Artificial Sequence
<220> FEATURE:
<223> OTHER INFORMATION: Leucine Rich Repeat Protein Consensus Sequence
<220> FEATURE:

-continued

```
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (10)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (15)..(16)
<223> OTHER INFORMATION: Xaa can be any naturally occurring amino acid
<220> FEATURE:
<221> NAME/KEY: misc_feature
<222> LOCATION: (19)..(20)
<223> OTHER INFORMATION: Xaa can be any naturally occurring amino acid
<220> FEATURE:
<221> NAME/KEY: MISC_FEATURE
<222> LOCATION: (21)..(21)
<223> OTHER INFORMATION: wherein "Xaa" equals a non-polar amino acid.
<220> FEATURE:
<221> NAME/KEY: misc_feature
<222> LOCATION: (23)..(24)
<223> OTHER INFORMATION: Xaa can be any naturally occurring amino acid

<400> SEQUENCE: 35

Leu Xaa Xaa Leu Xaa Xaa Leu Xaa Leu Xaa Xaa Asn Xaa Leu Xaa Xaa
1               5                   10                  15

Leu Pro Xaa Xaa Xaa Phe Xaa Xaa
            20
```

POLYNUCLEOTIDES ENCODING NOVEL HUMAN LEUCINE-RICH REPEAT CONTAINING PROTEIN EXPRESSED PREDOMINATELY IN BONE MARROW, HLRRBM1

This application claims benefit to provisional application U.S. Ser. No. 60/257,773, filed Dec. 22, 2000; and is a continuation in part of non-provisional U.S. Ser. No. 10/028,374, filed Dec. 20, 2001 now abandoned. The entire teachings of the referenced applications are incorporated herein by reference.

FIELD OF THE INVENTION

The present invention provides novel polynucleotides encoding HLRRBM1 polypeptides, fragments and homologues thereof. Also provided are vectors, host cells, antibodies, and recombinant and synthetic methods for producing said polypeptides. The invention further relates to diagnostic and therapeutic methods for applying these novel HLRRBM1 polypeptides to the diagnosis, treatment, and/or prevention of various diseases and/or disorders related to these polypeptides, particularly immune diseases and/or disorders. The invention further relates to screening methods for identifying agonists and antagonists of the polynucleotides and polypeptides of the present invention.

BACKGROUND OF THE INVENTION

Recently, a class of cell surface proteins have been described in both plants and animals that are involved in pathogen perception, MHC class II trans-activation, inflammation and the regulation of apoptosis (Inhere, N., Nunez, G, Cell, Death, Differ., 6(9):823–4, (1999); Inhere, N., Koneke, T., del, Peso, L., Hun, Y., Yee, C., Chen, S., Carrion, R., Merino, J., Liu, D., Ni, J., Nunez, G, J. Biol, Chem. 21., 274(21):14560–7, (1999); Inhere, N., Nunez, G, Cell, Death, Differ., 7(5):509–10, (2000); Harton, J A., Ting, J P, Mol, Cell, Biol., 20(17):6185–94, (2000); Dixon, J., Brakebusch, C., Fassler, R., Dixon, M J. Hum, Mol, Genet. 12., 9(10): 1473–80, (2000)). All of these proteins are modular in nature containing one or several domains that function in caspase recruitment (CARD), nucleotide binding and protein-protein interactions. Proteins within this group have also been found to play a role in cell adhesion during various developmental processes.

A common theme in all of these proteins are the presence of a leucine-repeat repeat (LLR) in the carboxy terminus of the polypeptide chain. LLRs are short protein modules characterized by a periodic distribution of hydrophobic amino acids, especially leucine residues separated by hydrophilic residues [Sean, 1996]. The basic structure of the repeat is as follows:

X-L-X-X-L-X-L-X-X-N-X-a-X-X-X-a-X-X-L-X (SEQ ID NO:34)

where X is any amino acid, L is leucine, N is asparagine and "a" denotes an aliphatic residue. The asparagine at position 10 can be replaced by cysteine, threonine or glutamine. The average repeat length is 24 amino acids but it can vary between 22 to 29 amino acids, though some LRR motifs have been reported to be at short as 20 amino acids. The motif often consists of leucine or other aliphatic residues at positions 2, 5, 7, 12, 16, 21, and 24 and asparagine, cysteine or threonine at position 10. X-ray structure determination of LRR motifs suggests that each LRR is composed of a beta-sheet and an alpha-helix. The largest subfamily of proteins that contain a leucine-rich domain are extracellular proteins having the following motif: LxxLxxLxLxxNxLxx-LPxxOFxx (SEQ ID NO:35), where "x" is any amino acid and "O" is a non-polar residue (Kajava, J. Mol. Biol. 277: 519 (1998)).

In transmembrane proteins, LLRs and their flanking sequence always occur in the presumed extracellular portions. In these situations the LLRs are generally flanked on either side by cysteine-rich regions. In general, these cysteines are present in the oxidized disulphide link form. An example of a transmembrane protein containing a LRR is Toll, a *Drosophila* gene the functions in establishment of dorsal-ventral patterning. Dominant, ventralizing mutants have been described that map to the cysteine-rich regions surrounding the LLR domain [Schneider, 1991]. Thus, the cysteine regions associated with LLRs act to regulate receptor activity. The LLRs the elves within the Toll protein have been shown to function in heterotypic cell adhesion, a process required for proper motorneuron and muscle development [Halfon, 1995]

Another *Drosophila* LLR containing transmembrane protein, 18 wheeler, which is regulated by homeotic genes also promotes heterophilic cell adhesion in cell migration events during development (Eldon, E., Kooyer, S., D'Evelyn, D., Duman, M., Lawinger, P., Botas, J., Bellen, H, Development., 120(4):885-99, (1994)). Mammalian CD14, which binds lipopolysaccharide (LPS), and signals through NF-κB, is thought to have analogies to the Toll signal transduction pathway. CD14 also contains a region of LLRs that have been shown in deletion mutants to be responsible for LPS binding.

Slit is another LLR containing *Drosophila* secreted protein that functions in the development of the midline glial cells and the commissural axon tracts the cross the midline. This is presumably accomplished by cell adhesion events (Jacobs, J R, J. Neurobiol. 24(5):611–26, (1993)). Mammalian homologues of *Drosophila* slit have been shown to bind the heparin sulfate proteoglycan, glypican-1 (Liang, Y., Annan, R S., Carr, S A., Popp, S., Mevissen, M., olis, R K., olis, R U, J. Biol, Chem. 18., 274(25):17885–92, (1999)). In general, heparan sulfate proteoglycans have been shown to accummulate in Alzheimer's disease brains and specifically, glypican-1 is component of both senile plaques and neurofibrillary tangles (Verbeek, M M., Otte, Holler, I., van, den, Born, J., van, den, Heuvel, L P.,David, G., Wesseling, P., de, Waal, R M, Am. J. Pathol., 155(6):2115–25, (1999)). Heparin sulfate proteoglycans are also implicated in the regulation of cytokine signaling in B cells through the activation of CD40 (van, der, Voort, R., Taher, T E., Derksen, P W., Spaargaren, M., van, der, Neut, R., Pals, S T, Adv, Cancer, Res., 79:39–90, (2000)).

p37NB is a 37 kDa LRR protein identified in human neuroblastoma cells (Kim, D. et al. (1996) Biochim. Biophys. Acta 1309: 183–188). Northern blot hybridization and RT-PCR studies show that p37NB is differentially expressed in several neuroblastoma cell lines. A related LRR protein, PRELP, is characterized as a 42 kDa secreted protein (Bengtsson, E. et al. (1995) J. Biol. Chem. 270: 25639–25644). PRELP consists of 10 LRR motifs ranging in length from 20 to 26 residues with asparigine at position 10. Northern analysis shows differential expression of PRELP in various tissues.

In addition, leucine-rich repeat containing proteins have also been implicated in various aspects of protein-protein interaction, such as cell-to-cell communication and signal transduction (for a review, see Kobe and Deisenhofer, TIBS 19: 415 (1994); Kobe and Deisenhofer, Curr. Opin. Struct. Biol. 5: 409 (1995); Kajava, J. Mol. Biol. 277: 519 (1998)).

Proteins that contain an LRR motif include hormone receptors, enzyme subunits, cell adhesion proteins, and ribosome-binding proteins.

A subfamily of the LRR superfamily, referred to as the Small Leucine Rich Proteoglycan family, illustrates the critical functions fulfilled by proteins containing an LRR motif. Members of this subfamily are believed to play essential biological roles during inflammation and cancer invasion, a regulatory role in collagen fibril formation, suppression of the malignant phenotype of cancer cells, and an inhibition of the growth of certain normal cells (see, for example, Iozzo, Annu. Rev Biochem. 67: 609 (1998)).

Kajava, et al., J. Mol. Biol. 277: 519 (1998), divided the LRR superfamily into subfamilies characterized by different lengths and consensus sequences of the leucine-rich repeats. Based upon this structural analysis, Kajava concluded that LRR proteins of different subfamilies probably emerged independently during evolution, indicating that proteins with the LRR motif provide a unique solution for a wide range of biological functions.

LLR containing proteins have been identified in prokaryotes, plants, yeast and mammals. Although such proteins were initially thought to be secreted proteins, it is now appreciated that they inhibit a variety of cellular locations and participate in a diverse set of critical functions in development and cellular homeostasis.

Such LRRs, being extracellular, are capable of directing protein-protein interactions with other receptors involved in apoptosis, inflammation and immune responses. LLR containing proteins may also bind other extracellular ligands derived from infectious agents and participate in the triggering and or modulating immune responses, particularly apoptosis.

The mechanisms that mediate apoptosis have been intensively studied. These mechanisms involve the activation of endogenous proteases, loss of mitochondrial function, and structural changes such as disruption of the cytoskeleton, cell shrinkage, membrane blebbing, and nuclear condensation due to degradation of DNA.

The various signals that trigger apoptosis are thought to bring about these events by converging on a common cell death pathway, the core components of which are highly conserved from worms, such as *C. elegans,* to humans. In fact, invertebrate model systems have been invaluable tools in identifying and characterizing the genes that control apoptosis. Despite this conservation of certain core components, apoptotic signaling in mammals is much more complex than in invertebrates. For example, in mammals there are multiple homologues of the core components in the cell death signaling pathway.

Caspases, a class of proteins central to the apoptotic program, are responsible for the degradation of cellular proteins that leads to the morphological changes seen in cells undergoing apoptosis. Caspases (cysteinyl aspartate-specific proteinases) are cysteine proteases having specificity for aspartate at the substrate cleavage site. Generally, caspases are classified as either initiator caspases or effector caspases, both of which are zymogens that are activated by proteolysis that generates an active species. An effector caspase is activated by an initiator caspase which cleaves the effector caspase.

Initiator caspases are activated by an autoproteolytic mechanism that is often dependent upon oligomerization directed by association of the caspase with an adapter molecule.

Apoptotic signaling is dependent on protein-protein interactions. At least three different protein-protein interaction domains, the death domain, the death effector domain and the caspase recruitment domain (CARD), have been identified within proteins involved in apoptosis. A fourth protein-protein interaction domain, the death recruiting domain (DRD) was recently identified in murine FLASH (Imai et al. (1999) Nature 398: 777–85).

Caspases comprise a multi-gene family having at least 12 distinct family members (Nicholson (1999) Cell Death and Differentiation 6: 1028). A relatively small fraction of cellular polypeptides (less than 200) are thought to serve as targets for cleavage by caspases. Because many of these caspase targets perform key cellular functions, their proteolysis is thought to account for the cellular and morphological events that occur during apoptosis. Members of the caspase gene family can be divided by phylogenetic analysis into two major subfamilies, based upon their relatedness to ICE (interleukin-1p converting enzyme; caspase-1) and CED-3. Alternate groupings of caspases can be made based upon their substrate specificities. Many caspases and proteins that interact with caspases possess a CARD domain.

Characterization of the HLRRBM1 polypeptide of the present invention led to the determination that it is involved in the modulation of the p21 G1/G2 cell cycle check point protein, either directly or indirectly.

Critical transitions through the cell cycle are highly regulated by distinct protein kinase complexes, each composed of a cyclin regulatory and a cyclin-dependent kinase (cdk) catalytic subunit (for review see Draetta, 1994). These proteins regulate the cell's progression through the stages of the cell cycle and are, in turn, regulated by numerous proteins, including p53, p21, p16, and cdc25. Downstream targets of cyclin-cdk complexes include pRb and E2F. The cell cycle often is dysregulated in neoplasia due to alterations either in oncogenes that indirectly affect the cell cycle, or in tumor suppressor genes or oncogenes that directly impact cell cycle regulation, such as pRb, p53, p16, cyclin D1, or mdm-2 (for review see Schafer, 1998).

P21, also known as CDNK1A (cyclin-dependent kinase inhibitor 1A), or CIP1 inhibits mainly the activity of cyclin CDK2 or CDK4 complexes. Therefore, p21 primarily blocks cell cycle progression at the G1 stage of the cell cycle. The expression of p21 is tightly controlled by the tumor suppressor protein p53, through which this protein mediates the cell cycle G1 phase arrest in response to a variety of stress stimuli. In addition, p21 protein interacts with the DNA polymerase accessory factor PCNA (proliferating cell nuclear antigen), and plays a regulatory role in S phase DNA replication and DNA damage repair.

After DNA damage, many cells appear to enter a sustained arrest in the G2 phase of the cell cycle. Bunz et al. (1998) demonstrated that this arrest could be sustained only when p53 was present in the cell and capable of transcriptionally activating the cyclin-dependent kinase inhibitor p21. After disruption of either the p53 or the p21 gene, gamma-radiated cells progressed into mitosis and exhibited a G2 DNA content only because of a failure of cytokinesis. Thus, p53 and p21 appear to be essential for maintaining the G2 cell cycle checkpoint in human cells.

Due to the connection between the transcriptional activity of p53 and p21 RNA expression, the readout of p21 RNA can be used to determine the effect of drugs or other insults (radiation, antisense for a specific gene, dominant negative expression) on a given cell system which contains wild type p53. Specifically, if a gene is removed using antisense products and this has an effect on the p53 activity, p21 will be upregulated and can serve therefore as an indirect marker for an influence on the cell cycle regulatory pathways and induction of cell cycle arrest.

In addition to cancer regulation of cell cycle activity has a role in numerous other systems. For example, hematopoietic stem cells are relative quiescent, while after receiving the required stimulus they undergo dramatic proliferation and inexorably move toward terminal differentiation. This is partly regulated by the presence of p21. Using p21 knockout mice Cheng et al. (2000) demonstrated its critical biologic importance in protecting the stem cell compartment. In the absence of p21, hematopoietic stem cell proliferation and absolute number were increased under normal homeostatic conditions. Exposing the animals to cell cycle-specific myelotoxic injury resulted in premature death due to hematopoietic cell depletion. Further, self-renewal of primitive cells was impaired in serially transplanted bone marrow from p21 −/− mice, leading to hematopoietic failure. Therefore it was concluded that p21 is the molecular switch governing the entry of stem cells into the cell cycle, and in its absence, increased cell cycling leads to stem cell exhaustion. Under conditions of stress, restricted cell cycling is crucial to prevent premature stem cell depletion and hematopoietic death. Therefore, genes involved in the downregulation of p21 expression could have a stimulatory effect and therefore be useful for the exploration of stem cell technologies.

Using the above examples, it is clear the availability of a novel cloned leucine-rich repeat containing protein provides an opportunity for adjunct or replacement therapy, and are useful for the identification of leucine-rich repeat containing protein agonists, or stimulators (which might stimulate and/or bias leucine-rich repeat containing protein action), as well as, in the identification of leucine-rich repeat containing protein inhibitors. Hence it can be reasoned that agonists and antagonists for these LLR containing proteins will be useful for therapeutic purposes The present invention also relates to recombinant vectors, which include the isolated nucleic acid molecules of the present invention, and to host cells containing the recombinant vectors, as well as to methods of making such vectors and host cells, in addition to their use in the production of HLRRBM1 polypeptides or peptides using recombinant techniques. Synthetic methods for producing the polypeptides and polynucleotides of the present invention are provided. Also provided are diagnostic methods for detecting diseases, disorders, and/or conditions related to the HLRRBM1 polypeptides and polynucleotides, and therapeutic methods for treating such diseases, disorders, and/or conditions. The invention further relates to screening methods for identifying binding partners of the polypeptides.

BRIEF SUMMARY OF THE INVENTION

The present invention provides isolated nucleic acid molecules, that comprise, or alternatively consist of, a polynucleotide encoding the HLRRBM1 protein having the amino acid sequence shown in FIGS. 1A–E (SEQ ID NO:2) or the amino acid sequence encoded by the cDNA clone, HLRRBM1 (also referred to as GPCR25, clone 25a, and/or BMLRR2), deposited as ATCC Deposit Number PTA-2676 on Nov. 15, 2000.

The present invention also relates to recombinant vectors, which include the isolated nucleic acid molecules of the present invention, and to host cells containing the recombinant vectors, as well as to methods of making such vectors and host cells, in addition to their use in the production of HLRRBM1 polypeptides or peptides using recombinant techniques. Synthetic methods for producing the polypeptides and polynucleotides of the present invention are provided. Also provided are diagnostic methods for detecting diseases, disorders, and/or conditions related to the HLRRBM1 polypeptides and polynucleotides, and therapeutic methods for treating such diseases, disorders, and/or conditions. The invention further relates to screening methods for identifying binding partners of the polypeptides.

The invention further provides an isolated HLRRBM1 polypeptide having an amino acid sequence encoded by a polynucleotide described herein.

The invention further relates to a polynucleotide encoding a polypeptide fragment of SEQ ID NO:2, or a polypeptide fragment encoded by the cDNA sequence included in the deposited clone, which is hybridizable to SEQ ID NO:1.

The invention further relates to a polynucleotide encoding a polypeptide domain of SEQ ID NO:2 or a polypeptide domain encoded by the cDNA sequence included in the deposited clone, which is hybridizable to SEQ ID NO:1.

The invention further relates to a polynucleotide encoding a polypeptide epitope of SEQ ID NO:2 or a polypeptide epitope encoded by the cDNA sequence included in the deposited clone, which is hybridizable to SEQ ID NO:1.

The invention further relates to a polynucleotide encoding a polypeptide of SEQ ID NO:2 or the cDNA sequence included in the deposited clone, which is hybridizable to SEQ ID NO:1, having biological activity.

The invention further relates to a polynucleotide which is a variant of SEQ ID NO:1.

The invention further relates to a polynucleotide which is an allelic variant of SEQ ID NO:1.

The invention further relates to a polynucleotide which encodes a species homologue of the SEQ ID NO:2.

The invention further relates to a polynucleotide which represents the complimentary sequence (antisense) of SEQ ID NO:1.

The invention further relates to a polynucleotide capable of hybridizing under stringent conditions to any one of the polynucleotides specified herein, wherein said polynucleotide does not hybridize under stringent conditions to a nucleic acid molecule having a nucleotide sequence of only A residues or of only T residues.

The invention further relates to an isolated nucleic acid molecule of SEQ ID NO:2, wherein the polynucleotide fragment comprises a nucleotide sequence encoding a leucine-rich repeat protein.

The invention further relates to an isolated nucleic acid molecule of SEQ ID NO:1, wherein the polynucleotide fragment comprises a nucleotide sequence encoding the sequence identified as SEQ ID NO:2 or the polypeptide encoded by the cDNA sequence included in the deposited clone, which is hybridizable to SEQ ID NO:1.

The invention further relates to an isolated nucleic acid molecule of SEQ ID NO:1, wherein the polynucleotide fragment comprises the entire nucleotide sequence of SEQ ID NO:1 or the cDNA sequence included in the deposited clone, which is hybridizable to SEQ ID NO:1.

The invention further relates to an isolated nucleic acid molecule of SEQ ID NO:1, wherein the nucleotide sequence comprises sequential nucleotide deletions from either the C-terminus or the N-terminus.

The invention further relates to an isolated polypeptide comprising an amino acid sequence that comprises a polypeptide fragment of SEQ ID NO:2 or the encoded sequence included in the deposited clone.

The invention further relates to a polypeptide fragment of SEQ ID NO:2 or the encoded sequence included in the deposited clone, having biological activity.

The invention further relates to a polypeptide domain of SEQ ID NO:2 or the encoded sequence included in the deposited clone.

The invention further relates to a polypeptide epitope of SEQ ID NO:2 or the encoded sequence included in the deposited clone.

The invention further relates to a full length protein of SEQ ID NO:2 or the encoded sequence included in the deposited clone.

The invention further relates to a variant of SEQ ID NO:2.

The invention further relates to an allelic variant of SEQ ID NO:2. The invention further relates to a species homologue of SEQ ID NO:2.

The invention further relates to the isolated polypeptide of SEQ ID NO:2, wherein the full length protein comprises sequential amino acid deletions from either the C-terminus or the N-terminus.

The invention further relates to an isolated antibody that binds specifically to the isolated polypeptide of SEQ ID NO:2.

The invention further relates to a method for preventing, treating, or ameliorating a medical condition, comprising administering to a mammalian subject a therapeutically effective amount of the polypeptide of SEQ ID NO:2 or the polynucleotide of SEQ ID NO:1.

The invention further relates to a method of diagnosing a pathological condition or a susceptibility to a pathological condition in a subject comprising the steps of (a) determining the presence or absence of a mutation in the polynucleotide of SEQ ID NO:1; and (b) diagnosing a pathological condition or a susceptibility to a pathological condition based on the presence or absence of said mutation.

The invention further relates to a method of diagnosing a pathological condition or a susceptibility to a pathological condition in a subject comprising the steps of (a) determining the presence or amount of expression of the polypeptide of SEQ ID NO:2 in a biological sample; and diagnosing a pathological condition or a susceptibility to a pathological condition based on the presence or amount of expression of the polypeptide.

The invention further relates to a method for identifying a binding partner to the polypeptide of SEQ ID NO:2 comprising the steps of (a) contacting the polypeptide of SEQ ID NO:2 with a binding partner; and (b) determining whether the binding partner effects an activity of the polypeptide.

The invention further relates to a gene corresponding to the cDNA sequence of SEQ ID NO:1.

The invention further relates to a method of identifying an activity in a biological assay, wherein the method comprises the steps of expressing SEQ ID NO:1 in a cell, (b) isolating the supernatant; (c) detecting an activity in a biological assay; and (d) identifying the protein in the supernatant having the activity.

The invention further relates to a process for making polynucleotide sequences encoding gene products having altered activity selected from the group consisting of SEQ ID NO:2 activity comprising the steps of (a) shuffling a nucleotide sequence of SEQ ID NO:1, (b) expressing the resulting shuffled nucleotide sequences and, (c) selecting for altered activity selected from the group consisting of SEQ ID NO:2 activity as compared to the activity selected from the group consisting of SEQ ID NO:2 activity of the gene product of said unmodified nucleotide sequence.

The invention further relates to a shuffled polynucleotide sequence produced by a shuffling process, wherein said shuffled DNA molecule encodes a gene product having enhanced tolerance to an inhibitor of any one of the activities selected from the group consisting of SEQ ID NO:2 activity.

The invention further relates to a method for preventing, treating, or ameliorating a medical condition with the polypeptide provided as SEQ ID NO:2, in addition to, its encoding nucleic acid, wherein the medical condition is a proliferative disorder.

The invention further relates to a method for preventing, treating, or ameliorating a medical condition with the polypeptide provided as SEQ ID NO:2, in addition to, its encoding nucleic acid, wherein the medical condition is an immune condition.

The invention further relates to a method for preventing, treating, or ameliorating a medical condition with the polypeptide provided as SEQ ID NO:2, in addition to, its encoding nucleic acid, wherein the medical condition is a disorder related to aberrant apoptosis modulation, either directly or indirectly.

The invention further relates to a method for preventing, treating, or ameliorating a medical condition with the polypeptide provided as SEQ ID NO:2, in addition to, its encoding nucleic acid, wherein the medical condition is a pulmonary disease.

The invention further relates to a method for preventing, treating, or ameliorating a medical condition with the polypeptide provided as SEQ ID NO:2, in addition to, its encoding nucleic acid, wherein the medical condition is a reproductive disease.

The invention further relates to a method for preventing, treating, or ameliorating a medical condition with the polypeptide provided as SEQ ID NO:2, in addition to, its encoding nucleic acid, wherein the medical condition is a hematopoietic disease.

The invention further relates to a method of identifying a compound that modulates the biological activity of HLRRBM1, comprising the steps of, (a) combining a candidate modulator compound with HLRRBM1 having the sequence set forth in one or more of SEQ ID NO:2; and measuring an effect of the candidate modulator compound on the activity of HLRRBM1.

The invention further relates to a method of identifying a compound that modulates the biological activity of a leucine-rich repeat protein, comprising the steps of, (a) combining a candidate modulator compound with a host cell expressing HLRRBM1 having the sequence as set forth in SEQ ID NO:2; and, (b) measuring an effect of the candidate modulator compound on the activity of the expressed HLRRBM1.

The invention further relates to a method of identifying a compound that modulates the biological activity of HLRRBM1, comprising the steps of, (a) combining a candidate modulator compound with a host cell containing a vector described herein, wherein HLRRBM1 is expressed by the cell; and, (b) measuring an effect of the candidate modulator compound on the activity of the expressed HLRRBM1.

The invention further relates to a method of screening for a compound that is capable of modulating the biological activity of HLRRBM1, comprising the steps of: (a) providing a host cell described herein; (b) determining the biological activity of HLRRBM1 in the absence of a modulator compound; (c) contacting the cell with the modulator compound; and (d)determining the biological activity of HLRRBM1 in the presence of the modulator compound;

wherein a difference between the activity of HLRRBM1 in the presence of the modulator compound and in the absence of the modulator compound indicates a modulating effect of the compound.

The invention further relates to a compound that modulates the biological activity of human HLRRBM1 as identified by the methods described herein.

The invention further relates to a method for preventing, treating, or ameliorating a medical condition with the polypeptide provided as SEQ ID NO:2, in addition to, its encoding nucleic acid, or a modulator thereof, wherein the medical condition is a disorder associated with aberrant p21 expression or activity.

The invention further relates to a method for preventing, treating, or ameliorating a medical condition with the polypeptide provided as SEQ ID NO:2, in addition to, its encoding nucleic acid, or a modulator thereof, wherein the medical condition is a cell cycle defect, disorders related to aberrant phosphorylation, disorders related to aberrant signal transduction, proliferating disorders, and/or cancers.

The invention further relates to a method for preventing, treating, or ameliorating a medical condition with the polypeptide provided as SEQ ID NO:2, in addition to, its encoding nucleic acid, or a modulator thereof, wherein the medical condition is a disorder associated with aberrant cell cycle regulation.

The invention further relates to a method for preventing, treating, or ameliorating a medical condition with the polypeptide provided as SEQ ID NO:2, in addition to, its encoding nucleic acid, or a modulator thereof, wherein the medical condition is a disorder associated with aberrant cell cycle regulation.

The invention further relates to a method of increasing the number of cells in the G1 phase of the cell cycle comprising the step of administering an antagonist of HLRRBM1.

The invention further relates to a method of increasing the number of cells in the G2 phase of the cell cycle comprising the step of administering an antagonist of HLRRBM1.

The invention further relates to a method of decreasing the number of cells that progress to the S phase of the cell cycle comprising the step of administering an antagonist of HLRRBM1.

The invention further relates to a method of increasing the number of cells that progress to the M phase of the cell cycle comprising the step of administering an antagonist of HLRRBM1.

The invention further relates to a method of inducing cells into G1 and/or G2 phase arrest comprising the step of administering an antagonist of HLRRBM1.

The invention further relates to a method for preventing, treating, or ameliorating a medical condition with the polypeptide provided as SEQ ID NO:2, in addition to, its encoding nucleic acid, or a modulator thereof, wherein the medical condition is ovarian cancer or related proliferative condition of the ovary.

The invention further relates to a method for preventing, treating, or ameliorating a medical condition with the polypeptide provided as SEQ ID NO:2, in addition to, its encoding nucleic acid, or a modulator thereof, wherein the medical condition is colon cancer or related proliferative condition of the colon.

The invention further relates to a method for preventing, treating, or ameliorating a medical condition with the polypeptide provided as SEQ ID NO:2, in addition to, its encoding nucleic acid, or a modulator thereof, wherein the medical condition is melanoma.

The invention further relates to a method for preventing, treating, or ameliorating a medical condition with the polypeptide provided as SEQ ID NO:2, in addition to, its encoding nucleic acid, or a modulator thereof, wherein the medical condition is a leukemia.

The invention further relates to a method of diagnosing a pathological condition or a susceptibility to a pathological condition in a subject comprising the steps of (a) determining the presence or amount of expression of the polypeptide of SEQ ID NO:2 in a biological sample; and diagnosing a pathological condition or a susceptibility to a pathological condition based on the presence or amount of expression of the polypeptide, wherein said condition is a member of the group consisting of ovarian cancer, colon cancer, leukemias, and melanoma.

The invention also relates to an antisense compound 8 to 30 nucleotides in length that specifically hybridizes to a nucleic acid molecule encoding the human HLRRBM1 polypeptide of the present invention, wherein said antisense compound inhibits the expression of the human HLRRBM1 polypeptide.

The invention further relates to a method of inhibiting the expression of the human HLRRBM1 polypeptide of the present invention in human cells or tissues comprising contacting said cells or tissues in vitro with an antisense compound of the present invention so that expression of the HLRRBM1 polypeptide is inhibited.

The invention further relates to a method of increasing the expression of p21 in human cells or tissues comprising contacting said cells or tissues in vitro with an antisense compound that specifically hybridizes to a nucleic acid molecule encoding the human HLRRBM1 polypeptide of the present invention so that expression of the HLRRBM1 polypeptide is inhibited.

BRIEF DESCRIPTION OF THE FIGURES/DRAWINGS

FIGS. 1A–E show the polynucleotide sequence (SEQ ID NO:1) and deduced amino acid sequence (SEQ ID NO:2) of the novel human leucine-rich repeat containing protein, HLRRBM1, of the present invention. The standard one-letter abbreviation for amino acids is used to illustrate the deduced amino acid sequence. The polynucleotide sequence contains a sequence of 4931 nucleotides (SEQ ID NO:1), encoding a polypeptide of 449 amino acids (SEQ ID NO:2). An analysis of the HLRRBM1 polypeptide determined that it comprised the following features: one transmembrane domain located from about amino acid 144 to about amino acid 159 (SEQ ID NO:6); of SEQ ID NO:2 (FIGS. 1A–E) represented by underlining; conserved leucine residues located at amino acid 13, 36, 69, 70, 73, 79, 85, 100, 207, 232, 264, 267, 268, 292, 364, 366, 406, 410, 419, 421, 438, 445, and 448 of SEQ ID NO:2 represented by shading; differentially conserved leucine residues located at amino acid 25, 28, 78, 93, 160, 210, 276, 312, 318, 355, 426, and 434 of SEQ ID NO:2 represented in bold; and conserved cysteine residues located at amino acid 147, 159, 317, and 443 of SEQ ID NO:2 represented by double underlining. The conserved leucine residues are characteristic of leucine-rich repeat proteins as described more particularly elsewhere herein. The conserved cysteine residues are diagnostic of conserved structural features of the protein to leucine-rich repeat containing proteins (particularly those referenced herein), and may be indicative of conserved protein function.

FIGS. 2A–C shows the regions of identity between the encoded HLRRBM1 protein (SEQ ID NO:2) to other leucine-rich repeat proteins, specifically, the human caspase recruitment protein 7 protein (caspase_recruitment_protein; Genbank Accession No:gi|10198209; SEQ ID NO:3); the human NOD caspase recruitment protein 4 protein (NOD1; Genbank Accession No:gi|5174617; SEQ ID NO:4); and the human cryopyrin protein (cryopyrin; Genbank Accession No:gi|17027237; SEQ ID NO:18). The alignment was performed using the CLUSTALW algorithm using default parameters as described herein (Vector NTI suite of programs). The darkly shaded amino acids represent regions of matching identity. The lightly shaded amino acids represent regions of matching similarity. Dots ("•") between residues indicate gapped regions of non-identity for the aligned polypeptides. The conserved leucine residues between HLRRBM1 and the other leucine-rich repeat containing proteins are noted.

FIG. 3 shows a hydrophobicity plot of HLRRBM1 according to the BioPlot Hydrophobicity algorithm of Vector NTI (version 5.5). The single transmembrane domain of the HLRRBM1 polypeptide is shown.

Figure 4:
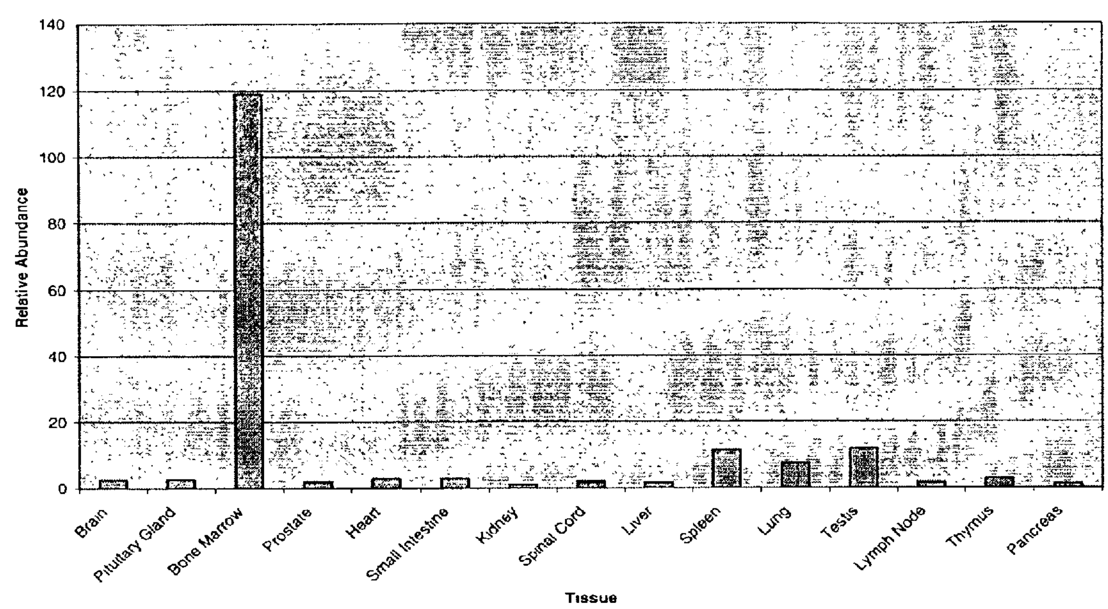

FIG. 4 shows an expression profile of the novel leucine-rich repeat containing protein, HLRRBM1. The figure illustrates the relative expression level of HLRRBM1 amongst various mRNA tissue sources. As shown, transcripts corresponding to HLRRBM1 expressed predominately high in the bone marrow, and to a lesser extent, in spleen, lung, and testis. Expression data was obtained by measuring the steady state HLRRBM1 mRNA levels by quantitative PCR using the PCR primer pair provided as SEQ ID NO:7 and 8 as described herein.

FIG. 5 shows a table illustrating the percent identity and percent similarity between the HLRRBM1 polypeptide of the present invention with other leucine-rich repeat containing proteins, specifically, the human caspase recruitment protein 7 protein (caspase_recruitment_protein; Genbank Accession No:gi|10198209; SEQ ID NO:3); the human NOD caspase recruitment protein 4 protein (NOD1; Genbank Accession No:gi|5174617; SEQ ID NO:4); and the human cryopyrin protein (cryopyrin; Genbank Accession No:gi|17027237; SEQ ID NO:18). The percent identity and percent similarity values were determined using the Gap algorithm using default parameters (Genetics Computer Group suite of programs; Needleman and Wunsch. J. Mol. Biol. 48; 443–453, 1970)).

Figure 6:
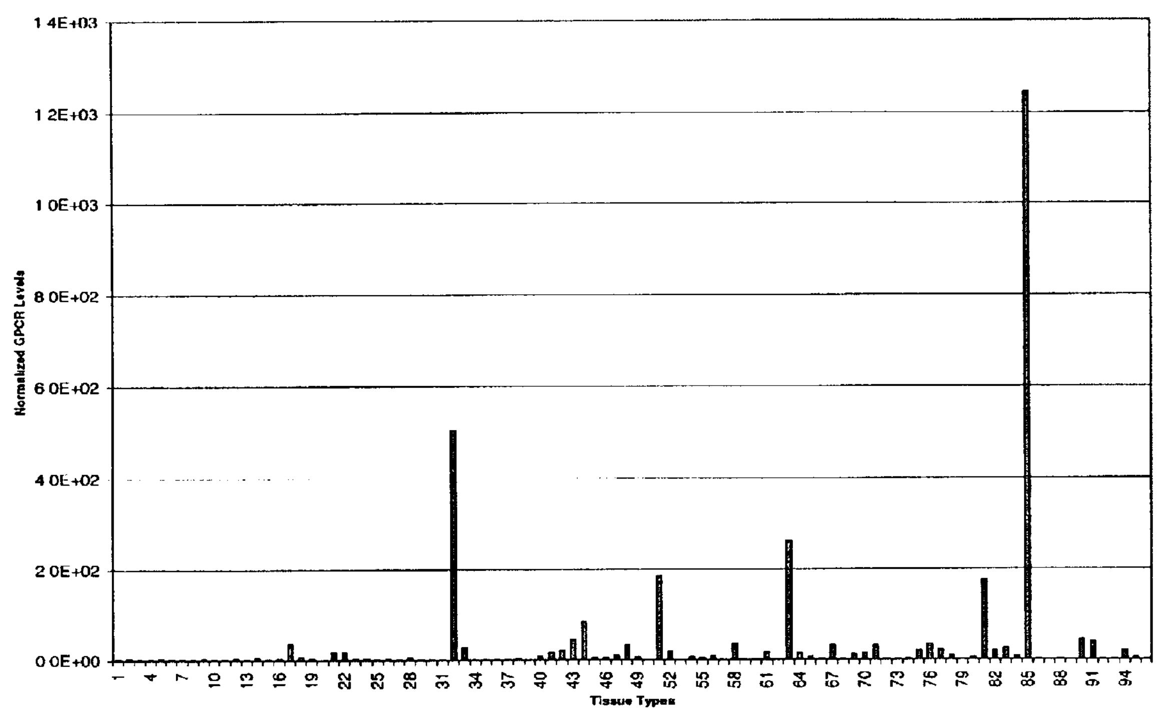

FIG. 6 shows an expanded expression profile of the novel human G-protein coupled receptor, HLRRBM1, of the present invention. The figure illustrates the relative expression level of HLRRBM1 amongst mRNA isolated from a number of cancer cell lines. As shown, the HLRRBM1 polypeptide was expressed in several colon cancer cell lines, significantly in a melanoma and a leukemia cell line, and to a lesser extent in other human tumor cell lines as shown. Moreover, the HLRRBM1 polypeptide was predominantly expressed in a Taxol resistant variant of an ovarian tumor cell line, suggesting HLRRBM1 may be diagnostic of aggressive transformed phenotypes. Expression data was obtained by measuring the steady state HLRRBM1 mRNA levels by quantitative PCR using the PCR primer pair provided as SEQ ID NO:7 and 8 as described in Example 5 herein.

Table I provides a summary of the novel polypeptides and their encoding polynucleotides of the present invention.

Table II illustrates the preferred hybridization conditions for the polynucleotides of the present invention. Other hybridization conditions may be known in the art or are described elsewhere herein.

Table III provides a summary of various conservative substitutions encompassed by the present invention.

Table IV provides the expression profiling results of HLRRBM1 in various cancer cell lines.

DETAILED DESCRIPTION OF THE INVENTION

The present invention may be understood more readily by reference to the following detailed description of the preferred embodiments of the invention and the Examples included herein.

The invention provides a novel human sequence that encodes a novel leucine-rich repeat containing protein, HLRRBM1, with substantial homology to the class of leucine-rich repeat containing proteins known as caspase recruitment proteins. Members of this class of leucine-rich repeat proteins have been implicated in a number of diseases and/or disorders, which include, but are not limited to, apoptosis and inflammatory disorders. Expression analysis indicates the HLRRBM1 has strong preferential expression in bone marrow, and to a lesser extent, in spleen, lung, and testis. Based on this information, we have provisionally named the gene and protein HLRRBM1 (Human Leucine-Rich Repeat Bone Marrow-1). The specificity by which the HLRRBM1 transcript is expressed that suggests its importance in various biological processes.

In the present invention, "isolated" refers to material removed from its original environment (e.g., the natural environment if it is naturally occurring), and thus is altered "by the hand of man" from its natural state. For example, an isolated polynucleotide could be part of a vector or a composition of matter, or could be contained within a cell, and still be "isolated" because that vector, composition of matter, or particular cell is not the original environment of the polynucleotide. The term "isolated" does not refer to genomic or cDNA libraries, whole cell total or mRNA preparations, genomic DNA preparations (including those separated by electrophoresis and transferred onto blots), sheared whole cell genomic DNA preparations or other compositions where the art demonstrates no distinguishing features of the polynucleotide/sequences of the present invention.

In specific embodiments, the polynucleotides of the invention are at least 15, at least 30, at least 50, at least 100, at least 125, at least 500, or at least 1000 continuous nucleotides but are less than or equal to 300 kb, 200 kb, 100 kb, 50 kb, 15 kb, 10 kb, 7.5 kb, 5 kb, 2.5 kb, 2.0 kb, or 1 kb, in length. In a further embodiment, polynucleotides of the invention comprise a portion of the coding sequences, as disclosed herein, but do not comprise all or a portion of any intron. In another embodiment, the polynucleotides comprising coding sequences do not contain coding sequences of a genomic flanking gene (i.e., 5' or 3' to the gene of interest in the genome). In other embodiments, the polynucleotides of the invention do not contain the coding sequence of more than 1000, 500, 250, 100, 50, 25, 20, 15, 10, 5, 4, 3, 2, or 1 genomic flanking gene(s).

As used herein, a "polynucleotide" refers to a molecule having a nucleic acid sequence contained in SEQ ID NO:1 or the cDNA contained within the clone deposited with the ATCC. For example, the polynucleotide can contain the nucleotide sequence of the full length cDNA sequence, including the 5' and 3' untranslated sequences, the coding region, with or without a signal sequence, the secreted protein coding region, as well as fragments, epitopes, domains, and variants of the nucleic acid sequence.

Moreover, as used herein, a "polypeptide" refers to a molecule having the translated amino acid sequence generated from the polynucleotide as broadly defined.

In the present invention, the full length sequence identified as SEQ ID NO:1 was often generated by overlapping sequences contained in one or more clones (contig analysis). A representative clone containing all or most of the sequence for SEQ ID NO:1 was deposited with the American Type Culture Collection ("ATCC"). As shown in Table I, each clone is identified by a cDNA Clone ID (Identifier) and the ATCC Deposit Number. The ATCC is located at 10801 University Boulevard, Manassas, Va. 20110-2209, USA. The ATCC deposit was made pursuant to the terms of the Budapest Treaty on the international recognition of the deposit of microorganisms for purposes of patent procedure. The deposited clone is inserted in the pSport1 plasmid (Life Technologies) using SalI and NotI restriction sites described herein.

Unless otherwise indicated, all nucleotide sequences determined by sequencing a DNA molecule herein were determined using an automated DNA sequencer (such as the Model 373 from Applied Biosystems, Inc.), and all amino acid sequences of polypeptides encoded by DNA molecules determined herein were predicted by translation of a DNA sequence determined above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

Using the information provided herein, such as the nucleotide sequence in FIGS. 1A–E (SEQ ID NO:1), a nucleic acid molecule of the present invention encoding the HLRRBM1 polypeptide may be obtained using standard cloning and screening procedures, such as those for cloning cDNAs using mRNA as starting material. Illustrative of the invention, the nucleic acid molecule described in FIGS. 1A–E (SEQ ID NO:1) was discovered in a human brain and testis cDNA library.

A "polynucleotide" of the present invention also includes those polynucleotides capable of hybridizing, under stringent hybridization conditions, to sequences contained in SEQ ID NO:1, the complement thereof, or the cDNA within the clone deposited with the ATCC. "Stringent hybridization conditions" refers to an overnight incubation at 42 degree C. in a solution comprising 50% formamide, 5×SSC (750 mM NaCl, 75 mM trisodium citrate), 50 mM sodium phosphate (pH 7.6), 5×Denhardt's solution, 10% dextran sulfate, and 20 μg/ml denatured, sheared salmon sperm DNA, followed by washing the filters in 0.1×SSC at about 65 degree C.

Also contemplated are nucleic acid molecules that hybridize to the polynucleotides of the present invention at lower stringency hybridization conditions. Changes in the stringency of hybridization and signal detection are primarily accomplished through the manipulation of formamide concentration (lower percentages of formamide result in lowered stringency); salt conditions, or temperature. For example, lower stringency conditions include an overnight incubation at 37 degree C. in a solution comprising 6×SSPE (20×SSPE=3M NaCl; 0.2M NaH2PO4; 0.02M EDTA, pH 7.4), 0.5% SDS, 30% formamide, 100 ug/ml salmon sperm blocking DNA; followed by washes at 50 degree C. with 1×SSPE, 0.1% SDS. In addition, to achieve even lower stringency, washes performed following stringent hybridization can be done at higher salt concentrations (e.g. 5×SSC).

Note that variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility.

Of course, a polynucleotide which hybridizes only to polyA+ sequences (such as any 3' terminal polyA+ tract of a cDNA shown in the sequence listing), or to a complementary stretch of T (or U) residues, would not be included in the definition of "polynucleotide," since such a polynucleotide would hybridize to any nucleic acid molecule containing a poly (A) stretch or the complement thereof (e.g., practically any double-stranded cDNA clone generated using oligo dT as a primer).

The polynucleotide of the present invention can be composed of any polyribonucleotide or polydeoxribonucleotide, which may be unmodified RNA or DNA or modified RNA or DNA. For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, the polynucleotide can be composed of triple-stranded regions comprising RNA or DNA or both RNA and DNA. A polynucleotide may also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

The polypeptide of the present invention can be composed of amino acids joined to each other by peptide bonds or modified peptide bonds, i.e., peptide isosteres, and may contain amino acids other than the 20 gene-encoded amino acids. The polypeptides may be modified by either natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched, for example, as a result of ubiquitination, and they may be cyclic, with or without branching. Cyclic, branched, and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, PROTEINS—STRUCTURE AND MOLECULAR PROPERTIES, 2nd Ed., T. E. Creighton, W. H. Freeman and Company, New York (1993); POSTTRANSLATIONAL COVALENT MODIFICATION OF PROTEINS, B. C. Johnson, Ed., Academic Press, New York, pgs. 1–12 (1983); Seifter et al., Meth Enzymol 182:626–646 (1990); Rattan et al., Ann N.Y. Acad Sci 663:48–62 (1992).)

"SEQ ID NO:1" refers to a polynucleotide sequence while "SEQ ID NO:2" refers to a polypeptide sequence, both sequences are identified by an integer specified in Table I.

"A polypeptide having biological activity" refers to polypeptides exhibiting activity similar, but not necessarily identical to, an activity of a polypeptide of the present invention, including mature forms, as measured in a particular biological assay, with or without dose dependency. In the case where dose dependency does exist, it need not be identical to that of the polypeptide, but rather substantially similar to the dose-dependence in a given activity as compared to the polypeptide of the present invention (i.e., the candidate polypeptide will exhibit greater activity or not more than about 25-fold less and, preferably, not more than about tenfold less activity, and most preferably, not more than about three-fold less activity relative to the polypeptide of the present invention.)

The term "organism" as referred to herein is meant to encompass any organism referenced herein, though preferably to eukaryotic organisms, more preferably to mammals, and most preferably to humans.

The present invention encompasses the identification of proteins, nucleic acids, or other molecules, that bind to polypeptides and polynucleotides of the present invention (for example, in a receptor-ligand interaction). The polynucleotides of the present invention can also be used in interaction trap assays (such as, for example, that described by Ozenberger and Young (Mol Endocrinol., 9(10): 1321–9, (1995); and Ann. N.Y. Acad. Sci., 7;766:279–81, (1995)).

The polynucleotide and polypeptides of the present invention are useful as probes for the identification and isolation of full-length cDNAs and/or genomic DNA which correspond to the polynucleotides of the present invention, as probes to hybridize and discover novel, related DNA sequences, as probes for positional cloning of this or a related sequence, as probe to "subtract-out" known sequences in the process of discovering other novel polynucleotides, as probes to quantify gene expression, and as probes for microarrays.

In addition, polynucleotides and polypeptides of the present invention may comprise one, two, three, four, five, six, seven, eight, or more membrane domains.

Also, in preferred embodiments the present invention provides methods for further refining the biological function of the polynucleotides and/or polypeptides of the present invention.

Specifically, the invention provides methods for using the polynucleotides and polypeptides of the invention to identify orthologs, homologs, paralogs, variants, and/or allelic variants of the invention. Also provided are methods of using the polynucleotides and polypeptides of the invention to identify the entire coding region of the invention, non-coding regions of the invention, regulatory sequences of the invention, and secreted, mature, pro-, prepro-, forms of the invention (as applicable).

In preferred embodiments, the invention provides methods for identifying the glycosylation sites inherent in the polynucleotides and polypeptides of the invention, and the subsequent alteration, deletion, and/or addition of said sites for a number of desirable characteristics which include, but are not limited to, augmentation of protein folding, inhibition of protein aggregation, regulation of intracellular trafficking to organelles, increasing resistance to proteolysis, modulation of protein antigenicity, and mediation of intercellular adhesion.

In further preferred embodiments, methods are provided for evolving the polynucleotides and polypeptides of the present invention using molecular evolution techniques in an effort to create and identify novel variants with desired structural, functional, and/or physical characteristics.

The present invention further provides for other experimental methods and procedures currently available to derive functional assignments. These procedures include but are not limited to spotting of clones on arrays, micro-array technology, PCR based methods (e.g., quantitative PCR), anti-sense methodology, gene knockout experiments, and other procedures that could use sequence information from clones to build a primer or a hybrid partner.

As used herein the terms "modulate" or "modulates" refer to an increase or decrease in the amount, quality or effect of a particular activity, DNA, RNA, or protein.

Polynucleotides and Polypeptides of the Invention

Features of the Polypeptide Encoded by Gene No:1

The polypeptide of this gene provided as SEQ ID NO:2 (FIGS. 1A–E), encoded by the polynucleotide sequence according to SEQ ID NO:1 (FIGS. 1A–E), and/or encoded by the polynucleotide contained within the deposited clone, HLRRBM1 (also refered to as GPCR25, clone 25a, and/or BMLRR2), has significant homology at the nucleotide and amino acid level to a number of leucine-rich repeat containing proteins, which include, for example, the human caspase recruitment protein 7 protein (caspase_recruitment_protein; Genbank Accession No:gi|10198209; SEQ ID NO:3); the human NOD caspase recruitment protein 4 protein (NOD1; Genbank Accession No:gi|5174617; SEQ ID NO:4); and the human cryopyrin protein (cryopyrin; Genbank Accession No:gi|17027237; SEQ ID NO:18). An alignment of the HLRRBM1 polypeptide with these proteins is provided in FIGS. 2A–C.

The human caspase recruitment protein 7 protein (caspase_recruitment_protein; Genbank Accession No:gi|10198209; SEQ ID NO:3) is a leucine-rich repeat protein. It comprises a pyrin domain which is a domain found primarily in proteins involved in apoptosis and inflammatory proteins.

The human NOD caspase recruitment protein 4 protein (NOD1; Genbank Accession No:gi|5174617; SEQ ID NO:4) is a leucine-rich repeat protein that contains a caspase-recruitment (CARD) and nucleotide-binding oligomerization domains. The CARD domain is linked to nucleotide-binding domain in the NH2-terminus and has multiple leucine-rich repeats in the COOH-terminus. Nod-1 was found to bind to multiple caspases with long prodomains, but specifically activated caspase-9 and promoted caspase-9-induced apoptosis. Thus, Nod1 is a leucine-rich repeat-containing protein that can regulate both apoptosis and NF-kappaB activation pathways (J. Biol. Chem. 274 (21), 14560–14567 (1999)). Nod1 is also referred to as CARD4 (J Biol Chem 1999 May 7;274(19):12955–8).

The human cryopyrin protein (cryopyrin; Genbank Accession No:gi|17027237; SEQ ID NO:18) is a leucine-rich repeat protein that contains a pyrin domain. Mutations in the cryopyrin protein have been associated with the incidence of familial cold autoinflammatory syndrome (FCAS, MIM 120100), commonly known as familial cold urticaria (FCU), which is an autosomal-dominant systemic inflammatory disease characterized by intermittent episodes of rash, arthralgia, fever and conjunctivitis after generalized exposure to cold. In addition, mutations in the cryopyrin protein were also associated with the incidence of Muckle-Wells syndrome (MWS; MIM 191900), which is an autosomal-dominant periodic fever syndrome with a similar phenotype except that symptoms are not precipitated by cold exposure and that sensorineural hearing loss is frequently also present. Additionally, the cryopyrin protein is also believed to play a role in the regulation of inflammation and apoptosis.

The determined nucleotide sequence of the HLRRBM1 cDNA in FIGS. 1A–E (SEQ ID NO:1) contains an open reading frame encoding a protein of about 449 amino acid residues, with a deduced molecular weight of about 51.3 kDa. The amino acid sequence of the predicted HLRRBM1 polypeptide is shown in FIGS. 1A–E (SEQ ID NO:2). The HLRRBM1 protein shown in FIGS. 1A–E was determined to share significant identity and similarity to several known leucine-rich repeat containing proteins, particularly, caspase recruitment proteins. Specifically, the HLRRBM1 protein shown in FIGS. 1A–E was determined to be about 35% identical and 48% similar to the human caspase recruitment protein 7 protein (caspase_recruitment_protein; Genbank Accession No:gi|10198209; SEQ ID NO:3); about 25% identical and 38% similar to the human NOD caspase recruitment protein 4 protein (NOD1; Genbank Accession No:gi|5174617; SEQ ID NO:4); and about 51.7% identical and 64.0% similar to the human cryopyrin protein (cryopyrin; Genbank Accession No:gi|17027237; SEQ ID NO:18); as shown in FIG. 5.

Analysis of the HLRRBM1 polypeptide indicates that it contains a canonical LLR domain in the carboxy terminal region of the protein that aligns with both caspase recruitment protein 7 and NOD. HLLRBM-1 and caspase recruitment protein 4 also share cysteine rich regions on both sides of the LLR domain. An additional domain of leucine-rich repeat region that does not follow classical spacing algorithms is also present between the amino terminus of HLLRBM-1 and caspase recruitment protein 7 and NOD. HLRRBM-1 contains no recognizable hydrophobic sequence (signal sequence) on its amino terminus and contains only one transmembrane domain. HLRRBM-1 is expressed mainly in the bone marrow and may function in the regulation of cell death during hemopoetic differentiation.

The HLRRBM1 polypeptide was predicted to comprise one transmembrane domain using the TMPRED program (K Hofmann, W Stoffel, Biol. Chem., 347:166, 1993). The predicted transmembrane domain of the HLRRBM1 polypeptide is located from about amino acid 144 to about amino acid 159 (SEQ ID NO:6) of SEQ ID NO:2 (FIGS. 1A–E). In this context, the term "about" may be construed to mean 1, 2, 3, 4, 5, 6, 7, 8, 9, or 10 amino acids beyond the N-Terminus and/or C-terminus of the above referenced polypeptide.

In preferred embodiments, the following transmembrane domain polypeptide is encompassed by the present invention: FTMCFVPLVCWVVCTC (SEQ ID NO:6). Polynucleotides encoding these polypeptides are also provided. The present invention also encompasses the use of the HLRRBM1 transmembrane domain polypeptide as an immunogenic and/or antigenic epitope as described elsewhere herein.

In preferred embodiments, the following N-terminal deletion mutants are encompassed by the present invention: F1-C16, T2-C16, M3-C16, C4-C16, F5-C16, V6-C16, P7-C 16, L8-C16, V9-C16, and/or C10-C16 of SEQ ID NO:6. Polynucleotide sequences encoding these polypeptides are also provided. The present invention also encompasses the use of the HLRRBM1 transmembrane domain N-terminal deletion polypeptides as immunogenic and/or antigenic epitopes as described elsewhere herein.

In preferred embodiments, the following C-terminal deletion mutants are encompassed by the present invention: F1-C16, F1-T15, F1-C14, F1-V13, F1-V12, F1-W11, F1-C10, F1-V9, F1-L8, and/or F1-P7 of SEQ ID NO:6. Polynucleotide sequences encoding these polypeptides are also provided. The present invention also encompasses the use of the HLRRBM1 transmembrane domain C-terminal deletion polypeptides as immunogenic and/or antigenic epitopes as described elsewhere herein.

Based upon the strong homology to members of the leucine-rich repeat containing proteins, the HLRRBM1 polypeptide is expected to share at least some biological activity with leucine-rich repeat containing proteins, preferably with members of the caspase recruitment protein family of leucine-rich repeat containing proteins, particularly the caspase recruitment protein family members referenced herein, preferably with pyrin domain containing proteins, and more preferably with leucine-rich repeat containing proteins found within bone marrow cells and tissues.

The HLRRBM1 polypeptide was also determined to comprise several conserved leucine residues, at amino acid 13, 36, 69, 70, 73, 79, 85, 100, 207, 232, 264, 267, 268, 292, 364, 366, 406, 410, 419, 421, 438, 445, and 448 of SEQ ID No: 2 (FIGS. 1A–E). Moreover, the HLRRBM1 polypeptide also was determined to comprise a few differentially conserved leucine residues, at amino acid 25, 28, 78, 93, 160, 210, 276, 312, 318, 355, 426, and 434 of SEQ ID No:2 (FIGS. 1A–E). The conservation of leucines at key amino acid residues is consistent with the HLRRBM1 polypeptide as being a member of the leucine-rich repeat containing protein family, and may be indicative of conserved structural features, which may correlate with conservation of protein function and/or activity.

The HLRRBM1 polypeptide was also determined to comprise several conserved cysteines, at amino acid 147, 159, 317, and 443 of SEQ ID No: 2 (FIGS. 1A–E). Conservation of cysteines at key amino acid residues is indicative of conserved structural features, which may correlate with conservation of protein function and/or activity.

Expression profiling designed to measure the steady state mRNA levels encoding the HLRRBM1 polypeptide showed predominately high expression levels in bone marrow tissue, and to a lesser extent, in spleen, lung, and testis tissue (See FIG. 4).

Addition expression profiling analysis of HLRRBM1 expression levels in various cancer cell lines by TaqMan™ quantitative PCR (see FIG. 6) determined that HLRRBM1 is expressed in several colon cancer cell lines, significantly in a melanoma and a leukemia cell line, and to a lesser extent in other human tumor cell lines as shown. Moreover, the HLRRBM1 polypeptide was predominately expressed in a Taxol resistant variant of an ovarian tumor cell line. suggesting HLRRBM1 may be diagnostic of aggressive transformed phenotypes. The data suggests the HLRRBM1 polypeptide may play a critical role in the development of a transformed phenotype leading to the development of cancers and/or a proliferative condition, either directly or indirectly. Alternatively, the HLRRBM1 polypeptide may play a protective role and could be activated in response to a cancerous or proliferative phenotype. Whether HLRRBM1 plays a role in directing transformation, or plays the role of protecting cells in response to a transformed phenotype, its role in ovarian tumors is likely to be enhanced. Therefore, antagonists or agonists of the HLRRBM1 polypeptide may be useful in the treatment, amelioration, and/or prevention of a variety of proliferative conditions, including, but not limited to ovarian, and colon tumors, in addition to melanoma and leukemias.

Characterization of the HLRRBM1 polypeptide of the present invention using antisense oligonucleotides led to the determination that HLRRBM1 is involved in the negative modulation of the p21 G1/G2 cell cycle check point modulatory protein as described in Example 6 herein.

These results suggest that inhibition of HLRRBM1 activity or expression with a modulator would induce differentiation, and stop cellular proliferation, as p21 is a cell cycle inhibitor and is known to be associated with committment down a differentiation pathway. Numerous known drugs in clinical trials (such as, for example, cdk2 inhibitors, dna methyltransferase inhibitors) also induce p21, and have been shown to have activity in patients with cancer. Thus, p21 induction is a plausable marker of anticancer potential when a target is appropriately modulated.

In preferred embodiments, HLRRBM1 polynucleotides and polypeptides, including fragments thereof, are useful for treating, diagnosing, and/or ameliorating cell cycle defects, disorders related to aberrant phosphorylation, disorders related to aberrant signal transduction, proliferating disorders, and/or cancers.

Moreover, HLRRBM1 polynucleotides and polypeptides, including fragments thereof, are useful for decreasing cellular proliferation, decreasing cellular proliferation in rapidly proliferating cells, increasing the number of cells in the G1 phase of the cell cycle, increasing the number of cells in the G2 phase of the cell cycle, decreasing the-number of cells that progress to the S phase of the cell cycle, decreasing the number of cells that progress to the M phase of the cell cycle, modulating DNA repair, and increasing hematopoietic stem cell expansion.

Moreover, antagonists directed against HLRRBM1 are useful for decreasing cellular proliferation, decreasing cellular proliferation in rapidly proliferating cells, increasing the number of cells in the G1 phase of the cell cycle, increasing the number of cells in the G2 phase of the cell cycle, decreasing the number of cells that progress to the S phase of the cell cycle, decreasing the number of cells that progress to the M phase of the cell cycle, and inducing cells into G1 and/or G2 phase arrest. Such antagonists would be particularly useful for transforming transformed cells normal cells.

The HLRRBM1 polynucleotides and polypeptides of the present invention, including agonists and/or fragments thereof, have uses that include detecting, prognosing, treating, preventing, and/or ameliorating the following diseases and/or disorders, disorders related to aberrant apoptosis regulation, disorders related to aberrant cell adhesion regulation, and disorders related to aberrant cellular proliferation, for example, in addition to, immune, pulmonary, and reproductive disorders.

Moreover, agonists directed against HLRRBM1 are useful for increasing cellular proliferation, increasing cellular proliferation in rapidly proliferating cells, decreasing the number of cells in the G1 phase of the cell cycle, decreasing the number of cells in the G2 phase of the cell cycle, increasing the number of cells that progress to the S phase of the cell cycle, increasing the number of cells that progress to the M phase of the cell cycle, and releasing cells from G1 and/or G2 phase arrest. Such antagonists would be particularly useful for transforming normal cells into immortalized cell lines, stimulating hematopoietic cells to grow and divide, increasing recovery rates of cancer patients that have undergone chemotherapy or other therapeutic regimen, by boosting their immune responses, etc. In addition, such antagonists of HLRRBM1 would also be useful for regenerating neural tissues (e.g., treatment of Parkinson's or Alzheimers patients with neural stem cells, or neural cells which have been activated by an HLRRBM1 antagonist).

The HLRRBM1 polynucleotides and polypeptides of the present invention, including agonists and/or fragments thereof, have uses that include modulating signal transduction activity, in various cells, tissues, and organisms, and particularly in mammalian bone marrow, lung, spleen, and testicular tissue, preferably human tissue.

The strong homology to human leucine-rich repeat containing proteins, particularly the strong homology to pyrin domain containing proteins, combined with the predominate localized expression in bone marrow tissue suggests the HLRRBM1 polynucleotides and polypeptides may be useful in treating, diagnosing, prognosing, and/or preventing immune and hematopoietic diseases and/or disorders, which include, but are not limited to, anemia, pancytopenia, leukopenia, thrombocytopenia or leukemia since stromal cells are important in the production of cells of hematopoietic lineages. Representative uses are described in the "Inmune Activity" and "Infectious Disease" sections below, the Examples, and elsewhere herein. Briefly, the uses include bone marrow cell ex-vivo culture, bone marrow transplantation, bone marrow reconstitution, radiotherapy or chemotherapy of neoplasia. The gene product may also be involved in lymphopoiesis, therefore, it can be used in immune disorders such as infection, inflammation, allergy, immunodeficiency etc. In addition, this gene product may have commercial utility in the expansion of stem cells and committed progenitors of various blood lineages, and in the differentiation and/or proliferation of various cell types.

Moreover, the HLRRBM1 polypeptide may be useful for modulating cytokine production, antigen presentation, or other processes, such as for boosting immune responses, etc. Expression in cells of lymphoid origin, indicates the natural gene product would be involved in immune functions. Therefore it would also be useful as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, and scleroderma. Moreover, the protein may represent a secreted factor that influences the differentiation or behavior of other blood cells, or that recruits hematopoietic cells to sites of injury. Thus, this gene product is thought to be useful in the expansion of stem cells and committed progenitors of various blood lineages, and in the differentiation and/or proliferation of various cell types. Furthermore, the protein may also be used to determine biological activity, raise antibodies, as tissuemarkers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

The HLRRBM1 polynucleotides and polypeptides, including agonists, antagonists, and/or fragments thereof, of the present invention have uses which include, for example, modulating cellular proliferation. Likewise, the HLRRBM1 polynucleotides and polypeptides, including agonists, antagonists, and/or fragments thereof, may be useful for the treatment, detection, amelioration, and/or prevention of disorders related, or directly linked to, aberrant cellular proliferation, such as, for example, cancers.

Alternatively, the strong homology to leucine-rich repeat containing proteins, combined with the significant localized expression in lung tissue suggests the HLRRBM1 polynucleotides and polypeptides may be useful in treating, diagnosing, prognosing, and/or preventing pulmonary diseases and/or disorders which include, but are not limited to, ARDS, chronic obstructive pulmonary disease, emphysema, cystic fibrosis, pulmonary embolism, pulmonary hypertension, pulmonary thrombosis, for example.

The HLRRBM1 polynucleotides and polypeptides may also be useful, either directly, or indirectly, including agonists and/or antagonists thereof, for treating, ameliorating, and/or preventing drug-induced pulmonary diseases and disorders for the following, non-limiting, drugs: Chemotherapeutic: Azathioprine, Bleomycin, Busulfan, Chlorambucil, Cyclophosphamide, Etoposide, Interleukin-2, Melphalan, Mitomycin C, Nitrosoamines, Procarbazine, Tumor necrosis factor, Vinblastine, Zinostatin, Bleomycin, Cytosine arabinoside, Methotrexate, Procarbazine, Amphotericin B, Nitrofurantoin, Sulfasalazine, Acetylsalicylic acid, Gold, Methotrexate, Penicillamine, Heroin, Methadone, Naloxone, Placidyl, Propoxyphene, Salicylates, Amoidarone, Angiotensin-converting enzyme inhibitors, Beta blockers, Dipyridamole, Flecainide, Protamine, Tocainide, Aspirated oil, Oxygen, Blood, Ethanolamide maolate (sodium morrhuate), Ethiodized oil (lymphangiogram), Talc, Bromocriptine, Dantrolene, Hydrocholorothiazide, Methysergide, Tocolytic agents, Tricyclics, L-Tryptophan, Radiation, Systemic lupus erythematosus (drug-induced), and Complement-mediated leukostasis.

In addition, the strong homology to leucine-rich repeat containing proteins, combined with the expression in testis tissue suggests a potential utility for HLRRBM1 polynucleotides and polypeptides in treating, diagnosing, prognosing, and/or preventing male reproductive disorders, such as, for example, male infertility, impotence, and/or testicular cancer. This gene product may also be useful in assays designed to identify binding agents, as such agents (antagonists) are useful as male contraceptive agents. The testes are also a site of active gene expression of transcripts that is expressed, particularly at low levels, in other tissues of the body. Therefore, this gene product may be expressed in other specific tissues or organs where it may play related functional roles in other processes, such as hematopoiesis, inflammation, bone formation, and kidney function, to name a few possible target indications.

Moreover, HLRRBM1 polynucleotides and polypeptides, including fragments and agonists thereof, may have uses which include treating, diagnosing, prognosing, and/or preventing hyperproliferative disorders, particularly of the immune, hematopoietic, pulmonary, and reproductive systems. Such disorders may include, for example, cancers, and metastasis.

The HLRRBM1 polynucleotides and polypeptides, including fragments and agonists thereof, may have uses which include, either directly or indirectly, for boosting immune responses.

The HLRRBM1 polynucleotides and polypeptides, including fragments and/or antagonsists thereof, may have uses which include identification of modulators of HLRRBM1 function including antibodies (for detection or neutralization), naturally-occurring modulators and small molecule modulators. Antibodies to domains of the HLRRBM1 protein could be used as diagnostic agents of hematopoietic and inflammatory conditions in patients, are useful in monitoring the activation of signal transduction pathways, and can be used as a biomarker for the involvement of leucine-rich repeat containing proteins in disease states, and in the evaluation of inhibitors of leucine-rich repeat containing proteins in vivo.

HLRRBM1 polypeptides and polynucleotides have additional uses which include diagnosing diseases related to the over and/or under expression of HLRRBM1 by identifying mutations in the HLRRBM1 gene by using HLRRBM1 sequences as probes or by determining HLRRBM1 protein or mRNA expression levels. HLRRBM1 polypeptides may be useful for screening compounds that affect the activity of the protein. HLRRBM1 peptides can also be used for the generation of specific antibodies and as bait in yeast two hybrid screens to find proteins the specifically interact with HLRRBM1 (described elsewhere herein).

In preferred embodiments, HLRRBM1 polypeptides, including antagonists, and fragments thereof, have uses which include, for example, the treatment, detection, prevention, prognosis, and/or amelioration of pulmonary diseases, which include, for example chronic obstructive pulmonary disease (COPD) (Lee, E., et al., Am. J. Respir. Crit. Care. Med.,160(6):2079–85 (1999)), bronchial hyperresponsiveness, bronchial hypersensitivity (Yoshida, S., et al., Clin. Exp. Allergy.,30(1):64–70 (2000)), allergic rhinitis (Meltzer, E. O., Ann. Allergy. Asthma. Immunol., 84(2):176–85 (2000)).

Recently, leucine-rich repeat containing proteins have been directly implicated in the pathogenesis of Bernard-Soulier syndrome (BSS), a hereditary qualitative platelet disorder. The disorder has been linked to the qualitative or quantitative abnormality of the platelet glycoprotein (GP) Ib/IX/V complex, which is formed by the aggregation of several leucine-rich repeat containing proteins (Hayashi, T.; Suzuki, K., Semin.Thromb. Hemost.,26(1): 53–9 (2000).

In preferred embodiments, HLRRBM1 polypeptides, including antagonists, and fragments thereof, have uses which include, for example, the treatment, detection, prevention, prognosis, and/or amelioration of platelet disorders, including, but not limited to, Bernard-Soulier syndrome (BSS)., As descussed elsewhere herein, the *Drosophia* Toll proteins, including the human homologues thereof, have been implicated in modulating development and in non-infectious disease (Schuster, J M., Nelson, P S, J. Leukoc, Biol., 67(6):767–73, (2000)).

In preferred embodiments, HLRRBM1 polypeptides, including antagonists, and fragments thereof, have uses which include, for example, the treatment, detection, prevention, prognosis, and/or amelioration of developmental disorders, and non-infectious disorders, such as innate immunity to bacterial pathogens, adaptive immune responses, and others as listed in Schuster, J M et al., supra.

Leucine-rich repeat proteins have also been implicated in the incidence of systemic lupus erythematosus (Koarada, S., Tada, Y., Ushiyama, O., Morito, F., Suzuki, N., Ohta, A.,Miyake, K., Kimoto, M., Nagasawa, K, Arthritis, Rheum., 42(12):2593–600, (1999)).

In preferred embodiments, HLRRBM1 polypeptides, including antagonists, and fragments thereof, have uses which include, for example, the treatment, detection, prevention, prognosis, and/or amelioration of immune and inflammatory disorders, which include, for example, systemic lupus erythematosus.

As described elsewhere herein, leucine-rich repeat proteins are also implicated in a number of processes related to pathogen and/or disease resistance in plants. This is of particular significance, since mammals, including, humans, have homologues of some of these proteins which are thought to function in innate immune responses ((Dixon, M S., Hatzixanthis, K., Jones, D A., Harrison, K., Jones, J D, Plant, Cell., 10(11):1915–25, (1998); Ellis, J., Jones, D, Curr, Opin, Plant, Biol., 1(4):288–93, (1998); Collins, N., Drake, J., Ayliffe, M., Sun, Q., Ellis, J., Hulbert, S., Pryor, T, Plant, Cell., 11(7):1365–76, (1999); Wang, Z X., Yano, M., Yamanouchi, U., Iwamoto, M., Monna, L.,Hayasaka, H., Katayose, Y., Sasaki, T, Plant, J., 19(1):55–64, (1999); Richter, T E., Ronald, P C, Plant, Mol, Biol., 42(1):195–204, (2000); Graham, M A., k, L F., Lohnes, D., Cregan, P., Shoemaker, R C, Genome., 43(1):86–93, (2000); and He, Z., Wang, Z Y., Li, J., Zhu, Q., Lamb, C., Ronald, P., Chory, J. Science. 30., 288(5475):2360–3, (2000)).

Moreover, the HLRRBM1 polypeptide shares significant homology with caspase recruitment proteins. Aberrations of such proteins have been implicated in the incidence of a number of disorders related to aberrant apoptosis regulation, and in various inflammatory disorders (Srinivasula, S M., Ahmad, M., Lin, J H., Poyet, J L., Fernandes, Alnemri, T., Tsichlis, P N., Alnemri, E S, J. Biol, Chem. 18., 274(25): 17946–54, (1999)).

In preferred embodiments, HLRRBM1 polypeptides, including antagonists, and fragments thereof, have uses which include, for example, the treatment, detection, prevention, prognosis, and/or amelioration of immune and inflammatory disorders, particularly proliferative disorders, in addition to disorders related to aberrant apoptosis regulation, including, but not limited to cancers.

Although it is believed the encoded polypeptide may share at least some biological activities with leucine-rich repeat containing proteins (particularly caspase recruitment proteins), a number of methods of determining the exact biological function of this clone are either known in the art or are described elsewhere herein. Briefly, the function of this clone may be determined by applying microarray methodology. Nucleic acids corresponding to the HLRRBM1 polynucleotides, in addition to, other clones of the present invention, may be arrayed on microchips for expression profiling. Depending on which polynucleotide probe is used to hybridize to the slides, a change in expression of a specific gene may provide additional insight into the function of this gene based upon the conditions being studied. For example, an observed increase or decrease in expression levels when the polynucleotide probe used comes from diseased bone marrow tissue, as compared to, normal tissue might indicate a function in modulating immune and/or hematopoietic function, for example. In the case of HLRRBM1, bone marrow, spleen, lung, and testis tissue should be used, for example, to extract RNA to prepare the probe.

In addition, the function of the protein may be assessed by applying quantitative PCR methodology, for example. Real time quantitative PCR would provide the capability of following the expression of the HLRRBM1 gene throughout development, for example. Quantitative PCR methodology requires only a nominal amount of tissue from each developmentally important step is needed to perform such experiments. Therefore, the application of quantitative PCR methodology to refining the biological function of this polypeptide is encompassed by the present invention. In the case of HLRRBM1, a disease correlation related to HLRRBM1 may be made by comparing the mRNA expression level of HLRRBM1 in normal tissue, as compared to diseased tissue (particularly diseased tissue isolated from the following: bone marrow, spleen, lung, and testis tissue). Significantly higher or lower levels of HLRRBM1 expression in the diseased tissue may suggest HLRRBM1 plays a role in disease progression, and antagonists against HLRRBM1 polypeptides would be useful therapeutically in treating, preventing, and/or ameliorating the disease. Alternatively, significantly higher or lower levels of HLRRBM1 expression in the diseased tissue may suggest HLRRBM1 plays a defensive role against disease progression, and agonists of HLRRBM1 polypeptides may be useful therapeutically in treating, preventing, and/or ameliorating the disease. Also encompassed by the present invention are quantitative PCR probes corresponding to the polynucleotide sequence provided as SEQ ID NO:1 (FIGS. 1A–E).

The function of the protein may also be assessed through complementation assays in yeast. For example, in the case of the HLRRBM1, transforming yeast deficient in leucine-rich repeat containing protein activity, preferably caspase recruitment protein activity, for example, and assessing their ability to grow would provide convincing evidence the HLRRBM1 polypeptide has leucine-rich repeat containing protein activity, and potentially caspase recruitment protein activity. Additional assay conditions and methods that may be used in assessing the function of the polynucleotides and polypeptides of the present invention are known in the art, some of which are disclosed elsewhere herein.

Alternatively, the biological function of the encoded polypeptide may be determined by disrupting a homologue of this polypeptide in Mice and/or rats and observing the resulting phenotype. Such knock-out experiments are known in the art, some of which are disclosed elsewhere herein.

Moreover, the biological function of this polypeptide may be determined by the application of antisense and/or sense methodology and the resulting generation of transgenic mice and/or rats. Expressing a particular gene in either sense or antisense orientation in a transgenic mouse or rat could lead to respectively higher or lower expression levels of that particular gene. Altering the endogenous expression levels of a gene can lead to the observation of a particular phenotype that can then be used to derive indications on the function of the gene. The gene can be either over-expressed or under expressed in every cell of the organism at all times using a strong ubiquitous promoter, or it could be expressed in one or more discrete parts of the organism using a well characterized tissue-specific promoter (e.g., a bone marrow, spleen, lung, or testis tissue specific promoter), or it can be expressed at a specified time of development using an inducible and/or a developmentally regulated promoter.

In the case of HLRRBM1 transgenic mice or rats, if no phenotype is apparent in normal growth conditions, observing the organism under diseased conditions (immune, hematopoietic, pulmonary, or reproductive disorders, in addition to cancers, etc.) may lead to understanding the function of the gene. Therefore, the application of antisense and/or sense methodology to the creation of transgenic mice or rats to refine the biological function of the polypeptide is encompassed by the present invention.

In preferred embodiments, the following N-terminal deletion mutants are encompassed by the present invention: M1-R449, N2-R449, Q3-R449, S4-R449, A5-R449, T6-R449, E7-R449, C8-R449, S9-R449, M10-R449, Q11-R449, D12-449, L13-R449, I14-R449, F15-R449, S16-R449, C17-R449, W18-R449, P19-R449, E20-R449, P21-R449, S22-R449, A23-R449, P24-R449, L25-R449, Q26-R449, E27-R449, L28-R449, I29-R449, R30-R449, V31-R449, P32-R449, E33-R449, R34-R449, L35-R449, L36-R449, F37-R449, I38-R449, I39-R449, D40-R449, G41-R449, F42-R449, D43-R449, E44-R449, L45-R449, K46-R449, P47-R449, S48-R449, F49-R449, H50-R449, D51-R449, P52-R449, Q53-R449, G54-R449, P55-R449, W56-R449, C57-R449, L58-R449, C59-R449, W60-R449, E61-R449, E62-R449, K63-R449, R64-R449, P65-R449, T66-R449, E67-R449, L68-R449, L69-R449, L70-449, N71-R449, S72-R449, L73-R449, I74-R449, R75-R449, K76-R449, K77-R449, L78-R449, L79-R449, P80-R449, E81-R449, L82-R449, S83-R449, L84-R449, L85-R449, I86-R449, T87-R449, T88-R449, R89-R449, P90-R449, T91-R449, A92-R449, L93-R449, E94-R449, K95-R449, L96-R449, H97-R449, R98-R449, L99-R449, L100-R449, E101-R449, H102-R449, P103-R449, R104-R449, H105-R449, V106-R449, E107-R449, I108-R449, L109-R449, G110-R449, F111-R449, S112-R449, E113-R449, A114-R449, E115-R449, R116-R449, K117-R449, E118-R449, Y119-R449, F120-R449, Y121-R449, K122-R449, Y123-R449, F124-R449, H125-R449, N126-R449, A127-R449, E128-R449, Q129-R449, A130-R449, G131-R449, Q132-R449, V133-R449, F134-R449, N135-R449, Y136-R449, V137-R449, R138-R449, D139-R449, N140-R449, E141-R449, P142-R449, L143-R449, F144-R449, T145-R449, M146-R449, C147-R449, F148-R449, V149-R449, P150-R449, L151-R449, V152-R449, C153-R449, W154-R449, V155-R449, V156-R449, C157-R449, T158-R449, C159-R449, L160-R449, Q161-R449, Q162-R449, Q163-R449, L164-R449, E165-R449, G166-R449, G167-R449, G168-R449, L169-R449, L170-R449, R171-R449, Q172-R449, T173-R449, S174-R449, R175-R449, T176-R449, T177-R449, T178-R449, A179-R449, V180-R449, Y181-R449, M182-R449, L183-R449, Y184-R449, L185-R449, L186-R449, S187-R449, L188-R449, M189-R449, Q190-R449, R449, P191-R449, K192-R449, P193-R449, G194-R449, A195-R449, P196-R449, R197-R449, L198-R449, Q199-R449, P200-R449, P201-R449, P202-R449, N203-R449, Q204-R449, R205-R449, G206-R449, L207-R449, C208-R449, S209-R449, L210-R449, A211-R449, A212-R449, D213-R449, G214-R449, L215-R449, W216-R449, N217-R449, Q218-R449, K219-R449, I220-R449, L221-R449, F222-R449, E223-R449, E224-R449, Q225-R449, D226-R449, L227-R449, R228-R449, K229-R449, H230-R449, G231-R449, L232-R449, D233-R449, G234-R449, E235-R449, D236-R449, V237-R449, S238-R449, A239-R449, F240-R449, L241-R449, N242-R449, M243-R449, N244-R449, I245-R449, F246-R449, Q247-R449, K248-R449, D249-R449, I250-R449, N251-R449, C252-R449, E253-R449, R254-R449, S255-R449, F256-R449, L257-R449, A258-R449, L259-R449, T260-R449, S261-R449, R262-R449, F263-R449, L264-R449, F265-R449, G266-R449, L267-R449, L268-R449, N269-R449, E270-R449, E271-R449, T272-R449, R273-R449, S274-R449, H275-R449, L276-R449, E277-R449, K278-R449, S279-R449, L280-R449, C281-R449, W282-R449, K283-R449, V284-R449, S285-R449, P286-R449, H287-R449, I288-R449, K289-R449, M290-R449, D291-R449, L292-R449, L293-R449, Q294-R449, W295-R449, I296-R449, Q297-R449, S298-R449, K299-R449, A300-R449, Q301-R449, S302-R449, D303-R449, G304-R449, S305-R449, T306-R449, L307-R449, Q308-R449, Q309-R449, G310-R449, S311-R449, L312-R449, E313-R449, F314-R449, F315-R449, S316-R449, C317-R449, L318-R449, Y319-R449, E320-R449, I321-R449, Q322-R449, E323-R449, E324-R449, E325-R449, F326-R449, I327-R449, Q328-R449, Q329-R449, A330-R449, L331-R449, S332-R449, H333-R449, F334-R449, Q335-R449, V336-R449, I337-R449, V338-R449, V339-R449, S340-R449, N341-R449, I342-R449, A343-R449, S344-R449, K345-R449, M346-R449, E347-R449, H348-R449, M349-R449, V350-R449, S351-R449, S352-R449, F353-R449, C354-R449, L355-R449, K356-R449, R357-R449, C358-R449, R359-R449, S360-R449, A361-R449, Q362-R449, V363-R449, L364-R449, H365-R449, L366-R449, Y367-R449, G368-R449, A369-R449, T370-R449, Y371-R449, S372R449, A373-R449, D374-R449, G375-R449, E376-R449, D377-R449, R378-R449, A379-R449, R380-R449, C381-R449, S382-R449, A383-R449, G384-R449, A385R449, H386-R449, T387-R449, L388-R449, L389-R449, V390-R449, Q391-R449, L392-R449, P393-R449, E394-R449, R395-R449, T396-R449, V397-R449, L398R449, L399-R449, D400-R449, A401-R449, Y402-R449, S403-R449, E404-R449, H405-R449, L406-R449, A407-R449, A408-R449, A409-R449, L410-R449, C411R449, T412-R449, N413-R449, P414-R449, N415-R449, L416-R449, I417-R449, E418R449, L419R449, S420R449, L421R449, Y422R449, R423R449, N424R449, A425R449, L426R449, G427R449, S428R449, R429R449, G430R449, V431R449, K432R449, L433R449, L4343R449, C435R449, Q436R449, G437R449, L438R449, R439R449, H440R449, P441R449, N442-R449, and/or C443-R449 of SEQ ID NO:2. Polynucleotide sequences encoding these polypeptides are also provided. The present invention also encompasses the use of the HLRRBM1 N-terminal deletion polypeptides as immunogenic and/or antigenic epitopes as described elsewhere herein.

In preferred embodiments, the following C-terminal deletion mutants are encompassed by the present invention: M1-R449, M1-L448, M1-N447, M1-Q446, M1-L445, M1-K444, M1-C443, M1-N442, M1-P441, M1-H440, M1-R439, M1-L438, M1-G437, M1-Q436, M1-C435, M1-L434, M1-L433, M1-K432, M1-431, M1-G430, M1-R429, M1-S428, M1-G427, M1-L426, M1-A425, M1-N424, M1-R423, M1-Y422, M1-L421, M1-S420, M1-L419, M1-E418, M1-I417, M1-L416, M1-N415, M1-P414, M1-N413, M1-T412, M1-C411, M1-L410, M1-A409, M1-A408, M1-A407, M1-L406, M1-H405, M1-E404, M1-S403, M1-Y402, M1-A401, M1-D400, M1-L399, M1-L398, M1-V397, M1-T396, M1-R395, M1-E394, M1-P393, M1-L392, M1-Q391, M1-V390, M1-L389, M1-L388, M1-T387, M1-H386, M1-A385, M1-G384, M1-A383, M1-S382, M1-C381, M1-R380, M1-A379, M1-R378, M1-D377, M1-E376, M1-G375, M1-D374, M1-A373, M1-S372, M1-Y371, M1-T370, M1-A369, M1-G368, M1-Y367, M1-L366, M1-H365, M1-L364, M1-V363, M1-Q362, M1-A361, M1-S360, M1-R359, M1-C358, M1-R357, M1-K356, M1-L355, M1-C354, M1-F353, M1-S352, M1-S351, M1-V350, M1-M349, M1-H348, M1-E347, M1-M346, M1-K345, M1-S344, M1-A343, M1-I342, M1-N341, M1-S340, M1-V339, M1-V338, M1-I337, M1-V336, M1-Q335, M1-F334, M1-H333, M1-S332, M1-L331, M1-A330, M1-Q329, M1-Q328, M1-I327, M1-F326, M1-E325, M1-E324, M1-E323, M1-Q322, M1-I321, M1-E320, M1-Y319, M1-L318, M1-C317, M1-S316, M1-F315, M1-F314, M1-E313, M1-L312, M1-S311, M1-G310, M1-Q309, M1-Q308, M1-L307, M1-T306, M1-S305, M1-G304, M1-D303, M1-S302, M1-Q301, M1-A300, M1-K299, M1-S298, M1-Q297, M1-I296, M1-W295, M1-Q294, M1-L293, M1-L292, M1-D291, M1-M290, M1-K289, M1-I288, M1-H287, M1-P286, M1-S285, M1-V284, M1-K283, M1-W282, M1-C281, M1-L280, M1-S279, M1-K278, M1-E277, M1-L276, M1-H275, M1-S274, M1-R273, M1-T272, M1-E271, M1-E270, M1-N269, M1-L268, M1-L267, M1-G266, M1-F265, M1-L264, M1-F263, M1-R262, M1-S261, M1-T260, M1-L259, M1-A258, M1-L257, M1-F256, M1-S255, M1-R254, M1-E253, M1-C252, M1-N251, M1-I250, M1-D249, M1-248, M1-Q247, M1-F246, M1-I245, M1-N244, M1-M243, M1-N242, M1-L241, M1-F240, M1-A239, M1-S238, M1-V237, M1-D236, M1-E235, M1-G234, M1-D233, M1-L232, M1-G231, M1-H230, M1-K229, M1-R228, M1-L227, M1-D226, M1-Q225, M1-E224, M1-E223, M1-F222, M1-L221, M1-I220, M1-K219, M1-Q218, M1-N217, M1-W216, M1-L215, M1-G214, M1-D213, M1-A212, M1-A211, M1-L210, M1-S209, M1-C208, M1-L207, M1-G206, M1-R205, M1-Q204, M1-N203, M1-P202, M1-P201, M1-P200, M1-Q199, M1-L198, M1-R197, M1-P196, M1-A195, M1-G194, M1-P193, M1-K192, M1-P191, M1-Q190, M1-M189, M1-L188, M1-S187, M1-L186, M1-L185, M1-Y184, M1-L183, M1-M182, M1-Y181, M1-V180, M1-A179, M1-T178, M1-T177, M1-T176, M1-R175, M1-S174, M1-T173, M1-Q172, M1-R171, M1-L170, M1-L169, M1-G168, M1-G167, M1-G166, M1-E165, M1-L164, M1-Q163, M1-Q162, M1-Q161, M1-L160, M1-C159, M1-T158, M1-C157, M1-V156, M1-V155, M1-W154, M1-C153, M1-V152, M1-L151, M1-P150, M1-V149, M1-F148, M1-C147, M1-M146, M1-T145, M1-F144, M1-L143, M1-P142, M1-E141, M1-N140, M1-D139, M1-R138, M1-V137, M1-Y136, M1-N135, M1-F134, M1-V133, M1-Q132, M1-G131, M1-A130, M1-Q129, M1-E128, M1-A127, M1-N126, M1-H125, M1-F124, M1-Y123, M1-K122, M1-Y121, M1-F120, M1-Y119, M1-E118, M1-K117, M1-R116, M1-E115, M1-A114, M1-E113, M1-S112, M1-F111, M1-G110, M1-L109, M1-I108, M1-E107, M1-V106, M1-H105, M1-R104, M1-P103, M1-H102, M1-E101, M1-L100, M1-L99, M1-R98, M1-H97, M1-L96, M1-K95, M1-E94, M1-L93, M1-A92, M1-T91, M1-P90, M1-R89, M1-T88, M1-T87, M1-186, M1-L85, M1-L84, M1-S83, M1-L82, M1-E81, M1-P80, M1-79, M1-L78, M1-K77, M1-K76, M1-R75, M1-I74, M1-L73, M1-S72, M1-N71, M1-70, M1-L69, M1-L68, M1-E67, M1-T66, M1-P65, M1-R64, M1-K63, M1-62, M1-61, M1-W60, M1-C59, M1-L58, M1-C57, M1-W56, M1-P55, M1-G54, M1-Q53, M1-P52, M1-D51, M1-H50, M1-F49, M1-S48, M1-P47, M1-K46, M1-L45, M1-E44, M1-D43, M1-F42, M1-G41, M1-D40, M1-I39, M1-I38, M1-F37, M1-L36, M1-35, M1-R34, M1-E33, M1-P32, M1-V31, M1-R30, M1-I29, M1-L28, M1-E27, M1-Q26, M1-L25, M1-P24, M1-A23, M1-S22, M1-P21, M1-E20, M1-P19, M1-W18, M1-C17, M1-S16, M1-F15, M1-I14, M1-L13, M1-D12, M1-Q11, M1-M10, M1-S9, M1-C8, and/or M1-E7 of SEQ ID NO:2. Polynucleotide sequences encoding these polypeptides are also provided. The present invention also encompasses the use of the HLRRBM1 C-terminal deletion polypeptides as immunogenic and/or antigenic epitopes as described elsewhere herein.

The present invention also encompasses immunogenic and/or antigenic epitopes of the HLRRBM1 polypeptide.

In preferred embodiments, the following immunogenic and/or antigenic epitope polypeptides are encompassed by the present invention: amino acid residues from about amino acid 144 to about amino acid 159, from about amino acid 144 to about amino acid 152, and/or from about amino acid 151 to about amino acid 159 of SEQ ID NO:2 (FIGS. 1A–E). In this context, the term "about" may be construed to mean 1, 2, 3, 4, 5, 6, 7, 8, 9, or 10 amino acids beyond the N-terminus and/or C-terminus of the above referenced polypeptides. Polynucleotides encoding these polypeptides are also provided.

The HLRRBM1 polypeptides of the present invention were determined to comprise several phosphorylation sites based upon the Motif algorithm (Genetics Computer Group, Inc.). The phosphorylation of such sites may regulate some biological activity of the HLRRBM1 polypeptide. For example, phosphorylation at specific sites may be involved in regulating the proteins ability to associate or bind to other molecules (e.g., proteins, ligands, substrates, DNA, etc.). In the present case, phosphorylation may modulate the ability of the HLRRBM1 polypeptide to associate with other polypeptides, particularly cognate ligand for HLRRBM1, or its ability to modulate certain cellular signal pathways.

The HLRRBM1 polypeptide was predicted to comprise three PKC phosphorylation sites using the Motif algorithm (Genetics Computer Group, Inc.). In vivo, protein kinase C exhibits a preference for the phosphorylation of serine or threonine residues. The PKC phosphorylation sites have the following consensus pattern: [ST]-x-[RK], where S or T represents the site of phosphorylation and 'x' an intervening amino acid residue. Additional information regarding PKC phosphorylation sites can be found in Woodget J. R., Gould K. L., Hunter T., Eur. J. Biochem. 161:177–184(1986), and Kishimoto A., Nishiyama K., Nakanishi H., Uratsuji Y., Nomura H., Takeyama Y., Nishizuka Y., J. Biol. Chem. 260:12492–12499(1985); which are hereby incorporated by reference herein.

In preferred embodiments, the following PKC phosphorylation site polypeptides are encompassed by the present invention: LSLLITTRPTALE (SEQ ID NO:10), GLLRQTSRTTTAV (SEQ ID NO:11), and/or SFLALTSRFLFGL (SEQ ID NO:12). Polynucleotides encoding these polypeptides are also provided. The present invention also encompasses the use of the HLRRBM1 PKC phosphorylation site polypeptides as immunogenic and/or antigenic epitopes as described elsewhere herein.

The HLRRBM1 polypeptide has been shown to comprise one glycosylation site according to the Motif algorithm (Genetics Computer Group, Inc.). As discussed more specifically herein, protein glycosylation is thought to serve a variety of functions including: augmentation of protein folding, inhibition of protein aggregation, regulation of intracellular trafficking to organelles, increasing resistance to proteolysis, modulation of protein antigenicity, and mediation of intercellular adhesion.

Asparagine phosphorylation sites have the following consensus pattern, N-{P}-[ST]-{P}, wherein N represents the glycosylation site. However, it is well known that that potential N-glycosylation sites are specific to the consensus sequence Asn-Xaa-Ser/Thr. However, the presence of the consensus tripeptide is not sufficient to conclude that an asparagine residue is glycosylated, due to the fact that the folding of the protein plays an important role in the regulation of N-glycosylation. It has been shown that the presence of proline between Asn and Ser/Thr will inhibit N-glycosylation; this has been confirmed by a recent statistical analysis of glycosylation sites, which also shows that about 50% of the sites that have a proline C-terminal to Ser/Thr are not glycosylated. Additional information relating to asparagine glycosylation may be found in reference to the following publications, which are hereby incorporated by reference herein: Marshall R. D., Annu. Rev. Biochem. 41:673–702(1972); Pless D. D., Lennarz W. J., Proc. Natl. Acad. Sci. U.S.A. 74:134–138(1977); Bause E., Biochem. J. 209:331–336(1983); Gavel Y., von Heijne G., Protein Eng. 3:433–442(1990); and Miletich J. P., Broze G. J. Jr., J. Biol. Chem. 265:11397–11404(1990).

In preferred embodiments, the following asparagine glycosylation site polypeptide is encompassed by the present invention: MNQSATECSM (SEQ ID NO:13). Polynucleotides encoding these polypeptides are also provided. The present invention also encompasses the use of the HLRRBM1 asparagine glycosylation site polypeptides as immunogenic and/or antigenic epitopes as described elsewhere herein.

The present invention encompasses the identification of compounds and drugs which stimulate HLRRBM1 on the one hand (i.e., agonists) and which inhibit the function of HLRRBM1 on the other hand (i.e., antagonists). In general, such screening procedures involve providing appropriate cells which express the polypeptide of the present invention. Such cells may include, for example, cells from mammals, yeast, *Drosophila* or *E. coli*. In a preferred embodiment, a polynucleotide encoding the polypeptide of the present invention may be employed to transfect cells to thereby express the HLRRBM1 polypeptide. The expressed protein may then be contacted with a test compound to observe binding, stimulation or inhibition of a functional response.

Many polynucleotide sequences, such as EST sequences, are publicly available and accessible through sequence databases. Some of these sequences are related to SEQ ID NO:1 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides consisting of a nucleotide sequence described by the general formula of a–b, where a is any integer between 1 to 4917 of SEQ ID NO:1, b is an integer between 15 to 4931, where both a and b correspond to the positions of nucleotide residues shown in SEQ ID NO:1, and where b is greater than or equal to a+14.

Table I summarizes the information corresponding to each "Gene No." described above. The nucleotide sequence identified as "NT SEQ ID NO:1" was assembled from partially homologous ("overlapping") sequences obtained from the "cDNA clone ID" identified in Table I and, in some cases, from additional related DNA clones. The overlapping sequences were assembled into a single contiguous sequence of high redundancy (usually several overlapping sequences at each nucleotide position), resulting in a final sequence identified as SEQ ID NO:1.

The cDNA Clone ID was deposited on the date and given the corresponding deposit number listed in "ATCC Deposit No:Z and Date." "Vector" refers to the type of vector contained in the cDNA Clone ID.

"Total NT Seq. Of Clone" refers to the total number of nucleotides in the clone contig identified by "Gene No." The deposited clone may contain all or most of the sequence of SEQ ID NO:1. The nucleotide position of SEQ ID NO:1 of the putative start codon (methionine) is identified as "5' NT of Start Codon of ORF."

The translated amino acid sequence, beginning with the methionine, is identified as "AA SEQ ID NO:2," although other reading frames can also be easily translated using known molecular biology techniques. The polypeptides produced by these alternative open reading frames are specifically contemplated by the present invention.

The total number of amino acids within the open reading frame of SEQ ID NO:2 is identified as "Total AA of ORF".

SEQ ID NO:1 (where X may be any of the polynucleotide sequences disclosed in the sequence listing) and the translated SEQ ID NO:2 (where Y may be any of the polypeptide sequences disclosed in the sequence listing) are sufficiently accurate and otherwise suitable for a variety of uses well known in the art and described further herein For instance, SEQ ID NO:1 is useful for designing nucleic acid hybridization probes that will detect nucleic acid sequences contained in SEQ ID NO:1 or the cDNA contained in the deposited clone. These probes will also hybridize to nucleic acid molecules in biological samples, thereby enabling a variety of forensic and diagnostic methods of the invention. Similarly, polypeptides identified from SEQ ID NO:2 may be used, for example, to generate antibodies which bind specifically to proteins containing the polypeptides and the proteins encoded by the cDNA clones identified in Table I.

Nevertheless, DNA sequences generated by sequencing reactions can contain sequencing errors. The errors exist as misidentified nucleotides, or as insertions or deletions of nucleotides in the generated DNA sequence. The erroneously inserted or deleted nucleotides may cause frame shifts in the reading frames of the predicted amino acid sequence. In these cases, the predicted amino acid sequence diverges from the actual amino acid sequence, even though the generated DNA sequence may be greater than 99.9% iden-

TABLE I

| Gene No. | CDNA Clone ID | ATCC Deposit No. Z and Date | Vector | NT SEQ ID. No. X | Total NT Seq of Clone | 5' NT of Start Codon of ORF | 3' NT of ORF | AA Seq ID No. Y | Total AA of ORF |
|---|---|---|---|---|---|---|---|---|---|
| 1. | HLRRBM1- (also known as GPCR25, clone 25a, and/or BMLRR2) | PTA-2676 Nov. 15, 2000 | PSport1 | 1 | 4931 | 1320 | 2666 | 2 | 449 |

tical to the actual DNA sequence (for example, one base insertion or deletion in an open reading frame of over 1000 bases).

Accordingly, for those applications requiring precision in the nucleotide sequence or the amino acid sequence, the present invention provides not only the generated nucleotide sequence identified as SEQ ID NO:1 and the predicted translated amino acid sequence identified as SEQ ID NO:2, but also a sample of plasmid DNA containing a cDNA of the invention deposited with the ATCC, as set forth in Table I. The nucleotide sequence of each deposited clone can readily be determined by sequencing the deposited clone in accordance with known methods. The predicted amino acid sequence can then be verified from such deposits. Moreover, the amino acid sequence of the protein encoded by a particular clone can also be directly determined by peptide sequencing or by expressing the protein in a suitable host cell containing the deposited cDNA, collecting the protein, and determining its sequence.

The present invention also relates to the genes corresponding to SEQ ID NO:1, SEQ ID NO:2, or the deposited clone. The corresponding gene can be isolated in accordance with known methods using the sequence information disclosed herein. Such methods include preparing probes or primers from the disclosed sequence and identifying or amplifying the corresponding gene from appropriate sources of genomic material.

Also provided in the present invention are species homologs, allelic variants, and/or orthologs. The skilled artisan could, using procedures well-known in the art, obtain the polynucleotide sequence corresponding to full-length genes (including, but not limited to the full-length coding region), allelic variants, splice variants, orthologs, and/or species homologues of genes corresponding to SEQ ID NO:1, SEQ ID NO:2, or a deposited clone, relying on the sequence from the sequences disclosed herein or the clones deposited with the ATCC. For example, allelic variants and/or species homologues may be isolated and identified by making suitable probes or primers which correspond to the 5', 3', or internal regions of the sequences provided herein and screening a suitable nucleic acid source for allelic variants and/or the desired homologue.

The polypeptides of the invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

The polypeptides may be in the form of the protein, or may be a part of a larger protein, such as a fusion protein (see below). It is often advantageous to include an additional amino acid sequence which contains secretory or leader sequences, pro-sequences, sequences which aid in purification, such as multiple histidine residues, or an additional sequence for stability during recombinant production.

The polypeptides of the present invention are preferably provided in an isolated form, and preferably are substantially purified. A recombinantly produced version of a polypeptide, can be substantially purified using techniques described herein or otherwise known in the art, such as, for example, by the one-step method described in Smith and Johnson, Gene 67:31–40 (1988). Polypeptides of the invention also can be purified from natural, synthetic or recombinant sources using protocols described herein or otherwise known in the art, such as, for example, antibodies of the invention raised against the full-length form of the protein.

The present invention provides a polynucleotide comprising, or alternatively consisting of, the sequence identified as SEQ ID NO:1, and/or a cDNA provided in ATCC Deposit No. Z:. The present invention also provides a polypeptide comprising, or alternatively consisting of, the sequence identified as SEQ ID NO:2, and/or a polypeptide encoded by the cDNA provided in ATCC Deposit NO:Z. The present invention also provides polynucleotides encoding a polypeptide comprising, or alternatively consisting of the polypeptide sequence of SEQ ID NO:2, and/or a polypeptide sequence encoded by the cDNA contained in ATCC Deposit No:Z.

Preferably, the present invention is directed to a polynucleotide comprising, or alternatively consisting of, the sequence identified as SEQ ID NO:1, and/or a cDNA provided in ATCC Deposit No.: that is less than, or equal to, a polynucleotide sequence that is 5 mega basepairs, 1 mega basepairs, 0.5 mega basepairs, 0.1 mega basepairs, 50,000 basepairs, 20,000 basepairs, or 10,000 basepairs in length.

The present invention encompasses polynucleotides with sequences complementary to those of the polynucleotides of the present invention disclosed herein. Such sequences may be complementary to the sequence disclosed as SEQ ID NO:1, the sequence contained in a deposit, and/or the nucleic acid sequence encoding the sequence disclosed as SEQ ID NO:2.

The present invention also encompasses polynucleotides capable of hybridizing, preferably under reduced stringency conditions, more preferably under stringent conditions, and most preferably under highly stringent conditions, to polynucleotides described herein. Examples of stringency conditions are shown in Table II below: highly stringent conditions are those that are at least as stringent as, for example, conditions A–F; stringent conditions are at least as stringent as, for example, conditions G–L; and reduced stringency conditions are at least as stringent as, for example, conditions M–R.

TABLE II

| Stringency Condition | Polynucleotide Hybrid± | Hybrid Length (bp)‡ | Hybridization Temperature and Buffer† | Wash Temperature and Buffer† |
|---|---|---|---|---|
| A | DNA:DNA | > or equal to 50 | 65° C.; 1xSSC -or- 42° C.; 1xSSC, 50% formamide | 65° C.; 0.3xSSC |
| B | DNA:DNA | <50 | Tb*; 1xSSC | Tb*; 1xSSC |
| C | DNA:RNA | > or equal to 50 | 67° C.; 1xSSC -or- 45° C.; 1xSSC, 50% formamide | 67° C.; 0.3xSSC |

TABLE II-continued

| Stringency Condition | Polynucleotide Hybrid± | Hybrid Length (bp)‡ | Hybridization Temperature and Buffer† | Wash Temperature and Buffer† |
|---|---|---|---|---|
| D | DNA:RNA | <50 | Td*; 1xSSC | Td*; 1xSSC |
| E | RNA:RNA | > or equal to 50 | 70° C.; 1xSSC -or- 50° C.; 1xSSC, 50% formamide | 70° C.; 0.3xSSC |
| F | RNA:RNA | <50 | Tf*; 1xSSC | Tf*; 1xSSC |
| G | DNA:DNA | > or equal to 50 | 65° C.; 4xSSC -or- 45° C.; 4xSSC, 50% formamide | 65° C.; 1xSSC |
| H | DNA:DNA | <50 | Th*; 4xSSC | Th*; 4xSSC |
| I | DNA:RNA | > or equal to 50 | 67° C.; 4xSSC -or- 45° C.; 4xSSC, 50% formamide | 67° C.; 1xSSC |
| J | DNA:RNA | <50 | Tj*; 4xSSC | Tj*; 4xSSC |
| K | RNA:RNA | > or equal to 50 | 70° C.; 4xSSC -or- 40° C.; 6xSSC, 50% formamide | 67° C.; 1xSSC |
| L | RNA:RNA | <50 | Tl*; 2xSSC | Tl*; 2xSSC |
| M | DNA:DNA | > or equal to 50 | 50° C.; 4xSSC -or- 40° C. 6xSSC, 50% formamide | 50° C.; 2xSSC |
| N | DNA:DNA | <50 | Tn*; 6xSSC | Tn*; 6xSSC |
| O | DNA:RNA | > or equal to 50 | 55° C.; 4xSSC -or- 42° C.; 6xSSC, 50% formamide | 55° C.; 2xSSC |
| P | DNA:RNA | <50 | Tp*; 6xSSC | Tp*; 6xSSC |
| Q | RNA:RNA | > or equal to 50 | 60° C.; 4xSSC -or- 45° C.; 6xSSC, 50% formamide | 60° C.; 2xSSC |
| R | RNA:RNA | <50 | Tr*; 4xSSC | Tr*; 4xSSC |

‡The "hybrid length" is the anticipated length for the hybridized region(s) of the hybridizing polynucleotides. When hybridizing a polynucletotide of unknown sequence, the hybrid is assumed to be that of the hybridizing polynucleotide of the present invention. When polynucleotides of known sequence are hybridized, the hybrid length can be determined by aligning the sequences of the polynucleotides and identifying the region or regions of optimal sequence complementarity. Methods of aligning two or more polynucleotide sequences and/or determining the percent identity between two polynucleotide sequences are well known in the art (e.g., MegAlign program of the DNA*Star suite of programs, etc).

†SSPE (1xSSPE is 0.15M NaCl, 10 mM NaH2PO4, and 1.25 mM EDTA, pH 7.4) can be substituted for SSC (1xSSC is 0.15M NaCl and 15 mM sodium citrate) in the hybridization and wash buffers; washes are performed for 15 minutes after hybridization is complete. The hybridizations and washes may additionally include 5X Denhardt's reagent, .5–1.0% SDS, 100 ug/ml denatured, fragmented salmon sperm DNA, 0.5% sodium pyrophosphate, and up to 50% formamide.

*Tb–Tr: The hybridization temperature for hybrids anticipated to be less than 50 base pairs in length should be 5–10° C. less than the melting temperature Tm of the hybrids there Tm is determined according to the following equations. For hybrids less than 18 base pairs in length, Tm (° C.) = 2 (# of A + T bases) + 4 (# of G + C bases). For hybrids between 18 and 49 base pairs in length, Tm (° C.) = 81.5 + 16.6 ($\log_{10}$[Na+]) + 0.41 (%G + C) − (600/N), where N is the number of bases in the hybrid, and [Na+] is the concentration of sodium ions in the hybridization buffer ([NA+] for 1xSSC = .165M).

±The present invention encompasses the substitution of any one, or more DNA or RNA hybrid partners with either a PNA, or a modified polynucleotide. Such modified polynucleotides are known in the art and are more particularly described elsewhere herein.

Additional examples of stringency conditions for polynucleotide hybridization are provided, for example, in Sambrook, J., E. F. Fritsch, and T. Maniatis, 1989, Molecular Cloning: A Laboratory Manual, Cold Spring Harbor Laboratory Press, Cold Spring Harbor, N.Y., chapters 9 and 11, and Current Protocols in Molecular Biology, 1995, F. M., Ausubel et al., eds, John Wiley and Sons, Inc., sections 2.10 and 6.3–6.4, which are hereby incorporated by reference herein.

Preferably, such hybridizing polynucleotides have at least 70% sequence identity (more preferably, at least 80% identity; and most preferably at least 90% or 95% identity) with the polynucleotide of the present invention to which they hybridize, where sequence identity is determined by comparing the sequences of the hybridizing polynucleotides when aligned so as to maximize overlap and identity while minimizing sequence gaps. The determination of identity is well known in the art, and discussed more specifically elsewhere herein.

The invention encompasses the application of PCR methodology to the polynucleotide sequences of the present invention, the clone deposited with the ATCC, and/or the cDNA encoding the polypeptides of the present invention. PCR techniques for the amplification of nucleic acids are described in U.S. Pat. No. 4,683,195 and Saiki et al., Science, 239:487–491 (1988). PCR, for example, may include the following steps, of denaturation of template nucleic acid (if double-stranded), annealing of primer to target, and polymerization. The nucleic acid probed or used as a template in the amplification reaction may be genomic DNA, cDNA, RNA, or a PNA. PCR may be used to amplify specific sequences from genomic DNA, specific RNA sequence, and/or cDNA transcribed from mRNA. References for the general use of PCR techniques, including specific method parameters, include Mullis et al., Cold Spring Harbor Symp. Quant. Biol., 51:263, (1987), Ehrlich (ed), PCR Technology, Stockton Press, NY, 1989; Ehrlich et al., Science, 252:1643–1650, (1991); and "PCR Protocols, A Guide to Methods and Applications", Eds., Innis et al., Academic Press, New York, (1990).

Polynucleotide and Polypeptide Variants

The present invention also encompasses variants (e.g., allelic variants, orthologs, etc.) of the polynucleotide sequence disclosed herein in SEQ ID NO:1, the complementary strand thereto, and/or the cDNA sequence contained in the deposited clone.

The present invention also encompasses variants of the polypeptide sequence, and/or fragments therein, disclosed in SEQ ID NO:2, a polypeptide encoded by the polynucleotide sequence in SEQ ID NO:1, and/or a polypeptide encoded by a cDNA in the deposited clone.

"Variant" refers to a polynucleotide or polypeptide differing from the polynucleotide or polypeptide of the present invention, but retaining essential properties thereof. Generally, variants are overall closely similar, and, in many regions, identical to the polynucleotide or polypeptide of the present invention.

Thus, one aspect of the invention provides an isolated nucleic acid molecule comprising, or alternatively consisting of, a polynucleotide having a nucleotide sequence selected from the group consisting of: (a) a nucleotide sequence encoding a HLRRBM1 related polypeptide having an amino acid sequence as shown in the sequence listing and described in SEQ ID NO:1 or the cDNA contained in ATCC deposit No:Z; (b) a nucleotide sequence encoding a mature HLRRBM1 related polypeptide having the amino acid sequence as shown in the sequence listing and described in SEQ ID NO:1 or the cDNA contained in ATCC deposit No:Z; (c) a nucleotide sequence encoding a biologically active fragment of a HLRRBM1 related polypeptide having an amino acid sequence shown in the sequence listing and described in SEQ ID NO:1 or the cDNA contained in ATCC deposit No:Z; (d) a nucleotide sequence encoding an antigenic fragment of a HLRRBM1 related polypeptide having an amino acid sequence sown in the sequence listing and described in SEQ ID NO:1 or the cDNA contained in ATCC deposit No:Z; (e) a nucleotide sequence encoding a HLRRBM1 related polypeptide comprising the complete amino acid sequence encoded by a human cDNA plasmid contained in SEQ ID NO:1 or the cDNA contained in ATCC deposit No:Z; (f) a nucleotide sequence encoding a mature HLRRBM1 related polypeptide having an amino acid sequence encoded by a human cDNA plasmid contained in SEQ ID NO:1 or the cDNA contained in ATCC deposit No:Z; (g) a nucleotide sequence encoding a biologically active fragment of a HLRRBM1 related polypeptide having an amino acid sequence encoded by a human cDNA plasmid contained in SEQ ID NO:1 or the cDNA contained in ATCC deposit No:Z; (h) a nucleotide sequence encoding an antigenic fragment of a HLRRBM1 related polypeptide having an amino acid sequence encoded by a human cDNA plasmid contained in SEQ ID NO:1 or the cDNA contained in ATCC deposit No:Z; (I) a nucleotide sequence complimentary to any of the nucleotide sequences in (a), (b), (c), (d), (e), (f), (g), or (h), above.

The present invention is also directed to polynucleotide sequences which comprise, or alternatively consist of, a polynucleotide sequence which is at least 80%, 85%, 90%, 91%, 92%, 93%, 94%, 95%, 96%, 97%, 98%, or 99% identical to, for example, any of the nucleotide sequences in (a), (b), (c), (d), (e), (f), (g), or (h), above. Polynucleotides encoded by these nucleic acid molecules are also encompassed by the invention. In another embodiment, the invention encompasses nucleic acid molecules which comprise, or alternatively, consist of a polynucleotide which hybridizes under stringent conditions, or alternatively, under lower stringency conditions, to a polynucleotide in (a), (b), (c), (d), (e), (f), (g), or (h), above. Polynucleotides which hybridize to the complement of these nucleic acid molecules under stringent hybridization conditions or alternatively, under lower stringency conditions, are also encompassed by the invention, as are polypeptides encoded by these polypeptides.

Another aspect of the invention provides an isolated nucleic acid molecule comprising, or alternatively, consisting of, a polynucleotide having a nucleotide sequence selected from the group consisting of: (a) a nucleotide sequence encoding a HLRRBM1 related polypeptide having an amino acid sequence as shown in the sequence listing and descried in Table I; (b) a nucleotide sequence encoding a mature HLRRBM1 related polypeptide having the amino acid sequence as shown in the sequence listing and descried in Table I; (c) a nucleotide sequence encoding a acid sequence as shown in the sequence listing and descried in Table I; (d) a nucleotide sequence encoding an antigenic fragment of a HLRRBM1 related polypeptide having an amino acid sequence as shown in the sequence listing and descried in Table I; (e) a nucleotide sequence encoding a HLRRBM1 related polypeptide comprising the complete amino acid sequence encoded by a human cDNA in a cDNA plasmid contained in the ATCC Deposit and described in Table I; (f) a nucleotide sequence encoding a mature HLRRBM1 related polypeptide having an amino acid sequence encoded by a human cDNA in a cDNA plasmid contained in the ATCC Deposit and described in Table I: (g) a nucleotide sequence encoding a biologically active fragment of a HLRRBM1 related polypeptide having an amino acid sequence encoded by a human cDNA in a cDNA plasmid contained in the ATCC Deposit and described in Table I; (h) a nucleotide sequence encoding an antigenic fragment of a HLRRBM1 related polypeptide having an amino acid sequence encoded by a human cDNA in a cDNA plasmid contained in the ATCC deposit and described in Table I; (i) a nucleotide sequence complimentary to any of the nucleotide sequences in (a), (b), (c), (d), (e), (f), (g), or (h) above.

The present invention is also directed to nucleic acid molecules which comprise, or alternatively, consist of, a nucleotide sequence which is at least 80%, 85%, 90%, 91%, 92%, 93%, 94%, 95%, 96%, 97%, 98%, or 99% identical to, for example, any of the nucleotide sequences in (a), (b), (c), (d), (e), (f), (g), or (h), above.

The present invention encompasses polypeptide sequences which comprise, or alternatively consist of, an amino acid sequence which is at least 80%, 98%, 90%, 91%, 92%, 93%, 94%, 95%, 96%, 97%, 98%, or 99% identical to, the following non-limited examples, the polypeptide sequence identified as SEQ ID NO:2, the polypeptide sequence encoded by a cDNA provided in the deposited clone, and/or polypeptide fragments of any of the polypeptides provided herein. Polynucleotides encoded by these nucleic acid molecules are also encompassed by the invention. In another embodiment, the, invention encompasses nucleic acid molecules which comprise, or alternatively, consist of a polynucleotide which hybridizes under stringent conditions, or alternatively, under lower stringency conditions, to a polynucleotide in (a), (b), (c), (d), (e), (f), (g), or (h), above. Polynucleotides which hybridize to the complement of these nucleic acid molecules under stringent hybridization conditions or alternatively, under lower stringency conditions, are also encompassed by the invention, as are polypeptides encoded by these polypeptides.

The present invention is also directed to polypeptides which comprise, or alternatively consist of, an amino acid sequence which is at least 80%, 98%, 90%, 91%, 92%, 93%, 94%, 95%, 96%, 97%, 98%, or 99% identical to, for example, the polypeptide sequence shown in SEQ ID NO:2, a polypeptide sequence encoded by the nucleotide sequence in SEQ ID NO:1, a polypeptide sequence encoded by the cDNA in cDNA plasmid:Z, and/or polypeptide fragments of any of these polypeptides (e.g., those fragments described herein). Polynucleotides which hybridize to the complement of the nucleic acid molecules encoding these polypeptides under stringent hybridization conditions or alternatively, under lower stringency conditions, are also encompasses by the present invention, as are the polypeptides encoded by these polynucleotides.

By a nucleic acid having a nucleotide sequence at least, for example, 95% "identical" to a reference nucleotide sequence of the present invention, it is intended that the nucleotide sequence of the nucleic acid is identical to the reference sequence except that the nucleotide sequence may include up to five point mutations per each 100 nucleotides of the reference nucleotide sequence encoding the polypeptide. In other words, to obtain a nucleic acid having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. The query sequence may be an entire sequence referenced in Table I, the ORF (open reading frame), or any fragment specified as described herein.

As a practical matter, whether any particular nucleic acid molecule or polypeptide is at least 80%, 85%, 90%, 91%, 92%, 93%, 94%, 95%, 96%, 97%, 98% or 99% identical to a nucleotide sequence of the present invention can be determined conventionally using known computer programs. A preferred method for determining the best overall match between a query sequence (a sequence of the present invention) and a subject sequence, also referred to as a global sequence alignment, can be determined using the CLUSTALW computer program (Thompson, J. D., et al., Nucleic Acids Research, 2(22):4673–4680, (1994)), which is based on the algorithm of Higgins, D. G., et al., Computer Applications in the Biosciences (CABIOS), 8(2):189–191, (1992). In a sequence alignment the query and subject sequences are both DNA sequences. An RNA sequence can be compared by converting U's to T's. However, the CLUSTALW algorithm automatically converts U's to T's when comparing RNA sequences to DNA sequences. The result of said global sequence alignment is in percent identity. Preferred parameters used in a CLUSTALW alignment of DNA sequences to calculate percent identity via pairwise alignments are: Matrix=IUB, k-tuple=1, Number of Top Diagonals=5, Gap Penalty=3, Gap Open Penalty 10, Gap Extension Penalty=0.1, Scoring Method=Percent, Window Size=5 or the length of the subject nucleotide sequence, whichever is shorter. For multiple alignments, the following CLUSTALW parameters are preferred: Gap Opening Penalty=10; Gap Extension Parameter=0.05; Gap Separation Penalty Range=8; End Gap Separation Penalty=Off; % Identity for Alignment Delay=40%; Residue Specific Gaps:Off; Hydrophilic Residue Gap=Off; and Transition Weighting=0. The pairwise and multple alignment parameters provided for CLUSTALW above represent the default parameters as provided with the AlignX software program (Vector NTI suite of programs, version 6.0).

The present invention encompasses the application of a manual correction to the percent identity results, in the instance where the subject sequence is shorter than the query sequence because of 5' or 3' deletions, not because of internal deletions. If only the local pairwise percent identity is required, no manual correction is needed. However, a manual correction may be applied to determine the global percent identity from a global polynucleotide alignment. Percent identity calculations based upon global polynucleotide alignments are often preferred since they reflect the percent identity between the polynucleotide molecules as a whole (i.e., including any polynucleotide overhangs, not just overlapping regions), as opposed to, only local matching polynucleotides. Manual corrections for global percent identity determinations are required since the CLUSTALW program does not account for 5' and 3' truncations of the subject sequence when calculating percent identity. For subject sequences truncated at the 5' or 3' ends, relative to the query sequence, the percent identify is corrected by calculating the number of bases of the query sequence that are 5' and 3' of the subject sequence, which are not matched/aligned, as a percent of the total bases of the query sequence. Whether a nucleotide is matched/aligned is determined by results of the CLUSTALW sequence alignment. This percentage is then subtracted from the percent identity, calculated by the above CLUSTALW program using the specified parameters, to arrive at a final percent identity score. This corrected score may be used for the purposes of the present invention. Only bases outside the 5' and 3' bases of the subject sequence, as displayed by the CLUSTALW alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the CLUSTALW alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the CLUSTALW program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by CLUSTALW is not manually corrected. Once again, only bases 5' and 3' of the subject sequence which are not matched/aligned with the query sequence are manually corrected for. No other manual corrections are required for the purposes of the present invention.

In addition to the above method of aligning two or more polynucleotide or polypeptide sequences to arrive at a percent identity value for the aligned sequences, it may be desirable in some circumstances to use a modified version of the CLUSTALW algorithm which takes into account known structural features of the sequences to be aligned, such as for example, the SWISS-PROT designations for each sequence. The result of such a modifed CLUSTALW algorithm may provide a more accurate value of the percent identity for two polynucleotide or polypeptide sequences. Support for such a modified version of CLUSTALW is provided within the CLUSTALW algorithm and would be readily appreciated to one of skill in the art of bioinformatics.

The variants may contain alterations in the coding regions, non-coding regions, or both. Especially preferred are polynucleotide variants containing alterations which produce silent substitutions, additions, or deletions, but do not alter the properties or activities of the encoded polypeptide. Nucleotide variants produced by silent substitutions due to the degeneracy of the genetic code are preferred. Moreover, variants in which 5–10, 1–5, or 1–2 amino acids are substituted, deleted, or added in any combination are also preferred. Polynucleotide variants can be produced for a variety of reasons, e.g., to optimize codon expression for a particular host (change codons in the mRNA to those preferred by a bacterial host such as *E. coli*).

Naturally occurring variants are called "allelic variants," and refer to one of several alternate forms of a gene occupying a given locus on a chromosome of an organism. (Genes II, Lewin, B., ed., John Wiley & Sons, New York (1985).) These allelic variants can vary at either the polynucleotide and/or polypeptide level and are included in the present invention. Alternatively, non-naturally occurring variants may be produced by mutagenesis techniques or by direct synthesis.

Using known methods of protein engineering and recombinant DNA technology, variants may be generated to improve or alter the characteristics of the polypeptides of the present invention. For instance, one or more amino acids can be deleted from the N-terminus or C-terminus of the protein without substantial loss of biological function. The authors of Ron et al., J. Biol. Chem. 268: 2984–2988 (1993), reported variant KGF proteins having heparin binding activity even after deleting 3, 8, or 27 amino-terminal amino acid residues. Similarly, Interferon gamma exhibited up to ten times higher activity after deleting 8–10 amino acid residues from the carboxy terminus of this protein (Dobeli et al., J. Biotechnology 7:199–216 (1988)).

Moreover, ample evidence demonstrates that variants often retain a biological activity similar to that of the naturally occurring protein. For example, Gayle and coworkers (J. Biol. Chem. 268:22105–22111 (1993)) conducted extensive mutational analysis of human cytokine IL-1a. They used random mutagenesis to generate over 3,500 individual IL-1a mutants that averaged 2.5 amino acid changes per variant over the entire length of the molecule. Multiple mutations were examined at every possible amino acid position. The investigators found that "[m]ost of the molecule could be altered with little effect on either [binding or biological activity]." In fact, only 23 unique amino acid sequences, out of more than 3,500 nucleotide sequences examined, produced a protein that significantly differed in activity from wild-type.

Furthermore, even if deleting one or more amino acids from the N-terminus or C-terminus of a polypeptide results in modification or loss of one or more biological functions, other biological activities may still be retained. For example, the ability of a deletion variant to induce and/or to bind antibodies which recognize the protein will likely be retained when less than the majority of the residues of the protein are removed from the N-terminus or C-terminus. Whether a particular polypeptide lacking N- or C-terminal residues of a protein retains such immunogenic activities can readily be determined by routine methods described herein and otherwise known in the art.

Alternatively, such N-terminus or C-terminus deletions of a polypeptide of the present invention may, in fact, result in a significant increase in one or more of the biological activities of the polypeptide(s). For example, biological activity of many polypeptides are governed by the presence of regulatory domains at either one or both termini. Such regulatory domains effectively inhibit the biological activity of such polypeptides in lieu of an activation event (e.g., binding to a cognate ligand or receptor, phosphorylation, proteolytic processing, etc.). Thus, by eliminating the regulatory domain of a polypeptide, the polypeptide may effectively be rendered biologically active in the absence of an activation event.

Thus, the invention further includes polypeptide variants that show substantial biological activity. Such variants include deletions, insertions, inversions, repeats, and substitutions selected according to general rules known in the art so as have little effect on activity. For example, guidance concerning how to make phenotypically silent amino acid substitutions is provided in Bowie et al., Science 247:1306–1310 (1990), wherein the authors indicate that there are two main strategies for studying the tolerance of an amino acid sequence to change.

The first strategy exploits the tolerance of amino acid substitutions by natural selection during the process of evolution. By comparing amino acid sequences in different species, conserved amino acids can be identified. These conserved amino acids are likely important for protein function. In contrast, the amino acid positions where substitutions have been tolerated by natural selection indicates that these positions are not critical for protein function. Thus, positions tolerating amino acid substitution could be modified while still maintaining biological activity of the protein.

The second strategy uses genetic engineering to introduce amino acid changes at specific positions of a cloned gene to identify regions critical for protein function. For example, site directed mutagenesis or alanine-scanning mutagenesis (introduction of single alanine mutations at every residue in the molecule) can be used. (Cunningham and Wells, Science 244:1081–1085 (1989).) The resulting mutant molecules can then be tested for biological activity.

As the authors state, these two strategies have revealed that proteins are surprisingly tolerant of amino acid substitutions. The authors further indicate which amino acid changes are likely to be permissive at certain amino acid positions in the protein. For example, most buried (within the tertiary structure of the protein) amino acid residues require nonpolar side chains, whereas few features of surface side chains are generally conserved.

The invention encompasses polypeptides having a lower degree of identity but having sufficient similarity so as to perform one or more of the same functions performed by the polypeptide of the present invention. Similarity is determined by conserved amino acid substitution. Such substitutions are those that substitute a given amino acid in a polypeptide by another amino acid of like characteristics (e.g., chemical properties). According to Cunningham et al above, such conservative substitutions are likely to be phenotypically silent. Additional guidance concerning which amino acid changes are likely to be phenotypically silent are found in Bowie et al., Science 247:1306–1310 (1990).

Tolerated conservative amino acid substitutions of the present invention involve replacement of the aliphatic or hydrophobic amino acids Ala, Val, Leu and Ile; replacement of the hydroxyl residues Ser and Thr; replacement of the acidic residues Asp and Glu; replacement of the amide residues Asn and Gln, replacement of the basic residues Lys, Arg, and His; replacement of the aromatic residues Phe, Tyr, and Trp, and replacement of the small-sized amino acids Ala, Ser, Thr, Met, and Gly.

In addition, the present invention also encompasses the conservative substitutions provided in Table III below.

TABLE III

| For Amino Acid | Code | Replace with any of: |
|---|---|---|
| Alanine | A | D-Ala, Gly, beta-Ala, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, β-Ala, Acp |
| Isoleucine | I | D-Ile, Val, D-Val, Leu, D-Leu, Met, D-Met |
| Leucine | L | D-Leu, Val, D-Val, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4, or 5-phenylproline, cis-3,4, or 5-phenylproline |
| Proline | P | D-Pro, L-1-thioazolidine-4-carboxylic acid, D- or L-1-oxazolidine-4-carboxylic acid |
| Serine | S | D-Ser, Thr, D-Thr, allo-Thr, Met, D-Met, Met(O), D-Met(O), L-Cys, D-Cys |
| Threonine | T | D-Thr, Ser, D-Ser, allo-Thr, Met, D-Met, Met(O), D-Met(O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met |

Aside from the uses described above, such amino acid substitutions may also increase protein or peptide stability. The invention encompasses amino acid substitutions that contain, for example, one or more non-peptide bonds (which replace the peptide bonds) in the protein or peptide sequence. Also included are substitutions that include amino acid residues other than naturally occurring L-amino acids, e.g., D-amino acids or non-naturally occurring or synthetic amino acids, e.g., β or γ amino acids.

Both identity and similarity can be readily calculated by reference to the following publications: Computational Molecular Biology, Lesk, A. M., ed., Oxford University Press, New York, 1988; Biocomputing: Informatics and Genome Projects, Smith, D. W., ed., Academic Press, New York, 1993; Informatics Computer Analysis of Sequence Data, Part 1, Griffin, A. M. and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991.

In addition, the present invention also encompasses substitution of amino acids based upon the probability of an amino acid substitution resulting in conservation of function. Such probabilities are determined by aligning multiple genes with related function and assessing the relative penalty of each substitution to proper gene function. Such probabilities are often described in a matrix and are used by some algorithms (e.g., BLAST, CLUSTALW, GAP, etc.) in calculating percent similarity wherein similarity refers to the degree by which one amino acid may substitute for another amino acid without lose of function. An example of such a matrix is the PAM250 or BLOSUM62 matrix.

Aside from the canonical chemically conservative substitutions referenced above, the invention also encompasses substitutions which are typically not classified as conservative, but that may be chemically conservative under certain circumstances. Analysis of enzymatic catalysis for proteases, for example, has shown that certain amino acids within the active site of some enzymes may have highly perturbed pKa's due to the unique microenvironment of the active site. Such perturbed pKa's could enable some amino acids to substitute for other amino acids while conserving enzymatic structure and function. Examples of amino acids that are known to have amino acids with perturbed pKa's are the Glu-35 residue of Lysozyme, the Ile-16 residue of Chymotrypsin, the His-159 residue of Papain, etc. The conservation of function relates to either anomalous protonation or anomalous deprotonation of such amino acids, relative to their canonical, non-perturbed pKa. The pKa perturbation may enable these amino acids to actively participate in general acid-base catalysis due to the unique ionization environment within the enzyme active site. Thus, substituting an amino acid capable of serving as either a general acid or general base within the microenvironment of an enzyme active site or cavity, as may be the case, in the same or similar capacity as the wild-type amino acid, would effectively serve as a conservative amino substitution.

Besides conservative amino acid substitution, variants of the present invention include, but are not limited to, the following: (i) substitutions with one or more of the non-conserved amino acid residues, where the substituted amino acid residues may or may not be one encoded by the genetic code, or (ii) substitution with one or more of amino acid residues having a substituent group, or (iii) fusion of the mature polypeptide with another compound, such as a compound to increase the stability and/or solubility of the polypeptide (for example, polyethylene glycol), or (iv) fusion of the polypeptide with additional amino acids, such as, for example, an IgG Fc fusion region peptide, or leader or secretory sequence, or a sequence facilitating purification. Such variant polypeptides are deemed to be within the scope of those skilled in the art from the teachings herein.

For example, polypeptide variants containing amino acid substitutions of charged amino acids with other charged or neutral amino acids may produce proteins with improved characteristics, such as less aggregation. Aggregation of pharmaceutical formulations both reduces activity and increases clearance due to the aggregate's immunogenic activity. (Pinckard et al., Clin. Exp. Immunol. 2:331–340 (1967); Robbins et al., Diabetes 36: 838–845 (1987); Cleland et al., Crit. Rev. Therapeutic Drug Carrier Systems 10:307–377 (1993).)

Moreover, the invention further includes polypeptide variants created through the application of molecular evolution ("DNA Shuffling") methodology to the polynucleotide disclosed as SEQ ID NO:1, the sequence of the clone submitted in a deposit, and/or the cDNA encoding the polypeptide disclosed as SEQ ID NO:2. Such DNA Shuffling technology is known in the art and more particularly described elsewhere herein (e.g., W P C, Stemmer, PNAS, 91:10747, (1994)), and in the Examples provided herein).

A further embodiment of the invention relates to a polypeptide which comprises the amino acid sequence of the present invention having an amino acid sequence which contains at least one amino acid substitution, but not more than 50 amino acid substitutions, even more preferably, not more than 40 amino acid substitutions, still more preferably, not more than 30 amino acid substitutions, and still even more preferably, not more than 20 amino acid substitutions. Of course, in order of ever-increasing preference, it is highly preferable for a peptide or polypeptide to have an amino acid sequence which comprises the amino acid sequence of the present invention, which contains at least one, but not more than 10, 9, 8, 7, 6, 5, 4, 3, 2 or 1 amino acid substitutions. In specific embodiments, the number of additions, substitutions, and/or deletions in the amino acid sequence of the present invention or fragments thereof (e.g., the mature form and/or other fragments described herein), is 1–5, 5–10, 5–25, 5–50, 10–50 or 50–150, conservative amino acid substitutions are preferable.

Polynucleotide and Polypeptide Fragments

The present invention is directed to polynucleotide fragments of the polynucleotides of the invention, in addition to polypeptides encoded therein by said polynucleotides and/or fragments.

In the present invention, a "polynucleotide fragment" refers to a short polynucleotide having a nucleic acid sequence which: is a portion of that contained in a deposited clone, or encoding the polypeptide encoded by the cDNA in a deposited clone; is a portion of that shown in SEQ ID NO:1 or the complementary strand thereto, or is a portion of a polynucleotide sequence encoding the polypeptide of SEQ ID NO:2. The nucleotide fragments of the invention are preferably at least about 15 nt, and more preferably at least about 20 nt, still more preferably at least about 30 nt, and even more preferably, at least about 40 nt, at least about 50 nt, at least about 75 nt, or at least about 150 nt in length. A fragment "at least 20 nt in length," for example, is intended to include 20 or more contiguous bases from the cDNA sequence contained in a deposited clone or the nucleotide sequence shown in SEQ ID NO:1. In this context "about" includes the particularly recited value, a value larger or smaller by several (5, 4, 3, 2, or 1) nucleotides, at either terminus, or at both termini. These nucleotide fragments have uses that include, but are not limited to, as diagnostic probes and primers as discussed herein. Of course, larger fragments (e.g., 50, 150, 500, 600, 2000 nucleotides) are preferred.

Moreover, representative examples of polynucleotide fragments of the invention, include, for example, fragments comprising, or alternatively consisting of, a sequence from about nucleotide number 1–50, 51–100, 101–150, 151–200, 201–250, 251–300, 301–350, 351–400, 401–450, 451–500, 501–550, 551–600, 651–700, 701–750, 751–800, 800–850, 851–900, 901–950, 951–1000, 1001–1050, 1051–1100, 1101–1150, 1151–1200, 1201–1250, 1251–1300, 1301–1350, 1351–1400, 1401–1450, 1451–1500, 1501–1550, 1551–1600, 1601–1650, 1651–1700, 1701–1750, 1751–1800, 1801–1850, 1851–1900, 1901–1950, 1951–2000, or 2001 to the end of SEQ ID NO:1, or the complementary strand thereto, or the cDNA contained in a deposited clone. In this context "about" includes the particularly recited ranges, and ranges larger or smaller by several (5, 4, 3, 2, or 1) nucleotides, at either terminus or at both termini. Preferably, these fragments encode a polypeptide which has biological activity. More preferably, these polynucleotides can be used as probes or primers as discussed herein. Also encompassed by the present invention are polynucleotides which hybridize to these nucleic acid molecules under stringent hybridization conditions or lower stringency conditions, as are the polypeptides encoded by these polynucleotides.

In the present invention, a "polypeptide fragment" refers to an amino acid sequence which is a portion of that contained in SEQ ID NO:2 or encoded by the cDNA contained in a deposited clone. Protein (polypeptide) fragments may be "free-standing," or comprised within a larger polypeptide of which the fragment forms a part or region, most preferably as a single continuous region. Representative examples of polypeptide fragments of the invention, include, for example, fragments comprising, or alternatively consisting of, from about amino acid number 1–20, 21–40, 41–60, 61–80, 81–100, 102–120, 121–140, 141–160, or 161 to the end of the coding region. Moreover, polypeptide fragments can be about 20, 30, 40, 50, 60, 70, 80, 90, 100, 110, 120, 130, 140, or 150 amino acids in length. In this context "about" includes the particularly recited ranges or values, and ranges or values larger or smaller by several (5, 4, 3, 2, or 1) amino acids, at either extreme or at both extremes. Polynucleotides encoding these polypeptides are also encompassed by the invention.

Preferred polypeptide fragments include the full-length protein. Further preferred polypeptide fragments include the full-length protein having a continuous series of deleted residues from the amino or the carboxy terminus, or both. For example, any number of amino acids, ranging from 1–60, can be deleted from the amino terminus of the full-length polypeptide. Similarly, any number of amino acids, ranging from 1–30, can be deleted from the carboxy terminus of the full-length protein. Furthermore, any combination of the above amino and carboxy terminus deletions are preferred. Similarly, polynucleotides encoding these polypeptide fragments are also preferred.

Also preferred are polypeptide and polynucleotide fragments characterized by structural or functional domains, such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions. Polypeptide fragments of SEQ ID NO:2 falling within conserved domains are specifically contemplated by the present invention. Moreover, polynucleotides encoding these domains are also contemplated.

Other preferred polypeptide fragments are biologically active fragments. Biologically active fragments are those exhibiting activity similar, but not necessarily identical, to an activity of the polypeptide of the present invention. The biological activity of the fragments may include an improved desired activity, or a decreased undesirable activity. Polynucleotides encoding these polypeptide fragments are also encompassed by the invention.

In a preferred embodiment, the functional activity displayed by a polypeptide encoded by a polynucleotide fragment of the invention may be one or more biological activities typically associated with the full-length polypeptide of the invention. Illustrative of these biological activities includes the fragments ability to bind to at least one of the same antibodies which bind to the full-length protein, the fragments ability to interact with at lease one of the same proteins which bind to the full-length, the fragments ability to elicit at least one of the same immune responses as the full-length protein (i.e., to cause the immune system to create antibodies specific to the same epitope, etc.), the fragments ability to bind to at least one of the same polynucleotides as the full-length protein, the fragments ability to bind to a receptor of the full-length protein, the fragments ability to bind to a ligand of the full-length protein, and the fragments ability to multimerize with the full-length protein. However, the skilled artisan would appreciate that some fragments may have biological activities which are desirable and directly inapposite to the biological activity of the full-length protein. The functional activity of polypeptides of the invention, including fragments, variants, derivatives, and analogs thereof can be determined by numerous methods available to the skilled artisan, some of which are described elsewhere herein.

The present invention encompasses polypeptides comprising, or alternatively consisting of, an epitope of the polypeptide having an amino acid sequence of SEQ ID NO:2, or an epitope of the polypeptide sequence encoded by a polynucleotide sequence contained in ATCC deposit No. Z or encoded by a polynucleotide that hybridizes to the complement of the sequence of SEQ ID NO:1 or contained in ATCC deposit No. Z under stringent hybridization conditions or lower stringency hybridization conditions as defined supra. The present invention further encompasses polynucleotide sequences encoding an epitope of a polypeptide sequence of the invention (such as, for example, the sequence disclosed in SEQ ID NO:1), polynucleotide sequences of the complementary strand of a polynucleotide sequence encoding an epitope of the invention, and polynucleotide sequences which hybridize to the complementary strand under stringent hybridization conditions or lower stringency hybridization conditions defined supra.

The term "epitopes," as used herein, refers to portions of a polypeptide having antigenic or immunogenic activity in an animal, preferably a mammal, and most preferably in a human. In a preferred embodiment, the present invention encompasses a polypeptide comprising an epitope, as well as the polynucleotide encoding this polypeptide. An "immunogenic epitope," as used herein, is defined as a portion of a protein that elicits an antibody response in an animal, as determined by any method known in the art, for example, by the methods for generating antibodies described infra. (See, for example, Geysen et al., Proc. Natl. Acad. Sci. USA 81:3998–4002 (1983)). The term "antigenic epitope," as used herein, is defined as a portion of a protein to which an antibody can immunospecifically bind its antigen as determined by any method well known in the art, for example, by the immunoassays described herein. Immunospecific binding excludes non-specific binding but does not necessarily exclude cross-reactivity with other antigens. Antigenic epitopes need not necessarily be immunogenic.

Fragments which function as epitopes may be produced by any conventional means. (See, e.g., Houghten, Proc. Natl. Acad. Sci. USA 82:5131–5135 (1985), further described in U.S. Pat. No. 4,631,211).

In the present invention, antigenic epitopes preferably contain a sequence of at least 4, at least 5, at least 6, at least 7, more preferably at least 8, at least 9, at least 10, at least 11, at least 12, at least 13, at least 14, at least 15, at least 20, at least 25, at least 30, at least 40, at least 50, and, most preferably, between about 15 to about 30 amino acids. Preferred polypeptides comprising immunogenic or antigenic epitopes are at least 10, 15, 20, 25, 30, 35, 40, 45, 50, 55, 60, 65, 70, 75, 80, 85, 90, 95, or 100 amino acid residues in length. Additional non-exclusive preferred antigenic epitopes include the antigenic epitopes disclosed herein, as well as portions thereof. Antigenic epitopes are useful, for example, to raise antibodies, including monoclonal antibodies, that specifically bind the epitope. Preferred antigenic epitopes include the antigenic epitopes disclosed herein, as well as any combination of two, three, four, five or more of these antigenic epitopes. Antigenic epitopes can be used as the target molecules in immunoassays. (See, for instance, Wilson et al., Cell 37:767–778 (1984); Sutcliffe et al., Science 219:660–666 (1983)).

Similarly, immunogenic epitopes can be used, for example, to induce antibodies according to methods well known in the art. (See, for instance, Sutcliffe et al., supra; Wilson et al., supra; Chow et al., Proc. Natl. Acad. Sci. USA 82:910–914; and Bittle et al., J. Gen. Virol. 66:2347–2354 (1985). Preferred immunogenic epitopes include the immunogenic epitopes disclosed herein, as well as any combination of two, three, four, five or more of these immunogenic epitopes. The polypeptides comprising one or more immunogenic epitopes may be presented for eliciting an antibody response together with a carrier protein, such as an albumin, to an animal system (such as rabbit or mouse), or, if the polypeptide is of sufficient length (at least about 25 amino acids), the polypeptide may be presented without a carrier. However, immunogenic epitopes comprising as few as 8 to 10 amino acids have been shown to be sufficient to raise antibodies capable of binding to, at the very least, linear epitopes in a denatured polypeptide (e.g., in Western blotting).

Epitope-bearing polypeptides of the present invention may be used to induce antibodies according to methods well known in the art including, but not limited to, in vivo immunization, in vitro immunization, and phage display methods. See, e.g., Sutcliffe et al., supra; Wilson et al., supra, and Bittle et al., J. Gen. Virol., 66:2347–2354 (1985). If in vivo immunization is used, animals may be immunized with free peptide; however, anti-peptide antibody titer may be boosted by coupling the peptide to a macromolecular carrier, such as keyhole limpet hemacyanin (KLH) or tetanus toxoid. For instance, peptides containing cysteine residues may be coupled to a carrier using a linker such as maleimidobenzoyl-N-hydroxysuccinimide ester (MBS), while other peptides may be coupled to carriers using a more general linking agent such as glutaraldehyde. Animals such as rabbits, rats and mice are immunized with either free or carrier-coupled peptides, for instance, by intraperitoneal and/or intradermal injection of emulsions containing about 100 $\mu$g of peptide or carrier protein and Freund's adjuvant or any other adjuvant known for stimulating an immune response. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

As one of skill in the art will appreciate, and as discussed above, the polypeptides of the present invention comprising an immunogenic or antigenic epitope can be fused to other polypeptide sequences. For example, the polypeptides of the present invention may be fused with the constant domain of immunoglobulins (IgA, IgE, IgG, IgM), or portions thereof (CH1, CH2, CH3, or any combination thereof and portions thereof) resulting in chimeric polypeptides. Such fusion proteins may facilitate purification and may increase half-life in vivo. This has been shown for chimeric proteins consisting of the first two domains of the human CD4-polypeptide and various domains of the constant regions of the heavy or light chains of mammalian immunoglobulins. See, e.g., EP 394,827; Traunecker et al., Nature, 331:84–86 (1988). Enhanced delivery of an antigen across the epithelial barrier to the immune system has been demonstrated for antigens (e.g., insulin) conjugated to an FcRn binding partner such as IgG or Fc fragments (see, e.g., PCT Publications WO 96/22024 and WO 99/04813). IgG Fusion proteins that have a disulfide-linked dimeric structure due to the IgG portion disulfide bonds have also been found to be more efficient in binding and neutralizing other molecules than monomcric polypeptides or fragments thereof alone. See, e.g., Fountoulakis et al., J. Biochem., 270:3958–3964 (1995). Nucleic acids encoding the above epitopes can also be recombined with a gene of interest as an epitope tag (e.g., the hemagglutinin ("HA") tag or flag tag) to aid in detection and purification of the expressed polypeptide. For example, a system described by Janknecht et al. allows for the ready purification of non-denatured fusion proteins expressed in human cell lines (Janknecht et al., 1991, Proc. Natl. Acad. Sci. USA 88:8972–897). In this system, the gene of interest is subcloned into a vaccinia recombination plasmid such that the open reading frame of the gene is translationally fused to an amino-terminal tag consisting of six histidine residues. The tag serves as a matrix binding domain for the fusion protein. Extracts from cells infected with the recombinant vaccinia virus are loaded onto Ni2+ nitriloacetic acid-agarose column and histidine-tagged proteins can be selectively eluted with imidazole-containing buffers.

Additional fusion proteins of the invention may be generated through the techniques of gene-shuffling, motif-shuffling, exon-shuffling, and/or codon-shuffling (collectively referred to as "DNA shuffling"). DNA shuffling may be employed to modulate the activities of polypeptides of the invention, such methods can be used to generate polypeptides with altered activity, as well as agonists and antagonists of the polypeptides. See, generally, U.S. Pat. Nos. 5,605,793; 5,811,238; 5,830,721; 5,834,252; and 5,837,458, and Patten et al., Curr. Opinion Biotechnol. 8:724–33 (1997); Harayama, Trends Biotechnol. 16(2): 76–82 (1998); Hansson, et al., J. Mol. Biol. 287:265–76 (1999); and Lorenzo and Blasco, Biotechniques 24(2): 308–13 (1998) (each of these patents and publications are hereby incorporated by reference in its entirety). In one embodiment, alteration of polynucleotides corresponding to SEQ ID NO:1 and the polypeptides encoded by these polynucleotides may be achieved by DNA shuffling. DNA shuffling involves the assembly of two or more DNA segments by homologous or site-specific recombination to generate variation in the polynucleotide sequence. In another embodiment, polynucleotides of the invention, or the encoded polypeptides, may be altered by being subjected to random mutagenesis by error-prone PCR, random nucleotide insertion or other methods prior to recombination. In another embodiment, one or more components, motifs, sections, parts, domains, fragments, etc., of a polynucleotide encoding a polypeptide of the invention may be recombined with one or more components, motifs, sections, parts, domains, fragments, etc. of one or more heterologous molecules.

Antibodies

Further polypeptides of the invention relate to antibodies and T-cell antigen receptors (TCR) which immunospecifically bind a polypeptide, polypeptide fragment, or variant of SEQ ID NO:Y, and/or an epitope, of the present invention (as determined by immunoassays well known in the art for assaying specific antibody-antigen binding). Antibodies of the invention include, but are not limited to, polyclonal, monoclonal, monovalent, bispecific, heteroconjugate, multispecific, human, humanized or chimeric antibodies, single chain antibodies, Fab fragments, F(ab') fragments, fragments produced by a Fab expression library, anti-idiotypic (anti-Id) antibodies (including, e.g., anti-Id antibodies to antibodies of the invention), and epitope-binding fragments of any of the above. The term "antibody," as used herein, refers to immunoglobulin molecules and immunologically active portions of immunoglobulin molecules, i.e., molecules that contain an antigen binding site that immunospecifically binds an antigen. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule. Moreover, the term "antibody" (Ab) or "monoclonal antibody" (Mab) is meant to include intact molecules, as well as, antibody fragments (such as, for example, Fab and F(ab')2 fragments) which are capable of specifically binding to protein. Fab and F(ab')2 fragments lack the Fc fragment of intact antibody, clear more rapidly from the circulation of the animal or plant, and may have less non-specific tissue binding than an intact antibody (Wahl et al., J. Nucl. Med. 24:316–325 (1983)). Thus, these fragments are preferred, as well as the products of a FAB or other immunoglobulin expression library. Moreover, antibodies of the present invention include chimeric, single chain, and humanized antibodies.

Most preferably the antibodies are human antigen-binding antibody fragments of the present invention and include, but are not limited to, Fab, Fab' and F(ab')2, Fd, single-chain Fvs (scFv), single-chain antibodies, disulfide-linked Fvs (sdFv) and fragments comprising either a VL or VH domain. Antigen-binding antibody fragments, including single-chain antibodies, may comprise the variable region(s) alone or in combination with the entirety or a portion of the following: hinge region, CH1, CH2, and CH3 domains. Also included in the invention are antigen-binding fragments also comprising any combination of variable region(s) with a hinge region, CH1, CH2, and CH3 domains. The antibodies of the invention may be from any animal origin including birds and mammals. Preferably, the antibodies are human, murine (e.g., mouse and rat), donkey, ship rabbit, goat, guinea pig, camel, horse, or chicken. As used herein, "human" antibodies include antibodies having the amino acid sequence of a human immunoglobulin and include antibodies isolated from human immunoglobulin libraries or from animals transgenic for one or more human immunoglobulin and that do not express endogenous immunoglobulins, as described infra and, for example in, U.S. Pat. No. 5,939,598 by Kucherlapati et al.

The antibodies of the present invention may be monospecific, bispecific, trispecific or of greater multispecificity. Multispecific antibodies may be specific for different epitopes of a polypeptide of the present invention or may be specific for both a polypeptide of the present invention as well as for a heterologous epitope, such as a heterologous polypeptide or solid support material. See, e.g., PCT publications WO 93/17715; WO 92/08802; WO 91/00360; WO 92/05793; Tutt, et al., J. Immunol. 147:60–69 (1991); U.S. Pat. Nos. 4,474,893; 4,714,681; 4,925,648; 5,573,920; 5,601,819; Kostelny et al., J. Immunol. 148:1547–1553 (1992).

Antibodies of the present invention may be described or specified in terms of the epitope(s) or portion(s) of a polypeptide of the present invention which they recognize or specifically bind. The epitope(s) or polypeptide portion(s) may be specified as described herein, e.g., by N-terminal and C-terminal positions, by size in contiguous amino acid residues, or listed in the Tables and Figures. Antibodies which specifically bind any epitope or polypeptide of the present invention may also be excluded. Therefore, the present invention includes antibodies that specifically bind polypeptides of the present invention, and allows for the exclusion of the same.

Antibodies of the present invention may also be described or specified in terms of their cross-reactivity. Antibodies that do not bind any other analog, ortholog, or homologue of a polypeptide of the present invention are included. Antibodies that bind polypeptides with at least 95%, at least 90%, at least 85%, at least 80%, at least 75%, at least 70%, at least 65%, at least 60%, at least 55%, and at least 50% identity (as calculated using methods known in the art and described herein) to a polypeptide of the present invention are also included in the present invention. In specific embodiments, antibodies of the present invention cross-react with murine, rat and/or rabbit homologues of human proteins and the corresponding epitopes thereof. Antibodies that do not bind polypeptides with less than 95%, less than 90%, less than 85%, less than 80%, less than 75%, less than 70%, less than 65%, less than 60%, less than 55%, and less than 50% identity (as calculated using methods known in the art and described herein) to a polypeptide of the present invention are also included in the present invention. In a specific embodiment, the above-described cross-reactivity is with respect to any single specific antigenic or immunogenic polypeptide, or combination(s) of 2, 3, 4, 5, or more of the specific antigenic and/or immunogenic polypeptides disclosed herein. Further included in the present invention are antibodies which bind polypeptides encoded by polynucleotides which hybridize to a polynucleotide of the present invention under stringent hybridization conditions (as described herein). Antibodies of the present invention may also be described or specified in terms of their binding affinity to a polypeptide of the invention. Preferred binding affinities include those with a dissociation constant or Kd less than 5×10−2 M, 10−2 M, 5×10−3 M, 10−3 M, 5×10−4 M, 10−4 M, 5×10−5 M, 5×10−6 M, 10−6M, 5×10−7 M, 107 M, 5×10−8 M, 10−8 M, 5×10−9 M, 10−9 M, 5×10−10 M, 10−10 M, 5×10−11 M, 10−11 M, 5×10−12 M, 10−12 M, 5×10−13 M, 10−13 M, 5×10−14 M, 10−14 M, 5×10−15 M, or 10−15 M.

The invention also provides antibodies that competitively inhibit binding of an antibody to an epitope of the invention as determined by any method known in the art for determining competitive binding, for example, the immunoassays described herein. In preferred embodiments, the antibody competitively inhibits binding to the epitope by at least 95%, at least 90%, at least 85%, at least 80%, at least 75%, at least 70%, at least 60%, or at least 50%.

Antibodies of the present invention may act as agonists or antagonists of the polypeptides of the present invention. For example, the present invention includes antibodies which disrupt the receptor/ligand interactions with the polypeptides of the invention either partially or fully. Preferably, antibodies of the present invention bind an antigenic epitope disclosed herein, or a portion thereof. The invention features both receptor-specific antibodies and ligand-specific antibodies. The invention also features receptor-specific antibodies which do not prevent ligand binding but prevent receptor activation. Receptor activation (i.e., signaling) may be determined by techniques described herein or otherwise known in the art. For example, receptor activation can be determined by detecting the phosphorylation (e.g., tyrosine or serine/threonine) of the receptor or its substrate by immunoprecipitation followed by western blot analysis (for example, as described supra). In specific embodiments, antibodies are provided that inhibit ligand activity or receptor activity by at least 95%, at least 90%, at least 85%, at least 80%, at least 75%, at least 70%, at least 60%, or at least 50% of the activity in absence of the antibody.

The invention also features receptor-specific antibodies which both prevent ligand binding and receptor activation as well as antibodies that recognize the receptor-ligand complex, and, preferably, do not specifically recognize the unbound receptor or the unbound ligand. Likewise, included in the invention are neutralizing antibodies which bind the ligand and prevent binding of the ligand to the receptor, as well as antibodies which bind the ligand, thereby preventing receptor activation, but do not prevent the ligand from binding the receptor. Further included in the invention are antibodies which activate the receptor. These antibodies may act as receptor agonists, i.e., potentiate or activate either all or a subset of the biological activities of the ligand-mediated receptor activation, for example, by inducing dimerization of the receptor. The antibodies may be specified as agonists, antagonists or inverse agonists for biological activities comprising the specific biological activities of the peptides of the invention disclosed herein. The above antibody agonists can be made using methods known in the art. See, e.g., PCT publication WO 96/40281; U.S. Pat. No. 5,811,097; Deng et al., Blood 92(6):1981–1988 (1998); Chen et al., Cancer Res. 58(16):3668–3678 (1998); Harrop et al., J. Immunol. 161 (4): 1786–1794 (1998); Zhu et al., Cancer Res. 58(15): 3209–3214 (1998); Yoon et al., J. Immunol. 160(7): 3170–3179 (1998); Prat et al., J. Cell. Sci. 111(Pt2): 237–247 (1998); Pitard et al., J. Immunol. Methods 205(2): 177–190 (1997); Liautard et al., Cytokine 9(4):233–241 (1997); Carlson et al., J. Biol. Chem. 272(17):11295–11301 (1997); Taryman et al., Neuron 14(4):755–762 (1995); Muller et al., Structure 6(9):1153–1167 (1998); Bartunck et al., Cytokine 8(1): 14–20 (1996) (which are all incorporated by reference herein in their entireties).

Antibodies of the present invention may be used, for example, but not limited to, to purify, detect, and target the polypeptides of the present invention, including both in vitro and in vivo diagnostic and therapeutic methods. For example, the antibodies have use in immunoassays for qualitatively and quantitatively measuring levels of the polypeptides of the present invention in biological samples. See, e.g., Harlow et al., Antibodies: A Laboratory Manual, (Cold Spring Harbor Laboratory Press, 2nd ed. 1988) (incorporated by reference herein in its entirety).

As discussed in more detail below, the antibodies of the present invention may be used either alone or in combination with other compositions. The antibodies may further be recombinantly fused to a heterologous polypeptide at the N- or C-terminus or chemically conjugated (including covalently and non-covalently conjugations) to polypeptides or other compositions. For example, antibodies of the present invention may be recombinantly fused or conjugated to molecules useful as labels in detection assays and effector molecules such as heterologous polypeptides, drugs, radionucleotides, or toxins. See, e.g., PCT publications WO 92/08495; WO 91/14438; WO 89/12624; U.S. Pat. No. 5,314,995; and EP 396,387.

The antibodies of the invention include derivatives that are modified, i.e., by the covalent attachment of any type of molecule to the antibody such that covalent attachment does not prevent the antibody from generating an anti-idiotypic response. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

The antibodies of the present invention may be generated by any suitable method known in the art.

The antibodies of the present invention may comprise polyclonal antibodies. Methods of preparing polyclonal antibodies are known to the skilled artisan (Harlow, et al., Antibodies: A Laboratory Manual, (Cold spring Harbor Laboratory Press, $2^{nd}$ ed. (1988); and Current Protocols, Chapter 2; which are hereby incorporated herein by reference in its entirety). In a preferred method, a preparation of the HLRRBM1 protein is prepared and purified to render it substantially free of natural contaminants. Such a preparation is then introduced into an animal in order to produce polyclonal antisera of greater specific activity. For example, a polypeptide of the invention can be administered to various host animals including, but not limited to, rabbits, mice, rats, etc. to induce the production of sera containing polyclonal antibodies specific for the antigen. The administration of the polypeptides of the present invention may entail one or more injections of an immunizing agent and, if desired, an adjuvant. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and corynebacterium parvum. Such adjuvants are also well known in the art. For the purposes of the invention, "immunizing agent" may be defined as a polypeptide of the invention, including fragments, variants, and/or derivatives thereof, in addition to fusions with heterologous polypeptides and other forms of the polypeptides described herein.

Typically, the immunizing agent and/or adjuvant will be injected in the mammal by multiple subcutaneous or intraperitoneal injections, though they may also be given intramuscularly, and/or through IV). The immunizing agent may include polypeptides of the present invention or a fusion protein or variants thereof. Depending upon the nature of the polypeptides (i.e., percent hydrophobicity, percent hydrophilicity, stability, net charge, isoelectric point etc.), it may be useful to conjugate the immunizing agent to a protein known to be immunogenic in the mammal being immunized. Such conjugation includes either chemical conjugation by derivitizing active chemical functional groups to both the polypeptide of the present invention and the immunogenic protein such that a covalent bond is formed, or through fusion-protein based methodology, or other methods known to the skilled artisan. Examples of such immunogenic proteins include, but are not limited to keyhole limpet hemocyanin, serum albumin, bovine thyroglobulin, and soybean trypsin inhibitor. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and Corynebacterium parvum. Additional examples of adjuvants which may be employed includes the MPL-TDM adjuvant (monophosphoryl lipid A, synthetic trehalose dicorynomycolate). The immunization protocol may be selected by one skilled in the art without undue experimentation.

The antibodies of the present invention may comprise monoclonal antibodies. Monoclonal antibodies may be prepared using hybridoma methods, such as those described by Kohler and Milstein, Nature, 256:495 (1975) and U.S. Pat. No. 4,376,110, by Harlow, et al., Antibodies: A Laboratory Manual, (Cold spring Harbor Laboratory Press, 2$^{nd}$ ed. (1988), by Hammerling, et al., Monoclonal Antibodies and T-Cell Hybridomas (Elsevier, N.Y., pp. 563–681 (1981); Köhler et al., Eur. J. Immunol. 6:511 (1976); Köhler et al., Eur. J. Immunol. 6:292 (1976), or other methods known to the artisan. Other examples of methods which may be employed for producing monoclonal antibodies includes, but are not limited to, the human B-cell hybridoma technique (Kosbor et al., 1983, Immunology Today 4:72; Cole et al., 1983, Proc. Natl. Acad. Sci. USA 80:2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In a hybridoma method, a mouse, a humanized mouse, a mouse with a human immune system, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include polypeptides of the present invention or a fusion protein thereof. Preferably, the immunizing agent consists of an HLRRBM1 polypeptide or, more preferably, with a HLRRBM1 polypeptide-expressing cell. Such cells may be cultured in any suitable tissue culture medium; however, it is preferable to culture cells in Earle's modified Eagle's medium supplemented with 10% fetal bovine serum (inactivated at about 56 degrees C.), and supplemented with about 10 g/l of nonessential amino acids, about 1,000 U/ml of penicillin, and about 100 ug/ml of streptomycin. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, Monoclonal Antibodies: Principles and Practice, Academic Press, (1986), pp. 59–103). Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. More preferred are the parent myeloma cell line (SP2O) as provided by the ATCC. As inferred throughout the specification, human myeloma and mouse-human heteromyeloma cell lines also have been described for the production of human monoclonal antibodies (Kozbor, J. Immunol., 133:3001 (1984); Brodeur et al., Monoclonal Antibody Production Techniques and Applications, Marcel Dekker, Inc., New York, (1987) pp. 51–63).

The culture medium in which the hybridoma cells are cultured can then be assayed for the presence of monoclonal antibodies directed against the polypeptides of the present invention. Preferably, the binding specificity of monoclonal antibodies produced by the hybridoma cells is determined by immunoprecipitation or by an in vitro binding assay, such as radioimmunoassay (RIA) or enzyme-linked immunoabsorbant assay (ELISA). Such techniques are known in the art and within the skill of the artisan. The binding affinity of the monoclonal antibody can, for example, be determined by the Scatchard analysis of Munson and Pollart, Anal. Biochem., 107:220 (1980).

After the desired hybridoma cells are identified, the clones may be subcloned by limiting dilution procedures and grown by standard methods (Goding, supra, and/or according to Wands et al. (Gastroenterology 80:225–232 (1981)). Suitable culture media for this purpose include, for example, Dulbecco's Modified Eagle's Medium and RPMI-1640. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-sepharose, hydroxyapatite chromatography, gel exclusion chromatography, gel electrophoresis, dialysis, or affinity chromatography.

The skilled artisan would acknowledge that a variety of methods exist in the art for the production of monoclonal antibodies and thus, the invention is not limited to their sole production in hydridomas. For example, the monoclonal antibodies may be made by recombinant DNA methods, such as those described in U.S. Pat. No. 4,816,567. In this context, the term "monoclonal antibody" refers to an antibody derived from a single eukaryotic, phage, or prokaryotic clone. The DNA encoding the monoclonal antibodies of the invention can be readily isolated and sequenced using conventional procedures (e.g., by using oligonucleotide probes that are capable of binding specifically to genes encoding the heavy and light chains of murine antibodies, or such chains from human, humanized, or other sources). The hydridoma cells of the invention serve as a preferred source of such DNA. Once isolated, the DNA may be placed into expression vectors, which are then transformed into host cells such as Simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences (U.S. Pat. No. 4,816,567; Morrison et al, supra) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art. Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563–681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art and are discussed in detail in the Examples described herein. In a non-limiting example, mice can be immunized with a polypeptide of the invention or a cell expressing such peptide. Once an immune response is detected, e.g., antibodies specific for the antigen are detected in the mouse serum, the mouse spleen is harvested and splenocytes isolated. The splenocytes are then fused by well known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

Accordingly, the present invention provides methods of generating monoclonal antibodies as well as antibodies produced by the method comprising culturing a hybridoma cell secreting an antibody of the invention wherein, preferably, the hybridoma is generated by fusing splenocytes isolated from a mouse immunized with an antigen of the invention with myeloma cells and then screening the hybridomas resulting from the fusion for hybridoma clones that secrete an antibody able to bind a polypeptide of the invention.

Antibody fragments which recognize specific epitopes may be generated by known techniques. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain.

For example, the antibodies of the present invention can also be generated using various phage display methods known in the art. In phage display methods, functional antibody domains are displayed on the surface of phage particles which carry the polynucleotide sequences encoding them. In a particular embodiment, such phage can be utilized to display antigen binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include those disclosed in Brinkman et al., J. Immunol. Methods 182:41–50 (1995); Ames et al., J. Immunol. Methods 184:177–186 (1995); Kettleborough et al., Eur. J. Immunol. 24:952–958 (1994); Persic et al., Gene 187 9–18 (1997); Burton et al., Advances in Immunology 57:191–280 (1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')2 fragments can also be employed using methods known in the art such as those disclosed in PCT publication WO 92/22324; Mullinax et al., BioTechniques 12(6):864–869 (1992); and Sawai et al., AJRI 34:26–34 (1995); and Better et al., Science 240:1041–1043 (1988) (said references incorporated by reference in their entireties). Examples of techniques which can be used to produce single-chain Fvs and antibodies include those described in U.S. Pat. Nos. 4,946,778 and 5,258,498; Huston et al., Methods in Enzymology 203:46–88 (1991); Shu et al., PNAS 90:7995–7999 (1993); and Skerra et al., Science 240:1038–1040 (1988).

For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See e.g., Morrison, Science 229:1202 (1985); Oi et al., BioTechniques 4:214 (1986); Gillies et al., (1989) J. Immunol. Methods 125:191–202; Cabilly et al., Taniguchi et al., EP 171496; Morrison et al., EP 173494; Neuberger et al., WO 8601533; Robinson et al., WO 8702671; Boulianne et al., Nature 312:643 (1984); Neuberger et al., Nature 314:268 (1985); U.S. Pat. Nos. 5,807,715; 4,816,567; and 4,816397, which are incorporated herein by reference in their entirety. Humanized antibodies are antibody molecules from non-human species antibody that binds the desired antigen having one or more complementarity determining regions (CDRs) from the non-human species and a framework regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., Nature 332:323 (1988), which are incorporated herein by reference in their entireties.) Antibodies can be humanized using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592,106; EP 519,596; Padlan, Molecular Immunology 28(4/5):489–498 (1991); Studnicka et al., Protein Engineering 7(6):805–814 (1994); Roguska. et al., PNAS 91:969–973 (1994)), and chain shuffling (U.S. Pat. No. 5,565,332). Generally, a humanized antibody has one or more amino acid residues introduced into it from a source that is non-human. These non-human amino acid residues are often referred to as "import" residues, which are typically taken from an "import" variable domain. Humanization can be essentially performed following the methods of Winter and co-workers (Jones et al., Nature, 321:522–525 (1986); Reichmann et al., Nature, 332:323–327 (1988); Verhoeyen et al., Science, 239:1534–1536 (1988), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possible some FR residues are substituted from analogous sites in rodent antibodies.

In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin (Jones et al., Nature, 321:522–525 (1986); Riechmann et al., Nature 332:323–329 (1988)l and Presta, Curr. Op. Struct. Biol., 2:593–596 (1992).

Completely human antibodies are particularly desirable for therapeutic treatment of human patients. Human antibodies can be made by a variety of methods known in the art including phage display methods described above using antibody libraries derived from human immunoglobulin sequences. See also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety. The techniques of cole et al., and Boerder et al., are also available for the preparation of human monoclonal antibodies (cole et al., Monoclonal Antibodies and Cancer Therapy, Alan R. Riss, (1985); and Boerner et al., J. Immunol., 147(1):86–95, (1991)).

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar, Int. Rev. Immunol. 13:65–93 (1995). For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,885,793; 5,916,771; and 5,939,598, which are incorporated by reference herein in their entirety. In addition, companies such as Abgenix, Inc. (Freemont, Calif.), Genpharm (San Jose, Calif.), and Medarex, Inc. (Princeton, N.J.) can be engaged to provide human antibodies directed against a selected antigen using technology similar to that described above.

Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and creation of an antibody repertoire. This approach is described, for example, in U.S. Pat. Nos. 5,545,807; 5,545,806; 5,569,825; 5,625,126; 5,633,425; 5,661,106, and in the following scientific publications: Marks et al., Biotechnol., 10:779–783 (1992); Lonberg et al., Nature 368:856–859 (1994); Fishwild et al., Nature Biotechnol., 14:845–51 (1996); Neuberger, Nature Biotechnol., 14:826 (1996); Lonberg and Huszer, Intern. Rev. Immunol., 13:65–93 (1995).

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., Bio/technology 12:899–903 (1988)).

Further, antibodies to the polypeptides of the invention can, in turn, be utilized to generate anti-idiotype antibodies that "mimic" polypeptides of the invention using techniques well known to those skilled in the art. (See, e.g., Greenspan & Bona, FASEB J. 7(5):437–444; (1989) and Nissinoff, J. Immunol. 147(8):2429–2438 (1991)). For example, antibodies which bind to and competitively inhibit polypeptide multimerization and/or binding of a polypeptide of the invention to a ligand can be used to generate anti-idiotypes that "mimic" the polypeptide multimerization and/or binding domain and, as a consequence, bind to and neutralize polypeptide and/or its ligand. Such neutralizing anti-idiotypes or Fab fragments of such anti-idiotypes can be used in therapeutic regimens to neutralize polypeptide ligand. For example, such anti-idiotypic antibodies can be used to bind a polypeptide of the invention and/or to bind its ligands/receptors, and thereby block its biological activity.

Such anti-idiotypic antibodies capable of binding to the HLRRBM1 polypeptide can be produced in a two-step procedure. Such a method makes use of the fact that antibodies are themselves antigens, and therefore, it is possible to obtain an antibody that binds to a second antibody. In accordance with this method, protein specific antibodies are used to immunize an animal, preferably a mouse. The splenocytes of such an animal are then used to produce hybridoma cells, and the hybridoma cells are screened to identify clones that produce an antibody whose ability to bind to the protein-specific antibody can be blocked by the polypeptide. Such antibodies comprise anti-idiotypic antibodies to the protein-specific antibody and can be used to immunize an animal to induce formation of further protein-specific antibodies.

The antibodies of the present invention may be bispecific antibodies. Bispecific antibodies are monoclonal, Preferably human or humanized, antibodies that have binding specificities for at least two different antigens. In the present invention, one of the binding specificities may be directed towards a polypeptide of the present invention, the other may be for any other antigen, and preferably for a cell-surface protein, receptor, receptor subunit, tissue-specific antigen, virally derived protein, virally encoded envelope protein, bacterially derived protein, or bacterial surface protein, etc.

Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello, Nature, 305:537–539 (1983). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., EMBO J., 10:3655–3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transformed into a suitable host organism. For further details of generating bispecific antibodies see, for example Suresh et al., Meth. In Enzym., 121:210 (1986).

Heteroconjugate antibodies are also contemplated by the present invention. Heteroconjugate antibodies are composed of two covalently joined antibodies. Such antibodies have, for example, been proposed to target immune system cells to unwanted cells (U.S. Pat. No. 4,676,980), and for the treatment of HIV infection (WO 91/00360; WO 92/20373; and EP03089). It is contemplated that the antibodies may be prepared in vitro using known methods in synthetic protein chemistry, including those involving crosslinking agents. For example, immunotoxins may be constructed using a disulfide exchange reaction or by forming a thioester bond.

Examples of suitable reagents for this purpose include iminothiolate and methyl-4-mercaptobutyrimidate and those disclosed, for example, in U.S. Pat. No. 4,676,980.

Polynucleotides Encoding Antibodies

The invention further provides polynucleotides comprising a nucleotide sequence encoding an antibody of the invention and fragments thereof. The invention also encompasses polynucleotides that hybridize under stringent or lower stringency hybridization conditions, e.g., as defined supra, to polynucleotides that encode an antibody, preferably, that specifically binds to a polypeptide of the invention, preferably, an antibody that binds to a polypeptide having the amino acid sequence of SEQ ID NO:Y.

The polynucleotides may be obtained, and the nucleotide sequence of the polynucleotides determined, by any method known in the art. For example, if the nucleotide sequence of the antibody is known, a polynucleotide encoding the antibody may be assembled from chemically synthesized oligonucleotides (e.g., as described in Kutmeier et al., BioTechniques 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody may be generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library, or a cDNA library generated from, or nucleic acid, preferably poly A+ RNA, isolated from, any tissue or cells expressing the antibody, such as hybridoma cells selected to express an antibody of the invention) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence and corresponding amino acid sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties ), to generate antibodies having a different amino acid sequence, for example to create amino acid substitutions, deletions, and/or insertions.

In a specific embodiment, the amino acid sequence of the heavy and/or light chain variable domains may be inspected to identify the sequences of the complementarity determining regions (CDRs) by methods that are well know in the art, e.g., by comparison to known amino acid sequences of other heavy and light chain variable regions to determine the regions of sequence hypervariability. Using routine recombinant DNA techniques, one or more of the CDRs may be inserted within framework regions, e.g., into human framework regions to humanize a non-human antibody, as described supra. The framework regions may be naturally occurring or consensus framework regions, and preferably human framework regions (see, e.g., Chothia et al., J. Mol. Biol. 278: 457–479 (1998) for a listing of human framework regions). Preferably, the polynucleotide generated by the combination of the framework regions and CDRs encodes an antibody that specifically binds a polypeptide of the invention. Preferably, as discussed supra, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

In addition, techniques developed for the production of "chimeric antibodies" (Morrison et al., Proc. Natl. Acad. Sci. 81:851–855 (1984); Neuberger et al., Nature 312:604–608 (1984); Takeda et al., Nature 314:452–454 (1985)) by splicing genes from a mouse antibody molecule of appropriate antigen specificity together with genes from a human antibody molecule of appropriate biological activity can be used. As described supra, a chimeric antibody is a molecule in which different portions are derived from different animal species, such as those having a variable region derived from a murine mAb and a human immunoglobulin constant region, e.g., humanized antibodies.

Alternatively, techniques described for the production of single chain antibodies (U.S. Pat. No. 4,946,778; Bird, Science 242:423–42 (1988); Huston et al., Proc. Natl. Acad. Sci. USA 85:5879–5883 (1988); and Ward et al., Nature 334:544–54 (1989)) can be adapted to produce single chain antibodies. Single chain antibodies are formed by linking the heavy and light chain fragments of the Fv region via an amino acid bridge, resulting in a single chain polypeptide. Techniques for the assembly of functional Fv fragments in *E. coli* may also be used (Skerra et al., Science 242:1038–1041 (1988)).

More preferably, a clone encoding an antibody of the present invention may be obtained according to the method described in the Example section herein.

Methods of Producing Antibodies

The antibodies of the invention can be produced by any method known in the art for the synthesis of antibodies, in particular, by chemical synthesis or preferably, by recombinant expression techniques.

Recombinant expression of an antibody of the invention, or fragment, derivative or analog thereof, (e.g., a heavy or light chain of an antibody of the invention or a single chain antibody of the invention), requires construction of an expression vector containing a polynucleotide that encodes the antibody. Once a polynucleotide encoding an antibody molecule or a heavy or light chain of an antibody, or portion thereof (preferably containing the heavy or light chain variable domain), of the invention has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464) and the variable domain of the antibody may be cloned into such a vector for expression of the entire heavy or light chain.

The expression vector is transferred to a host cell by conventional techniques and the transfected cells are then cultured by conventional techniques to produce an antibody of the invention. Thus, the invention includes host cells containing a polynucleotide encoding an antibody of the invention, or a heavy or light chain thereof, or a single chain antibody of the invention, operably linked to a heterologous promoter. In preferred embodiments for the expression of double-chained antibodies, vectors encoding both the heavy and light chains may be co-expressed in the host cell for expression of the entire immunoglobulin molecule, as detailed below.

A variety of host-expression vector systems may be utilized to express the antibody molecules of the invention. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., Saccharomyces, Pichia) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., Gene 45:101 (1986); Cockett et al., Bio/Technology 8:2 (1990)).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited, to the *E. coli* expression vector pUR278 (Ruther et al., EMBO J. 2:1791 (1983)), in which the antibody coding sequence may be ligated individually into the vector in frame with the lac Z coding region so that a fusion protein is produced; pIN vectors (Inouye & Inouye, Nucleic Acids Res. 13:3101–3109 (1985); Van Heeke & Schuster, J. Biol. Chem. 24:5503–5509 (1989)); and the like. pGEX vectors may also be used to express foreign polypeptides as fusion proteins with glutathione S-transferase (GST). In general, such fusion proteins are soluble and can easily be purified from lysed cells by adsorption and binding to matrix glutathione-agarose beads followed by elution in the presence of free glutathione. The pGEX vectors are designed to include thrombin or factor Xa protease cleavage sites so that the cloned target gene product can be released from the GST moiety.

In an insect system, Autographa californica nuclear polyhedrosis virus (AcNPV) is used as a vector to express foreign genes. The virus grows in Spodoptera frugiperda cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts. (e.g., see Logan & Shenk, Proc. Natl. Acad. Sci. USA 81:355–359 (1984)). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., Methods in Enzymol. 153:51–544 (1987)).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, HeLa, COS, MDCK, 293, 3T3, WI38, and in particular, breast cancer cell lines such as, for example, BT483, Hs578T, HTB2, BT20 and T47D, and normal mammary gland cell line such as, for example, CRL7030 and Hs578Bst.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compounds that interact directly or indirectly with the antibody molecule.

A number of selection systems may be used, including but not limited to the herpes simplex virus thymidine kinase (Wigler et al., Cell 11:223 (1977)), hypoxanthine-guanine phosphoribosyltransferase (Szybalska & Szybalski, Proc. Natl. Acad. Sci. USA 48:202 (1992)), and adenine phosphoribosyltransferase (Lowy et al., Cell 22:817 (1980)) genes can be employed in tk-, hgprt- or aprt-cells, respectively. Also, antimetabolite resistance can be used as the basis of selection for the following genes: dhfr, which confers resistance to methotrexate (Wigler et al., Natl. Acad. Sci. USA 77:357 (1980); O'Hare et al., Proc. Natl. Acad. Sci. USA 78:1527 (1981)); gpt, which confers resistance to mycophenolic acid (Mulligan & Berg, Proc. Natl. Acad. Sci. USA 78:2072 (1981)); neo, which confers resistance to the aminoglycoside G-418 Clinical Pharmacy 12:488–505; Wu and Wu, Biotherapy 3:87–95 (1991); Tolstoshev, Ann. Rev. Pharmacol. Toxicol. 32:573–596 (1993); Mulligan, Science 260:926–932 (1993); and Morgan and Anderson, Ann. Rev. Biochem. 62:191–217 (1993); May, 1993, TIB TECH 11(5): 155–215); and hygro, which confers resistance to hygromycin (Santerre et al., Gene 30:147 (1984)). Methods commonly known in the art of recombinant DNA technology may be routinely applied to select the desired recombinant clone, and such methods are described, for example, in Ausubel et al. (eds.), Current Protocols in Molecular Biology, John Wiley & Sons, NY (1993); Kriegler, Gene Transfer and Expression, A Laboratory Manual, Stockton Press, NY (1990); and in Chapters 12 and 13, Dracopoli et al. (eds), Current Protocols in Human Genetics, John Wiley & Sons, NY (1994); Colberre-Garapin et al., J. Mol. Biol. 150:1 (1981), which are incorporated by reference herein in their entireties.

The expression levels of an antibody molecule can be increased by vector amplification (for a review, see Bebbington and Hentschel, The use of vectors based on gene amplification for the expression of cloned genes in mammalian cells in DNA cloning, Vol.3. (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., Mol. Cell. Biol. 3:257 (1983)).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain should be placed before the heavy chain to avoid an excess of toxic free heavy chain (Proudfoot, Nature 322:52 (1986); Kohler, Proc. Natl. Acad. Sci. USA 77:2197 (1980)). The coding sequences for the heavy and light chains may comprise cDNA or genomic DNA.

Once an antibody molecule of the invention has been produced by an animal, chemically synthesized, or recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. In addition the antibodies of the present invention or fragments thereof can be fused to heterologous polypeptide sequences described herein or otherwise known in the art, to facilitate purification.

The present invention encompasses antibodies recombinantly fused or chemically conjugated (including both covalently and non-covalently conjugations) to a polypeptide (or portion thereof, preferably at least 10, 20, 30, 40, 50, 60, 70, 80, 90 or 100 amino acids of the polypeptide) of the present invention to generate fusion proteins. The fusion does not necessarily need to be direct, but may occur through linker sequences. The antibodies may be specific for antigens other than polypeptides (or portion thereof, preferably at least 10, 20, 30, 40, 50, 60, 70, 80, 90 or 100 amino acids of the polypeptide) of the present invention. For example, antibodies may be used to target the polypeptides of the present invention to particular cell types, either in vitro or in vivo, by fusing or conjugating the polypeptides of the present invention to antibodies specific for particular cell surface receptors. Antibodies fused or conjugated to the polypeptides of the present invention may also be used in in vitro immunoassays and purification methods using methods known in the art. See e.g., Harbor et al., supra, and PCT publication WO 93/21232; EP 439,095; Naramura et al., Immunol. Lett. 39:91–99 (1994); U.S. Pat. No. 5,474,981; Gillies et al., PNAS 89:1428–1432 (1992); Fell et al., J. Immunol. 146:2446–2452(1991), which are incorporated by reference in their entireties.

The present invention further includes compositions comprising the polypeptides of the present invention fused or conjugated to antibody domains other than the variable regions. For example, the polypeptides of the present invention may be fused or conjugated to an antibody Fc region, or portion thereof. The antibody portion fused to a polypeptide of the present invention may comprise the constant region, hinge region, CH1 domain, CH2 domain, and CH3 domain or any combination of whole domains or portions thereof. The polypeptides may also be fused or conjugated to the above antibody portions to form multimers. For example, Fc portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art. See, e.g., U.S. Pat. Nos. 5,336,603; 5,622,929; 5,359,046; 5,349,053; 5,447,851; 5,112,946; EP 307,434; EP 367,166; PCT publications WO 96/04388; WO 91/06570; Ashkenazi et al., Proc. Natl. Acad. Sci. USA 88:10535–10539 (1991); Zheng et al., J. Immunol. 154:5590–5600 (1995); and Vil et al., Proc. Natl. Acad. Sci. USA 89:11337–11341(1992) (said references incorporated by reference in their entireties).

As discussed, supra, the polypeptides corresponding to a polypeptide, polypeptide fragment, or a variant of SEQ ID NO:Y may be fused or conjugated to the above antibody portions to increase the in vivo half life of the polypeptides or for use in immunoassays using methods known in the art. Further, the polypeptides corresponding to SEQ ID NO:Y may be fused or conjugated to the above antibody portions to facilitate purification. One reported example describes chimeric proteins consisting of the first two domains of the human CD4-polypeptide and various domains of the constant regions of the heavy or light chains of mammalian immunoglobulins. (EP 394,827; Traunecker et al., Nature 331:84–86 (1988). The polypeptides of the present invention fused or conjugated to an antibody having disulfide-linked dimeric structures (due to the IgG) may also be more efficient in binding and neutralizing other molecules, than the monomeric secreted protein or protein fragment alone. (Fountoulakis et al., J. Biochem. 270:3958–3964 (1995)). In many cases, the Fc part in a fusion protein is beneficial in therapy and diagnosis, and thus can result in, for example, improved pharmacokinetic properties. (EP A 232,262). Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, Bennett et al., J. Molecular Recognition 8:52–58 (1995); Johanson et al., J. Biol. Chem. 270:9459–9471 (1995).

Moreover, the antibodies or fragments thereof of the present invention can be fused to marker sequences, such as a peptide to facilitate purification. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821–824 (1989), for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., Cell 37:767 (1984)) and the "flag" tag.

The present invention further encompasses antibodies or fragments thereof conjugated to a diagnostic or therapeutic agent. The antibodies can be used diagnostically to, for example, monitor the development or progression of a tumor as part of a clinical testing procedure to, e.g., determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the antibody (or fragment thereof) or indirectly, through an intermediate (such as, for example, a linker known in the art) using techniques known in the art. See, for example, U.S. Pat. No. 4,741,900 for metal ions which can be conjugated to antibodies for use as diagnostics according to the present invention. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include 125I, 131I, 111In or 99Tc.

Further, an antibody or fragment thereof may be conjugated to a therapeutic moiety such as a cytotoxin, e.g., a cytostatic or cytocidal agent, a therapeutic agent or a radioactive metal ion, e.g., alpha-emitters such as, for example, 213Bi. A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologues thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the therapeutic agent or drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, a-interferon, β-interferon, nerve growth factor, platelet derived growth factor, tissue plasminogen activator, an apoptotic agent, e.g., TNF-alpha, TNF-beta, AIM I (See, International Publication No. WO 97/33899), AIM II (See, International Publication No. WO 97/34911), Fas Ligand (Takahashi et al., Int. Immunol., 6:1567–1574 (1994)), VEGI (See, International Publication No. WO 99/23105), a thrombotic agent or an anti-angiogenic agent, e.g., angiostatin or endostatin; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243–56 (Alan R. Liss, Inc. 1985); Hellstrom et al., "Antibodies For Drug Delivery", in Controlled Drug Delivery (2nd Ed.), Robinson et al. (eds.), pp. 623–53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475–506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303–16 (Academic Press 1985), and Thorpe et al., "The Preparation And Cytotoxic Properties Of Antibody-Toxin Conjugates", Immunol. Rev. 62:119–58 (1982).

Alternatively, an antibody can be conjugated to a second antibody to form an antibody heteroconjugate as described by Segal in U.S. Pat. No. 4,676,980, which is incorporated herein by reference in its entirety.

An antibody, with or without a therapeutic moiety conjugated to it, administered alone or in combination with cytotoxic factor(s) and/or cytokine(s) can be used as a therapeutic.

The present invention also encompasses the creation of synthetic antibodies directed against the polypeptides of the present invention. One example of synthetic antibodies is described in Radrizzani, M., et al., Medicina, (Aires), 59(6): 753–8, (1999)). Recently, a new class of synthetic antibodies has been described and are referred to as molecularly imprinted polymers (MIPs) (Semorex, Inc.). Antibodies, peptides, and enzymes are often used as molecular recognition elements in chemical and biological sensors. However, their lack of stability and signal transduction mechanisms limits their use as sensing devices. Molecularly imprinted polymers (MIPs) are capable of mimicking the function of biological receptors but with less stability constraints. Such polymers provide high sensitivity and selectivity while maintaining excellent thermal and mechanical stability. MIPs have the ability to bind to small molecules and to target molecules such as organics and proteins' with equal or greater potency than that of natural antibodies. These "super" MIPs have higher affinities for their target and thus require lower concentrations for efficacious binding.

During synthesis, the MIPs are imprinted so as to have complementary size, shape, charge and functional groups of the selected target by using the target molecule itself (such as a polypeptide, antibody, etc.), or a substance having a very similar structure, as its "print" or "template." MIPs can be derivatized with the same reagents afforded to antibodies. For example, fluorescent 'super' MIPs can be coated onto beads or wells for use in highly sensitive separations or assays, or for use in high throughput screening of proteins.

Moreover, MIPs based upon the structure of the polypeptide(s) of the present invention may be useful in screening for compounds that bind to the polypeptide(s) of the invention. Such a MIP would serve the role of a synthetic "receptor" by minimicking the native architecture of the polypeptide. In fact, the ability of a MIP to serve the role of a synthetic receptor has already been demonstrated for the estrogen receptor (Ye, L., Yu, Y., Mosbach, K, Analyst., 126(6):760–5, (2001); Dickert, F, L., Hayden, O., Halikias, K, P, Analyst., 126(6):766–71, (2001)). A synthetic receptor may either be mimicked in its entirety (e.g., as the entire protein), or mimicked as a series of short peptides corresponding to the protein (Rachkov, A., Minoura, N, Biochim, Biophys, Acta., 1544(1–2):255–66, (2001)). Such a synthetic receptor MIPs may be employed in any one or more of the screening methods described elsewhere herein.

MIPs have also been shown to be useful in "sensing" the presence of its mimicked molecule (Cheng, Z., Wang, E., Yang, X, Biosens, Bioelectron., 16(3):179–85, (2001); Jenkins, A, L., Yin, R., Jensen, J. L, Analyst., 126(6): 798–802, (2001); Jenkins, A, L., Yin, R., Jensen, J. L, Analyst., 126(6):798–802, (2001)). For example, a MIP designed using a polypeptide of the present invention may be used in assays designed to identify, and potentially quantitate, the level of said polypeptide in a sample. Such a MIP may be used as a substitute for any component described in the assays, or kits, provided herein (e.g., ELISA, etc.).

A number of methods may be employed to create MIPs to a specific receptor, ligand, polypeptide, peptide, organic molecule. Several preferred methods are described by Esteban et al in J. Anal, Chem., 370(7):795–802, (2001), which is hereby incorporated herein by reference in its entirety in addition to any references cited therein. Additional methods are known in the art and are encompassed by the present invention, such as for example, Hart, B, R., Shea, K, J. J. Am. Chem, Soc., 123(9):2072–3, (2001); and Quaglia, M., Chenon, K., Hall, A, J., De, Lorenzi, E., Sellergren, B, J. Am. Chem, Soc., 123(10):2146–54, (2001); which are hereby incorporated by reference in their entirety herein.

Uses for Antibodies Directed Against Polypeptides of the Invention

The antibodies of the present invention have various utilities. For example, such antibodies may be used in diagnostic assays to detect the presence or quantification of the polypeptides of the invention in a sample. Such a diagnostic assay may be comprised of at least two steps. The first, subjecting a sample with the antibody, wherein the sample is a tissue (e.g., human, animal, etc.), biological fluid (e.g., blood, urine, sputum, semen, amniotic fluid, saliva, etc.), biological extract (e.g., tissue or cellular homogenate, etc.), a protein microchip (e.g., See Arenkov P, et al., Anal Biochem., 278(2):123–131 (2000)), or a chromatography column, etc. And a second step involving the quantification of antibody bound to the substrate. Alternatively, the method may additionally involve a first step of attaching the antibody, either covalently, electrostatically, or reversibly, to a solid support, and a second step of subjecting the bound antibody to the sample, as defined above and elsewhere herein.

Various diagnostic assay techniques are known in the art, such as competitive binding assays, direct or indirect sandwich assays and immunoprecipitation assays conducted in either heterogeneous or homogenous phases (Zola, Monoclonal Antibodies: A Manual of Techniques, CRC Press, Inc., (1987), pp 147–158). The antibodies used in the diagnostic assays can be labeled with a detectable moiety. The detectable moiety should be capable of producing, either directly or indirectly, a detectable signal. For example, the detectable moiety may be a radioisotope, such as 2H, 14C, 32P, or 125I, a florescent or chemiluminescent compound, such as fluorescein isothiocyanate, rhodamine, or luciferin, or an enzyme, such as alkaline phosphatase, beta-galactosidase, green fluorescent protein, or horseradish peroxidase. Any method known in the art for conjugating the antibody to the detectable moiety may be employed, including those methods described by Hunter et al., Nature, 144:945 (1962); Dafvid et al., Biochem., 13:1014 (1974); Pain et el., J. Immunol. Metho., 40:219(1981); and Nygren, J. Histochem. And Cytochem., 30:407 (1982).

Antibodies directed against the polypeptides of the present invention are useful for the affinity purification of such polypeptides from recombinant cell culture or natural sources. In this process, the antibodies against a particular polypeptide are immobilized on a suitable support, such as a Sephadex resin or filter paper, using methods well known in the art. The immobilized antibody then is contacted with a sample containing the polypeptides to be purified, and thereafter the support is washed with a suitable solvent that will remove substantially all the material in the sample except for the desired polypeptides, which are bound to the immobilized antibody. Finally, the support is washed with another suitable solvent that will release the desired polypeptide from the antibody.

Immunophenotyping

The antibodies of the invention may be utilized for immunophenotyping of cell lines and biological samples. The translation product of the gene of the present invention may be useful as a cell specific marker, or more specifically as a cellular marker that is differentially expressed at various stages of differentiation and/or maturation of particular cell types. Monoclonal antibodies directed against a specific epitope, or combination of epitopes, will allow for the screening of cellular populations expressing the marker. Various techniques can be utilized using monoclonal antibodies to screen for cellular populations expressing the marker(s), and include magnetic separation using antibody-coated magnetic beads, "panning" with antibody attached to a solid matrix (i.e., plate), and flow cytometry (See, e.g., U.S. Pat. No. 5,985,660; and Morrison et al., Cell, 96:737–49 (1999)).

These techniques allow for the screening of particular populations of cells, such as might be found with hematological malignancies (i.e. minimal residual disease (MRD) in acute leukemic patients) and "non-self" cells in transplantations to prevent Graft-versus-Host Disease (GVHD). Alternatively, these techniques allow for the screening of hematopoietic stem and progenitor cells capable of undergoing proliferation and/or differentiation, as might be found in human umbilical cord blood.

Assays for Antibody Binding

The antibodies of the invention may be assayed for immunospecific binding by any method known in the art. The immunoassays which can be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1–4 hours) at 4° C., adding protein A and/or protein G sepharose beads to the cell lysate, incubating for about an hour or more at 4° C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al, eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%–20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., 32P or 125I) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al, eds, 1994, Current Protocols in Molecular Biology, Vol. 1, John Wiley & Sons, Inc., New York at 10.8.1.

ELISAs comprise preparing antigen, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al, eds, 1994, Current Protocols in Molecular Biology, Vol. 1, John Wiley & Sons, Inc., New York at 11.2.1.

The binding affinity of an antibody to an antigen and the off-rate of an antibody-antigen interaction can be determined by competitive binding assays. One example of a competitive binding assay is a radioimmunoassay comprising the incubation of labeled antigen (e.g., 3H or 125I) with the antibody of interest in the presence of increasing amounts of unlabeled antigen, and the detection of the antibody bound to the labeled antigen. The affinity of the antibody of interest for a particular antigen and the binding off-rates can be determined from the data by scatchard plot analysis. Competition with a second antibody can also be determined using radioimmunoassays. In this case, the antigen is incubated with antibody of interest conjugated to a labeled compound (e.g., 3H or 125I) in the presence of increasing amounts of an unlabeled second antibody.

Therapeutic Uses of Antibodies

The present invention is further directed to antibody-based therapies which involve administering antibodies of the invention to an animal, preferably a mammal, and most preferably a human, patient for treating one or more of the disclosed diseases, disorders, or conditions. Therapeutic compounds of the invention include, but are not limited to, antibodies of the invention (including fragments, analogs and derivatives thereof as described herein) and nucleic acids encoding antibodies of the invention (including fragments, analogs and derivatives thereof and anti-idiotypic antibodies as described herein). The antibodies of the invention can be used to treat, inhibit or prevent diseases, disorders or conditions associated with aberrant expression and/or activity of a polypeptide of the invention, including, but not limited to, any one or more of the diseases, disorders, or conditions described herein. The treatment and/or prevention of diseases, disorders, or conditions associated with aberrant expression and/or activity of a polypeptide of the invention includes, but is not limited to, alleviating symptoms associated with those diseases, disorders or conditions. Antibodies of the invention may be provided in pharmaceutically acceptable compositions as known in the art or as described herein.

A summary of the ways in which the antibodies of the present invention may be used therapeutically includes binding polynucleotides or polypeptides of the present invention locally or systemically in the body or by direct cytotoxicity of the antibody, e.g. as mediated by complement (CDC) or by effector cells (ADCC). Some of these approaches are described in more detail below. Armed with the teachings provided herein, one of ordinary skill in the art will know how to use the antibodies of the present invention for diagnostic, monitoring or therapeutic purposes without undue experimentation.

The antibodies of this invention may be advantageously utilized in combination with other monoclonal or chimeric antibodies, or with lymphokines or hematopoietic growth factors (such as, e.g., IL-2, IL-3 and IL-7), for example, which serve to increase the number or activity of effector cells which interact with the antibodies.

The antibodies of the invention may be administered alone or in combination with other types of treatments (e.g., radiation therapy, chemotherapy, hormonal therapy, immunotherapy and anti-tumor agents). Generally, administration of products of a species origin or species reactivity (in the case of antibodies) that is the same species as that of the patient is preferred. Thus, in a preferred embodiment, human antibodies, fragments derivatives, analogs, or nucleic acids, are administered to a human patient for therapy or prophylaxis.

It is preferred to use high affinity and/or potent in vivo inhibiting and/or neutralizing antibodies against polypeptides or polynucleotides of the present invention, fragments or regions thereof, for both immunoassays directed to and therapy of disorders related to polynucleotides or polypeptides, including fragments thereof, of the present invention. Such antibodies, fragments, or regions, will preferably have an affinity for polynucleotides or polypeptides of the invention, including fragments thereof. Preferred binding affinities include those with a dissociation constant or Kd less than 5×10−2 M, 10−2 M, 5×10−3 M, 10−3 M, 5×10−4 M, 10−4 M, 5×10−5 M, 10−5 M, 5×10−6 M, 10−6 M, 5×10−7 M, 10−7 M, 5×10−8 M, 10−8 M, 5×10−9 M, 10−9 M, 5×10−10 M, 10−10 M, 5×10−11 M, 10−11 M, 5×10−12 M, 10−12 M, 5×10−13 M, 10−13 M, 5×10−14 M, 10−14 M, 5×10−15 M, and 10−15 M.

Antibodies directed against polypeptides of the present invention are useful for inhibiting allergic reactions in animals. For example, by administering a therapeutically acceptable dose of an antibody, or antibodies, of the present invention, or a cocktail of the present antibodies, or in combination with other antibodies of varying sources, the animal may not elicit an allergic response to antigens.

Likewise, one could envision cloning the gene encoding an antibody directed against a polypeptide of the present invention, said polypeptide having the potential to elicit an allergic and/or immune response in an organism, and transforming the organism with said antibody gene such that it is expressed (e.g., constitutively, inducibly, etc.) in the organism. Thus, the organism would effectively become resistant to an allergic response resulting from the ingestion or presence of such an immune/allergic reactive polypeptide. Moreover, such a use of the antibodies of the present invention may have particular utility in preventing and/or ameliorating autoimmune diseases and/or disorders, as such conditions are typically a result of antibodies being directed against endogenous proteins. For example, in the instance where the polypeptide of the present invention is responsible for modulating the immune response to auto-antigens, transforming the organism and/or individual with a construct comprising any of the promoters disclosed herein or otherwise known in the art, in addition, to a polynucleotide encoding the antibody directed against the polypeptide of the present invention could effective inhibit the organisms immune system from eliciting an immune response to the auto-antigen(s). Detailed descriptions of therapeutic and/or gene therapy applications of the present invention are provided elsewhere herein.

Alternatively, antibodies of the present invention could be produced in a plant (e.g., cloning the gene of the antibody directed against a polypeptide of the present invention, and transforming a plant with a suitable vector comprising said gene for constitutive expression of the antibody within the plant), and the plant subsequently ingested by an animal, thereby conferring temporary immunity to the animal for the specific antigen the antibody is directed towards (See, for example, U.S. Pat. Nos. 5,914,123 and 6,034,298).

In another embodiment, antibodies of the present invention, preferably polyclonal antibodies, more preferably monoclonal antibodies, and most preferably single-chain antibodies, can be used as a means of inhibiting gene expression of a particular gene, or genes, in a human, mammal, and/or other organism. See, for example, International Publication Number WO 00/05391, published Feb. 3, 2000, to Dow Agrosciences LLC. The application of such methods for the antibodies of the present invention are known in the art, and are more particularly described elsewhere herein.

In yet another embodiment, antibodies of the present invention may be useful for multimerizing the polypeptides of the present invention. For example, certain proteins may confer enhanced biological activity when present in a multimeric state (i.e., such enhanced activity may be due to the increased effective concentration of such proteins whereby more protein is available in a localized location).

Antibody-Based Gene Therapy

In a specific embodiment, nucleic acids comprising sequences encoding antibodies or functional derivatives thereof, are administered to treat, inhibit or prevent a disease or disorder associated with aberrant expression and/or activity of a polypeptide of the invention, by way of gene therapy. Gene therapy refers to therapy performed by the administration to a subject of an expressed or expressible nucleic acid. In this embodiment of the invention, the nucleic acids produce their encoded protein that mediates a therapeutic effect.

Any of the methods for gene therapy available in the art can be used according to the present invention. Exemplary methods are described below.

For general reviews of the methods of gene therapy, see Goldspiel et al., Clinical Pharmacy 12:488–505 (1993); Wu and Wu, Biotherapy 3:87–95 (1991); Tolstoshev, Ann. Rev. Pharmacol. Toxicol. 32:573–596 (1993); Mulligan, Science 260:926–932 (1993); and Morgan and Anderson, Ann. Rev. Biochem. 62:191–217 (1993); May, TIBTECH 11(5): 155–215 (1993). Methods commonly known in the art of recombinant DNA technology which can be used are described in Ausubel et al. (eds.), Current Protocols in Molecular Biology, John Wiley & Sons, NY (1993); and Kriegler, Gene Transfer and Expression, A Laboratory Manual, Stockton Press, NY (1990).

In a preferred aspect, the compound comprises nucleic acid sequences encoding an antibody, said nucleic acid sequences being part of expression vectors that express the antibody or fragments or chimeric proteins or heavy or light chains thereof in a suitable host. In particular, such nucleic acid sequences have promoters operably linked to the antibody coding region, said promoter being inducible or constitutive, and, optionally, tissue-specific. In another particular embodiment, nucleic acid molecules are used in which the antibody coding sequences and any other desired sequences are flanked by regions that promote homologous recombination at a desired site in the genome, thus providing for intrachromosomal expression of the antibody encoding nucleic acids (Koller and Smithies, Proc. Natl. Acad. Sci. USA 86:8932–8935 (1989); Zijlstra et al., Nature 342:435–438 (1989). In specific embodiments, the expressed antibody molecule is a single chain antibody; alternatively, the nucleic acid sequences include sequences encoding both the heavy and light chains, or fragments thereof, of the antibody.

Delivery of the nucleic acids into a patient may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors (see U.S. Pat. No. 4,980, 286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, J. Biol. Chem. 262:4429–4432 (1987)) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180; WO 92/22635; WO92/20316; WO93/14188, WO 93/20221). Alternatively, the nucleic acid can be introduced intracellularly and incorporated within host cell DNA for expression, by homologous recombination (Koller and Smithies, Proc. Natl. Acad. Sci. USA 86:8932–8935 (1989); Zijlstra et al., Nature 342:435–438 (1989)).

In a specific embodiment, viral vectors that contains nucleic acid sequences encoding an antibody of the invention are used. For example, a retroviral vector can be used (see Miller et al., Meth. Enzymol. 217:581–599 (1993)). These retroviral vectors contain the components necessary for the correct packaging of the viral genome and integration into the host cell DNA. The nucleic acid sequences encoding the antibody to be used in gene therapy are cloned into one or more vectors, which facilitates delivery of the gene into a patient. More detail about retroviral vectors can be found in Boesen et al., Biotherapy 6:291–302 (1994), which describes the use of a retroviral vector to deliver the mdr1 gene to hematopoietic stem cells in order to make the stem cells more resistant to chemotherapy. Other references illustrating the use of retroviral vectors in gene therapy are: Clowes et al., J. Clin. Invest. 93:644–651 (1994); Kiem et al., Blood 83:1467–1473 (1994); Salmons and Gunzberg, Human Gene Therapy 4:129–141 (1993); and Grossman and Wilson, Curr. Opin. in Genetics and Devel. 3:110–114 (1993).

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, Current Opinion in Genetics and Development 3:499–503 (1993) present a review of adenovirus-based gene therapy. Bout et al., Human Gene Therapy 5:3–10 (1994) demonstrated the use of adenovirus vectors to transfer genes to the respiratory epithelia of rhesus monkeys. Other instances of the use of adenoviruses in gene therapy can be found in Rosenfeld et al., Science 252:431–434 (1991); Rosenfeld et al., Cell 68:143–155 (1992); Mastrangeli et al., J. Clin. Invest. 91:225–234 (1993); PCT Publication WO94/12649; and Wang, et al., Gene Therapy 2:775–783 (1995). In a preferred embodiment, adenovirus vectors are used.

Adeno-associated virus (AAV) has also been proposed for use in gene therapy (Walsh et al., Proc. Soc. Exp. Biol. Med. 204:289–300 (1993); U.S. Pat. No. 5,436,146).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc.

Numerous techniques are known in the art for the introduction of foreign genes into cells (see, e.g., Loeffler and Behr, Meth. Enzymol. 217:599–618 (1993); Cohen et al., Meth. Enzymol. 217:618–644 (1993); Cline, Pharmac. Ther. 29:69–92m (1985) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as Tlymphocytes, Blymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the patient.

In an embodiment in which recombinant cells are used in gene therapy, nucleic acid sequences encoding an antibody are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see e.g. PCT Publication WO 94/08598; Stemple and Anderson, Cell 71:973–985 (1992); Rheinwald, Meth. Cell Bio. 21A:229 (1980); and Pittelkow and Scott, Mayo Clinic Proc. 61:771 (1986)).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription. Demonstration of Therapeutic or Prophylactic Activity The compounds or pharmaceutical compositions of the invention are preferably tested in vitro, and then in vivo for the desired therapeutic or prophylactic activity, prior to use in humans. For example, in vitro assays to demonstrate the therapeutic or prophylactic utility of a compound or pharmaceutical composition include, the effect of a compound on a cell line or a patient tissue sample. The effect of the compound or composition on the cell line and/or tissue sample can be determined utilizing techniques known to those of skill in the art including, but not limited to, rosette formation assays and cell lysis assays. In accordance with the invention, in vitro assays which can be used to determine whether administration of a specific compound is indicated, include in vitro cell culture assays in which a patient tissue sample is grown in culture, and exposed to or otherwise administered a compound, and the effect of such compound upon the tissue sample is observed.

Therapeutic/Prophylactic Administration and Compositions

The invention provides methods of treatment, inhibition and prophylaxis by administration to a subject of an effective amount of a compound or pharmaceutical composition of the invention, preferably an antibody of the invention. In a preferred aspect, the compound is substantially purified (e.g., substantially free from substances that limit its effect or produce undesired side-effects). The subject is preferably an animal, including but not limited to animals such as cows, pigs, horses, chickens, cats, dogs, etc., and is preferably a mammal, and most preferably human.

Formulations and methods of administration that can be employed when the compound comprises a nucleic acid or an immunoglobulin are described above; additional appropriate formulations and routes of administration can be selected from among those described herein below.

Various delivery systems are known and can be used to administer a compound of the invention, e.g., encapsulation in liposomes, microparticles, microcapsules, recombinant cells capable of expressing the compound, receptor-mediated endocytosis (see, e.g., Wu and Wu, J. Biol. Chem. 262:4429–4432 (1987)), construction of a nucleic acid as part of a retroviral or other vector, etc. Methods of introduction include but are not limited to intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compounds or compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compounds or compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the invention, care must be taken to use materials to which the protein does not absorb.

In another embodiment, the compound or composition can be delivered in a vesicle, in particular a liposome (see Langer, Science 249:1527–1533 (1990); Treat et al., in Liposomes in the Therapy of Infectious Disease and Cancer, Lopez-Berestein and Fidler (eds.), Liss, N.Y., pp. 353–365 (1989); Lopez-Berestein, ibid., pp. 317–327; see generally ibid.)

In yet another embodiment, the compound or composition can be delivered in a controlled release system. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J., Macromol. Sci. Rev. Macromol. Chem. 23:61 (1983); see also Levy et al., Science 228:190 (1985); During et al., Ann. Neurol. 25:351 (1989); Howard et al., J. Neurosurg. 71:105 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115–138 (1984)).

Other controlled release systems are discussed in the review by Langer (Science 249:1527–1533 (1990)).

In a specific embodiment where the compound of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., Proc. Natl. Acad. Sci. USA 88:1864–1868 (1991)), etc. Alternatively, a nucleic acid can be introduced intracellularly and incorporated within host cell DNA for expression, by homologous recombination.

The present invention also provides pharmaceutical compositions. Such compositions comprise a therapeutically effective amount of a compound, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of the compound of the invention which will be effective in the treatment, inhibition and prevention of a disease or disorder associated with aberrant expression and/or activity of a polypeptide of the invention can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

For antibodies, the dosage administered to a patient is typically 0.1 mg/kg to 100 mg/kg of the patient's body weight. Preferably, the dosage administered to a patient is between 0.1 mg/kg and 20 mg/kg of the patient's body weight, more preferably 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the invention may be reduced by enhancing uptake and tissue penetration (e.g., into the brain) of the antibodies by modifications such as, for example, lipidation.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

Diagnosis and Imaging with Antibodies

Labeled antibodies, and derivatives and analogs thereof, which specifically bind to a polypeptide of interest can be used for diagnostic purposes to detect, diagnose, or monitor diseases, disorders, and/or conditions associated with the aberrant expression and/or activity of a polypeptide of the invention. The invention provides for the detection of aberrant expression of a polypeptide of interest, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of aberrant expression.

The invention provides a diagnostic assay for diagnosing a disorder, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of a particular disorder. With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Antibodies of the invention can be used to assay protein levels in a biological sample using classical immunohistological methods known to those of skill in the art (e.g., see Jalkanen, et al., J. Cell. Biol. 101:976–985 (1985); Jalkanen, et al., J. Cell. Biol. 105:3087–3096 (1987)). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine (125I, 121I), carbon (14C), sulfur (35S), tritium (3H), indium (112In), and technetium (99Tc); luminescent labels, such as luminol; and fluorescent labels, such as fluorescein and rhodamine, and biotin.

One aspect of the invention is the detection and diagnosis of a disease or disorder associated with aberrant expression of a polypeptide of interest in an animal, preferably a mammal and most preferably a human. In one embodiment, diagnosis comprises: a) administering (for example, parenterally, subcutaneously, or intraperitoneally) to a subject an effective amount of a labeled molecule which specifically binds to the polypeptide of interest; b) waiting for a time interval following the administering for permitting the labeled molecule to preferentially concentrate at sites in the subject where the polypeptide is expressed (and for unbound labeled molecule to be cleared to background level); c) determining background level; and d) detecting the labeled molecule in the subject, such that detection of labeled molecule above the background level indicates that the subject has a particular disease or disorder associated with aberrant expression of the polypeptide of interest. Background level can be determined by various methods including, comparing the amount of labeled molecule detected to a standard value previously determined for a particular system.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of 99mTc. The labeled antibody or antibody fragment will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).

Depending on several variables, including the type of label used and the mode of administration, the time interval following the administration for permitting the labeled molecule to preferentially concentrate at sites in the subject and for unbound labeled molecule to be cleared to background level is 6 to 48 hours or 6 to 24 hours or 6 to 12 hours. In another embodiment the time interval following administration is 5 to 20 days or 5 to 10 days.

In an embodiment, monitoring of the disease or disorder is carried out by repeating the method for diagnosing the disease or disease, for example, one month after initial diagnosis, six months after initial diagnosis, one year after initial diagnosis, etc.

Presence of the labeled molecule can be detected in the patient using methods known in the art for in vivo scanning. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patent using positron emission-tomography. In yet another embodiment, the molecule is labeled with a paramagnetic label and is detected in a patient using magnetic resonance imaging (MRI).

Kits

The present invention provides kits that can be used in the above methods. In one embodiment, a kit comprises an antibody of the invention, preferably a purified antibody, in one or more containers. In a specific embodiment, the kits of the present invention contain a substantially isolated polypeptide comprising an epitope which is specifically immunoreactive with an antibody included in the kit. Preferably, the kits of the present invention further comprise a control antibody which does not react with the polypeptide of interest. In another specific embodiment, the kits of the present invention contain a means for detecting the binding of an antibody to a polypeptide of interest (e.g., the antibody may be conjugated to a detectable substrate such as a fluorescent compound, an enzymatic substrate, a radioactive compound or a luminescent compound, or a second antibody which recognizes the first antibody may be conjugated to a detectable substrate).

In another specific embodiment of the present invention, the kit is a diagnostic kit for use in screening serum containing antibodies specific against proliferative and/or cancerous polynucleotides and polypeptides. Such a kit may include a control antibody that does not react with the polypeptide of interest. Such a kit may include a substantially isolated polypeptide antigen comprising an epitope which is specifically immunoreactive with at least one anti-polypeptide antigen antibody. Further, such a kit includes means for detecting the binding of said antibody to the antigen (e.g., the antibody may be conjugated to a fluorescent compound such as fluorescein or rhodamine which can be detected by flow cytometry). In specific embodiments, the kit may include a recombinantly produced or chemically synthesized polypeptide antigen. The polypeptide antigen of the kit may also be attached to a solid support.

In a more specific embodiment the detecting means of the above-described kit includes a solid support to which said polypeptide antigen is attached. Such a kit may also include a non-attached reporter-labeled anti-human antibody. In this embodiment, binding of the antibody to the polypeptide antigen can be detected by binding of the said reporter-labeled antibody.

In an additional embodiment, the invention includes a diagnostic kit for use in screening serum containing antigens of the polypeptide of the invention. The diagnostic kit includes a substantially isolated antibody specifically immunoreactive with polypeptide or polynucleotide antigens, and means for detecting the binding of the polynucleotide or polypetide antigen to the antibody. In one embodiment, the antibody is attached to a solid support. In a specific embodiment, the antibody may be a monoclonal antibody. The detecting means of the kit may include a second, labeled monoclonal antibody. Alternatively, or in addition, the detecting means may include a labeled, competing antigen.

In one diagnostic configuration, test serum is reacted with a solid phase reagent having a surface-bound antigen obtained by the methods of the present invention. After binding with specific antigen antibody to the reagent and removing unbound serum components by washing, the reagent is reacted with reporter-labeled anti-human antibody to bind reporter to the reagent in proportion to the amount of bound anti-antigen antibody on the solid support. The reagent is again washed to remove unbound labeled antibody, and the amount of reporter associated with the reagent is determined. Typically, the reporter is an enzyme which is detected by incubating the solid phase in the presence of a suitable fluorometric, luminescent or colorimetric substrate (Sigma, St. Louis, Mo.).

The solid surface reagent in the above assay is prepared by known techniques for attaching protein material to solid support material, such as polymeric beads, dip sticks, 96-well plate or filter material. These attachment methods generally include non-specific adsorption of the protein to the support or covalent attachment of the protein, typically through a free amine group, to a chemically reactive group on the solid support, such as an activated carboxyl, hydroxyl, or aldehyde group. Alternatively, streptavidin coated plates can be used in conjunction with biotinylated antigen(s).

Thus, the invention provides an assay system or kit for carrying out this diagnostic method. The kit generally includes a support with surface-bound recombinant antigens, and a reporter-labeled anti-human antibody for detecting surface-bound anti-antigen antibody.

Fusion Proteins

Any polypeptide of the present invention can be used to generate fusion proteins. For example, the polypeptide of the present invention, when fused to a second protein, can be used as an antigenic tag. Antibodies raised against the polypeptide of the present invention can be used to indirectly detect the second protein by binding to the polypeptide. Moreover, because certain proteins target cellular locations based on trafficking signals, the polypeptides of the present invention can be used as targeting molecules once fused to other proteins.

Examples of domains that can be fused to polypeptides of the present invention include not only heterologous signal sequences, but also other heterologous functional regions. The fusion does not necessarily need to be direct, but may occur through linker sequences.

Moreover, fusion proteins may also be engineered to improve characteristics of the polypeptide of the present invention. For instance, a region of additional amino acids, particularly charged amino acids, may be added to the N-terminus of the polypeptide to improve stability and persistence during purification from the host cell or subsequent handling and storage. Peptide moieties may be added to the polypeptide to facilitate purification. Such regions may be removed prior to final preparation of the polypeptide. Similarly, peptide cleavage sites can be introduced in-between such peptide moieties, which could additionally be subjected to protease activity to remove said peptide(s) from the protein of the present invention. The addition of peptide moieties, including peptide cleavage sites, to facilitate handling of polypeptides are familiar and routine techniques in the art.

Moreover, polypeptides of the present invention, including fragments, and specifically epitopes, can be combined with parts of the constant domain of immunoglobulins (IgA, IgE, IgG, IgM) or portions thereof (CH1, CH2, CH3, and any combination thereof, including both entire domains and portions thereof), resulting in chimeric polypeptides. These fusion proteins facilitate purification and show an increased half-life in vivo. One reported example describes chimeric proteins consisting of the first two domains of the human CD4-polypeptide and various domains of the constant regions of the heavy or light chains of mammalian immunoglobulins. (EP A 394,827; Traunecker et al., Nature 331:84–86 (1988).) Fusion proteins having disulfide-linked dimeric structures (due to the IgG) can also be more efficient in binding and neutralizing other molecules, than the monomeric secreted protein or protein fragment alone. (Fountoulakis et al., J. Biochem. 270:3958–3964 (1905).)

Similarly, EP-A-O 464 533 (Canadian counterpart 2045869) discloses fusion proteins comprising various portions of the constant region of immunoglobulin molecules together with another human protein or part thereof. In many cases, the Fc part in a fusion protein is beneficial in therapy and diagnosis, and thus can result in, for example, improved pharmacokinetic properties. (EP-A 0232 262.) Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5.(See, D. Bennett et al., J. Molecular Recognition 8:52–58 (1995); K. Johanson et al., J. Biol. Chem. 270:9459–9471 (1995).)

Moreover, the polypeptides of the present invention can be fused to marker sequences (also referred to as "tags"). Due to the availability of antibodies specific to such "tags", purification of the fused polypeptide of the invention, and/or its identification is significantly facilitated since antibodies specific to the polypeptides of the invention are not required. Such purification may be in the form of an affinity purification whereby an anti-tag antibody or another type of affinity matrix (e.g., anti-tag antibody attached to the matrix of a flow-thru column) that binds to the epitope tag is present. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821–824 (1989), for instance, hexa-histidine provides for convenient purification of the fusion protein. Another peptide tag useful for purification, the "HA" tag, corresponds to an epitope derived from the influenza hemagglutinin protein. (Wilson et al., Cell 37:767 (1984)).

The skilled artisan would acknowledge the existence of other "tags" which could be readily substituted for the tags referred to supra for purification and/or identification of polypeptides of the present invention (Jones C., et al., J Chromatogr A. 707(1):3–22 (1995)). For example, the c-myc tag and the 8F9, 3C7, 6E10, G4m B7 and 9E10 antibodies thereto (Evan et al., Molecular and Cellular Biology 5:3610–3616 (1985)); the Herpes Simplex virus glycoprotein D (gD) tag and its antibody (Paborsky et al., Protein Engineering, 3(6):547–553 (1990), the Flag-peptide—i.e., the octapeptide sequence DYKDDDDK (SEQ ID NO:16), (Hopp et al., Biotech. 6:1204–1210 (1988); the KT3 epitope peptide (Martin et al., Science, 255:192–194 (1992)); a-tubulin epitope peptide (Skinner et al., J. Biol. Chem., 266:15136–15166, (1991)); the T7 gene 10 protein peptide tag (Lutz-Freyermuth et al., Proc. Natl. Sci. USA, 87:6363–6397 (1990)), the FITC epitope (Zymed, Inc.), the GFP epitope (Zymed, Inc.), and the Rhodamine epitope (Zymed, Inc.).

The present invention also encompasses the attachment of up to nine codons encoding a repeating series of up to nine arginine amino acids to the coding region of a polynucleotide of the present invention. The invention also encompasses chemically derivitizing a polypeptide of the present invention with a repeating series of up to nine arginine amino acids. Such a tag, when attached to a polypeptide, has recently been shown to serve as a universal pass, allowing compounds access to the interior of cells without additional derivitization or manipulation (Wender, P., et al., unpublished data).

Protein fusions involving polypeptides of the present invention, including fragments and/or variants thereof, can be used for the following, non-limiting examples, subcellular localization of proteins, determination of protein-protein interactions via immunoprecipitation, purification of proteins via affinity chromatography, functional and/or structural characterization of protein. The present invention also encompasses the application of hapten specific antibodies for any of the uses referenced above for epitope fusion proteins. For example, the polypeptides of the present invention could be chemically derivatized to attach hapten molecules (e.g., DNP, (Zymed, Inc.)). Due to the availability of monoclonal antibodies specific to such haptens, the protein could be readily purified using immunoprecipation, for example.

Polypeptides of the present invention, including fragments and/or variants thereof, in addition to, antibodies directed against such polypeptides, fragments, and/or variants, may be fused to any of a number of known, and yet to be determined, toxins, such as ricin, saporin (Mashiba H, et al., Ann. N.Y. Acad. Sci. 1999;886:233–5), or HC toxin (Tonukari N J, et al., Plant Cell. 2000 February;12(2): 237–248), for example. Such fusions could be used to deliver the toxins to desired tissues for which a ligand or a protein capable of binding to the polypeptides of the invention exists.

The invention encompasses the fusion of antibodies directed against polypeptides of the present invention, including variants and fragments thereof, to said toxins for delivering the toxin to specific locations in a cell, to specific tissues, and/or to specific species. Such bifunctional antibodies are known in the art, though a review describing additional advantageous fusions, including citations for methods of production, can be found in P. J. Hudson, Curr. Opp. In. Imm. 11:548–557, (1999); this publication, in addition to the references cited therein, are hereby incorporated by reference in their entirety herein. In this context, the term "toxin" may be expanded to include any heterologous protein, a small molecule, radionucleotides, cytotoxic drugs, liposomes, adhesion molecules, glycoproteins, ligands, cell or tissue-specific ligands, enzymes, of bioactive agents, biological response modifiers, anti-fungal agents, hormones, steroids, vitamins, peptides, peptide analogs, anti-allergenic agents, anti-tubercular agents, anti-viral agents, antibiotics, anti-protozoan agents, chelates, radioactive particles, radioactive ions, X-ray contrast agents, monoclonal antibodies, polyclonal antibodies and genetic material. In view of the present disclosure, one skilled in the art could determine whether any particular "toxin" could be used in the compounds of the present invention. Examples of suitable "toxins" listed above are exemplary only and are not intended to limit the "toxins" that may be used in the present invention.

Thus, any of these above fusions can be engineered using the polynucleotides or the polypeptides of the present invention.

Vectors, Host Cells, and Protein Production

The present invention also relates to vectors containing the polynucleotide of the present invention, host cells, and the production of polypeptides by recombinant techniques. The vector may be, for example, a phage, plasmid, viral, or retroviral vector. Retroviral vectors may be replication competent or replication defective. In the latter case, viral propagation generally will occur only in complementing host cells.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The polynucleotide insert should be operatively linked to an appropriate promoter, such as the phage lambda PL promoter, the *E. coli* lac, trp, phoA and tac promoters, the SV40 early and late promoters and promoters of retroviral LTRs, to name a few. Other suitable promoters will be known to the skilled artisan. The expression constructs will further contain sites for transcription initiation, termination, and, in the transcribed region, a ribosome binding site for translation. The coding portion of the transcripts expressed by the constructs will preferably include a translation initiating codon at the beginning and a termination codon (UAA, UGA or UAG) appropriately positioned at the end of the polypeptide to be translated.

As indicated, the expression vectors will preferably include at least one selectable marker. Such markers include dihydrofolate reductase, G418 or neomycin resistance for eukaryotic cell culture and tetracycline, kanamycin or ampicillin resistance genes for culturing in *E. coli* and other bacteria. Representative examples of appropriate hosts include, but are not limited to, bacterial cells, such as *E. coli*, Streptomyces and *Salmonella typhimurium* cells; fungal cells, such as yeast cells (e.g., *Saccharomyces cerevisiae* or

*Pichia pastoris* (ATCC Accession No. 201178)); insect cells such as *Drosophila* S2 and Spodoptera Sf9 cells; animal cells such as CHO, COS, 293, and Bowes melanoma cells; and plant cells. Appropriate culture mediums and conditions for the above-described host cells are known in the art.

Among vectors preferred for use in bacteria include pQE70, pQE60 and pQE9, available from QIAGEN, Inc.; pBluescript vectors, Phagescript vectors, pNH8A, pNH16a, pNH18A, pNH46A, available from Stratagene Cloning Systems, Inc.; and ptrc99a, pKK223-3, pKK233-3, pDR540, pRIT5 available from Pharmacia Biotech, Inc. Among preferred eukaryotic vectors are pWLNEO, pSV2CAT, pOG44, pXT1 and pSG available from Stratagene; and pSVK3, pBPV, pMSG and pSVL available from Pharmacia. Preferred expression vectors for use in yeast systems include, but are not limited to pYES2, pYD1, pTEF1/Zeo, pYES2/GS, pPICZ, pGAPZ, pGAPZalph, pPIC9, pPIC3.5, pHIL-D2, pHIL-S1, pPIC3.5K, pPIC9K, and PAO815 (all available from Invitrogen, Carlsbad, Calif.). Other suitable vectors will be readily apparent to the skilled artisan.

Introduction of the construct into the host cell can be effected by calcium phosphate transfection, DEAE-dextran mediated transfection, cationic lipid-mediated transfection, electroporation, transduction, infection, or other methods. Such methods are described in many standard laboratory manuals, such as Davis et al., Basic Methods In Molecular Biology (1986). It is specifically contemplated that the polypeptides of the present invention may in fact be expressed by a host cell lacking a recombinant vector.

A polypeptide of this invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

Polypeptides of the present invention, and preferably the secreted form, can also be recovered from: products purified from natural sources, including bodily fluids, tissues and cells, whether directly isolated or cultured; products of chemical synthetic procedures; and products produced by recombinant techniques from a prokaryotic or eukaryotic host, including, for example, bacterial, yeast, higher plant, insect, and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes. Thus, it is well known in the art that the N-terminal methionine encoded by the translation initiation codon generally is removed with high efficiency from any protein after translation in all eukaryotic cells. While the N-terminal methionine on most proteins also is efficiently removed in most prokaryotes, for some proteins, this prokaryotic removal process is inefficient, depending on the nature of the amino acid to which the N-terminal methionine is covalently linked.

In one embodiment, the yeast *Pichia pastoris* is used to express the polypeptide of the present invention in a eukaryotic system. *Pichia pastoris* is a methylotrophic yeast which can metabolize methanol as its sole carbon source. A main step in the methanol metabolization pathway is the oxidation of methanol to formaldehyde using O2. This reaction is catalyzed by the enzyme alcohol oxidase. In order to metabolize methanol as its sole carbon source, *Pichia pastoris* must generate high levels of alcohol oxidase due, in part, to the relatively low affinity of alcohol oxidase for O2. Consequently, in a growth medium depending on methanol as a main carbon source, the promoter region of one of the two alcohol oxidase genes (AOX1) is highly active. In the presence of methanol, alcohol oxidase produced from the AOX1 gene comprises up to approximately 30% of the total soluble protein in *Pichia pastoris*. See, Ellis, S. B., et al., Mol. Cell. Biol. 5:1111–21 (1985); Koutz, P. J, et al., Yeast 5:167–77 (1989); Tschopp, J. F., et al., Nucl. Acids Res. 15:3859–76 (1987). Thus, a heterologous coding sequence, such as, for example, a polynucleotide of the present invention, under the transcriptional regulation of all or part of the AOX1 regulatory sequence is expressed at exceptionally high levels in Pichia yeast grown in the presence of methanol.

In one example, the plasmid vector pPIC9K is used to express DNA encoding a polypeptide of the invention, as set forth herein, in a Pichea yeast system essentially as described in "Pichia Protocols: Methods in Molecular Biology," D. R. Higgins and J. Cregg, eds. The Humana Press, Totowa, N.J., 1998. This expression vector allows expression and secretion of a protein of the invention by virtue of the strong AOX1 promoter linked to the *Pichia pastoris* alkaline phosphatase (PHO) secretory signal peptide (i.e., leader) located upstream of a multiple cloning site.

Many other yeast vectors could be used in place of pPIC9K, such as, pYES2, pYD1, pTEF1/Zeo, pYES2/GS, pPICZ, pGAPZ, pGAPZalpha, pPIC9, pPIC3.5, pHIL-D2, pHIL-S1, pPIC3.5K, and PAO815, as one skilled in the art would readily appreciate, as long as the proposed expression construct provides appropriately located signals for transcription, translation, secretion (if desired), and the like, including an in-frame AUG, as required.

In another embodiment, high-level expression of a heterologous coding sequence, such as, for example, a polynucleotide of the present invention, may be achieved by cloning the heterologous polynucleotide of the invention into an expression vector such as, for example, pGAPZ or pGAPZalpha, and growing the yeast culture in the absence of methanol.

In addition to encompassing host cells containing the vector constructs discussed herein, the invention also encompasses primary, secondary, and immortalized host cells of vertebrate origin, particularly mammalian origin, that have been engineered to delete or replace endogenous genetic material (e.g., coding sequence), and/or to include genetic material (e.g., heterologous polynucleotide sequences) that is operably associated with the polynucleotides of the invention, and which activates, alters, and/or amplifies endogenous polynucleotides. For example, techniques known in the art may be used to operably associate heterologous control regions (e.g., promoter and/or enhancer) and endogenous polynucleotide sequences via homologous recombination, resulting in the formation of a new transcription unit (see, e.g., U.S. Pat. No. 5,641,670, issued Jun. 24, 1997; U.S. Pat. No. 5,733,761, issued Mar. 31, 1998; International Publication No. WO 96/29411, published Sep. 26, 1996; International Publication No. WO 94/12650, published Aug. 4, 1994; Koller et al., Proc. Natl. Acad. Sci. USA 86:8932–8935 (1989); and Zijlstra et al., Nature 342:435–438 (1989), the disclosures of each of which are incorporated by reference in their entireties).

In addition, polypeptides of the invention can be chemically synthesized using techniques known in the art (e.g., see Creighton, 1983, Proteins: Structures and Molecular Principles, W. H. Freeman & Co., N.Y., and Hunkapiller et al., Nature, 310:105–111 (1984)). For example, a polypeptide corresponding to a fragment of a polypeptide sequence of the invention can be synthesized by use of a peptide synthesizer. Furthermore, if desired, nonclassical amino acids or chemical amino acid analogs can be introduced as a substitution or addition into the polypeptide sequence. Non-classical amino acids include, but are not limited to, to the D-isomers of the common amino acids, 2,4-diaminobutyric acid, a-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, b-alanine, fluoro-amino acids, designer amino acids such as b-methyl amino acids, Ca-methyl amino acids, Na-methyl amino acids, and amino acid analogs in general. Furthermore, the amino acid can be D (dextrorotary) or L (levorotary).

The invention encompasses polypeptides which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited, to specific chemical cleavage by cyanogen bromide, trypsin, chymotrypsin, papain, V8 protease, NaBH4; acetylation, formylation, oxidation, reduction; metabolic synthesis in the presence of tunicamycin; etc.

Additional post-translational modifications encompassed by the invention include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of prokaryotic host cell expression. The polypeptides may also be modified with a detectable label, such as an enzymatic, fluorescent, isotopic or affinity label to allow for detection and isolation of the protein, the addition of epitope tagged peptide fragments (e.g., FLAG, HA, GST, thioredoxin, maltose binding protein, etc.), attachment of affinity tags such as biotin and/or streptavidin, the covalent attachment of chemical moieties to the amino acid backbone, N- or C-terminal processing of the polypeptides ends (e.g., proteolytic processing), deletion of the N-terminal methionine residue, etc.

Also provided by the invention are chemically modified derivatives of the polypeptides of the invention which may provide additional advantages such as increased solubility, stability and circulating time of the polypeptide, or decreased immunogenicity (see U.S. Pat. No. 4,179,337). The chemical moieties for derivitization may be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties.

The invention further encompasses chemical derivitization of the polypeptides of the present invention, preferably where the chemical is a hydrophilic polymer residue. Exemplary hydrophilic polymers, including derivatives, may be those that include polymers in which the repeating units contain one or more hydroxy groups (polyhydroxy polymers), including, for example, poly(vinyl alcohol); polymers in which the repeating units contain one or more amino groups (polyamine polymers), including, for example, peptides, polypeptides, proteins and lipoproteins, such as albumin and natural lipoproteins; polymers in which the repeating units contain one or more carboxy groups (polycarboxy polymers), including, for example, carboxymethylcellulose, alginic acid and salts thereof, such as sodium and calcium alginate, glycosaminoglycans and salts thereof, including salts of hyaluronic acid, phosphorylated and sulfonated derivatives of carbohydrates, genetic material, such as interleukin-2 and interferon, and phosphorothioate oligomers; and polymers in which the repeating units contain one or more saccharide moieties (polysaccharide polymers), including, for example, carbohydrates.

The molecular weight of the hydrophilic polymers may vary, and is generally about 50 to about 5,000,000, with polymers having a molecular weight of about 100 to about 50,000 being preferred. The polymers may be branched or unbranched. More preferred polymers have a molecular weight of about 150 to about 10,000, with molecular weights of 200 to about 8,000 being even more preferred.

For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog).

Additional preferred polymers which may be used to derivatize polypeptides of the invention, include, for example, poly(ethylene glycol) (PEG), poly (vinylpyrrolidine), polyoxomers, polysorbate and poly(vinyl alcohol), with PEG polymers being particularly preferred. Preferred among the PEG polymers are PEG polymers having a molecular weight of from about 100 to about 10,000. More preferably, the PEG polymers have a molecular weight of from about 200 to about 8,000, with PEG 2,000, PEG 5,000 and PEG 8,000, which have molecular weights of 2,000, 5,000 and 8,000, respectively, being even more preferred. Other suitable hydrophilic polymers, in addition to those exemplified above, will be readily apparent to one skilled in the art based on the present disclosure. Generally, the polymers used may include polymers that can be attached to the polypeptides of the invention via alkylation or acylation reactions.

The polyethylene glycol molecules (or other chemical moieties) should be attached to the protein with consideration of effects on functional or antigenic domains of the protein. There are a number of attachment methods available to those skilled in the art, e.g., EP 0 401 384, herein incorporated by reference (coupling PEG to G-CSF), see also Malik et al., Exp. Hematol. 20:1028–1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

One may specifically desire proteins chemically modified at the N-terminus. Using polyethylene glycol as an illustration of the present composition, one may select from a variety of polyethylene glycol molecules (by molecular weight, branching, etc.), the proportion of polyethylene glycol molecules to protein (polypeptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective proteins chemically modified at the N-terminus modification may be accomplished by reductive alkylation which exploits differential reactivity of different types of primary amino groups (lysine versus the N-terminus) available for derivatization in a particular protein. Under the appropriate reaction conditions, substantially selective derivatization of the protein at the N-terminus with a carbonyl group containing polymer is achieved.

As with the various polymers exemplified above, it is contemplated that the polymeric residues may contain functional groups in addition, for example, to those typically involved in linking the polymeric residues to the polypeptides of the present invention. Such functionalities include, for example, carboxyl, amine, hydroxy and thiol groups. These functional groups on the polymeric residues can be further reacted, if desired, with materials that are generally reactive with such functional groups and which can assist in targeting specific tissues in the body including, for example, diseased tissue. Exemplary materials which can be reacted with the additional functional groups include, for example, proteins, including antibodies, carbohydrates, peptides, glycopeptides, glycolipids, lectins, and nucleosides.

In addition to residues of hydrophilic polymers, the chemical used to derivatize the polypeptides of the present invention can be a saccharide residue. Exemplary saccharides which can be derived include, for example, monosaccharides or sugar alcohols, such as erythrose, threose, ribose, arabinose, xylose, lyxose, fructose, sorbitol, mannitol and sedoheptulose, with preferred monosaccharides being fructose, mannose, xylose, arabinose, mannitol and sorbitol; and disaccharides, such as lactose, sucrose, maltose and cellobiose. Other saccharides include, for example, inositol and ganglioside head groups. Other suitable saccharides, in addition to those exemplified above, will be readily apparent to one skilled in the art based on the present disclosure. Generally, saccharides which may be used for derivitization include saccharides that can be attached to the polypeptides of the invention via alkylation or acylation reactions.

Moreover, the invention also encompasses derivitization of the polypeptides of the present invention, for example, with lipids (including cationic, anionic, polymerized, charged, synthetic, saturated, unsaturated, and any combination of the above. etc.). stabilizing agents.

The invention encompasses derivitization of the polypeptides of the present invention, for example, with compounds that may serve a stabilizing function (e.g., to increase the polypeptides half-life in solution, to make the polypeptides more water soluble, to increase the polypeptides hydrophilic or hydrophobic character, etc.). Polymers useful as stabilizing materials may be of natural, semi-synthetic (modified natural) or synthetic origin. Exemplary natural polymers include naturally occurring polysaccharides, such as, for example, arabinans, fructans, fucans, galactans, galacturonans, glucans, mannans, xylans (such as, for example, inulin), levan, fucoidan, carrageenan, galatocarolose, pectic acid, pectins, including amylose, pullulan, glycogen, amylopectin, cellulose, dextran, dextrin, dextrose, glucose, polyglucose, polydextrose, pustulan, chitin, agarose, keratin, chondroitin, dermatan, hyaluronic acid, alginic acid, xanthin gum, starch and various other natural homopolymer or heteropolymers, such as those containing one or more of the following aldoses, ketoses, acids or amines: erythose, threose, ribose, arabinose, xylose, lyxose, allose, altrose, glucose, dextrose, mannose, gulose, idose, galactose, talose, erythrulose, ribulose, xylulose, psicose, fructose, sorbose, tagatose, mannitol, sorbitol, lactose, sucrose, trehalose, maltose, cellobiose, glycine, serine, threonine, cysteine, tyrosine, asparagine, glutamine, aspartic acid, glutamic acid, lysine, arginine, histidine, glucuronic acid, gluconic acid, glucaric acid, galacturonic acid, mannuronic acid, glucosamine, galactosamine, and neuraminic acid, and naturally occurring derivatives thereof Accordingly, suitable polymers include, for example, proteins, such as albumin, polyalginates, and polylactide-coglycolide polymers. Exemplary semi-synthetic polymers include carboxymethylcellulose, hydroxymethylcellulose, hydroxypropylmethylcellulose, methylcellulose, and methoxycellulose. Exemplary synthetic polymers include polyphosphazenes, hydroxyapatites, fluoroapatite polymers, polyethylenes (such as, for example, polyethylene glycol (including for example, the class of compounds referred to as Pluronics.RTM., commercially available from BASF, Parsippany, N.J.), polyoxyethylene, and polyethylene terephthlate), polypropylenes (such as, for example, polypropylene glycol), polyurethanes (such as, for example, polyvinyl alcohol (PVA), polyvinyl chloride and polyvinylpyrrolidone), polyamides including nylon, polystyrene, polylactic acids, fluorinated hydrocarbon polymers, fluorinated carbon polymers (such as, for example, polytetrafluoroethylene), acrylate, methacrylate, and polymethylmethacrylate, and derivatives thereof. Methods for the preparation of derivatized polypeptides of the invention which employ polymers as stabilizing compounds will be readily apparent to one skilled in the art, in view of the present disclosure, when coupled with information known in the art, such as that described and referred to in Unger, U.S. Pat. No. 5,205,290, the disclosure of which is hereby incorporated by reference herein in its entirety.

Moreover, the invention encompasses additional modifications of the polypeptides of the present invention. Such additional modifications are known in the art, and are specifically provided, in addition to methods of derivitization, etc., in U.S. Pat. No. 6,028,066, which is hereby incorporated in its entirety herein.

The polypeptides of the invention may be in monomers or multimers (i.e., dimers, trimers, tetramers and higher multimers). Accordingly, the present invention relates to monomers and multimers of the polypeptides of the invention, their preparation, and compositions (preferably, Therapeutics) containing them. In specific embodiments, the polypeptides of the invention are monomers, dimers, trimers or tetramers. In additional embodiments, the multimers of the invention are at least dimers, at least trimers, or at least tetramers.

Multimers encompassed by the invention may be homomers or heteromers. As used herein, the term homomer, refers to a multimer containing only polypeptides corresponding to the amino acid sequence of SEQ ID NO:2 or encoded by the cDNA contained in a deposited clone (including fragments, variants, splice variants, and fusion proteins, corresponding to these polypeptides as described herein). These homomers may contain polypeptides having identical or different amino acid sequences. In a specific embodiment, a homomer of the invention is a multimer containing only polypeptides having an identical amino acid sequence. In another specific embodiment, a homomer of the invention is a multimer containing polypeptides having different amino acid sequences. In specific embodiments, the multimer of the invention is a homodimer (e.g., containing polypeptides having identical or different amino acid sequences) or a homotrimer (e.g., containing polypeptides having identical and/or different amino acid sequences). In additional embodiments, the homomeric multimer of the invention is at least a homodimer, at least a homotrimer, or at least a homotetramer.

As used herein, the term heteromer refers to a multimer containing one or more heterologous polypeptides (i.e., polypeptides of different proteins) in addition to the polypeptides of the invention. In a specific embodiment, the multimer of the invention is a heterodimer, a heterotrimer, or a heterotetramer. In additional embodiments, the heteromeric multimer of the invention is at least a heterodimer, at least a heterotrimer, or at least a heterotetramer.

Multimers of the invention may be the result of hydrophobic, hydrophilic, ionic and/or covalent associations and/or may be indirectly linked, by for example, liposome formation. Thus, in one embodiment, multimers of the invention, such as, for example, homodimers or homotrimers, are formed when polypeptides of the invention contact one another in solution. In another embodiment, heteromultimers of the invention, such as, for example, heterotrimers or heterotetramers, are formed when polypeptides of the invention contact antibodies to the polypeptides of the invention (including antibodies to the heterologous polypeptide sequence in a fusion protein of the invention) in solution. In other embodiments, multimers of the invention are formed by covalent associations with and/or between the polypeptides of the invention. Such covalent associations may involve one or more amino acid residues contained in the polypeptide sequence (e.g., that recited in the sequence listing, or contained in the polypeptide encoded by a deposited clone). In one instance, the covalent associations are cross-linking between cysteine residues located within the polypeptide sequences which interact in the native (i.e., naturally occurring) polypeptide. In another instance, the covalent associations are the consequence of chemical or recombinant manipulation. Alternatively, such covalent associations may involve one or more amino acid residues contained in the heterologous polypeptide sequence in a fusion protein of the invention.

In one example, covalent associations are between the heterologous sequence contained in a fusion protein of the invention (see, e.g., U.S. Pat. No. 5,478,925). In a specific example, the covalent associations are between the heterologous sequence contained in an Fc fusion protein of the invention (as described herein). In another specific example, covalent associations of fusion proteins of the invention are between heterologous polypeptide sequence from another protein that is capable of forming covalently associated multimers, such as for example, osteoprotegerin (see, e.g., International Publication NO: WO 98/49305, the contents of which are herein incorporated by reference in its entirety). In another embodiment, two or more polypeptides of the invention are joined through peptide linkers. Examples include those peptide linkers described in U.S. Pat. No. 5,073,627 (hereby incorporated by reference). Proteins comprising multiple polypeptides of the invention separated by peptide linkers may be produced using conventional recombinant DNA technology.

Another method for preparing multimer polypeptides of the invention involves use of polypeptides of the invention fused to a leucine zipper or isoleucine zipper polypeptide sequence. Leucine zipper and isoleucine zipper domains are polypeptides that promote multimerization of the proteins in which they are found. Leucine zippers were originally identified in several DNA-binding proteins (Landschulz et al., Science 240:1759, (1988)), and have since been found in a variety of different proteins. Among the known leucine zippers are naturally occurring peptides and derivatives thereof that dimerize or trimerize. Examples of leucine zipper domains suitable for producing soluble multimeric proteins of the invention are those described in PCT application WO 94/10308, hereby incorporated by reference. Recombinant fusion proteins comprising a polypeptide of the invention fused to a polypeptide sequence that dimerizes or trimerizes in solution are expressed in suitable host cells, and the resulting soluble multimeric fusion protein is recovered from the culture supernatant using techniques known in the art.

Trimeric polypeptides of the invention may offer the advantage of enhanced biological activity. Preferred leucine zipper moieties and isoleucine moieties are those that preferentially form trimers. One example is a leucine zipper derived from lung surfactant protein D (SPD), as described in Hoppe et al. (FEBS Letters 344:191, (1994)) and in U.S. patent application Ser. No. 08/446,922, hereby incorporated by reference. Other peptides derived from naturally occurring trimeric proteins may be employed in preparing trimeric polypeptides of the invention.

In another example, proteins of the invention are associated by interactions between Flag® polypeptide sequence contained in fusion proteins of the invention containing Flag® polypeptide sequence. In a further embodiment, associations proteins of the invention are associated by interactions between heterologous polypeptide sequence contained in Flag® fusion proteins of the invention and anti-Flag® antibody.

The multimers of the invention may be generated using chemical techniques known in the art. For example, polypeptides desired to be contained in the multimers of the invention may be chemically cross-linked using linker molecules and linker molecule length optimization techniques known in the art (see, e.g., U.S. Pat. No. 5,478,925, which is herein incorporated by reference in its entirety). Additionally, multimers of the invention may be generated using techniques known in the art to form one or more inter-molecule cross-links between the cysteine residues located within the sequence of the polypeptides desired to be contained in the multimer (see, e.g., U.S. Pat. No. 5,478,925, which is herein incorporated by reference in its entirety). Further, polypeptides of the invention may be routinely modified by the addition of cysteine or biotin to the C terminus or N-terminus of the polypeptide and techniques known in the art may be applied to generate multimers containing one or more of these modified polypeptides (see, e.g., U.S. Pat. No. 5,478,925, which is herein incorporated by reference in its entirety). Additionally, techniques known in the art may be applied to generate liposomes containing the polypeptide components desired to be contained in the multimer of the invention (see, e.g., U.S. Pat. No. 5,478,925, which is herein incorporated by reference in its entirety).

Alternatively, multimers of the invention may be generated using genetic engineering techniques known in the art. In one embodiment, polypeptides contained in multimers of the invention are produced recombinantly using fusion protein technology described herein or otherwise known in the art (see, e.g., U.S. Pat. No. 5,478,925, which is herein incorporated by reference in its entirety). In a specific embodiment, polynucleotides coding for a homodimer of the invention are generated by ligating a polynucleotide sequence encoding a polypeptide of the invention to a sequence encoding a linker polypeptide and then further to a synthetic polynucleotide encoding the translated product of the polypeptide in the reverse orientation from the original C-terminus to the N-terminus (lacking the leader sequence) (see, e.g., U.S. Pat. No. 5,479,925, which is herein incorporated by reference in its entirety). In another embodiment, recombinant techniques described herein or otherwise known in the art are applied to generate recombinant polypeptides of the invention which contain a transmembrane domain (or hydrophobic or signal peptide) and which can be incorporated by membrane reconstitution techniques into liposomes (see, e.g., U.S. Pat. No. 5,478,925, which is herein incorporated by reference in its entirety).

In addition, the polynucleotide insert of the present invention could be operatively linked to "artificial" or chimeric promoters and transcription factors. Specifically, the artificial promoter could comprise, or alternatively consist, of any combination of cis-acting DNA sequence elements that are recognized by trans-acting transcription factors. Preferably, the cis acting DNA sequence elements and trans-acting transcription factors are operable in mammals. Further, the trans-acting transcription factors of such "artificial" promoters could also be "artificial" or chimeric in design themselves and could act as activators or repressors to said "artificial" promoter.

Uses of the Polynucleotides

Each of the polynucleotides identified herein can be used in numerous ways as reagents. The following description should be considered exemplary and utilizes known techniques.

The polynucleotides of the present invention are useful for chromosome identification. There exists an ongoing need to identify new chromosome markers, since few chromosome marking reagents, based on actual sequence data (repeat polymorphisms), are presently available. Each polynucleotide of the present invention can be used as a chromosome marker.

Briefly, sequences can be mapped to chromosomes by preparing PCR primers (preferably 15–25 bp) from the sequences shown in SEQ ID NO:1. Primers can be selected using computer analysis so that primers do not span more than one predicted exon in the genomic DNA. These primers are then used for PCR screening of somatic cell hybrids containing individual human chromosomes. Only those hybrids containing the human gene corresponding to the SEQ ID NO:1 will yield an amplified fragment.

Similarly, somatic hybrids provide a rapid method of PCR mapping the polynucleotides to particular chromosomes. Three or more clones can be assigned per day using a single thermal cycler. Moreover, sublocalization of the polynucleotides can be achieved with panels of specific chromosome fragments. Other gene mapping strategies that can be used include in situ hybridization, prescreening with labeled flow-sorted chromosomes, and preselection by hybridization to construct chromosome specific-cDNA libraries.

Precise chromosomal location of the polynucleotides can also be achieved using fluorescence in situ hybridization (FISH) of a metaphase chromosomal spread. This technique uses polynucleotides as short as 500 or 600 bases; however, polynucleotides 2,000–4,000 bp are preferred. For a review of this technique, see Verma et al., "Human Chromosomes: a Manual of Basic Techniques," Pergamon Press, New York (1988).

For chromosome mapping, the polynucleotides can be used individually (to mark a single chromosome or a single site on that chromosome) or in panels (for marking multiple sites and/or multiple chromosomes). Preferred polynucleotides correspond to the noncoding regions of the cDNAs because the coding sequences are more likely conserved within gene families, thus increasing the chance of cross hybridization during chromosomal mapping.

Once a polynucleotide has been mapped to a precise chromosomal location, the physical position of the polynucleotide can be used in linkage analysis. Linkage analysis establishes coinheritance between a chromosomal location and presentation of a particular disease. Disease mapping data are known in the art. Assuming 1 megabase mapping resolution and one gene per 20 kb, a cDNA precisely localized to a chromosomal region associated with the disease could be one of 50–500 potential causative genes.

Thus, once coinheritance is established, differences in the polynucleotide and the corresponding gene between affected and unaffected organisms can be examined. First, visible structural alterations in the chromosomes, such as deletions or translocations, are examined in chromosome spreads or by PCR. If no structural alterations exist, the presence of point mutations are ascertained. Mutations observed in some or all affected organisms, but not in normal organisms, indicates that the mutation may cause the disease. However, complete sequencing of the polypeptide and the corresponding gene from several normal organisms is required to distinguish the mutation from a polymorphism. If a new polymorphism is identified, this polymorphic polypeptide can be used for further linkage analysis.

Furthermore, increased or decreased expression of the gene in affected organisms as compared to unaffected organisms can be assessed using polynucleotides of the present invention. Any of these alterations (altered expression, chromosomal rearrangement, or mutation) can be used as a diagnostic or prognostic marker.

Thus, the invention also provides a diagnostic method useful during diagnosis of a disorder, involving measuring the expression level of polynucleotides of the present invention in cells or body fluid from an organism and comparing the measured gene expression level with a standard level of polynucleotide expression level, whereby an increase or decrease in the gene expression level compared to the standard is indicative of a disorder.

By "measuring the expression level of a polynucleotide of the present invention" is intended qualitatively or quantitatively measuring or estimating the level of the polypeptide of the present invention or the level of the mRNA encoding the polypeptide in a first biological sample either directly (e.g., by determining or estimating absolute protein level or mRNA level) or relatively (e.g., by comparing to the polypeptide level or mRNA level in a second biological sample). Preferably, the polypeptide level or mRNA level in the first biological sample is measured or estimated and compared to a standard polypeptide level or mRNA level, the standard being taken from a second biological sample obtained from an individual not having the disorder or being determined by averaging levels from a population of organisms not having a disorder. As will be appreciated in the art, once a standard polypeptide level or mRNA level is known, it can be used repeatedly as a standard for comparison.

By "biological sample" is intended any biological sample obtained from an organism, body fluids, cell line, tissue culture, or other source which contains the polypeptide of the present invention or mRNA. As indicated, biological samples include body fluids (such as the following non-limiting examples, sputum, amniotic fluid, urine, saliva, breast milk, secretions, interstitial fluid, blood, serum, spinal fluid, etc.) which contain the polypeptide of the present invention, and other tissue sources found to express the polypeptide of the present invention. Methods for obtaining tissue biopsies and body fluids from organisms are well known in the art. Where the biological sample is to include mRNA, a tissue biopsy is the preferred source.

The method(s) provided above may Preferably be applied in a diagnostic method and/or kits in which polynucleotides and/or polypeptides are attached to a solid support. In one exemplary method, the support may be a "gene chip" or a "biological chip" as described in U.S. Pat. Nos. 5,837,832, 5,874,219, and 5,856,174. Further, such a gene chip with polynucleotides of the present invention attached may be used to identify polymorphisms between the polynucleotide sequences, with polynucleotides isolated from a test subject. The knowledge of such polymorphisms (i.e. their location, as well as, their existence) would be beneficial in identifying disease loci for many disorders, including proliferative diseases and conditions. Such a method is described in U.S. Pat. Nos. 5,858,659 and 5,856,104. The US patents referenced supra are hereby incorporated by reference in their entirety herein.

The present invention encompasses polynucleotides of the present invention that are chemically synthesized, or reproduced as peptide nucleic acids (PNA), or according to other methods known in the art. The use of PNAs would serve as the preferred form if the polynucleotides are incorporated onto a solid support, or gene chip. For the purposes of the present invention, a peptide nucleic acid (PNA) is a polyamide type of DNA analog and the monomeric units for adenine, guanine, thymine and cytosine are available commercially (Perceptive Biosystems). Certain components of DNA, such as phosphorus, phosphorus oxides, or deoxyribose derivatives, are not present in PNAs. As disclosed by P. E. Nielsen, M. Egholm, R. H. Berg and O. Buchardt, Science 254, 1497 (1991); and M. Egholm, O. Buchardt, L. Christensen, C. Behrens, S. M. Freier, D. A. Driver, R. H. Berg, S. K. Kim, B. Norden, and P. E. Nielsen, Nature 365, 666 (1993), PNAs bind specifically and tightly to complementary DNA strands and are not degraded by nucleases. In fact, PNA binds more strongly to DNA than DNA itself does. This is probably because there is no electrostatic repulsion between the two strands, and also the polyamide backbone is more flexible. Because of this, PNA/DNA duplexes bind under a wider range of stringency conditions than DNA/DNA duplexes, making it easier to perform multiplex hybridization. Smaller probes can be used than with DNA due to the stronger binding characteristics of PNA:DNA hybrids. In addition, it is more likely that single base mismatches can be determined with PNA/DNA hybridization because a single mismatch in a PNA/DNA 15-mer lowers the melting point (T.sub.m) by 8°–20° C., vs. 4°–16° C. for the DNA/DNA 15-mer duplex. Also, the absence of charge groups in PNA means that hybridization can be done at low ionic strengths and reduce possible interference by salt during the analysis.

In addition to the foregoing, a polynucleotide can be used to control gene expression through triple helix formation or antisense DNA or RNA. Antisense techniques are discussed, for example, in Okano, J. Neurochem. 56: 560 (1991); "Oligodeoxynucleotides as Antisense Inhibitors of Gene Expression, CRC Press, Boca Raton, Fla. (1988). Triple helix formation is discussed in, for instance Lee et al., Nucleic Acids Research 6: 3073 (1979); Cooney et al., Science 241: 456 (1988); and Dervan et al., Science 251: 1360 (1991). Both methods rely on binding of the polynucleotide to a complementary DNA or RNA. For these techniques, preferred polynucleotides are usually oligonucleotides 20 to 40 bases in length and complementary to either the region of the gene involved in transcription (triple helix—see Lee et al., Nucl. Acids Res. 6:3073 (1979); Cooney et al., Science 241:456 (1988); and Dervan et al., Science 251:1360 (1991)) or to the mRNA itself (antisense—Okano, J. Neurochem. 56:560 (1991); Oligodeoxy-nucleotides as Antisense Inhibitors of Gene Expression, CRC Press, Boca Raton, Fla. (1988).) Triple helix formation optimally results in a shut-off of RNA transcription from DNA, while antisense RNA hybridization blocks translation of an mRNA molecule into polypeptide. Both techniques are effective in model systems, and the information disclosed herein can be used to design antisense or triple helix polynucleotides in an effort to treat or prevent disease.

The present invention encompasses the addition of a nuclear localization signal, operably linked to the 5' end, 3' end, or any location therein, to any of the oligonucleotides, antisense oligonucleotides, triple helix oligonucleotides, ribozymes, PNA oligonucleotides, and/or polynucleotides, of the present invention. See, for example, G. Cutrona, et al., Nat. Biotech., 18:300–303, (2000); which is hereby incorporated herein by reference.

Polynucleotides of the present invention are also useful in gene therapy. One goal of gene therapy is to insert a normal gene into an organism having a defective gene, in an effort to correct the genetic defect. The polynucleotides disclosed in the present invention offer a means of targeting such genetic defects in a highly accurate manner. Another goal is to insert a new gene that was not present in the host genome, thereby producing a new trait in the host cell. In one example, polynucleotide sequences of the present invention may be used to construct chimeric RNA/DNA oligonucleotides corresponding to said sequences, specifically designed to induce host cell mismatch repair mechanisms in an organism upon systemic injection, for example (Bartlett, R. J., et al., Nat. Biotech, 18:615–622 (2000), which is hereby incorporated by reference herein in its entirety). Such RNA/DNA oligonucleotides could be designed to correct genetic defects in certain host strains, and/or to introduce desired phenotypes in the host (e.g., introduction of a specific polymorphism within an endogenous gene corresponding to a polynucleotide of the present invention that may ameliorate and/or prevent a disease symptom and/or disorder, etc.). Alternatively, the polynucleotide sequence of the present invention may be used to construct duplex oligonucleotides corresponding to said sequence, specifically designed to correct genetic defects in certain host strains, and/or to introduce desired phenotypes into the host (e.g., introduction of a specific polymorphism within an endogenous gene corresponding to a polynucleotide of the present invention that may ameliorate and/or prevent a disease symptom and/or disorder, etc). Such methods of using duplex oligonucleotides are known in the art and are encompassed by the present invention (see EP1007712, which is hereby incorporated by reference herein in its entirety).

The polynucleotides are also useful for identifying organisms from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identifying personnel. This method does not suffer from the current limitations of "Dog Tags" which can be lost, switched, or stolen, making positive identification difficult. The polynucleotides of the present invention can be used as additional DNA markers for RFLP.

The polynucleotides of the present invention can also be used as an alternative to RFLP, by determining the actual base-by-base DNA sequence of selected portions of an organisms genome. These sequences can be used to prepare PCR primers for amplifying and isolating such selected DNA, which can then be sequenced. Using this technique, organisms can be identified because each organism will have a unique set of DNA sequences. Once an unique ID database is established for an organism, positive identification of that organism, living or dead, can be made from extremely small tissue samples. Similarly, polynucleotides of the present invention can be used as polymorphic markers, in addition to, the identification of transformed or non-transformed cells and/or tissues.

There is also a need for reagents capable of identifying the source of a particular tissue. Such need arises, for example, when presented with tissue of unknown origin. Appropriate reagents can comprise, for example, DNA probes or primers specific to particular tissue prepared from the sequences of the present invention. Panels of such reagents can identify tissue by species and/or by organ type. In a similar fashion, these reagents can be used to screen tissue cultures for contamination. Moreover, as mentioned above, such reagents can be used to screen and/or identify transformed and non-transformed cells and/or tissues.

In the very least, the polynucleotides of the present invention can be used as molecular weight markers on Southern gels, as diagnostic probes for the presence of a specific mRNA in a particular cell type, as a probe to "subtract-out" known sequences in the process of discovering novel polynucleotides, for selecting and making oligomers for attachment to a "gene chip" or other support, to raise anti-DNA antibodies using DNA immunization techniques, and as an antigen to elicit an immune response.

Uses of the Polypeptides

Each of the polypeptides identified herein can be used in numerous ways. The following description should be considered exemplary and utilizes known techniques.

A polypeptide of the present invention can be used to assay protein levels in a biological sample using antibody-based techniques. For example, protein expression in tissues can be studied with classical immunohistological methods. (Jalkanen, M., et al., J. Cell. Biol. 101:976–985 (1985); Jalkanen, M., et al., J. Cell. Biol. 105:3087–3096 (1987).) Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase, and radioisotopes, such as iodine (125I,121I), carbon (14C), sulfur (35S), tritium (3H), indium (112In), and technetium (99mTc), and fluorescent labels, such as fluorescein and rhodamine, and biotin.

In addition to assaying protein levels in a biological sample, proteins can also be detected in vivo by imaging. Antibody labels or markers for in vivo imaging of protein include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma.

A protein-specific antibody or antibody fragment which has been labeled with an appropriate detectable imaging moiety, such as a radioisotope (for example, 131I, 112In, 99mTc), a radio-opaque substance, or a material detectable by nuclear magnetic resonance, is introduced (for example, parenterally, subcutaneously, or intraperitoneally) into the mammal. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of 99mTc. The labeled antibody or antibody fragment will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer. S. W. Burchiel and B. A Rhodes eds., Masson Publishing Inc. (1982).)

Thus, the invention provides a diagnostic method of a disorder, which involves (a) assaying the expression of a polypeptide of the present invention in cells or body fluid of an individual; (b) comparing the level of gene expression with a standard gene expression level, whereby an increase or decrease in the assayed polypeptide gene expression level compared to the standard expression level is indicative of a disorder. With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Moreover, polypeptides of the present invention can be used to treat, prevent, and/or diagnose disease. For example, patients can be administered a polypeptide of the present invention in an effort to replace absent or decreased levels of the polypeptide (e.g., insulin), to supplement absent or decreased levels of a different polypeptide (e.g., hemoglobin S for hemoglobin B, SOD, catalase, DNA repair proteins), to inhibit the activity of a polypeptide (e.g., an oncogene or tumor suppressor), to activate the activity of a polypeptide (e.g., by binding to a receptor), to reduce the activity of a membrane bound receptor by competing with it for free ligand (e.g., soluble TNF receptors used in reducing inflammation), or to bring about a desired response (e.g., blood vessel growth inhibition, enhancement of the immune response to proliferative cells or tissues).

Similarly, antibodies directed to a polypeptide of the present invention can also be used to treat, prevent, and/or diagnose disease. For example, administration of an antibody directed to a polypeptide of the present invention can bind and reduce overproduction of the polypeptide. Similarly, administration of an antibody can activate the polypeptide, such as by binding to a polypeptide bound to a membrane (receptor).

At the very least, the polypeptides of the present invention can be used as molecular weight markers on SDS-PAGE gels or on molecular sieve gel filtration columns using methods well known to those of skill in the art. Polypeptides can also be used to raise antibodies, which in turn are used to measure protein expression from a recombinant cell, as a way of assessing transformation of the host cell. Moreover, the polypeptides of the present invention can be used to test the following biological activities.

Gene Therapy Methods

Another aspect of the present invention is to gene therapy methods for treating or preventing disorders, diseases and conditions. The gene therapy methods relate to the introduction of nucleic acid (DNA, RNA and antisense DNA or RNA) sequences into an animal to achieve expression of a polypeptide of the present invention. This method requires a polynucleotide which codes for a polypeptide of the invention that operatively linked to a promoter and any other genetic elements necessary for the expression of the polypeptide by the target tissue. Such gene therapy and delivery techniques are known in the art, see, for example, WO90/11092, which is herein incorporated by reference.

Thus, for example, cells from a patient may be engineered with a polynucleotide (DNA or RNA) comprising a promoter operably linked to a polynucleotide of the invention ex vivo, with the engineered cells then being provided to a patient to be treated with the polypeptide. Such methods are well-known in the art. For example, see Belldegrun et al., J. Natl. Cancer Inst., 85:207–216 (1993); Ferrantini et al., Cancer Research, 53:107–1112 (1993); Ferrantini et al., J. Immunology 153: 4604–4615 (1994); Kaido, T., et al., Int. J. Cancer 60: 221–229 (1995); Ogura et al., Cancer Research 50: 5102–5106 (1990); Santodonato, et al., Human Gene Therapy 7:1–10 (1996); Santodonato, et al., Gene Therapy 4:1246–1255 (1997); and Zhang, et al., Cancer Gene Therapy 3: 31–38 (1996)), which are herein incorporated by reference. In one embodiment, the cells which are engineered are arterial cells. The arterial cells may be reintroduced into the patient through direct injection to the artery, the tissues surrounding the artery, or through catheter injection.

As discussed in more detail below, the polynucleotide constructs can be delivered by any method that delivers injectable materials to the cells of an animal, such as, injection into the interstitial space of tissues (heart, muscle, skin, lung, liver, and the like). The polynucleotide constructs may be delivered in a pharmaceutically acceptable liquid or aqueous carrier.

In one embodiment, the polynucleotide of the invention is delivered as a naked polynucleotide. The term "naked" polynucleotide, DNA or RNA refers to sequences that are free from any delivery vehicle that acts to assist, promote or facilitate entry into the cell, including viral sequences, viral particles, liposome formulations, lipofectin or precipitating agents and the like. However, the polynucleotides of the invention can also be delivered in liposome formulations and lipofectin formulations and the like can be prepared by methods well known to those skilled in the art. Such methods are described, for example, in U.S. Pat. Nos. 5,593,972, 5,589,466, and 5,580,859, which are herein incorporated by reference.

The polynucleotide vector constructs of the invention used in the gene therapy method are preferably constructs that will not integrate into the host genome nor will they contain sequences that allow for replication. Appropriate vectors include pWLNEO, pSV2CAT, pOG44, pXT1 and pSG available from Stratagene; pSVK3, pBPV, pMSG and pSVL available from Pharmacia; and pEF1/V5, pcDNA3.1, and pRc/CMV2 available from Invitrogen. Other suitable vectors will be readily apparent to the skilled artisan.

Any strong promoter known to those skilled in the art can be used for driving the expression of polynucleotide sequence of the invention. Suitable promoters include adenoviral promoters, such as the adenoviral major late promoter; or heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs; the b-actin promoter; and human growth hormone promoters. The promoter also may be the native promoter for the polynucleotides of the invention.

Unlike other gene therapy techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The polynucleotide construct of the invention can be delivered to the interstitial space of tissues within the an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular, fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the naked nucleic acid sequence injection, an effective dosage amount of DNA or RNA will be in the range of from about 0.05 mg/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration.

The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked DNA constructs can be delivered to arteries during angioplasty by the catheter used in the procedure.

The naked polynucleotides are delivered by any method known in the art, including, but not limited to, direct needle injection at the delivery site, intravenous injection, topical administration, catheter infusion, and so-called "gene guns". These delivery methods are known in the art.

The constructs may also be delivered with delivery vehicles such as viral sequences, viral particles, liposome formulations, lipofectin, precipitating agents, etc. Such methods of delivery are known in the art.

In certain embodiments, the polynucleotide constructs of the invention are complexed in a liposome preparation. Liposomal preparations for use in the instant invention include cationic (positively charged), anionic (negatively charged) and neutral preparations. However, cationic liposomes are particularly preferred because a tight charge complex can be formed between the cationic liposome and the polyanionic nucleic acid. Cationic liposomes have been shown to mediate intracellular delivery of plasmid DNA (Felgner et al., Proc. Natl. Acad. Sci. USA, 84:7413–7416 (1987), which is herein incorporated by reference); mRNA (Malone et al., Proc., Natl. Acad. Sci. USA, 86:6077–6081 (1989), which is herein incorporated by reference); and purified transcription factors (Debs et al., J. Biol. Chem., 265:10189–10192 (1990), which is herein incorporated by reference), in functional form.

Cationic liposomes are readily available. For example, N[1-2,3-dioleyloxy) propyl]-N,N,N-triethylammonium (DOTMA) liposomes are particularly useful and are available under the trademark Lipofectin, from GIBCO BRL, Grand Island, N.Y. (See, also, Felgner et al., Proc. Natl. Acad. Sci. USA, 84:7413–7416 (1987), which is herein incorporated by reference). Other commercially available liposomes include transfectace (DDAB/DOPE) and DOTAP/DOPE (Boehringer).

Other cationic liposomes can be prepared from readily available materials using techniques well known in the art. See, e.g. PCT Publication NO: WO 90/11092 (which is herein incorporated by reference) for a description of the synthesis of DOTAP (1,2-bis(oleoyloxy)-3-(trimethylammonio)propane) liposomes. Preparation of DOTMA liposomes is explained in the literature, see, e.g., Felgner et al., Proc. Natl. Acad. Sci. USA, 84:7413–7417, which is herein incorporated by reference. Similar methods can be used to prepare liposomes from other cationic lipid materials.

Similarly, anionic and neutral liposomes are readily available, such as from Avanti Polar Lipids (Birmingham, Ala.), or can be easily prepared using readily available materials. Such materials include phosphatidyl, choline, cholesterol, phosphatidyl ethanolamine, dioleoylphosphatidyl choline (DOPC), dioleoylphosphatidyl glycerol (DOPG), dioleoylphoshatidyl ethanolamine (DOPE), among others. These materials can also be mixed with the DOTMA and DOTAP starting materials in appropriate ratios. Methods for making liposomes using these materials are well known in the art.

For example, commercially dioleoylphosphatidyl choline (DOPC), dioleoylphosphatidyl glycerol (DOPG), and dioleoylphosphatidyl ethanolamine (DOPE) can be used in various combinations to make conventional liposomes, with or without the addition of cholesterol. Thus, for example, DOPG/DOPC vesicles can be prepared by drying 50 mg each of DOPG and DOPC under a stream of nitrogen gas into a sonication vial. The sample is placed under a vacuum pump overnight and is hydrated the following day with deionized water. The sample is then sonicated for 2 hours in a capped vial, using a Heat Systems model 350 sonicator equipped with an inverted cup (bath type) probe at the maximum setting while the bath is circulated at 15 EC. Alternatively, negatively charged vesicles can be prepared without sonication to produce multilamellar vesicles or by extrusion through nucleopore membranes to produce unilamellar vesicles of discrete size. Other methods are known and available to those of skill in the art.

The liposomes can comprise multilamellar vesicles (MLVs), small unilamellar vesicles (SUVs), or large unilamellar vesicles (LUVs), with SUVs being preferred. The various liposome-nucleic acid complexes are prepared using methods well known in the art. See, e.g., Straubinger et al., Methods of Immunology, 101:512–527 (1983), which is herein incorporated by reference. For example, MLVs containing nucleic acid can be prepared by depositing a thin film of phospholipid on the walls of a glass tube and subsequently hydrating with a solution of the material to be encapsulated. SUVs are prepared by extended sonication of MLVs to produce a homogeneous population of unilamellar liposomes. The material to be entrapped is added to a suspension of preformed MLVs and then sonicated. When using liposomes containing cationic lipids, the dried lipid film is resuspended in an appropriate solution such as sterile water or an isotonic buffer solution such as 10 mM Tris/NaCl, sonicated, and then the preformed liposomes are mixed directly with the DNA. The liposome and DNA form a very stable complex due to binding of the positively charged liposomes to the cationic DNA. SUVs find use with small nucleic acid fragments. LUVs are prepared by a number of methods, well known in the art. Commonly used methods include Ca2+-EDTA chelation (Papahadjopoulos et al., Biochim. Biophys. Acta, 394:483 (1975); Wilson et al., Cell, 17:77 (1979)); ether injection (Deamer et al., Biochim. Biophys. Acta, 443:629 (1976); Ostro et al., Biochem. Biophys. Res. Commun., 76:836 (1977); Fraley et al., Proc. Natl. Acad. Sci. USA, 76:3348 (1979)); detergent dialysis (Enoch et al., Proc. Natl. Acad. Sci. USA, 76:145 (1979)); and reverse-phase evaporation (REV) (Fraley et al., J. Biol. Chem., 255:10431 (1980); Szoka et al., Proc. Natl. Acad. Sci. USA, 75:145 (1978); Schaefer-Ridder et al., Science, 215:166 (1982)), which are herein incorporated by reference.

Generally, the ratio of DNA to liposomes will be from about 10:1 to about 1:10. Preferably, the ration will be from about 5:1 to about 1:5. More preferably, the ration will be about 3:1 to about 1:3. Still more preferably, the ratio will be about 1:1.

U.S. Pat. No. 5,676,954 (which is herein incorporated by reference) reports on the injection of genetic material, complexed with cationic liposomes carriers, into mice. U.S. Pat. Nos. 4,897,355, 4,946,787, 5,049,386, 5,459,127, 5,589,466, 5,693,622, 5,580,859, 5,703,055, and international publication NO: WO 94/9469 (which are herein incorporated by reference) provide cationic lipids for use in transfecting DNA into cells and mammals. U.S. Pat. Nos. 5,589,466, 5,693,622, 5,580,859, 5,703,055, and international publication NO: WO 94/9469 (which are herein incorporated by reference) provide methods for delivering DNA-cationic lipid complexes to mammals.

In certain embodiments, cells are engineered, ex vivo or in vivo, using a retroviral particle containing RNA which comprises a sequence encoding polypeptides of the invention. Retroviruses from which the retroviral plasmid vectors may be derived include, but are not limited to, Moloney Murine Leukemia Virus, spleen necrosis virus, Rous sarcoma Virus, Harvey Sarcoma Virus, avian leukosis virus, gibbon ape leukemia virus, human immunodeficiency virus, Myeloproliferative Sarcoma Virus, and mammary tumor virnis The retroviral plasmid vector is employed to transduce packaging cell lines to form producer cell lines. Examples of packaging cells which may be transfected include, but are not limited to, the PE501, PA317, R-2, R-AM, PA12, T19-14X, VT-19-17-H2, RCRE, RCRIP, GP+E-86, GP+envAm12, and DAN cell lines as described in Miller, Human Gene Therapy, 1:5–14 (1990), which is incorporated herein by reference in its entirety. The vector may transduce the packaging cells through any means known in the art. Such means include, but are not limited to, electroporation, the use of liposomes, and CaPO4 precipitation. In one alternative, the retroviral plasmid vector may be encapsulated into a liposome, or coupled to a lipid, and then administered to a host.

The producer cell line generates infectious retroviral vector particles which include polynucleotide encoding polypeptides of the invention. Such retroviral vector particles then may be employed, to transduce eukaryotic cells, either in vitro or in vivo. The transduced eukaryotic cells will express polypeptides of the invention.

In certain other embodiments, cells are engineered, ex vivo or in vivo, with polynucleotides of the invention contained in an adenovirus vector. Adenovirus can be manipulated such that it encodes and expresses polypeptides of the invention, and at the same time is inactivated in terms of its ability to replicate in a normal lytic viral life cycle. Adenovirus expression is achieved without integration of the viral DNA into the host cell chromosome, thereby alleviating concerns about insertional mutagenesis. Furthermore, adenoviruses have been used as live enteric vaccines for many years with an excellent safety profile (Schwartzet al., Am. Rev. Respir. Dis., 109:233–238 (1974)). Finally, adenovirus mediated gene transfer has been demonstrated in a number of instances including transfer of alpha-1-antitrypsin and CFTR to the lungs of cotton rats (Rosenfeld et al., Science, 252:431–434 (1991); Rosenfeld et al., Cell, 68:143–155 (1992)). Furthermore, extensive studies to attempt to establish adenovirus as a causative agent in human cancer were uniformly negative (Green et al. Proc. Natl. Acad. Sci. USA, 76:6606 (1979)).

Suitable adenoviral vectors useful in the present invention are described, for example, in Kozarsky and Wilson, Curr. Opin. Genet. Devel., 3:499–503 (1993); Rosenfeld et al., Cell, 68:143–155 (1992); Engelhardt et al., Human Genet. Ther., 4:759–769 (1993); Yang et al., Nature Genet., 7:362–369 (1994); Wilson et al., Nature, 365:691–692 (1993); and U.S. Pat. No. 5,652,224, which are herein incorporated by reference. For example, the adenovirus vector Ad2 is useful and can be grown in human 293 cells. These cells contain the E1 region of adenovirus and constitutively express E1a and E1b, which complement the defective adenoviruses by providing the products of the genes deleted from the vector. In addition to Ad2, other varieties of adenovirus (e.g., Ad3, Ad5, and Ad7) are also useful in the present invention.

Preferably, the adenoviruses used in the present invention are replication deficient. Replication deficient adenoviruses require the aid of a helper virus and/or packaging cell line to form infectious particles. The resulting virus is capable of infecting cells and can express a polynucleotide of interest which is operably linked to a promoter, but cannot replicate in most cells. Replication deficient adenoviruses may be deleted in one or more of all or a portion of the following genes: E1a, E1b, E3, E4, E2a, or L1 through L5.

In certain other embodiments, the cells are engineered, ex vivo or in vivo, using an adeno-associated virus (AAV). AAVs are naturally occurring defective viruses that require helper viruses to produce infectious particles (Muzyczka, Curr. Topics in Microbiol. Immunol., 158:97 (1992)). It is also one of the few viruses that may integrate its DNA into non-dividing cells. Vectors containing as little as 300 base pairs of AAV can be packaged and can integrate, but space for exogenous DNA is limited to about 4.5 kb. Methods for producing and using such AAVs are known in the art. See, for example, U.S. Pat. Nos. 5,139,941, 5,173,414, 5,354,678, 5,436,146, 5,474,935, 5,478,745, and 5,589,377.

For example, an appropriate AAV vector for use in the present invention will include all the sequences necessary for DNA replication, encapsidation, and host-cell integration. The polynucleotide construct containing polynucleotides of the invention is inserted into the AAV vector using standard cloning methods, such as those found in Sambrook et al., Molecular Cloning: A Laboratory Manual, Cold Spring Harbor Press (1989). The recombinant AAV vector is then transfected into packaging cells which are infected with a helper virus, using any standard technique, including lipofection, electroporation, calcium phosphate precipitation, etc. Appropriate helper viruses include adenoviruses, cytomegaloviruses, vaccinia viruses, or herpes viruses. Once the packaging cells are transfected and infected they will produce infectious AAV viral particles which contain the polynucleotide construct of the invention. These viral particles are then used to transduce eukaryotic cells, either ex vivo or in vivo. The transduced cells will contain the polynucleotide construct integrated into its genome, and will express the desired gene product.

Another method of gene therapy involves operably associating heterologous control regions and endogenous polynucleotide sequences (e.g. encoding the polypeptide sequence of interest) via homologous recombination (see, e.g., U.S. Pat. No. 5,641,670, issued Jun. 24, 1997; International Publication NO: WO 96/29411, published Sep. 26, 1996; International Publication NO: WO 94/12650, published Aug. 4, 1994; Koller et al., Proc. Natl. Acad. Sci. USA, 86:8932–8935 (1989); and Zijlstra et al., Nature, 342:435–438 (1989). This method involves the activation of a gene which is present in the target cells, but which is not normally expressed in the cells, or is expressed at a lower level than desired.

Polynucleotide constructs are made, using standard techniques known in the art, which contain the promoter with targeting sequences flanking the promoter. Suitable promoters are described herein. The targeting sequence is sufficiently complementary to an endogenous sequence to permit homologous recombination of the promoter-targeting sequence with the endogenous sequence. The targeting sequence will be sufficiently near the 5' end of the desired endogenous polynucleotide sequence so the promoter will be operably linked to the endogenous sequence upon homologous recombination.

The promoter and the targeting sequences can be amplified using PCR. Preferably, the amplified promoter contains distinct restriction enzyme sites on the 5' and 3' ends. Preferably, the 3' end of the first targeting sequence contains the same restriction enzyme site as the 5' end of the amplified promoter and the 5' end of the second targeting sequence contains the same restriction site as the 3' end of the amplified promoter. The amplified promoter and targeting sequences are digested and ligated together.

The promoter-targeting sequence construct is delivered to the cells, either as naked polynucleotide, or in conjunction with transfection-facilitating agents, such as liposomes, viral sequences, viral particles, whole viruses, lipofection, precipitating agents, etc., described in more detail above. The P promoter-targeting sequence can be delivered by any method, included direct needle injection, intravenous injection, topical administration, catheter infusion, particle accelerators, etc. The methods are described in more detail below.

The promoter-targeting sequence construct is taken up by cells. Homologous recombination between the construct and the endogenous sequence takes place, such that an endogenous sequence is placed under the control of the promoter. The promoter then drives the expression of the endogenous sequence.

The polynucleotides encoding polypeptides of the present invention may be administered along with other polynucleotides encoding angiogenic proteins. Angiogenic proteins include, but are not limited to, acidic and basic fibroblast growth factors, VEGF-1, VEGF-2 (VEGF-C), VEGF-3 (VEGF-B), epidermal growth factor alpha and beta, platelet-derived endothelial cell growth factor, platelet-derived growth factor, tumor necrosis factor alpha, hepatocyte growth factor, insulin like growth factor, colony stimulating factor, macrophage colony stimulating factor, granulocyte/macrophage colony stimulating factor, and nitric oxide synthase.

Preferably, the polynucleotide encoding a polypeptide of the invention contains a secretory signal sequence that facilitates secretion of the protein. Typically, the signal sequence is positioned in the coding region of the polynucleotide to be expressed towards or at the 5' end of the coding region. The signal sequence may be homologous or heterologous to the polynucleotide of interest and may be homologous or heterologous to the cells to be transfected. Additionally, the signal sequence may be chemically synthesized using methods known in the art.

Any mode of administration of any of the above-described polynucleotides constructs can be used so long as the mode results in the expression of one or more molecules in an amount sufficient to provide a therapeutic effect. This includes direct needle injection, systemic injection, catheter infusion, biolistic injectors, particle accelerators (i.e., "gene guns"), gelfoam sponge depots, other commercially available depot materials, osmotic pumps (e.g., Alza minipumps), oral or suppositorial solid (tablet or pill) pharmaceutical formulations, and decanting or topical applications during surgery. For example, direct injection of naked calcium phosphate-precipitated plasmid into rat liver and rat spleen or a protein-coated plasmid into the portal vein has resulted in gene expression of the foreign gene in the rat livers. (Kaneda et al., Science, 243:375 (1989)).

A preferred method of local administration is by direct injection. Preferably, a recombinant molecule of the present invention complexed with a delivery vehicle is administered by direct injection into or locally within the area of arteries. Administration of a composition locally within the area of arteries refers to injecting the composition centimeters and preferably, millimeters within arteries.

Another method of local administration is to contact a polynucleotide construct of the present invention in or around a surgical wound. For example, a patient can undergo surgery and the polynucleotide construct can be coated on the surface of tissue inside the wound or the construct can be injected into areas of tissue inside the wound.

Therapeutic compositions useful in systemic administration, include recombinant molecules of the present invention complexed to a targeted delivery vehicle of the present invention. Suitable delivery vehicles for use with systemic administration comprise liposomes comprising ligands for targeting the vehicle to a particular site.

Preferred methods of systemic administration, include intravenous injection, aerosol, oral and percutaneous (topical) delivery. Intravenous injections can be performed using methods standard in the art. Aerosol delivery can also be performed using methods standard in the art (see, for example, Stribling et al., Proc. Natl. Acad. Sci. USA, 189:11277–11281 (1992), which is incorporated herein by reference). Oral delivery can be performed by complexing a polynucleotide construct of the present invention to a carrier capable of withstanding degradation by digestive enzymes in the gut of an animal. Examples of such carriers, include plastic capsules or tablets, such as those known in the art. Topical delivery can be performed by mixing a polynucleotide construct of the present invention with a lipophilic reagent (e.g., DMSO) that is capable of passing into the skin.

Determining an effective amount of substance to be delivered can depend upon a number of factors including, for example, the chemical structure and biological activity of the substance, the age and weight of the animal, the precise condition requiring treatment and its severity, and the route of administration. The frequency of treatments depends unon a number of factors, such as the amount of polynucleotide constructs administered per dose, as well as the health and history of the subject. The precise amount, number of doses, and timing of doses will be determined by the attending physician or veterinarian. Therapeutic compositions of the present invention can be administered to any animal, preferably to mammals and birds. Preferred mammals include humans, dogs, cats, mice, rats, rabbits sheep, cattle, horses and pigs, with humans being particularly preferred.

Biological Activities

The polynucleotides or polypeptides, or agonists or antagonists of the present invention can be used in assays to test for one or more biological activities. If these polynucleotides and polypeptides do exhibit activity in a particular assay, it is likely that these molecules may be involved in the diseases associated with the biological activity. Thus, the polynucleotides or polypeptides, or agonists or antagonists could be used to treat the associated disease.

Immune Activity

The polynucleotides or polypeptides, or agonists or antagonists of the present invention may be useful in treating, preventing, and/or diagnosing diseases, disorders, and/or conditions of the immune system, by activating or inhibiting the proliferation, differentiation, or mobilization (chemotaxis) of immune cells. Immune cells develop through a process called hematopoiesis, producing myeloid (platelets, red blood cells, neutrophils, and macrophages) and lymphoid (B and T lymphocytes) cells from pluripotent stem cells. The etiology of these immune diseases, disorders, and/or conditions may be genetic, somatic, such as cancer or some autoimmune diseases, disorders, and/or conditions, acquired (e.g., by chemotherapy or toxins), or infectious. Moreover, a polynucleotides or polypeptides, or agonists or antagonists of the present invention can be used as a marker or detector of a particular immune system disease or disorder.

A polynucleotides or polypeptides, or agonists or antagonists of the present invention may be useful in treating, preventing, and/or diagnosing diseases, disorders, and/or conditions of hematopoietic cells. A polynucleotides or polypeptides, or agonists or antagonists of the present invention could be used to increase differentiation and proliferation of hematopoietic cells, including the pluripotent stem cells, in an effort to treat or prevent those diseases, disorders, and/or conditions associated with a decrease in certain (or many) types hematopoietic cells. Examples of immunologic deficiency syndromes include, but are not limited to: blood protein diseases, disorders, and/or conditions (e.g. agammaglobulinemia, dysgammaglobulinemia), ataxia telangiectasia, common variable immunodeficiency, Digeorge Syndrome, HIV infection, HTLV-BLV infection, leukocyte adhesion deficiency syndrome, lymphopenia, phagocyte bactericidal dysfunction, severe combined immunodeficiency (SCIDs), Wiskott-Aldrich Disorder, anemia, thrombocytopenia, or hemoglobinuria.

Moreover, a polynucleotides or polypeptides, or agonists or antagonists of the present invention could also be used to modulate hemostatic (the stopping of bleeding) or thrombolytic activity (clot formation). For example, by increasing hemostatic or thrombolytic activity, a polynucleotides or polypeptides, or agonists or antagonists of the present invention could be used to treat or prevent blood coagulation diseases, disorders, and/or conditions (e.g., afibrinogenemia, factor deficiencies, arterial thrombosis, venous thrombosis, etc.), blood platelet diseases, disorders, and/or conditions (e.g. thrombocytopenia), or wounds resulting from trauma, surgery, or other causes. Alternatively, a polynucleotides or polypeptides, or agonists or antagonists of the present invention that can decrease hemostatic or thrombolytic activity could be used to inhibit or dissolve clotting. Polynucleotides or polypeptides, or agonists or antagonists of the present invention are may also be useful for the detection, prognosis, treatment, and/or prevention of heart attacks (infarction), strokes, scarring, fibripolysis, uncontrolled bleeding, uncontrolled coagulation, uncontrolled complement fixation, and/or inflammation.

A polynucleotides or polypeptides, or agonists or antagonists of the present invention may also be useful in treating, preventing, and/or diagnosing autoimmune diseases, disorders, and/or conditions. Many autoimmune diseases, disorders, and/or conditions result from inappropriate recognition of self as foreign material by immune cells. This inappropriate recognition results in an immune response leading to the destruction of the host tissue. Therefore, the administration of a polynucleotides or polypeptides, or agonists or antagonists of the present invention that inhibits an immune response, particularly the proliferation, differentiation, or chemotaxis of T-cells, may be an effective therapy in preventing autoimmune diseases, disorders, and/or conditions.

Examples of autoimmune diseases, disorders, and/or conditions that can be treated, prevented, and/or diagnosed or detected by the present invention include, but are not limited to: Addison's Disease, hemolytic anemia, antiphospholipid syndrome, rheumatoid arthritis, dermatitis, allergic encephalomyelitis, glomerulonephritis, Goodpasture's Syndrome, Graves' Disease, Multiple Sclerosis, Myasthenia Gravis, Neuritis, Ophthalmia, Bullous Pemphigoid, Pemphigus, Polyendocrinopathies, Purpura, Reiter's Disease, Stiff-Man Syndrome, Autoimmune Thyroiditis, Systemic Lupus Erythematosus, Autoimmune Pulmonary Inflammation, Guillain-Barre Syndrome, insulin dependent diabetes mellitis, and autoimmune inflammatory eye disease.

Similarly, allergic reactions and conditions, such as asthma (particularly allergic asthma) or other respiratory problems, may also be treated, prevented, and/or diagnosed by polynucleotides or polypeptides, or agonists or antagonists of the present invention. Moreover, these molecules can be used to treat anaphylaxis, hypersensitivity to an antigenic molecule, or blood group incompatibility.

A polynucleotides or polypeptides, or agonists or antagonists of the present invention may also be used to treat, prevent, and/or diagnose organ rejection or graft-versus-host disease (GVHD). Organ rejection occurs by host immune cell destruction of the transplanted tissue through an immune response. Similarly, an immune response is also involved in GVHD, but, in this case, the foreign transplanted immune cells destroy the host tissues. The administration of a polynucleotides or polypeptides, or agonists or antagonists of the present invention that inhibits an immune response, particularly the proliferation, differentiation, or chemotaxis of T-cells, may be an effective therapy in preventing organ rejection or GVHD.

Similarly, a polynucleotides or polypeptides, or agonists or antagonists of the present invention may also be used to modulate inflammation. For example, the polypeptide or polynucleotide or agonists or antagonist may inhibit the proliferation and differentiation of cells involved in an inflammatory response. These molecules can be used to treat, prevent, and/or diagnose inflammatory conditions, both chronic and acute conditions, including chronic prostatitis, granulomatous prostatitis and malacoplakia, inflammation associated with infection (e.g., septic shock, sepsis, or systemic inflammatory response syndrome (SIRS)), ischemia-reperfusion injury, endotoxin lethality, arthritis, complement-mediated hyperacute rejection, nephritis, cytokine or chemokine induced lung injury, inflammatory bowel disease, Crohn's disease, or resulting from over production of cytokines (e.g., TNF or IL-1.)

Hyperproliferative Disorders

A polynucleotides or polypeptides, or agonists or antagonists of the invention can be used to treat, prevent, and/or diagnose hyperproliferative diseases, disorders, and/or conditions, including neoplasms. A polynucleotides or polypeptides, or agonists or antagonists of the present invention may inhibit the proliferation of the disorder through direct or indirect interactions. Alternatively, a polynucleotides or polypeptides, or agonists or antagonists of the present invention may proliferate other cells which can inhibit the hyperproliferative disorder.

For example, by increasing an immune response, particularly increasing antigenic qualities of the hyperproliferative disorder or by proliferating, differentiating, or mobilizing T-cells, hyperproliferative diseases, disorders, and/or conditions can be treated, prevented, and/or diagnosed. This immune response may be increased by either enhancing an existing immune response, or by initiating a new immune response. Alternatively, decreasing an immune response may also be a method of treating, preventing, and/or diagnosing hyperproliferative diseases, disorders, and/or conditions, such as a chemotherapeutic agent.

Examples of hyperproliferative diseases, disorders, and/or conditions that can be treated, prevented, and/or diagnosed by polynucleotides or polypeptides, or agonists or antagonists of the present invention include, but are not limited to neoplasms located in the: colon, abdomen, bone, breast, digestive system, liver, pancreas, peritoneum, endocrine glands (adrenal, parathyroid, pituitary, testicles, ovary, thymus, thyroid), eye, head and neck, nervous (central and peripheral), lymphatic system, pelvic, skin, soft tissue, spleen, thoracic, and urogenital.

Similarly, other hyperproliferative diseases, disorders, and/or conditions can also be treated, prevented, and/or diagnosed by a polynucleotides or polypeptides, or agonists or antagonists of the present invention. Examples of such hyperproliferative diseases, disorders, and/or conditions include, but are not limited to: hypergammaglobulinemia, lymphoproliferative diseases, disorders, and/or conditions, paraproteinemias, purpura, sarcoidosis, Sezary Syndrome, Waldenstron's Macroglobulinemia, Gaucher's Disease, histiocytosis, and any other hyperproliferative disease, besides neoplasia, located in an organ system listed above.

One preferred embodiment utilizes polynucleotides of the present invention to inhibit aberrant cellular division, by gene therapy using the present invention, and/or protein fusions or fragments thereof.

Thus, the present invention provides a method for treating or preventing cell proliferative diseases, disorders, and/or conditions by inserting into an abnormally proliferating cell a polynucleotide of the present invention, wherein said polynucleotide represses said expression.

Another embodiment of the present invention provides a method of treating or preventing cell-proliferative diseases, disorders, and/or conditions in individuals comprising administration of one or more active gene copies of the present invention to an abnormally proliferating cell or cells. In a preferred embodiment, polynucleotides of the present invention is a DNA construct comprising a recombinant expression vector effective in expressing a DNA sequence encoding said polynucleotides. In another preferred embodiment of the present invention, the DNA construct encoding the polynucleotides of the present invention is inserted into cells to be treated utilizing a retrovirus, or more Preferably an adenoviral vector (See G J. Nabel, et. al., PNAS 1999 96: 324–326, which is hereby incorporated by reference). In a most preferred embodiment, the viral vector is defective and will not transform non-proliferating cells, only proliferating cells. Moreover, in a preferred embodiment, the polynucleotides of the present invention inserted into proliferating cells either alone, or in combination with or fused to other polynucleotides, can then be modulated via an external stimulus (i.e. magnetic, specific small molecule, chemical, or drug administration, etc.), which acts upon the promoter upstream of said polynucleotides to induce expression of the encoded protein product. As such the beneficial therapeutic affect of the present invention may be expressly modulated (i.e. to increase, decrease, or inhibit expression of the present invention) based upon said external stimulus.

Polynucleotides of the present invention may be useful in repressing expression of oncogenic genes or antigens. By "repressing expression of the oncogenic genes" is intended the suppression of the transcription of the gene, the degradation of the gene transcript (pre-message RNA), the inhibition of splicing, the destruction of the messenger RNA, the prevention of the post-translational modifications of the protein, the destruction of the protein, or the inhibition of the normal function of the protein.

For local administration to abnormally proliferating cells, polynucleotides of the present invention may be administered by any method known to those of skill in the art including, but not limited to transfection, electroporation, microinjection of cells, or in vehicles such as liposomes, lipofectin, or as naked polynucleotides, or any other method described throughout the specification. The polynucleotide of the present invention may be delivered by known gene delivery systems such as, but not limited to, retroviral vectors (Gilboa, J. Virology 44:845 (1982); Hocke, Nature 320:275 (1986); Wilson, et al., Proc. Natl. Acad. Sci. U.S.A. 85:3014), vaccinia virus system (Chakrabarty et al., Mol. Cell Biol. 5:3403 (1985) or other efficient DNA delivery systems (Yates et al., Nature 313:812 (1985)) known to those skilled in the art. These references are exemplary only and are hereby incorporated by reference. In order to specifically deliver or transfect cells which are abnormally proliferating and spare non-dividing cells, it is preferable to utilize a retrovirus, or adenoviral (as described in the art and elsewhere herein) delivery system known to those of skill in the art. Since host DNA replication is required for retroviral DNA to integrate and the retrovirus will be unable to self replicate due to the lack of the retrovirus genes needed for its life cycle. Utilizing such a retroviral delivery system for polynucleotides of the present invention will target said gene and constructs to abnormally proliferating cells and will spare the non-dividing normal cells.

The polynucleotides of the present invention may be delivered directly to cell proliferative disorder/disease sites in internal organs, body cavities and the like by use of imaging devices used to guide an injecting needle directly to the disease site. The polynucleotides of the present invention may also be administered to disease sites at the time of surgical intervention.

By "cell proliferative disease" is meant any human or animal disease or disorder, affecting any one or any combination of organs, cavities, or body parts, which is characterized by single or multiple local abnormal proliferations of cells, groups of cells, or tissues, whether benign or malignant.

Any amount of the polynucleotides of the present invention may be administered as long as it has a biologically inhibiting effect on the proliferation of the treated cells. Moreover, it is possible to administer more than one of the polynucleotide of the present invention simultaneously to the same site. By "biologically inhibiting" is meant partial or total growth inhibition as well as decreases in the rate of proliferation or growth of the cells. The biologically inhibitory dose may be determined by assessing the effects of the polynucleotides of the present invention on target malignant or abnormally proliferating cell growth in tissue culture, tumor growth in animals and cell cultures, or any other method known to one of ordinary skill in the art.

The present invention is further directed to antibody-based therapies which involve administering of anti-polypeptides and anti-polynucleotide antibodies to a mammalian, preferably human, patient for treating, preventing, and/or diagnosing one or more of the described diseases, disorders, and/or conditions. Methods for producing anti-polypeptides and anti-polynucleotide antibodies polyclonal and monoclonal antibodies are described in detail elsewhere herein. Such antibodies may be provided in pharmaceutically acceptable compositions as known in the art or as described herein.

A summary of the ways in which the antibodies of the present invention may be used therapeutically includes binding polynucleotides or polypeptides of the present invention locally or systemically in the body or by direct cytotoxicity of the antibody, e.g. as mediated by complement (CDC) or by effector cells (ADCC). Some of these approaches are described in more detail below. Armed with the teachings provided herein, one of ordinary skill in the art will know how to use the antibodies of the present invention for diagnostic, monitoring or therapeutic purposes without undue experimentation.

In particular, the antibodies, fragments and derivatives of the present invention are useful for treating, preventing, and/or diagnosing a subject having or developing cell proliferative and/or differentiation diseases, disorders, and/or conditions as described herein. Such treatment comprises administering a single or multiple doses of the antibody, or a fragment, derivative, or a conjugate thereof.

The antibodies of this invention may be advantageously utilized in combination with other monoclonal or chimeric antibodies, or with lymphokines or hematopoietic growth factors, for example, which serve to increase the number or activity of effector cells which interact with the antibodies.

It is preferred to use high affinity and/or potent in vivo inhibiting and/or neutralizing antibodies against polypeptides or polynucleotides of the present invention, fragments or regions thereof, for both immunoassays directed to and therapy of diseases, disorders, and/or conditions related to polynucleotides or polypeptides, including fragments thereof, of the present invention. Such antibodies, fragments, or regions, will preferably have an affinity for polynucleotides or polypeptides, including fragments thereof. Preferred binding affinities include those with a dissociation constant or Kd less than 5×10−6M, 10−6M, 5×10−7M, 10−7M, 5×10−8M, 10−8M, 5×10−9M, 10−9M, 5×10−10M, 10−10M, 5×10−11M, 10−11M, 5×10−12M, 10−12M, 5×10−13M, 10−13M, 5×10−14M, 10−14M, 5×10−15M, and 10−15M.

Moreover, polypeptides of the present invention may be useful in inhibiting the angiogenesis of proliferative cells or tissues, either alone, as a protein fusion, or in combination with other polypeptides directly or indirectly, as described elsewhere herein. In a most preferred embodiment, said anti-angiogenesis effect may be achieved indirectly, for example, through the inhibition of hematopoietic, tumor-specific cells, such as tumor-associated macrophages (See Joseph I B, et al. J Natl Cancer Inst, 90(21):1648–53 (1998), which is hereby incorporated by reference). Antibodies directed to polypeptides or polynucleotides of the present invention may also result in inhibition of angiogenesis directly, or indirectly (See Witte L, et al., Cancer Metastasis Rev. 17(2): 155–61 (1998), which is hereby incorporated by reference)).

Polypeptides, including protein fusions, of the present invention, or fragments thereof may be useful in inhibiting proliferative cells or tissues through the induction of apoptosis. Said polypeptides may act either directly, or indirectly to indirectly to induce apoptosis of proliferative cells and tissues, for example in the activation of a death-domain receptor, such as tumor necrosis factor (TNF) receptor-1, CD95 (Fas/APO-1), TNF-receptor-related apoptosis-mediated protein (TRAMP) and TNF-related apoptosis-inducing ligand (TRAIL) receptor-1 and -2 (See Schulze-Osthoff K, et al., Eur J Biochem 254(3):439–59 (1998), which is hereby incorporated by reference). Moreover, in another preferred embodiment of the present invention, said polypeptides may induce apoptosis through other mechanisms, such as in the activation of other proteins which will activate apoptosis, or through stimulating the expression of said proteins, either alone or in combination with small molecule drugs or adjuvants, such as apoptonin, galectins, thioredoxins, antiinflammatory proteins (See for example, Mutat. Res. 400(1–2):447–55 (1998), Med Hypotheses.50(5):423–33 (1998), Chem. Biol. Interact. April 24;111–112:23–34 (1998), J Mol Med.76(6):402–12 (1998), Int. J. Tissue React. 20(1):3–15 (1998), which are all hereby incorporated by reference).

Polypeptides, including protein fusions to, or fragments thereof, of the present invention are useful in inhibiting the metastasis of proliferative cells or tissues. Inhibition may occur as a direct result of administering polypeptides, or antibodies directed to said polypeptides as described elsewhere herein, or indirectly, such as activating the expression of proteins known to inhibit metastasis, for example alpha 4 integrins, (See, e.g., Curr Top Microbiol Immunol 1998;231:125–41, which is hereby incorporated by reference). Such therapeutic affects of the present invention may be achieved either alone, or in combination with small molecule drugs or adjuvants.

In another embodiment, the invention provides a method of delivering compositions containing the polypeptides of the invention (e.g., compositions containing polypeptides or polypeptide antibodies associated with heterologous polypeptides, heterologous nucleic acids, toxins, or prodrugs) to targeted cells expressing the polypeptide of the present invention. Polypeptides or polypeptide antibodies of the invention may be associated with heterologous polypeptides, heterologous nucleic acids, toxins, or prodrugs via hydrophobic, hydrophilic, ionic and/or covalent interactions.

Polypeptides, protein fusions to, or fragments thereof, of the present invention are useful in enhancing the immunogenicity and/or antigenicity of proliferating cells or tissues, either directly, such as would occur if the polypeptides of the present invention 'vaccinated' the immune response to respond to proliferative antigens and immunogens, or indirectly, such as in activating the expression of proteins known to enhance the immune response (e.g. chemokines), to said antigens and immunogens.

Diseases at the Cellular Level

Diseases associated with increased cell survival or the inhibition of apoptosis that could be treated, prevented, and/or diagnosed by the polynucleotides or polypeptides and/or antagonists or agonists of the invention, include cancers (such as follicular lymphomas, carcinomas with p53 mutations, and hormone-dependent tumors, including, but not limited to colon cancer, cardiac tumors, pancreatic cancer, melanoma, retinoblastoma, glioblastoma, lung cancer, intestinal cancer, testicular cancer, stomach cancer, neuroblastoma, myxoma, myoma, lymphoma, endothelioma, osteoblastoma, osteoclastoma, osteosarcoma, chondrosarcoma, adenoma, breast cancer, prostate cancer, Kaposi's sarcoma and ovarian cancer); autoimmune diseases, disorders, and/or conditions (such as, multiple sclerosis, Sjogren's syndrome, Hashimoto's thyroiditis, biliary cirrhosis, Behcet's disease, Crohn's disease, polymyositis, systemic lupus erythematosus and immune-related glomerulonephritis and rheumatoid arthritis) and viral infections (such as herpes viruses, pox viruses and adenoviruses), inflammation, graft v. host disease, acute graft rejection, and chronic graft rejection. In preferred embodiments, the polynucleotides or polypeptides, and/or agonists or antagonists of the invention are used to inhibit growth, progression, and/or metastasis of cancers, in particular those listed above.

Additional diseases or conditions associated with increased cell survival that could be treated, prevented or diagnosed by the polynucleotides or polypeptides, or agonists or antagonists of the invention, include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

Diseases associated with increased apoptosis that could be treated, prevented, and/or diagnosed by the polynucleotides or polypeptides, and/or agonists or antagonists of the invention, include AIDS; neurodegenerative diseases, disorders, and/or conditions (such as Alzheimer's disease, Parkinson's disease, Amyotrophic lateral sclerosis, Retinitis pigmentosa, Cerebellar degeneration and brain tumor or prior associated disease); autoimmune diseases, disorders, and/or conditions (such as, multiple sclerosis, Sjogren's syndrome, Hashimoto's thyroiditis, biliary cirrhosis, Behcet's disease, Crohn's disease, polymyositis, systemic lupus erythematosus and immune-related glomerulonephritis and rheumatoid arthritis) myelodysplastic syndromes (such as aplastic anemia), graft v. host disease, ischemic injury (such as that caused by myocardial infarction, stroke and reperfusion injury), liver injury (e.g., hepatitis related liver injury, ischemia/reperfusion injury, cholestosis (bile duct injury) and liver cancer); toxin-induced liver disease (such as that caused by alcohol), septic shock, cachexia and anorexia.

Wound Healing and Epithelial Cell Proliferation

In accordance with yet a further aspect of the present invention, there is provided a process for utilizing the polynucleotides or polypeptides, and/or agonists or antagonists of the invention, for therapeutic purposes, for example, to stimulate epithelial cell proliferation and basal keratinocytes for the purpose of wound healing, and to stimulate hair follicle production and healing of dermal wounds. Polynucleotides or polypeptides, as well as agonists or antagonists of the invention, may be clinically useful in stimulating wound healing including surgical wounds, excisional wounds, deep wounds involving damage of the dermis and epidermis, eye tissue wounds, dental tissue wounds, oral cavity wounds, diabetic ulcers, dermal ulcers, cubitus ulcers, arterial ulcers, venous stasis ulcers, burns resulting from heat exposure or chemicals, and other abnormal wound healing conditions such as uremia, malnutrition, vitamin deficiencies and complications associated with systemic treatment with steroids, radiation therapy and antineoplastic drugs and antimetabolites. Polynucleotides or polypeptides, and/or agonists or antagonists of the invention, could be used to promote dermal reestablishment subsequent to dermal loss The polynucleotides or polypeptides, and/or agonists or antagonists of the invention, could be used to increase the adherence of skin grafts to a wound bed and to stimulate re-epithelialization from the wound bed. The following are a non-exhaustive list of grafts that polynucleotides or polypeptides, agonists or antagonists of the invention, could be used to increase adherence to a wound bed: autografts, artificial skin, allografts, autodermic graft, autoepidermic grafts, avacular grafts, Blair-Brown grafts, bone graft, brephoplastic grafts, cutis graft, delayed graft, dermic graft, epidermic graft, fascia graft, full thickness graft, heterologous graft, xenograft, homologous graft, hyperplastic graft, lamellar graft, mesh graft, mucosal graft, Ollier-Thiersch graft, omenpal graft, patch graft, pedicle graft, penetrating graft, split skin graft, thick split graft. The polynucleotides or polypeptides, and/or agonists or antagonists of the invention, can be used to promote skin strength and to improve the appearance of aged skin.

It is believed that the polynucleotides or polypeptides, and/or agonists or antagonists of the invention, will also produce changes in hepatocyte proliferation, and epithelial cell proliferation in the lung, breast, pancreas, stomach, small intestine, and large intestine. The polynucleotides or polypeptides, and/or agonists or antagonists of the invention, could promote proliferation of epithelial cells such as sebocytes, hair follicles, hepatocytes, type II pneumocytes, mucin-producing goblet cells, and other epithelial cells and their progenitors contained within the skin, lung, liver, and gastrointestinal tract. The polynucleotides or polypeptides, and/or agonists or antagonists of the invention, may promote proliferation of endothelial cells, keratinocytes, and basal keratinocytes.

The polynucleotides or polypeptides, and/or agonists or antagonists of the invention, could also be used to reduce the side effects of gut toxicity that result from radiation, chemotherapy treatments or viral infections. The polynucleotides or polypeptides, and/or agonists or antagonists of the invention, may have a cytoprotective effect on the small intestine mucosa. The polynucleotides or polypeptides, and/or agonists or antagonists of the invention, may also stimulate healing of mucositis (mouth ulcers) that result from chemotherapy and viral infections.

The polynucleotides or polypeptides, and/or agonists or antagonists of the invention, could further be used in full regeneration of skin in full and partial thickness skin defects, including burns, (i.e., repopulation of hair follicles, sweat glands, and sebaceous glands), treatment of other skin defects such as psoriasis. The polynucleotides or polypeptides, and/or agonists or antagonists of the invention, could be used to treat epidermolysis bullosa, a defect in adherence of the epidermis to the underlying dermis which results in frequent, open and painful blisters by accelerating reepithelialization of these lesions. The polynucleotides or polypeptides, and/or agonists or antagonists of the invention, could also be used to treat gastric and doudenal ulcers and help heal by scar formation of the mucosal lining and regeneration of glandular mucosa and duodenal mucosal lining more rapidly. Inflamamatory bowel diseases, such as Crohn's disease and ulcerative colitis, are diseases which result in destruction of the mucosal surface of the small or large intestine, respectively. Thus, the polynucleotides or polypeptides, and/or agonists or antagonists of the invention, could be used to promote the resurfacing of the mucosal surface to aid more rapid healing and to prevent progression of inflammatory bowel disease. Treatment with the polynucleotides or polypeptides, and/or agonists or antagonists of the invention, is expected to have a significant effect on the production of mucus throughout the gastrointestinal tract and could be used to protect the intestinal mucosa from injurious substances that are ingested or following surgery. The polynucleotides or polypeptides, and/or agonists or antagonists of the invention, could be used to treat diseases associate with the under expression of the polynucleotides of the invention.

Moreover, the polynucleotides or polypeptides, and/or agonists or antagonists of the invention, could be used to prevent and heal damage to the lungs due to various pathological states. A growth factor such as the polynucleotides or polypeptides, and/or agonists or antagonists of the invention, which could stimulate proliferation and differentiation and promote the repair of alveoli and brochiolar epithelium to prevent or treat acute or chronic lung damage. For example, emphysema, which results in the progressive loss of aveoli, and inhalation injuries, i.e., resulting from smoke inhalation and burns, that cause necrosis of the bronchiolar epithelium and alveoli could be effectively treated, prevented, and/or diagnosed using the polynucleotides or polypeptides, and/or agonists or antagonists of the invention. Also, the polynucleotides or polypeptides, and/or agonists or antagonists of the invention, could be used to stimulate the proliferation of and differentiation of type II pneumocytes, which may help treat or prevent disease such as hyaline membrane diseases, such as infant respiratory distress syndrome and bronchopulmonary displasia, in premature infants.

The polynucleotides or polypeptides, and/or agonists or antagonists of the invention, could stimulate the proliferation and differentiation of hepatocytes and, thus, could be used to alleviate or treat liver diseases and pathologies such as fulminant liver failure caused by cirrhosis, liver damage caused by viral hepatitis and toxic substances (i.e., acetaminophen, carbon tetraholoride and other hepatotoxins known in the art).

In addition, the polynucleotides or polypeptides, and/or agonists or antagonists of the invention, could be used treat or prevent the onset of diabetes mellitus. In patients with newly diagnosed Types I and II diabetes, where some islet cell function remains, the polynucleotides or polypeptides, and/or agonists or antagonists of the invention, could be used to maintain the islet function so as to alleviate, delay or prevent permanent manifestation of the disease. Also, the polynucleotides or polypeptides, and/or agonists or antagonists of the invention, could be used as an auxiliary in islet cell transplantation to improve or promote islet cell function.

Infectious Disease

A polypeptide or polynucleotide and/or agonist or antagonist of the present invention can be used to treat, prevent, and/or diagnose infectious agents. For example, by increasing the immune response, particularly increasing the proliferation and differentiation of B and/or T cells, infectious diseases may be treated, prevented, and/or diagnosed. The immune response may be increased by either enhancing an existing immune response, or by initiating a new immune response. Alternatively, polypeptide or polynucleotide and/or agonist or antagonist of the present invention may also directly inhibit the infectious agent, without necessarily eliciting an immune response.

Viruses are one example of an infectious agent that can cause disease or symptoms that can be treated, prevented, and/or diagnosed by a polynucleotide or polypeptide and/or agonist or antagonist of the present invention. Examples of viruses, include, but are not limited to Examples of viruses, include, but are not limited to the following DNA and RNA viruses and viral families: Arbovirus, Adenoviridae, Arenaviridae, Arterivirus, Birnaviridae, Bunyaviridae, Caliciviridae, Circoviridae, Coronaviridae, Dengue, EBV, HIV, Flaviviridae, Hepadnaviridae (Hepatitis), Herpesviridae (such as, Cytomegalovirus, Herpes Simplex, Herpes Zoster), Mononegavirus (e.g., Paramyxoviridae, Morbillivirus, Rhabdoviridae), Orthomyxoviridae (e.g., Influenza A, Influenza B, and parainfluenza), Papiloma virus, Papovaviridae, Parvoviridae, Picornaviridae, Poxviridae (such as Smallpox or Vaccinia), Reoviridae (e.g., Rotavirus), Retroviridae (HTLV-I, HTLV-II, Lentivirus), and Togaviridae (e.g., Rubivirus). Viruses falling within these families can cause a variety of diseases or symptoms, including, but not limited to: arthritis, bronchiollitis, respiratory syncytial virus, encephalitis, eye infections (e.g., conjunctivitis, keratitis), chronic fatigue syndrome, hepatitis (A, B, C, E, Chronic Active, Delta), Japanese B encephalitis, Junin, Chikungunya, Rift Valley fever, yellow fever, meningitis, opportunistic infections (e.g., AIDS), pneumonia, Burkitt's Lymphoma, chickenpox, hemorrhagic fever, Measles, Mumps, Parainfluenza, Rabies, the common cold, Polio, leukemia, Rubella, sexually transmitted diseases, skin diseases (e.g., Kaposi's, warts) and viremia. polynucleotides or polypeptides, or agonists or antagonists of the invention, can be used to treat, prevent, and/or diagnose any of these symptoms or diseases. In specific embodiments, polynucleotides, polypeptides, or agonists or antagonists of the invention are used to treat, prevent, and/or diagnose: meningitis, Dengue, EBV, and/or hepatitis (e.g., hepatitis B). In an additional specific embodiment polynucleotides, polypeptides, or agonists or antagonists of the invention are used to treat patients nonresponsive to one or more other commercially available hepatitis vaccines. In a further specific embodiment polynucleotides, polypeptides, or agonists or antagonists of the invention are used to treat, prevent, and/or diagnose AIDS.

Similarly, bacterial or fungal agents that can cause disease or symptoms and that can be treated, prevented, and/or diagnosed by a polynucleotide or polypeptide and/or agonist or antagonist of the present invention include, but not limited to, include, but not limited to, the following Gram-Negative and Gram-positive bacteria and bacterial families and fungi: Actinomycetales (e.g., Corynebacterium, Mycobacterium, Norcardia), *Cryptococcus neoformans*, Aspergillosis, Bacillaceae (e.g., Anthrax, Clostridium), Bacteroidaceae, Blastomycosis, Bordetella, Borrelia (e.g., *Borrelia burgdorferi*), Brucellosis, Candidiasis, Campylobacter, Coccidioidomycosis, Cryptococcosis, Dermatocycoses, *E. coli* (e.g., Enterotoxigenic *E. coli* and Enterohemorrhagic *E. coli*), Enterobacteriaceae (Klebsiella, Salmonella (e.g., *Salmonella typhi*, and *Salmonella paratyphi*), Serratia, Yersinia), Erysipelothrix, Helicobacter, Legionellosis, Leptospirosis, Listeria, Mycoplasmatales, *Mycobacterium leprae, Vibrio cholerae*, Neisseriaceae (e.g., Acinetobacter, Gonorrhea, Menigococcal), *Meisseria meningitidis*, Pasteurellacea Infections (e.g., Actinobacillus, Heamophilus (e.g., Heamophilus influenza type B), Pasteurella), Pseudomonas, Rickettsiaceae, Chlamydiaceae, Syphilis, Shigella spp., Staphylococcal, Meningiococcal, Pneumococcal and Streptococcal (e.g., *Streptococcus pneumoniae* and Group B Streptococcus). These bacterial or fungal families can cause the following diseases or symptoms, including, but not limited to: bacteremia, endocarditis, eye infections (conjunctivitis, tuberculosis, uveitis), gingivitis, opportunistic infections (e.g., AIDS related infections), paronychia, prosthesis-related infections, Reiter's Disease, respiratory tract infections, such as Whooping Cough or Empyema, sepsis, Lyme Disease, Cat-Scratch Disease, Dysentery, Paratyphoid Fever, food poisoning, Typhoid, pneumonia, Gonorrhea, meningitis (e.g., mengitis types A and B), Chlamydia, Syphilis, Diphtheria, Leprosy, Paratuberculosis, Tuberculosis, Lupus, Botulism, gangrene, tetanus, impetigo, Rheumatic Fever, Scarlet Fever, sexually transmitted diseases, skin diseases (e.g., cellulitis, dermatocycoses), toxemia, urinary tract infections, wound infections. Polynucleotides or polypeptides, agonists or antagonists of the invention, can be used to treat, prevent, and/or diagnose any of these symptoms or diseases. In specific embodiments, polynucleotides, polypeptides, agonists or antagonists of the invention are used to treat, prevent, and/or diagnose: tetanus, Diptheria, botulism, and/or meningitis type B.

Moreover, parasitic agents causing disease or symptoms that can be treated, prevented, and/or diagnosed by a polynucleotide or polypeptide and/or agonist or antagonist of the present invention include, but not limited to, the following families or class: Amebiasis, Babesiosis, Coccidiosis, Cryptosporidiosis, Dientamoebiasis, Dourine, Ectoparasitic, Giardiasis, Helminthiasis, Leishmaniasis, Theileriasis, Toxoplasmosis, Trypanosomiasis, and Trichomonas and Sporozoans (e.g., *Plasmodium virax, Plasmodium falciparium, Plasmodium malariae* and *Plasmodium ovale*). These parasites can cause a variety of diseases or symptoms, including, but not limited to: Scabies, Trombiculiasis, eye infections, intestinal disease (e.g., dysentery, giardiasis), liver disease, lung disease, opportunistic infections (e.g., AIDS related), malaria, pregnancy complications, and toxoplasmosis. polynucleotides or polypeptides, or agonists or antagonists of the invention, can be used to treat, prevent, and/or diagnose any of these symptoms or diseases. In specific embodiments, polynucleotides, polypeptides, or agonists or antagonists of the invention are used to treat, prevent, and/or diagnose malaria.

Preferably, treatment or prevention using a polypeptide or polynucleotide and/or agonist or antagonist of the present invention could either be by administering an effective amount of a polypeptide to the patient, or by removing cells from the patient, supplying the cells with a polynucleotide of the present invention, and returning the engineered cells to the patient (ex vivo therapy). Moreover, the polypeptide or polynucleotide of the present invention can be used as an antigen in a vaccine to raise an immune response against infectious disease.

Regeneration

A polynucleotide or polypeptide and/or agonist or antagonist of the present invention can be used to differentiate, proliferate, and attract cells, leading to the regeneration of tissues. (See, Science 276:59–87 (1997).) The regeneration of tissues could be used to repair, replace, or protect tissue damaged by congenital defects, trauma (wounds, burns, incisions, or ulcers), age, disease (e.g. osteoporosis, osteocarthritis, periodontal disease, liver failure), surgery, including cosmetic plastic surgery, fibrosis, reperfusion injury, or systemic cytokine damage.

Tissues that could be regenerated using the present invention include organs (e.g., pancreas, liver, intestine, kidney, skin, endothelium), muscle (smooth, skeletal or cardiac), vasculature (including vascular and lymphatics), nervous, hematopoietic, and skeletal (bone, cartilage, tendon, and ligament) tissue. Preferably, regeneration occurs without or decreased scarring. Regeneration also may include angiogenesis.

Moreover, a polynucleotide or polypeptide and/or agonist or antagonist of the present invention may increase regeneration of tissues difficult to heal. For example, increased tendon/ligament regeneration would quicken recovery time after damage. A polynucleotide or polypeptide and/or agonist or antagonist of the present invention could also be used prophylactically in an effort to avoid damage. Specific diseases that could be treated, prevented, and/or diagnosed include of tendinitis, carpal tunnel syndrome, and other tendon or ligament defects. A further example of tissue regeneration of non-healing wounds includes pressure ulcers, ulcers associated with vascular insufficiency, surgical, and traumatic wounds.

Similarly, nerve and brain tissue could also be regenerated by using a polynucleotide or polypeptide and/or agonist or antagonist of the present invention to proliferate and differentiate nerve cells. Diseases that could be treated, prevented, and/or diagnosed using this method include central and peripheral nervous system diseases, neuropathies, or mechanical and traumatic diseases, disorders, and/or conditions (e.g., spinal cord disorders, head trauma, cerebrovascular disease, and stoke). Specifically, diseases associated with peripheral nerve injuries, peripheral neuropathy (e.g., resulting from chemotherapy or other medical therapies), localized neuropathies, and central nervous system diseases (e.g., Alzheimer's disease, Parkinson's disease, Huntington's disease, amyotrophic lateral sclerosis, and Shy-Drager syndrome), could all be treated, prevented, and/or diagnosed using the polynucleotide or polypeptide and/or agonist or antagonist of the present invention.

Chemotaxis

A polynucleotide or polypeptide and/or agonist or antagonist of the present invention may have chemotaxis activity. A chemotaxic molecule attracts or mobilizes cells (e.g., monocytes, fibroblasts, neutrophils, T-cells, mast cells, eosinophils, epithelial and/or endothelial cells) to a particular site in the body, such as inflammation, infection, or site of hyperproliferation. The mobilized cells can then fight off and/or heal the particular trauma or abnormality.

A polynucleotide or polypeptide and/or agonist or antagonist of the present invention may increase chemotaxic activity of particular cells. These chemotactic molecules can then be used to treat, prevent, and/or diagnose inflammation, infection, hyperproliferative diseases, disorders, and/or conditions, or any immune system disorder by increasing the number of cells targeted to a particular location in the body. For example, chemotaxic molecules can be used to treat, prevent, and/or diagnose wounds and other trauma to tissues by attracting immune cells to the injured location. Chemotactic molecules of the present invention can also attract fibroblasts, which can be used to treat, prevent, and/or diagnose wounds.

It is also contemplated that a polynucleotide or polypeptide and/or agonist or antagonist of the present invention may inhibit chemotactic activity. These molecules could also be used to treat, prevent, and/or diagnose diseases, disorders, and/or conditions. Thus, a polynucleotide or polypeptide and/or agonist or antagonist of the present invention could be used as an inhibitor of chemotaxis.

Binding Activity

A polypeptide of the present invention may be used to screen for molecules that bind to the polypeptide or for molecules to which the polypeptide binds. The binding of the polypeptide and the molecule may activate (agonist), increase, inhibit (antagonist), or decrease activity of the polypeptide or the molecule bound. Examples of such molecules include antibodies, oligonucleotides, proteins (e.g., receptors), or small molecules.

Preferably, the molecule is closely related to the natural ligand of the polypeptide, e.g., a fragment of the ligand, or a natural substrate, a ligand, a structural or functional mimetic. (See, Coligan et al., Current Protocols in Immunology 1(2):Chapter 5 (1991).) Similarly, the molecule can be closely related to the natural receptor to which the polypeptide binds, or at least, a fragment of the receptor capable of being bound by the polypeptide (e.g., active site). In either case, the molecule can be rationally designed using known techniques.

Preferably, the screening for these molecules involves producing appropriate cells which express the polypeptide, either as a secreted protein or on the cell membrane. Preferred cells include cells from mammals, yeast, *Drosophila,* or *E. coli*. Cells expressing the polypeptide (or cell membrane containing the expressed polypeptide) are then preferably contacted with a test compound potentially containing the molecule to observe binding, stimulation, or inhibition of activity of either the polypeptide or the molecule.

The assay may simply test binding of a candidate compound to the polypeptide, wherein binding is detected by a label, or in an assay involving competition with a labeled competitor. Further, the assay may test whether the candidate compound results in a signal generated by binding to the polypeptide.

Alternatively, the assay can be carried out using cell-free preparations, polypeptide/molecule affixed to a solid support, chemical libraries, or natural product mixtures. The assay may also simply comprise the steps of mixing a candidate compound with a solution containing a polypeptide, measuring polypeptide/molecule activity or binding, and comparing the polypeptide/molecule activity or binding to a standard.

Preferably, an ELISA assay can measure polypeptide level or activity in a sample (e.g., biological sample) using a monoclonal or polyclonal antibody. The antibody can measure polypeptide level or activity by either binding, directly or indirectly, to the polypeptide or by competing with the polypeptide for a substrate.

Additionally, the receptor to which a polypeptide of the invention binds can be identified by numerous methods known to those of skill in the art, for example, ligand panning and FACS sorting (Coligan, et al., Current Protocols in Immun., 1(2), Chapter 5, (1991)). For example, expression cloning is employed wherein polyadenylated RNA is prepared from a cell responsive to the polypeptides, for example, NIH3T3 cells which are known to contain multiple receptors for the FGF family proteins, and SC-3 cells, and a cDNA library created from this RNA is divided into pools and used to transfect COS cells or other cells that are not responsive to the polypeptides. Transfected cells which are grown on glass slides are exposed to the polypeptide of the present invention, after they have been labeled. The polypeptides can be labeled by a variety of means including iodination or inclusion of a recognition site for a site-specific protein kinase.

Following fixation and incubation, the slides are subjected to auto-radiographic analysis. Positive pools are identified and sub-pools are prepared and re-transfected using an iterative sub-pooling and re-screening process, eventually yielding a single clones that encodes the putative receptor.

As an alternative approach for receptor identification, the labeled polypeptides can be photoaffinity linked with cell membrane or extract preparations that express the receptor molecule. Cross-linked material is resolved by PAGE analysis and exposed to X-ray film. The labeled complex containing the receptors of the polypeptides can be excised, resolved into peptide fragments, and subjected to protein microsequencing. The amino acid sequence obtained from microsequencing would be used to design a set of degenerate oligonucleotide probes to screen a cDNA library to identify the genes encoding the putative receptors.

Moreover, the techniques of gene-shuffling, motif-shuffling, exon-shuffling, and/or codon-shuffling (collectively referred to as "DNA shuffling") may be employed to modulate the activities of polypeptides of the invention thereby effectively generating agonists and antagonists of polypeptides of the invention. See generally, U.S. Pat. Nos. 5,605,793, 5,811,238, 5,830,721, 5,834,252, and 5,837,458, and Patten, P. A., et al., Curr. Opinion Biotechnol. 8:724–33 (1997); Harayama, S. Trends Biotechnol. 16(2):76–82 (1998); Hansson, L. O., et al., J. Mol. Biol. 287:265–76 (1999); and Lorenzo, M. M. and Blasco, R. Biotechniques 24(2):308–13 (1998) (each of these patents and publications are hereby incorporated by reference). In one embodiment, alteration of polynucleotides and corresponding polypeptides of the invention may be achieved by DNA shuffling. DNA shuffling involves the assembly of two or more DNA segments into a desired polynucleotide sequence of the invention molecule by homologous, or site-specific, recombination. In another embodiment, polynucleotides and corresponding polypeptides of the invention may be altered by being subjected to random mutagenesis by error-prone PCR, random nucleotide insertion or other methods prior to recombination. In another embodiment, one or more components, motifs, sections, parts, domains, fragments, etc., of the polypeptides of the invention may be recombined with one or more components, motifs, sections, parts, domains, fragments, etc. of one or more heterologous molecules. In preferred embodiments, the heterologous molecules are family members. In further preferred embodiments, the heterologous molecule is a growth factor such as, for example, platelet-derived growth factor (PDGF), insulin-like growth factor (IGF-I), transforming growth factor (TGF)-alpha, epidermal growth factor (EGF), fibroblast growth factor (FGF), TGF-beta, bone morphogenetic protein (BMP)-2, BMP-4, BMP-5, BMP-6, BMP-7, activins A and B, decapentaplegic(dpp), 60A, OP-2, dorsalin, growth differentiation factors (GDFs), nodal, MIS, inhibin-alpha, TGF-beta1, TGF-beta2, TGF-beta3, TGF-beta5, and glial-derived neurotrophic factor (GDNF).

Other preferred fragments are biologically active fragments of the polypeptides of the invention. Biologically active fragments are those exhibiting activity similar, but not necessarily identical, to an activity of the polypeptide. The biological activity of the fragments may include an improved desired activity, or a decreased undesirable activity.

Additionally, this invention provides a method of screening compounds to identify those which modulate the action of the polypeptide of the present invention. An example of such an assay comprises combining a mammalian fibroblast cell, a the polypeptide of the present invention, the compound to be screened and 3[H] thymidine under cell culture conditions where the fibroblast cell would normally proliferate. A control assay may be performed in the absence of the compound to be screened and compared to the amount of fibroblast proliferation in the presence of the compound to determine if the compound stimulates proliferation by determining the uptake of 3[H] thymidine in each case. The amount of fibroblast cell proliferation is measured by liquid scintillation chromatography which measures the incorporation of 3[H] thymidine. Both agonist and antagonist compounds may be identified by this procedure.

In another method, a mammalian cell or membrane preparation expressing a receptor for a polypeptide of the present invention is incubated with a labeled polypeptide of the present invention in the presence of the compound. The ability of the compound to enhance or block this interaction could then be measured. Alternatively, the response of a known second messenger system following interaction of a compound to be screened and the receptor is measured and the ability of the compound to bind to the receptor and elicit a second messenger response is measured to determine if the compound is a potential agonist or antagonist. Such second messenger systems include but are not limited to, cAMP guanylate cyclase, ion channels or phosphoinositide hydrolysis.

All of these above assays can be used as diagnostic or prognostic markers. The molecules discovered using these assays can be used to treat, prevent, and/or diagnose disease or to bring about a particular result in a patient (e.g., blood vessel growth) by activating or inhibiting the polypeptide/molecule. Moreover, the assays can discover agents which may inhibit or enhance the production of the polypeptides of the invention from suitably manipulated cells or tissues. Therefore, the invention includes a method of identifying compounds which bind to the polypeptides of the invention comprising the steps of: (a) incubating a candidate binding compound with the polypeptide; and (b) determining if binding has occurred. Moreover, the invention includes a method of identifying agonists/antagonists comprising the steps of: (a) incubating a candidate compound with the polypeptide, (b) assaying a biological activity, and (b) determining if a biological activity of the polypeptide has been altered.

Also, one could identify molecules bind a polypeptide of the invention experimentally by using the beta-pleated sheet regions contained in the polypeptide sequence of the protein. Accordingly, specific embodiments of the invention are directed to polynucleotides encoding polypeptides which comprise, or alternatively consist of, the amino acid sequence of each beta pleated sheet regions in a disclosed polypeptide sequence. Additional embodiments of the invention are directed to polynucleotides encoding polypeptides which comprise, or alternatively consist of, any combination or all of contained in the polypeptide sequences of the invention. Additional preferred embodiments of the invention are directed to polypeptides which comprise, or alternatively consist of, the amino acid sequence of each of the beta pleated sheet regions in one of the polypeptide sequences of the invention. Additional embodiments of the invention are directed to polypeptides which comprise, or alternatively consist of, any combination or all of the beta pleated sheet regions in one of the polypeptide sequences of the invention.

Targeted Delivery

In another embodiment, the invention provides a method of delivering compositions to targeted cells expressing a receptor for a polypeptide of the invention, or cells expressing a cell bound form of a polypeptide of the invention.

As discussed herein, polypeptides or antibodies of the invention may be associated with heterologous polypeptides, heterologous nucleic acids, toxins, or prodrugs via hydrophobic, hydrophilic, ionic and/or covalent interactions. In one embodiment, the invention provides a method for the specific delivery of compositions of the invention to cells by administering polypeptides of the invention (including antibodies) that are associated with heterologous polypeptides or nucleic acids. In one example, the invention provides a method for delivering a therapeutic protein into the targeted cell. In another example, the invention provides a method for delivering a single stranded nucleic acid (e.g., antisense or ribozymes) or double stranded nucleic acid (e.g., DNA that can integrate into the cell's genome or replicate episomally and that can be transcribed) into the targeted cell.

In another embodiment, the invention provides a method for the specific destruction of cells (e.g., the destruction of tumor cells) by administering polypeptides of the invention (e.g., polypeptides of the invention or antibodies of the invention) in association with toxins or cytotoxic prodrugs.

By "toxin" is meant compounds that bind and activate endogenous cytotoxic effector systems, radioisotopes, holotoxins, modified toxins, catalytic subunits of toxins, or any molecules or enzymes not normally present in or on the surface of a cell that under defined conditions cause the cell's death. Toxins that may be used according to the methods of the invention include, but are not limited to, radioisotopes known in the art, compounds such as, for example, antibodies (or complement fixing containing portions thereof) that bind an inherent or induced endogenous cytotoxic effector system, thymidine kinase, endonuclease, RNAse, alpha toxin, ricin, abrin, Pseudomonas exotoxin A, diphtheria toxin, saporin, momordin, gelonin, pokeweed antiviral protein, alpha-sarcin and cholera toxin. By "cytotoxic prodrug" is meant a non-toxic compound that is converted by an enzyme, normally present in the cell, into a cytotoxic compound. Cytotoxic prodrugs that may be used according to the methods of the invention include, but are not limited to, glutamyl derivatives of benzoic acid mustard alkylating agent, phosphate derivatives of etoposide or mitomycin C, cytosine arabinoside, daunorubisin, and phenoxyacetamide derivatives of doxorubicin.

Drug Screening

Further contemplated is the use of the polypeptides of the present invention, or the polynucleotides encoding these polypeptides, to screen for molecules which modify the activities of the polypeptides of the present invention. Such a method would include contacting the polypeptide of the present invention with a selected compound(s) suspected of having antagonist or agonist activity, and assaying the activity of these polypeptides following binding.

This invention is particularly useful for screening therapeutic compounds by using the polypeptides of the present invention, or binding fragments thereof, in any of a variety of drug screening techniques. The polypeptide or fragment employed in such a test may be affixed to a solid support, expressed on a cell surface, free in solution, or located intracellularly. One method of drug screening utilizes eukaryotic or prokaryotic host cells which are stably transformed with recombinant nucleic acids expressing the polypeptide or fragment. Drugs are screened against such transformed cells in competitive binding assays. One may measure, for example, the formulation of complexes between the agent being tested and a polypeptide of the present invention.

Thus, the present invention provides methods of screening for drugs or any other agents which affect activities mediated by the polypeptides of the present invention. These methods comprise contacting such an agent with a polypeptide of the present invention or a fragment thereof and assaying for the presence of a complex between the agent and the polypeptide or a fragment thereof, by methods well known in the art. In such a competitive binding assay, the agents to screen are typically labeled. Following incubation, free agent is separated from that present in bound form, and the amount of free or uncomplexed label is a measure of the ability of a particular agent to bind to the polypeptides of the present invention.

Another technique for drug screening provides high throughput screening for compounds having suitable binding affinity to the polypeptides of the present invention, and is described in great detail in European Patent Application 84/03564, published on Sep. 13, 1984, which is incorporated herein by reference herein. Briefly stated, large numbers of different small peptide test compounds are synthesized on a solid substrate, such as plastic pins or some other surface. The peptide test compounds are reacted with polypeptides of the present invention and washed. Bound polypeptides are then detected by methods well known in the art. Purified polypeptides are coated directly onto plates for use in the aforementioned drug screening techniques. In addition, nonneutralizing antibodies may be used to capture the peptide and immobilize it on the solid support.

This invention also contemplates the use of competitive drug screening assays in which neutralizing antibodies capable of binding polypeptides of the present invention specifically compete with a test compound for binding to the polypeptides or fragments thereof. In this manner, the antibodies are used to detect the presence of any peptide which shares one or more antigenic epitopes with a polypeptide of the invention.

The human HLRRBM1 polypeptides and/or peptides of the present invention, or immunogenic fragments or oligopeptides thereof, can be used for screening therapeutic drugs or compounds in a variety of drug screening techniques. The fragment employed in such a screening assay may be free in solution, affixed to a solid support, borne on a cell surface, or located intracellularly. The reduction or abolition of activity of the formation of binding complexes between the ion channel protein and the agent being tested can be measured. Thus, the present invention provides a method for screening or assessing a plurality of compounds for their specific binding affinity with a HLRRBM1 polypeptide, or a bindable peptide fragment, of this invention, comprising providing a plurality of compounds, combining the HLRRBM1 polypeptide, or a bindable peptide fragment, with each of a plurality of compounds for a time sufficient to allow binding under suitable conditions and detecting binding of the HLRRBM1 polypeptide or peptide to each of the plurality of test compounds, thereby identifying the compounds that specifically bind to the HLRRBM1 polypeptide or peptide.

Methods of identifying compounds that modulate the activity of the novel human HLRRBM1 polypeptides and/or peptides are provided by the present invention and comprise combining a potential or candidate compound or drug modulator of leucine-rich repeat protein biological activity with an HLRRBM1 polypeptide or peptide, for example, the HLRRBM1 amino acid sequence as set forth in SEQ ID NOS:2, and measuring an effect of the candidate compound or drug modulator on the biological activity of the HLRRBM1 polypeptide or peptide. Such measurable effects include, for example, physical binding interaction; the ability to cleave a suitable leucine-rich repeat protein substrate; effects on native and cloned HLRRBM1-expressing cell line; and effects of modulators or other leucine-rich repeat protein-mediated physiological measures.

Another method of identifying compounds that modulate the biological activity of the novel HLRRBM1 polypeptides of the present invention comprises combining a potential or candidate compound or drug modulator of a leucine-rich repeat protein biological activity with a host cell that expresses the HLRRBM1 polypeptide and measuring an effect of the candidate compound or drug modulator on the biological activity of the HLRRBM1 polypeptide. The host cell can also be capable of being induced to express the HLRRBM1 polypeptide, e.g., via inducible expression. Physiological effects of a given modulator candidate on the HLRRBM1 polypeptide can also be measured. Thus, cellular assays for particular leucine-rich repeat protein modulators may be either direct measurement or quantification of the physical biological activity of the HLRRBM1 polypeptide, or they may be measurement or quantification of a physiological effect. Such methods preferably employ a HLRRBM1 polypeptide as described herein, or an overexpressed recombinant HLRRBM1 polypeptide in suitable host cells containing an expression vector as described herein, wherein the HLRRBM1 polypeptide is expressed, overexpressed, or undergoes upregulated expression.

Another aspect of the present invention embraces a method of screening for a compound that is capable of modulating the biological activity of a HLRRBM1 polypeptide, comprising providing a host cell containing an expression vector harboring a nucleic acid sequence encoding a HLRRBM1 polypeptide, or a functional peptide or portion thereof (e.g., SEQ ID NOS:2); determining the biological activity of the expressed HLRRBM1 polypeptide in the absence of a modulator compound; contacting the cell with the modulator compound and determining the biological activity of the expressed HLRRBM1 polypeptide in the presence of the modulator compound. In such a method, a difference between the activity of the HLRRBM1 polypeptide in the presence of the modulator compound and in the absence of the modulator compound indicates a modulating effect of the compound.

Essentially any chemical compound can be employed as a potential modulator or ligand in the assays according to the present invention. Compounds tested as leucine-rich repeat protein modulators can be any small chemical compound, or biological entity (e.g., protein, sugar, nucleic acid, lipid). Test compounds will typically be small chemical molecules and peptides. Generally, the compounds used as potential modulators can be dissolved in aqueous or organic (e.g., DMSO-based) solutions. The assays are designed to screen large chemical libraries by automating the assay steps and providing compounds from any convenient source. Assays are typically run in parallel, for example, in microtiter formats on microtiter plates in robotic assays. There are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs, Switzerland), for example. Also, compounds may be synthesized by methods known in the art.

High throughput screening methodologies are particularly envisioned for the detection of modulators of the novel HLRRBM1 polynucleotides and polypeptides described herein. Such high throughput screening methods typically involve providing a combinatorial chemical or peptide library containing a large number of potential therapeutic compounds (e.g., ligand or modulator compounds). Such combinatorial chemical libraries or ligand libraries are then screened in one or more assays to identify those library members (e.g., particular chemical species or subclasses) that display a desired characteristic activity. The compounds so identified can serve as conventional lead compounds, or can themselves be used as potential or actual therapeutics.

A combinatorial chemical library is a collection of diverse chemical compounds generated either by chemical synthesis or biological synthesis, by combining a number of chemical building blocks (i.e., reagents such as amino acids). As an example, a linear combinatorial library, e.g., a polypeptide or peptide library, is formed by combining a set of chemical building blocks in every possible way for a given compound length (i.e., the number of amino acids in a polypeptide or peptide compound). Millions of chemical compounds can be synthesized through such combinatorial mixing of chemical building blocks.

The preparation and screening of combinatorial chemical libraries is well known to those having skill in the pertinent art. Combinatorial libraries include, without limitation, peptide libraries (e.g. U.S. Pat. No. 5,010,175; Furka, 1991, *Int. J. Pept. Prot. Res.*, 37:487–493; and Houghton et al., 1991, *Nature*, 354:84–88). Other chemistries for generating chemical diversity libraries can also be used. Nonlimiting examples of chemical diversity library chemistries include, peptoids (PCT Publication No. WO 91/019735), encoded peptides (PCT Publication No. WO 93/20242), random bio-oligomers (PCT Publication No. WO 92/00091), benzodiazepines (U.S. Pat. No. 5,288,514), diversomers such as hydantoins, benzodiazepines and dipeptides (Hobbs et al., 1993, *Proc. Natl. Acad. Sci. USA*, 90:6909–6913), vinylogous polypeptides (Hagihara et al., 1992, *J. Amer. Chem. Soc.*, 114:6568), nonpeptidal peptidomimetics with glucose scaffolding (Hirschmann et al., 1992, *J. Amer. Chem. Soc.*, 114:9217–9218), analogous organic synthesis of small compound libraries (Chem. et al., 1994, *J. Amer. Chem. Soc.*, 116:2661), oligocarbamates (Cho et al., 1993, *Science*, 261:1303), and/or peptidyl phosphonates (Campbell et al., 1994, *J. Org. Chem.*, 59:658), nucleic acid libraries (see Ausubel, Berger and Sambrook, all supra), peptide nucleic acid libraries (U.S. Pat. No. 5,539,083), antibody libraries (e.g., Vaughn et al., 1996, *Nature Biotechnology*, 14(3): 309–314) and PCT/US96/10287), carbohydrate libraries (e.g., Liang et al., 1996, *Science*, 274–1520–1522) and U.S. Pat. No. 5,593,853) small organic molecule libraries (e.g., benzodiazepines, Baum C&EN, Jan. 18, 1993, page 33; and U.S. Pat. No. 5,288,514; isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; and the like).

Devices for the preparation of combinatorial libraries are commercially available (e.g., 357 MPS, 390 MPS, Advanced Chem Tech, Louisville Ky.; Symphony, Rainin, Woburn, Mass.; 433A Applied Biosystems, Foster City, Calif.; 9050 Plus, Millipore, Bedford, Mass.). In addition, a large number of combinatorial libraries are commercially available (e.g., ComGenex, Princeton, N.J.; Asinex, Moscow, Russia; Tripos, Inc., St. Louis, Mo.; ChemStar, Ltd., Moscow, Russia; 3D Pharmaceuticals, Exton, Pa.; Martek Biosciences, Columbia, Md., and the like).

In one embodiment, the invention provides solid phase based in vitro assays in a high throughput format, where the cell or tissue expressing an ion channel is attached to a solid phase substrate. In such high throughput assays, it is possible to screen up to several thousand different modulators or ligands in a single day. In particular, each well of a microtiter plate can be used to perform a separate assay against a selected potential modulator, or, if concentration or incubation time effects are to be observed, every 5–10 wells can test a single modulator. Thus, a single standard microtiter plate can assay about 96 modulators. If 1536 well plates are used, then a single plate can easily assay from about 100 to about 1500 different compounds. It is possible to assay several different plates per day; thus, for example, assay screens for up to about 6,000–20,000 different compounds are possible using the described integrated systems.

In another of its aspects, the present invention encompasses screening and small molecule (e.g., drug) detection assays which involve the detection or identification of small molecules that can bind to a given protein, i.e., a HLRRBM1 polypeptide or peptide. Particularly preferred are assays suitable for high throughput screening methodologies.

In such binding-based detection, identification, or screening assays, a functional assay is not typically required. All that is needed is a target protein, preferably substantially purified, and a library or panel of compounds (e.g., ligands, drugs, small molecules) or biological entities to be screened or assayed for binding to the protein target. Preferably, most small molecules that bind to the target protein will modulate activity in some manner, due to preferential, higher affinity binding to functional areas or sites on the protein.

An example of such an assay is the fluorescence based thermal shift assay (3-Dimensional Pharmaceuticals, Inc., 3DP, Exton, Pa.) as described in U.S. Pat. Nos. 6,020,141 and 6,036,920 to Pantoliano et al.; see also, J. Zimmerman, 2000, *Gen. Eng. News*, 20(8)). The assay allows the detection of small molecules (e.g., drugs, ligands) that bind to expressed, and preferably purified, ion channel polypeptide based on affinity of binding determinations by analyzing thermal unfolding curves of protein-drug or ligand complexes. The drugs or binding molecules determined by this technique can be further assayed, if desired, by methods, such as those described herein, to determine if the molecules affect or modulate function or activity of the target protein.

To purify a HLRRBM1 polypeptide or peptide to measure a biological binding or ligand binding activity, the source may be a whole cell lysate that can be prepared by successive freeze-thaw cycles (e.g., one to three) in the presence of standard protease inhibitors. The HLRRBM1 polypeptide may be partially or completely purified by standard protein purification methods, e.g., affinity chromatography using specific antibody described infra, or by ligands specific for an epitope tag engineered into the recombinant HLRRBM1 polypeptide molecule, also as described herein. Binding activity can then be measured as described.

Compounds which are identified according to the methods provided herein, and which modulate or regulate the biological activity or physiology of the HLRRBM1 polypeptides according to the present invention are a preferred embodiment of this invention. It is contemplated that such modulatory compounds may be employed in treatment and therapeutic methods for treating a condition that is mediated by the novel HLRRBM1 polypeptides by administering to an individual in need of such treatment a therapeutically effective amount of the compound identified by the methods described herein.

In addition, the present invention provides methods for treating an individual in need of such treatment for a disease, disorder, or condition that is mediated by the HLRRBM1 polypeptides of the invention, comprising administering to the individual a therapeutically effective amount of the HLRRBM1-modulating compound identified by a method provided herein.

Antisense and Ribozyme (Antagonists)

In specific embodiments, antagonists according to the present invention are nucleic acids corresponding to the sequences contained in SEQ ID NO:1, or the complementary strand thereof, and/or to nucleotide sequences contained a deposited clone. In one embodiment, antisense sequence is generated internally by the organism, in another embodiment, the antisense sequence is separately administered (see, for example, O'Connor, Neurochem., 56:560 (1991). Oligodeoxynucleotides as Antisense Inhibitors of Gene Expression, CRC Press, Boca Raton, Fla. (1988). Antisense technology can be used to control gene expression through antisense DNA or RNA, or through triple-helix formation. Antisense techniques are discussed for example, in Okano, Neurochem., 56:560 (1991); Oligodeoxynucleotides as Antisense Inhibitors of Gene Expression, CRC Press, Boca Raton, Fla. (1988). Triple helix formation is discussed in, for instance, Lee et al., Nucleic Acids Research, 6:3073 (1979); Cooney et al., Science, 241:456 (1988); and Dervan et al., Science, 251:1300 (1991). The methods are based on binding of a polynucleotide to a complementary DNA or RNA.

For example, the use of c-myc and c-myb antisense RNA constructs to inhibit the growth of the non-lymphocytic leukemia cell line HL-60 and other cell lines was previously described. (Wickstrom et al. (1988); Anfossi et al. (1989)). These experiments were performed in vitro by incubating cells with the oligoribonucleotide. A similar procedure for in vivo use is described in WO 91/15580. Briefly, a pair of oligonucleotides for a given antisense RNA is produced as follows: A sequence complimentary to the first 15 bases of the open reading frame is flanked by an EcoR1 site on the 5 end and a HindIII site on the 3 end. Next, the pair of oligonucleotides is heated at 90° C. for one minute and then annealed in 2×ligation buffer (20 mM TRIS HCl pH 7.5, 10 mM MgCl2, 10 MM dithiothreitol (DTT) and 0.2 mM ATP) and then ligated to the EcoR1/Hind III site of the retroviral vector PMV7 (WO 91/15580).

For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of the receptor. The antisense RNA oligonucleotide hybridizes to the mRNA in vivo and blocks translation of the mRNA molecule into receptor polypeptide.

In one embodiment, the antisense nucleic acid of the invention is produced intracellularly by transcription from an exogenous sequence. For example, a vector or a portion thereof, is transcribed, producing an antisense nucleic acid (RNA) of the invention. Such a vector would contain a sequence encoding the antisense nucleic acid of the invention. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in vertebrate cells. Expression of the sequence encoding a polypeptide of the invention, or fragments thereof, can be by any promoter known in the art to act in vertebrate, preferably human cells. Such promoters can be inducible or constitutive. Such promoters include, but are not limited to, the SV40 early promoter region (Bernoist and Chambon, Nature, 29:304–310 (1981), the promoter contained in the 3' long terminal repeat of Rous sarcoma virus (Yamamoto et al., Cell, 22:787–797 (1980), the herpes thymidine promoter (Wagner et al., Proc. Natl. Acad. Sci. U.S.A., 78:1441–1445 (1981), the regulatory sequences of the metallothionein gene (Brinster et al., Nature, 296:39–42 (1982)), etc.

The antisense nucleic acids of the invention comprise a sequence complementary to at least a portion of an RNA transcript of a gene of interest. However, absolute complementarity, although preferred, is not required. A sequence "complementary to at least a portion of an RNA," referred to herein, means a sequence having sufficient complementarity to be able to hybridize with the RNA, forming a stable duplex; in the case of double stranded antisense nucleic acids of the invention, a single strand of the duplex DNA may thus be tested, or triplex formation may be assayed. The ability to hybridize will depend on both the degree of complementarity and the length of the antisense nucleic acid Generally, the larger the hybridizing nucleic acid, the more base mismatches with a RNA sequence of the invention it may contain and still form a stable duplex (or triplex as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have been shown to be effective at inhibiting translation of mRNAs as well. See generally, Wagner, R., Nature, 372:333–335 (1994). Thus, oligonucleotides complementary to either the 5'- or 3'-non-translated, non-coding regions of a polynucleotide sequence of the invention could be used in an antisense approach to inhibit translation of endogenous mRNA. Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Whether designed to hybridize to the 5'-, 3'- or coding region of mRNA, antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

The polynucleotides of the invention can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al., Proc. Natl. Acad. Sci. U.S.A. 86:6553–6556 (1989); Lemaitre et al., Proc. Natl. Acad. Sci., 84:648–652 (1987); PCT Publication NO: WO88/09810, published Dec. 15, 1988) or the blood-brain barrier (see, e.g., PCT Publication NO: WO89/10134, published Apr. 25, 1988), hybridization-triggered cleavage agents. (See, e.g., Krol et al., BioTechniques, 6:958–976 (1988)) or intercalating agents. (See, e.g., Zon, Pharm. Res., 5:539–549 (1988)). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including, but not limited to, 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6 -diaminopurine.

The antisense oligonucleotide may also comprise at least one modified sugar moiety selected from the group including, but not limited to, arabinose, 2-fluoroarabinose, xylulose, and hexose.

In yet another embodiment, the antisense oligonucleotide comprises at least one modified phosphate backbone selected from the group including, but not limited to, a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an a-anomeric oligonucleotide. An a-anomeric oligonucleotide forms specific double-stranded hybrids with complementary RNA in which, contrary to the usual b-units, the strands run parallel to each other (Gautier et al., Nucl. Acids Res., 15:6625–6641 (1987)). The oligonucleotide is a 2-0-methylribonucleotide (Inoue et al., Nucl. Acids Res., 15:6131–6148 (1987)), or a chimeric RNA-DNA analogue (Inoue et al., FEBS Lett. 215:327–330 (1987)).

Polynucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (Nucl. Acids Res., 16:3209 (1988)), methylphosphonate oligonucleotides can be prepared by use of controlled pore glass polymer supports (Sarin et al., Proc. Natl. Acad. Sci. U.S.A., 85:7448–7451 (1988)), etc.

While antisense nucleotides complementary to the coding region sequence of the invention could be used, those complementary to the transcribed untranslated region are most preferred.

Potential antagonists according to the invention also include catalytic RNA, or a ribozyme (See, e.g., PCT International Publication WO 90/11364, published Oct. 4, 1990; Sarver et al, Science, 247:1222–1225 (1990). While ribozymes that cleave mRNA at site specific recognition sequences can be used to destroy mRNAs corresponding to the polynucleotides of the invention, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, Nature, 334:585–591 (1988). There are numerous potential hammerhead ribozyme cleavage sites within each nucleotide sequence disclosed in the sequence listing. Preferably, the ribozyme is engineered so that the cleavage recognition site is located near the 5' end of the mRNA corresponding to the polynucleotides of the invention; i.e., to increase efficiency and minimize the intracellular accumulation of non-functional mRNA transcripts.

As in the antisense approach, the ribozymes of the invention can be composed of modified oligonucleotides (e.g. for improved stability, targeting, etc.) and should be delivered to cells which express the polynucleotides of the invention in vivo. DNA constructs encoding the ribozyme may be introduced into the cell in the same manner as described above for the introduction of antisense encoding DNA. A preferred method of delivery involves using a DNA construct "encoding" the ribozyme under the control of a strong constitutive promoter such as, for example, pol III or pol II promoter, so that transfected cells will produce sufficient quantities of the ribozyme to destroy endogenous messages and inhibit translation. Since ribozymes unlike antisense molecules, are catalytic, a lower intracellular concentration is required for efficiency.

Antagonist/agonist compounds may be employed to inhibit the cell growth and proliferation effects of the polypeptides of the present invention on neoplastic cells and tissues, i.e. stimulation of angiogenesis of tumors, and, therefore, retard or prevent abnormal cellular growth and proliferation, for example, in tumor formation or growth.

The antagonist/agonist may also be employed to prevent hyper-vascular diseases, and prevent the proliferation of epithelial lens cells after extracapsular cataract surgery. Prevention of the mitogenic activity of the polypeptides of the present invention may also be desirous in cases such as restenosis after balloon angioplasty.

The antagonist/agonist may also be employed to prevent the growth of scar tissue during wound healing.

The antagonist/agonist may also be employed to treat, prevent, and/or diagnose the diseases described herein.

Thus, the invention provides a method of treating or preventing diseases, disorders, and/or conditions, including but not limited to the diseases, disorders, and/or conditions listed throughout this application, associated with overexpression of a polynucleotide of the present invention by administering to a patient (a) an antisense molecule directed to the polynucleotide of the present invention, and/or (b) a ribozyme directed to the polynucleotide of the present invention.

invention, and/or (b) a ribozyme directed to the polynucleotide of the present invention.

Biotic Associations

A polynucleotide or polypeptide and/or agonist or antagonist of the present invention may increase the organisms ability, either directly or indirectly, to initiate and/or maintain biotic associations with other organisms. Such associations may be symbiotic, nonsymbiotic, endosymbiotic, macrosymbiotic, and/or microsymbiotic in nature. In general, a polynucleotide or polypeptide and/or agonist or antagonist of the present invention may increase the organisms ability to form biotic associations wit h any member of the fungal, bacterial, lichen, mycorrhizal, cyanobacterial, dinoflaggellate, and/or algal, kingdom, phylums, families, classes, genuses, and/or species.

The mechanism by which a polynucleotide or polypeptide and/or agonist or antagonist of the present invention may increase the host organisms ability, either directly or indirectly, to initiate and/or maintain biotic associations is variable, though may include, modulating osmolarity to desirable levels for the symbiont, modulating pH to desirable levels for the symbiont, modulating secretions of organic acids, modulating the secretion of specific proteins, phenolic compounds, nutrients, or the increased expression of a protein required for host-biotic organisms interactions (e.g., a receptor, ligand, etc.). Additional mechanisms are known in the art and are encompassed by the invention (see, for example, "Microbial Signalling and Communication", eds., R. England, G. Hobbs, N. Bainton, and D. McL. Roberts, Cambridge University Press, Cambridge, (1999); which is hereby incorporated herein by reference).

In an alternative embodiment, a polynucleotide or polypeptide and/or agonist or antagonist of the present invention may decrease the host organisms ability to form biotic associations with another organism, either directly or indirectly. The mechanism by which a polynucleotide or polypeptide and/or agonist or antagonist of the present invention may decrease the host organisms ability, either directly or indirectly, to initiate and/or maintain biotic associations with another organism is variable, though may include, modulating osmolarity to undesirable levels, modulating pH to undesirable levels, modulating secretions of organic acids, modulating the secretion of specific proteins, phenolic compounds, nutrients, or the decreased expression of a protein required for host-biotic organisms interactions (e.g., a receptor, ligand, etc.). Additional mechanisms are known in the art and are encompassed by the invention (see, for example, "Microbial Signalling and Communication", eds., R. England, G. Hobbs, N. Bainton, and D. McL. Roberts, Cambridge University Press, Cambridge, (1999); which is hereby incorporated herein by reference).

The hosts ability to maintain biotic associations with a particular pathogen has significant implications for the overall health and fitness of the host. For example, human hosts have symbiosis with enteric bacteria in their gastrointestinal tracts, particularly in the small and large intestine. In fact, bacteria counts in feces of the distal colon often approach $10^{12}$ per milliliter of feces. Examples of bowel flora in the gastrointestinal tract are members of the Enterobacteriaceae, Bacteriodes, in addition to a-hemolytic streptococci, *E. coli*, Bifobacteria, *Anaerobic cocci*, Eubacteria, Costridia, lactobacilli, and yeasts. Such bacteria, among other things, assist the host in the assimilation of nutrients by breaking down food stuffs not typically broken down by the hosts digestive system, particularly in the hosts bowel. Therefore, increasing the hosts ability to maintain such a biotic association would help assure proper nutrition for the host.

Aberrations in the enteric bacterial population of mammals, particularly humans, has been associated with the following disorders: diarrhea, ileus, chronic inflammatory disease, bowel obstruction, duodenal diverticula, biliary calculous disease, and malnutrition. A polynucleotide or polypeptide and/or agonist or antagonist of the present invention are useful for treating, detecting, diagnosing, prognosing, and/or ameliorating, either directly or indirectly, and of the above mentioned diseases and/or disorders associated with aberrant enteric flora population.

The composition of the intestinal flora, for example, is based upon a variety of factors, which include, but are not limited to, the age, race, diet, malnutrition, gastric acidity, bile salt excretion, gut motility, and immune mechanisms. As a result, the polynucleotides and polypeptides, including agonists, antagonists, and fragments thereof, may modulate the ability of a host to form biotic associations by affecting, directly or indirectly, at least one or more of these factors.

Although the predominate intestinal flora comprises anaerobic organisms, an underlying percentage represents aerobes (e.g., *E. coli*). This is significant as such aerobes rapidly become the predominate organisms in intraabdominal infections—effectively becoming opportunistic early in infection pathogenesis. As a result, there is an intrinsic need to control aerobe populations, particularly for immune comprised individuals.

In a preferred embodiment, a polynucleotides and polypeptides, including agonists, antagonists, and fragments thereof, are useful for inhibiting biotic associations with specific enteric symbiont organisms in an effort to control the population of such organisms.

Biotic associations occur not only in the gastrointestinal tract, but also on an in the integument. As opposed to the gastrointestinal flora, the cutaneous flora is comprised almost equally with aerobic and anaerobic organisms. Examples of cutaneous flora are members of the gram-positive cocci (e.g., *S. aureus*, coagulase-negative staphylococci, micrococcus, *M. sedentarius*), gram-positive bacilli (e.g., Corynebacterium species, *C. minutissimum*, Brevibacterium species, Propoionibacterium species, *P. acnes*), gram-negative bacilli (e.g., Acinebacter species), and fungi (*Pityrosporum orbiculare*). The relatively low number of flora associated with the integument is based upon the inability of many organisms to adhere to the skin. The organisms referenced above have acquired this unique ability. Therefore, the polynucleotides and polypeptides of the present invention may have uses which include modulating the population of the cutaneous flora, either directly or indirectly.

Aberrations in the cutaneous flora are associated with a number of significant diseases and/or disorders, which include, but are not limited to the following: impetigo, ecthyma, blistering distal dactulitis, pustules, folliculitis, cutaneous abscesses, pitted keratolysis, trichomycosis axcillaris, dermatophytosis complex, axillary odor, erthyrasma, cheesy foot odor, acne, tinea versicolor, seborrheic dermitits, and *Pityrosporum folliculitis*, to name a few. A polynucleotide or polypeptide and/or agonist or antagonist of the present invention are useful for treating, detecting, diagnosing, prognosing, and/or ameliorating, either directly or indirectly, and of the above mentioned diseases and/or disorders associated with aberrant cutaneous flora population.

Additional biotic associations, including diseases and disorders associated with the aberrant growth of such associations, are known in the art and are encompassed by the invention. See, for example, "Infectious Disease", Second Edition, Eds., S. L., Gorbach, J. G., Bartlett, and N. R., Blacklow, W. B. Saunders Company, Philadelphia, (1998); which is hereby incorporated herein by reference).

Pheromones

In another embodiment, a polynucleotide or polypeptide and/or agonist or antagonist of the present invention may increase the organisms ability to synthesize and/or release a pheromone. Such a pheromone may, for example, alter the organisms behavior and/or metabolism.

A polynucleotide or polypeptide and/or agonist or antagonist of the present invention may modulate the biosynthesis and/or release of pheromones, the organisms ability to respond to pheromones (e.g., behaviorally, and/or metabolically), and/or the organisms ability to detect pheromones. Preferably, any of the pheromones, and/or volatiles released from the organism, or induced, by a polynucleotide or polypeptide and/or agonist or antagonist of the invention have behavioral effects the organism.

Other Activities

The polypeptide of the present invention, as a result of the ability to stimulate vascular endothelial cell growth, may be employed in treatment for stimulating re-vascularization of ischemic tissues due to various disease conditions such as thrombosis, arteriosclerosis, and other cardiovascular conditions. These polypeptide may also be employed to stimulate angiogenesis and limb regeneration, as discussed above.

The polypeptide may also be employed for treating wounds due to injuries, burns, post-operative tissue repair, and ulcers since they are mitogenic to various cells of different origins, such as fibroblast cells and skeletal muscle cells, and therefore, facilitate the repair or replacement of damaged or diseased tissue.

The polypeptide of the present invention may also be employed stimulate neuronal growth and to treat, prevent, and/or diagnose neuronal damage which occurs in certain neuronal disorders or neuro-degenerative conditions such as Alzheimer's disease, Parkinson's disease, and AIDS-related complex. The polypeptide of the invention may have the ability to stimulate chondrocyte growth, therefore, they may be employed to enhance bone and periodontal regeneration and aid in tissue transplants or bone grafts.

The polypeptide of the present invention may be also be employed to prevent skin aging due to sunburn by stimulating keratinocyte growth.

The polypeptide of the invention may also be employed for preventing hair loss, since FGF family members activate hair-forming cells and promotes melanocyte growth. Along the same lines, the polypeptides of the present invention may be employed to stimulate growth and differentiation of hematopoietic cells and bone marrow cells when used in combination with other cytokines.

The polypeptide of the invention may also be employed to maintain organs before transplantation or for supporting cell culture of primary tissues.

The polypeptide of the present invention may also be employed for inducing tissue of mesodermal origin to differentiate in early embryos.

The polypeptide or polynucleotides and/or agonist or antagonists of the present invention may also increase or decrease the differentiation or proliferation of embryonic stem cells, besides, as discussed above, hematopoietic lineage.

The polypeptide or polynucleotides and/or agonist or antagonists of the present invention may also be used to modulate mammalian characteristics, such as body height, weight, hair color, eye color, skin, percentage of adipose tissue, pigmentation, size, and shape (e.g., cosmetic surgery). Similarly, polypeptides or polynucleotides and/or agonist or antagonists of the present invention may be used to modulate mammalian metabolism affecting catabolism, anabolism, processing, utilization, and storage of energy.

Polypeptide or polynucleotides and/or agonist or antagonists of the present invention may be used to change a mammal's mental state or physical state by influencing biorhythms, caricadic rhythms, depression (including depressive diseases, disorders, and/or conditions), tendency for violence, tolerance for pain, reproductive capabilities (preferably by Activin or Inhibin-like activity), hormonal or endocrine levels, appetite, libido, memory, stress, or other cognitive qualities.

Polypeptide or polynucleotides and/or agonist or antagonists of the present invention may also be used as a food additive or preservative, such as to increase or decrease storage capabilities, fat content, lipid, protein, carbohydrate, vitamins, minerals, cofactors or other nutritional components.

Polypeptide or polynucleotides and/or agonist or antagonists of the present invention may also be used to prepare individuals for extraterrestrial travel, low gravity environments, prolonged exposure to extraterrestrial radiation levels, low oxygen levels, reduction of metabolic activity, exposure to extraterrestrial pathogens, etc. Such a use may be administered either prior to an extraterrestrial event, during an extraterrestrial event, or both. Moreover, such a use may result in a number of beneficial changes in the recipient, such as, for example, any one of the following, non-limiting, effects: an increased level of hematopoietic cells, particularly red blood cells which would aid the recipient in coping with low oxygen levels; an increased level of B-cells, T-cells, antigen presenting cells, and/or macrophages, which would aid the recipient in coping with exposure to extraterrestrial pathogens, for example; a temporary (i.e., reversible) inhibition of hematopoietic cell production which would aid the recipient in coping with exposure to extraterrestrial radiation levels; increase and/or stability of bone mass which would aid the recipient in coping with low gravity environments; and/or decreased metabolism which would effectively facilitate the recipients ability to prolong their extraterrestrial travel by any one of the following, non-limiting means: (i) aid the recipient by decreasing their basal daily energy requirements; (ii) effectively lower the level of oxidative and/or metabolic stress in recipient (i.e., to enable recipient to cope with increased extraterrestial radiation levels by decreasing the level of internal oxidative/metabolic damage acquired during normal basal energy requirements; and/or (iii) enabling recipient to subsist at a lower metabolic temperature (i.e., cryogenic, and/or sub-cryogenic environment).

Polypeptide or polynucleotides and/or agonist or antagonists of the present invention may also be used to increase the efficacy of a pharmaceutical composition, either directly or indirectly. Such a use may be administered in simultaneous conjunction with said pharmaceutical, or separately through either the same or different route of administration (e.g., intravenous for the polynucleotide or polypeptide of the present invention, and orally for the pharmaceutical, among others described herein.).

Also preferred is a method of treatment of an individual in need of an increased level of a protein activity, which method comprises administering to such an individual a pharmaceutical composition comprising an amount of an isolated polypeptide, polynucleotide, or antibody of the claimed invention effective to increase the level of said protein activity in said individual.

Having generally described the invention, the same will be more readily understood by reference to the following examples, which are provided by way of illustration and are not intended as limiting.

References:

S F Altschul, T L Madden, A A Schaffer, J Zhang, Z Zhang, W Miller, D J Lipman. Gapped BLAST and PSI-BLAST: a new generation of protein database search programs. Nucleic Acids Res 25:3389–3402, 1997.

K Hofmann, W Stoffel. TMbase—A database of membrane spanning proteins segments. Biol. Chem. Hoppe-Seyler 347:166, 1993.

Bertin, J., and DiStefano, P. S. (2000). The PYRIN Domain: A novel Motif found in apoptosis and inflammation proteins. Cell Death Differ. In press.

Dixon, M. S., Golstein, C., Thomas, C. M., van der Biezen, E. A., and Jones, J. D. G. (2000). Genetic complexity of pathogen perception by plants: The example of Rcr3, a tomato gene required specifically by Cf-2. Proc. Natl. Acad. Sci. USA 97, 8807–8814.

Eldon, E., Kooyer, S., D'Evelyn, D., Duman, M., Lawinger, P., Botas, J., and Bellen, H. (1994). The *Drosophila* 18 wheeler is required for morphogenesis and has striking similarities to Toll. Development 120, 885–899.

Gavrieli, Y., Sherman, Y., and Ben-Sasson, S. A. (1992). Identification of programmed cell death in situ via specific labeling of nuclear DNA fragmentation. J. Cell Biol. 119, 493–501.

Halfon, M., Hashimoto, C., and Keshishian, H. (1995). The *Drosophila* Toll gene functions zygotically and is necessary for proper motoneuron and muscle development. Dev. Biol. 169, 151–167.

Harton, J. A., and Ting, J. P. (2000). Class II transactivator: Mastering the art of major histocompatibility complex expression. Molecular and Cellular Biology 20, 6185–6194.

Inohara, N., Koseki, T., Lin, J., Peso, L., Lucas, P. C., Chen, F. F., Ogura, Y., and Nunez, G. (2000). An induced proximity model for NF-kB activation in the Nod1/RICK and RIP signaling pathways. Journal of Biological Chemistry 275, 27823–27831.

Inohara, N., Koseki, T., Peso, L., Hu, Y., Yee, C., Chen, S., Carrio, R., Merina, J., Liu, D., Ni, J., and Nunez, G. (1999). Nod1, an Apaf-1-like activator of caspase-9 and nuclear factor-kb. Journal of Biological Chemistry 274, 14560–14567.

Jacobs, J., and Goodman, C. (1989). Embryonic development of axon pathways in the *Drosophila* CNS. I. A glial cell scaffold appears before the first growth cones. J. Neurosci. 9, 2402–2411.

Jones, D. A., McIntire, L. V., Smith, C. W., and Picker, L. J. (1994). A two step adhesion cascade for T-cell/endothelial cell interaction under flow conditions. J. Clin. Invest. 94, 2443–2450.

Liang, Y., Annan, R. S., Carr, S. A., Popp, S., Mevissen, M., Margolis, R. K., and Margolis, R. U. (1999). Mammalina homologues of the *Drosophila* slit protein are ligands of the herparan sulfate proteoglycan-i in brain. J. Biol. Chem. 274, 17885–1792.

Schneider, D. S., Hudson, K. L., Lin, T., and Anderson, K. V. (1991). Dominant and recessive mutations define functional domains of Toll, a transmembrane protein required for dorsal-ventral polarity in the *Drosophila* embryo. Genes and Development 5, 797–807.

Sean, G. S., Buchanan, C., and Gay, N. J. (1996). Structural and functional diversity in the leucine rich repeat family of proteins. Prog. Biophys. Molec. Biol. 65, 1–44.

Tong, Z. B., and Nelson, L. M. (1999). A mouse gene encoding an oocyte antigen associated with autoimmune premature ovarian failure. Endocrinology 140, 3720–3726.

van Der Voort, R., Keehnen, R. M., Beuling, E. A., Spaargaren, M., and Pals, S. T. (2000). Regulation of cytokine signaling by B cell antigen receptor and CD40-controlled expression of heparan sulfate proteoglycans. J. Exp. Med. 192, 1115–1124.

Verbeek, M. M., Otte-Holler, I., van den Born, J., van den Heuvel, L. P., Wesseling, P., and M., d. W. R. (1999). Agrin is a major heparan sulfate proteoglycan accummulating in Alzheimer's disease brain. Am. J. Pathol. 155, 2115–2125.

EXAMPLES

Description of the Preferred Embodiments

Example 1

Bioinformatics Analysis.

A Leucine-rich repeat (LLR) domain containing protein, annotated as Angiotensin/Vasopressin receptor AII/AVP (Genbank Accession: AAC39910; SEQ ID NO:14) and other LLR-domain containing proteins such as KIAA0926 (Genbank Accession: NP_055737; SEQ ID NO:15) were used as probes to search the EST databases from Incyte and the public domain, in addition to the genomic database from the Human Genome Project. The search program used was BLAST (Basic Local Alignment Search Tool). From this analysis, ESTs and exons encoding potential novel candidates, related to Angiotensin/Vasopressin receptor, were identified based on sequence homology. The potential candidates (Incyte ESTs: 6109483 and Public domain EST GI number: g201045) were sequenced and the full-length clone encoding the novel HLRRBM-1 protein was obtained using the EST sequence information. The complete protein sequences of these proteins were analyzed for potential transmembrane domains. TMPRED program (5) was used for transmembrane prediction. Also, these proteins were analyzed for potential motifs and protein domains. Motifs program in GCG (GCG is a software package from Genetics Computer Group of Wisconsin) was used for identifying the potential motifs in the protein. Protein domains were analyzed by using HMMER. HMMER is a freely distributable implementation of profile Hidden Markov Model (HMM) software for protein sequence analysis (http://hmmer.wustl.edu/). The protein domain search set used was Pfam (http://pfam.wustl.edu/). Pfam is a large collection of multiple sequence alignments and hidden Markov models of protein domains covering 2478 protein families. By these analyses, the HLRRBM1 protein has been predicted to comprise one or more leucine-rich repeat domains.

Example 2

Method for Constructing a Size Fractionated Brain and Testis Cdna Library.

Brain and testis poly A+ RNA was purchased from Clontech and converted into double stranded cDNA using the SuperScript™ Plasmid System for cDNA Synthesis and Plasmid Cloning (Life Technologies) except that no radioisotope was incorporated in either of the cDNA synthesis steps and that the cDNA was fractionated by HPLC. This was accomplished on a TransGenomics HPLC system equipped with a size exclusion column (TosoHass) with dimensions of 7.8 mm×30 cm and a particle size of 10 μm. Tris buffered saline was used as the mobile phase, and the column was run at a flow rate of 0.5 mL/min. The resulting chromatograms were analyzed to determine which fractions should be pooled to obtain the largest cDNA's; generally fractions that eluted in the range of 12 to 15 minutes were pooled. The cDNA was precipitated prior to ligation into the Sal I/Not I sites in the pSport vector supplied with the kit. Using a combination of PCR with primers directed to the ends of the vector and Sal I/Not I restriction enzyme digestion of mini-prep DNA, it was determined that the average insert size of the library was greater the 3.5 Kb. The overall complexity of the library was greater than $10^7$ independent clones. The library was amplified in semi-solid agar for 2 days at 30° C.

An aliquot (200 microliters) of the amplified library was inoculated into a 200 ml culture for single-stranded DNA isolation by super-infection with a f1 helper phage. After overnight grow, the released phage particles with precipitated with PEG and the DNA isolated with proteinase K, SDS and phenol extractions. The single stranded circular DNA was concentrated by ethanol precipitation and used for the cDNA capture experiments described below.

Example 3

Cloning of the Novel Human HLRRBM1 Polynucleotide.

Using the following EST sequence, the following PCR primer pairs and antisense 80 bp 5' biotinylated oligonucleotides (shown in Table IV) were designed and obtained from Genset Oligos (San Diego, Calif.) for use in the cloning methods described below.

BMS Clone #25
INCYTE g2010458 6109483
EST Sequence:

```
                                       (SEQ ID NO:4)
CCACCTGGAGAAGAGTCTCTGCTGGAAGGTCTCGCCGCACATCAAGATGG

ACCTGTTGCAGTGGATCCAAAGCAAAGCTCAGAGCGACGGCTCCACCCTG

CAGCAGGGCTCCTTTGAGTTCTTCAGTTGCTTGTACGAGATCCAGGAGGA
```

-continued

```
GGAGTTTATCCAGCAGGCCCTGAGCCACTTCCAGGTGATCGTGGTCAGCA

ACATTGCCTCCAAGATGGAGCACATGGTCTCCTCGTTCTGTCTGATGCGC

TGCAGGAGCGCCCAGGTGGTGCACTTGTATGGCGCCACCTACAGCGCGGA

CGGGGAAG
```

Oligonucleotides.

| Oligo No. | Oligo Name | Oligonucleotide Sequence | Length | SEQ ID NO: |
|---|---|---|---|---|
| 375 | GPCR-25s | GATGGACCTGTTGCAGTGGAT | 21 | 7 |
| 376 | GPCR-25a | GACCACGATCACCTGGAAGTG | 21 | 8 |
| 603 | GPCR-25 | TGAAGAACTCAAAGGAGCCCT GCTGCAGGGTGGAGCCGTCGCT CTGAGCTTTGCTTTGGATCCAC TGCAACAGGTCCATC | 80 | 9 |

One microliter (one hundred and fifty nanograms) of a biotinylated oligo (SEQ ID NO:9) was added to six microliters (six micrograms) of a mixture of the single-stranded covalently closed circular brain and testis cDNA libraries described herein, and seven microliters of 100% formamide in a 0.5 ml PCR tube. The mixture was heated in a thermal cycler to 95° C. for 2 mins. Fourteen microliters of 2× hybridization buffer (50% formamide, 1.5 M NaCl, 0.04 M $NaPO_4$, pH 7.2, 5 mM EDTA, 0.2% SDS) was added to the heated probe/cDNA library mixture and incubated at 42° C. for 26 hours. Hybrids between the biotinylated oligo and the circular cDNA were isolated by diluting the hybridization mixture to 220 microliters in a solution containing 1 M NaCl, 10 mM Tris-HCl pH 7.5, 1 nm EDTA, pH 8.0 and adding 125 microliters of streptavidin magnetic beads. This solution was incubated at 42° C. for 60 mins, mixing every 5 mins to resuspend the beads. The beads were separated from the solution with a magnet and the beads washed three times in 200 microliters of 0.1×SSPE, 0.1% SDS at 45° C.

The single stranded cDNAs were released from the biotinlyated oligo/streptavidin magnetic bead complex by adding 50 microliters of 0.1 N NaOH and incubating at room temperature for 10 mins. Six microliters of 3 M Sodium Acetate was added along with 15 micrograms of glycogen and the solution ethanol precipitated with 120 microliters of 100% ethanol. The DNA was resuspend in 12 microliters of TE (10 mM Tris-HCl, pH 8.0), 1 mM EDTA, pH 8.0). The single stranded cDNA was converted into double strands in a thermal cycler by mixing 5 microliters of the captured DNA with 1.5 microliters 10 micromolar standard SP6 primer (homologous to a sequence on the cDNA cloning vector) and 1.5 microliters of 10×PCR buffer. The mixture was heated to 95° C. for 20 seconds, then ramped down to 59° C. At this time 15 microliters of a repair mix, that was preheated to 70° C. (Repair mix contains 4 microliters of 5 mM dNTPs (1.25 mM each), 1.5 microliters of 10×PCR buffer, 9.25 microliters of water, and 0.25 microliters of Taq polymerase). The solution was ramped back to 73° C. and incubated for 23 mins. The repaired DNA was ethanol precipitate and resuspended in 10 microliters of TE. Two microliters were electroporated in *E. coli* DH12S cells and resulting colonies were screen by PCR, using a primer pairs designed from the EST sequences to identify the proper cDNAs. Those cDNA clones that were positive by PCR had the inserts sized and two clones for each probe were chosen for DNA sequencing.

The full-length nucleotide sequence and the encoded polypeptide for HLRRBM1 is shown in FIGS. 1A–E.

Example 4

Expression Profiling of the Novel Human HLRRBM1 Polypeptide.

The following PCR primer pair was used to measure the steady state levels of HLRRBM1 mRNA by quantitative PCR:

```
Sense:
5'-GATGGACCTGTTGCAGTGGAT-3'     (SEQ ID NO:7)

Antisense:
5'-GACCACGATCACCTGGAAGTG-3'     (SEQ ID NO:8)
```

Briefly, first strand cDNA was made from commercially available mRNA (Clontech) and subjected to real time quantitative PCR using a PE 5700 instrument (Applied Biosystems, Foster City, Calif.) which detects the amount of DNA amplified during each cycle by the fluorescent output of SYBR green, a DNA binding dye specific for double strands. The primer pairs provided above were used in the PCR reaction. The specificity of the primer pair for its target was verified by performing a thermal denaturation profile at the end of the run which gave an indication of the number of different DNA hybridization complexes present by determining melting Tm. In the case of the novel HLRRBM1 gene primer pairs, only one DNA fragment was detected having a homogeneous melting point. Contributions of contaminating genomic DNA to the assessment of tissue abundance is controlled by performing the PCR with first strand cDNA made with and without reverse transcriptase. In all cases, the contribution of material amplified in the no reverse transcriptase controls was negligible.

Small variations in the amount of cDNA used in each tube was determined by performing a parallel experiment using a primer pair for a gene expressed in equal amounts in all tissues, cyclophilin. These data were used to normalize the data obtained with the HLRRBM1 primer pairs described herein. The PCR data was converted into a relative assessment of the difference in transcript abundance amongst the tissues tested and the data are presented in bar graph form in FIG. 4. As shown, transcripts corresponding to HLRRBM1 were expressed highly in the bone marrow, and to a lesser extent, in spleen, lung, and testis.

Example 5

Method of Assessing the Expression Profile of the Novel HLRRBM1 Polypeptides of the Present Invention in a Variety of Cancer Cell Lines.

RNA quantification may be performed using the Taqman® real-time-PCR fluorogenic assay. The Taqman® assay is one of the most precise methods for assaying the concentration of nucleic acid templates.

All cell lines were grown using standard conditions: RPMI 1640 supplemented with 10% fetal bovine serum, 100 IU/ml penicillin, 100 mg/ml streptomycin, and 2 mM L-glutamine, 10 mM Hepes (all from GibcoBRL; Rockville, Md.). Eighty percent confluent cells were washed twice with phosphate-buffered saline (GibcoBRL) and harvested using 0.25% trypsin (GibcoBRL). RNA was prepared using the RNeasy Maxi Kit from Qiagen (Valencia, Calif.).

cDNA template for real-time PCR may be generated using the Superscript™ First Strand Synthesis system for RT-PCR.

SYBR Green real-time PCR reactions were prepared as follows: The reaction mix consisted of 20 ng first strand cDNA; 50 nM Forward Primer; 50 nM Reverse Primer; 0.75×SYBR Green I (Sigma); 1×SYBR Green PCR Buffer (50 mMTris-HCl pH8.3, 75 mM KCl); 10% DMSO; 3 mM $MgCl_2$; 300 μM each dATP, dGTP, dTTP, dCTP; 1 U Platinum® Taq DNA Polymerase High Fidelity (Cat# 11304-029; Life Technologies; Rockville, Md.); 1:50 dilution; ROX (Life Technologies). Real-time PCR was performed using an Applied Biosystems 5700 Sequence Detection System. Conditions were 95° C. for 10 min (denaturation and activation of Platinum® Taq DNA Polymerase), 40 cycles of PCR (95° C. for 15 sec, 60° C. for 1 min). PCR products are analyzed for uniform melting using an analysis algorithm built into the 5700 Sequence Detection System.

```
Forward primer: GPCR749-F:
5'-GATGGACCTGTTGCAGTGGAT-3'; (SEQ ID NO:7)

and
Reverse primer: GPCR750-R:
5'-GACCACGATCACCTGGAAGTG-3' (SEQ ID NO:8)
```

cDNA quantification used in the normalization of template quantity was performed using Taqman® technology. Taqman® reactions are prepared as follows: The reaction mix consisted of 20 ng first strand cDNA; 25 nM GAPDH-F3, Forward Primer; 250 nM GAPDH-R1 Reverse Primer; 200 nM GAPDH-PVIC Taqman® Probe (fluorescent dye labeled oligonucleotide primer); 1× Buffer A (Applied Biosystems); 5.5 mM MgCl2; 300 μM dATP, dGTP, dTTP, dCTP; 1 U Amplitaq Gold (Applied Biosystems). GAPDH, D-glyceraldehyde-3-phosphate dehydrogenase, was used as control to normalize mRNA levels.

Real-time PCR was performed using an Applied Biosystems 7700 Sequence Detection System. Conditions were 95° C. for 10 min. (denaturation and activation of Amplitaq Gold), 40 cycles of PCR (95° C. for 15 sec, 60° C. for 1 min).

The sequences for the GAPDH oligonucleotides used in the Taqman® reactions are as follows:

```
GAPDH-F3-                              (SEQ ID NO:28)
5'-AGCCGAGCCACATCGCT-3'

GAPDH-R1-                              (SEQ ID NO:29)
5'-GTGACCAGGCGCCCAATAC-3'

GAPDH-PVIC Taqman ® Probe-VIC- (SEQ ID NO:30)
5'-CAAATCCGTTGACTCCGACCTTCACCTT-3'TAMRA.
```

The Sequence Detection System generates a Ct (threshold cycle) value that is used to calculate a concentration for each input cDNA template. cDNA levels for each gene of interest are normalized to GAPDH cDNA levels to compensate for variations in total cDNA quantity in the input sample. This is done by generating GAPDH Ct values for each cell line. Ct values for the gene of interest and GAPDH are inserted into a modified version of the δδCt equation (Applied Biosystems Prism® 7700 Sequence Detection System User Bulletin #2), which is used to calculate a GAPDH normalized relative cDNA level for each specific cDNA. The δδCt equation is as follows: relative quantity of nucleic acid template$=2^{\delta\delta Ct}=2^{(\delta Cta-\delta Ctb)}$, where δCta=Ct target−Ct GAPDH, and δCtb=Ct reference−Ct GAPDH. (No reference cell line was used for the calculation of relative quantity; δCtb was defined as 21).

The results of the Taqman® experiments for HLRRBM1 are provided in Table IV, and are shown in graphical form in FIG. 6. In brief, HLRRBM1 was expressed at low levels in most of the human tumor cell lines tested. Significantly, enhanced expression of HLRRBM1 was observed in several colon tumor cell lines, as well as, a melanoma and a leukemia cell line. Moreover, the highest expression of HLRRBM1 (GPCR-25) was observed in a Taxol resistant variant of an ovarian tumor cell line.

TABLE IV

| Graph # | Name | Tissue | CtGAPDH | CtGPCR85 | dCt | ddCt | Quant. |
|---|---|---|---|---|---|---|---|
| 1 | AIN 4 | breast | 17.49 | 38.58 | 21.09 | 0.09 | 9.4E−01 |
| 2 | AIN 4T | breast | 17.15 | 36.45 | 19.3 | −1.7 | 3.2E+00 |
| 3 | AIN4/myc | breast | 17.81 | 40 | 22.19 | 1.19 | 4.4E−01 |
| 4 | BT-20 | breast | 17.9 | 40 | 22.1 | 1.1 | 4.7E−01 |
| 5 | BT-474 | breast | 17.65 | 36.83 | 19.18 | −1.82 | 3.5E+00 |
| 6 | BT-483 | breast | 17.45 | 37.75 | 20.3 | −0.7 | 1.6E+00 |
| 7 | BT-549 | breast | 17.55 | 37.59 | 20.04 | −0.96 | 1.9E+00 |
| 8 | DU4475 | breast | 18.1 | 40 | 21.9 | 0.9 | 5.4E−01 |
| 9 | H3396 | breast | 18.04 | 37.22 | 19.18 | −1.82 | 3.5E+00 |
| 10 | HBL100 | breast | 17.02 | 37.06 | 20.04 | −0.96 | 1.9E+00 |
| 11 | Her2 MCF-7 | breast | 19.26 | 40 | 20.74 | −0.26 | 1.2E+00 |
| 12 | HS 578T | breast | 17.83 | 37.43 | 19.6 | −1.4 | 2.6E+00 |
| 13 | MCF7 | breast | 17.83 | 38.16 | 20.33 | −0.67 | 1.6E+00 |
| 14 | MCF-7/AdrR | breast | 17.23 | 35.9 | 18.67 | −2.33 | 5.0E+00 |
| 15 | MDAH 2774 | breast | 16.87 | 40 | 23.13 | 2.13 | 2.3E−01 |
| 16 | MDA-MB-175-VII | breast | 15.72 | 35.36 | 19.64 | −1.36 | 2.6E+00 |
| 17 | MDA-MB-231 | breast | 17.62 | 33.49 | 15.87 | −5.13 | 3.5E+01 |
| 18 | MDA-MB-453 | breast | 17.9 | 36.07 | 18.17 | −2.83 | 7.1E+00 |
| 19 | MDA-MB-468 | breast | 17.49 | 37.05 | 19.56 | −1.44 | 2.7E+00 |
| 20 | Pat-21 R60 | breast | 35.59 | 40 | 4.41 | −16.59 | ND |
| 21 | SKBR3 | breast | 17.12 | 34.04 | 16.92 | −4.08 | 1.7E+01 |
| 22 | T47D | breast | 18.86 | 35.84 | 16.98 | −4.02 | 1.6E+01 |
| 23 | UACC-812 | breast | 17.06 | 36.45 | 19.39 | −1.61 | 3.1E+00 |
| 24 | ZR-75-1 | breast | 15.95 | 35.05 | 19.1 | −1.9 | 3.7E+00 |
| 25 | C-33A | cervical | 17.49 | 40 | 22.51 | 1.51 | 3.5E−01 |
| 26 | Ca Ski | cervical | 17.38 | 36.4 | 19.02 | −1.98 | 3.9E+00 |

TABLE IV-continued

| Graph # | Name | Tissue | CtGAPDH | CtGPCR85 | dCt | ddCt | Quant. |
|---|---|---|---|---|---|---|---|
| 27 | HeLa | cervical | 17.59 | 40 | 22.41 | 1.41 | 3.8E−01 |
| 28 | HT-3 | cervical | 17.42 | 36.26 | 18.84 | −2.16 | 4.5E+00 |
| 29 | ME−180 | cervical | 16.86 | 37.02 | 20.16 | −0.84 | 1.8E+00 |
| 30 | SiHa | cervical | 18.07 | 40 | 21.93 | 0.93 | 5.2E−01 |
| 31 | SW756 | cervical | 15.59 | 40 | 24.41 | 3.41 | 9.4E−02 |
| 32 | CACO-2 | colon | 17.56 | 29.58 | 12.02 | −8.98 | 5.0E+02 |
| 33 | CCD-112Co | colon | 18.03 | 34.27 | 16.24 | −4.76 | 2.7E+01 |
| 34 | CCD-33Co | colon | 17.07 | 38.57 | 21.5 | 0.5 | 7.1E−01 |
| 35 | Colo 205 | colon | 18.02 | 40 | 21.98 | 0.98 | 5.1E−01 |
| 36 | Colo 320DM | colon | 17.01 | 37.88 | 20.87 | −0.13 | 1.1E+00 |
| 37 | Colo201 | colon | 17.89 | 38.87 | 20.98 | −0.02 | 1.0E+00 |
| 38 | Cx-1 | colon | 18.79 | 38.29 | 19.5 | −1.5 | 2.8E+00 |
| 39 | ddH2O | colon | 40 | 40 | 0 | −21 | ND |
| 40 | HCT116 | colon | 17.59 | 35.51 | 17.92 | −3.08 | 8.5E+00 |
| 41 | HCT116/epo5 | colon | 17.71 | 34.71 | 17 | −4 | 1.6E+01 |
| 42 | HCT116/ras | colon | 17.18 | 33.89 | 16.71 | −4.29 | 2.0E+01 |
| 43 | HCT116/TX15 CR | colon | 17.36 | 32.82 | 15.46 | 5.54 | 4.7E+01 |
| 44 | HCT116/vivo | colon | 17.7 | 32.28 | 14.58 | -6.42 | 8.6E+01 |
| 45 | HCT116/VM46 | colon | 17.87 | 36.31 | 18.44 | -2.56 | 5.9E+00 |
| 46 | HCT116/VP35 | colon | 17.3 | 35.83 | 18.53 | -2.47 | 5.5E+00 |
| 47 | HCT-8 | colon | 17.44 | 35.06 | 17.62 | −3.38 | 1.0E+01 |
| 48 | HT-29 | colon | 17.9 | 33.91 | 16.01 | −4.99 | 3.2E+01 |
| 49 | LoVo | colon | 17.64 | 36.01 | 18.37 | −2.63 | 6.2E+00 |
| 50 | LS 174T | colon | 17.93 | 40 | 22.07 | 1.07 | 4.8E−01 |
| 51 | LS123 | colon | 17.65 | 31.12 | 13.47 | −7.53 | 1.8E+02 |
| 52 | MIP | colon | 16.92 | 33.73 | 16.81 | −4.19 | 1.8E+01 |
| 53 | SK-CO-1 | colon | 17.75 | 40 | 22.25 | 1.25 | 4.2E−01 |
| 54 | SW1417 | colon | 17.22 | 35.54 | 18.32 | −2.68 | 6.4E+00 |
| 55 | SW403 | colon | 18.39 | 37.08 | 18.69 | −2.31 | 5.0E+00 |
| 56 | SW480 | colon | 17 | 35.17 | 18.17 | −2.83 | 7.1E+00 |
| 57 | SW620 | colon | 17.16 | 40 | 22.84 | 1.84 | 2.8E−01 |
| 58 | SW837 | colon | 18.35 | 34.19 | 15.84 | −5.16 | 3.6E+01 |
| 59 | T84 | colon | 16.44 | 38.03 | 21.59 | 0.59 | 6.6E−01 |
| 60 | CCD-18Co | colon, fibroblast | 17.19 | 40 | 22.81 | 1.81 | 2.9E−01 |
| 61 | HT-1080 | fibrosarcoma | 17.16 | 34.08 | 16.92 | −4.08 | 1.7E+01 |
| 62 | CCRF-CEM | leukemia | 17.07 | 39.75 | 22.68 | 1.68 | 3.1E−0l |
| 63 | HL-60 | leukemia | 17.54 | 30.51 | 12.97 | −8.03 | 2.6E+02 |
| 64 | K562 | leukemia | 18.42 | 35.56 | 17.14 | −3.86 | 1.5E+01 |
| 65 | A-427 | lung | 18 | 36.27 | 18.27 | −2.73 | 6.6E+00 |
| 66 | A549 | lung | 17.63 | 38.4 | 20.77 | −0.23 | 1.2E+00 |
| 67 | Calu-3 | lung | 18.09 | 34.14 | 16.05 | −4.95 | 3.1E+01 |
| 68 | Calu-6 | lung | 16.62 | 40 | 23.38 | 2.38 | 1.9E−01 |
| 69 | ChaGo-K-1 | lung | 17.79 | 35.29 | 17.5 | −3.5 | 1.1E+01 |
| 70 | DMS 114 | lung | 18.14 | 35.15 | 17.01 | −3.99 | 1.6E+01 |
| 71 | LX-1 | lung | 18.17 | 34.24 | 16.07 | −4.93 | 3.0E+01 |
| 72 | MRC-5 | lung | 17.3 | 40 | 22.7 | 1.7 | 3.1E−01 |
| 73 | MSTO-211H | lung | 16.81 | 40 | 23.19 | 2.19 | 2.2E−01 |
| 74 | NCI-H596 | lung | 17.73 | 37.56 | 19.83 | −1.17 | 2.3E+00 |
| 75 | SHP-77 | lung | 18.66 | 35.47 | 16.81 | −4.19 | 1.8E+01 |
| 76 | Sk-LU-1 | lung | 15.81 | 31.74 | 15.93 | −5.07 | 3.4E+01 |
| 77 | SK-MES-1 | lung | 17.1 | 33.72 | 16.62 | −4.38 | 2.1E+01 |
| 78 | SW1271 | lung | 16.45 | 34.33 | 17.88 | −3.12 | 8.7E+00 |
| 79 | SW1573 | lung | 17.14 | 38.41 | 21.27 | 0.27 | 8.3E−01 |
| 80 | SW900 | lung | 18.17 | 36.92 | 18.75 | −2.25 | 4.8E+00 |
| 81 | Hs 294T | melanoma | 17.73 | 31.28 | 13.55 | −7.45 | 1.7E+02 |
| 82 | A2780/DDP-R | ovarian | 21.51 | 38.24 | 16.73 | -4.27 | 1.9E+01 |
| 83 | A2780/DDP-S | ovarian | 17.89 | 34.25 | 16.36 | -4.64 | 2.5E+01 |
| 84 | A2780/cpo5 | ovarian | 17.54 | 35.58 | 18.04 | −2.96 | 7.8E+00 |
| 85 | A2780/TAX-R | ovarian | 18.4 | 29.12 | 10.72 | −10.28 | 1.2E+03 |
| 86 | A2780/TAX-S | ovarian | 17.83 | 38 | 20.17 | −0.83 | 1.8E+00 |
| 87 | Caov-3 | ovarian | 15.5 | 40 | 24.5 | 3.5 | 8.8E−02 |
| 88 | ES-2 | ovarian | 17.22 | 37.98 | 20.76 | −0.24 | 1.2E+00 |
| 89 | HOC-76 | ovarian | 34.3 | 40 | 5.7 | −15.3 | Mouse |
| 90 | OVCAR-3 | ovarian | 17.09 | 32.64 | 15.55 | −5.45 | 4.4E+01 |
| 91 | PA-1 | ovarian | 17.33 | 33.05 | 15.72 | −5.28 | 3.9E+01 |
| 92 | SW 626 | ovarian | 16.94 | 37.5 | 20.56 | −0.44 | 1.4E+00 |
| 93 | UPN251 | ovarian | 17.69 | 37.57 | 19.88 | −1.12 | 2.2E+00 |
| 94 | LNCAP | prostate | 18.17 | 34.94 | 16.77 | −4.23 | 1.9E+01 |
| 95 | PC-3 | prostate | 17.25 | 36.27 | 19.02 | −1.98 | 3.9E+00 |
| 96 | A431 | squamous | 19.85 | 40 | 20.15 | −0.85 | 1.8E+00 |

Example 6

Complementary Polynucleotides

Antisense molecules or nucleic acid sequences complementary to the HLRRBM1 protein-encoding sequence, or any part thereof, is used to decrease or to inhibit the expression of naturally occurring HLRRBM1. Although the use of antisense or complementary oligonucleotides comprising about 15 to 35 base-pairs is described, essentially the same procedure is used with smaller or larger nucleic acid sequence fragments. An oligonucleotide based on the coding sequence of HLRRBM1 protein, as shown in FIGS. 1A–E, or as depicted in SEQ ID NO:1, for example, is used to inhibit expression of naturally occurring HLRRBM1. The complementary oligonucleotide is typically designed from the most unique 5' sequence and is used either to inhibit transcription by preventing promoter binding to the coding sequence, or to inhibit translation by preventing the ribosome from binding to the HLRRBM1 protein-encoding transcript, among others. However, other regions may also be targeted.

Using an appropriate portion of the signal and 5' sequence of SEQ ID NO:1, an effective antisense oligonucleotide includes any of about 15–35 nucleotides spanning the region which translates into the signal or 5' coding sequence, among other regions, of the polypeptide as shown in FIGS. 1A–E (SEQ ID NO:2). Apropriate oligonucleotides are designed using OLIGO 4.06 software and the HLRRBM1 protein coding sequence (SEQ ID NO:1). Preferred oligonucleotides are deoxynucleotide, or chimeric deoxynucleotide/ribonucleotide based and are provided below. The oligonucleotides were synthesized using chemistry essentially as described in U.S. Pat. No. 5,849,902; which is hereby incorporated herein by reference in its entirety.

| ID# | Sequence | |
|---|---|---|
| 13723 | GCCCACTCCGGUCUUAGAGAUGCUC | (SEQ ID NO:23) |
| 13724 | GCTGCCTCTCAGUAGACUAAACGGA | (SEQ ID NO:24) |
| 13725 | TTGACTGGTUCCCAAGUGAGGACGG | (SEQ ID NO:25) |
| 13726 | ATACCAGAGCUUUGAGAGGUCGAGG | (SEQ ID NO:26) |
| 13727 | TTACAGATGGAGAUGGAGGCCCAGG | (SEQ ID NO:27) |

The HLRRBM1 polypeptide has been shown to be involved in the regulation of mammalian cell cycle pathways. Subjecting cells with an effective amount of a pool of all five of the above antisense oligoncleotides resulted in a significant increase in p21 expression/activity providing convincing evidence that HLRRBM1 at least regulates the activity and/or expression of p21 either directly, or indirectly. Moreover, the results suggest that HLRRBM1 is involved in the negative regulation of p21 activity and/or expression, either directly or indirectly. The p21 assay used is described below and was based upon the analysis of p21 activity as a downstream marker for proliferative signal transduction events.

Transfection of Post-Quiescent A549 Cells with AntiSense Oligonucleotides.

Materials Needed:

A549 cells maintained in DMEM with high glucose (Gibco-BRL) supplemented with 10% Fetal Bovine Serum, 2 mM L-Glutamine, and 1× penicillin/streptomycin.

Opti-MEM (Gibco-BRL)

Lipofectamine 2000 (Invitrogen)

Antisense oligomers (Sequitur)

Polystyrene tubes.

Tissue culture treated plates.

Quiescent cells were prepared as follows:

Day 0: 300, 000 A549 cells were seeded in a T75 tissue culture flask in 10 ml of A549 media (as specified above), and incubated in at 37° C., 5% $CO_2$ in a humidified incubator for 48 hours.

Day 2: The T75 flasks were rocked to remove any loosely adherent cells, and the A549 growth media removed and replenished with 10 ml of fresh A549 media. The cells were cultured for six days without changing the media to create a quiescent cell population.

Day 8: Quiescent cells were plated in multi-well format and transfected with antisense oligonucleotides.

A549 cells were transfected according to the following:

1. Trypsinize T75 flask containing quiescent population of A549 cells.
2. Count the cells and seed 24-well plates with 60K quiescent A549 cells per well.
3. Allow the cells to adhere to the tissue culture plate (approximately 4 hours).
4. Transfect the cells with antisense and control oligonucleotides according to the following:
   a. A 10× stock of lipofectamine 2000 (10 ug/ml is 10×) was prepared, and diluted lipid was allowed to stand at RT for 15 minutes.
      Stock solution of lipofectamine 2000 was 1 mg/ml.
      10× solution for transfection was 10 ug/ml.
      To prepare 10× solution, dilute 10 ul of lipofectamine 2000 stock per 1 ml of Opti-MEM (serum free media).
   b. A 10× stock of each oligomer was prepared to be used in the transfection.
      Stock solutions of oligomers were at 100 uM in 20 mM HEPES, pH 7.5.
      10× concentration of oligomer was 0.25 uM.
      To prepare the 10× solutions, dilute 2.5 ul of oligomer per 1 ml of Opti-MEM.
   c. Equal volumes of the 10× lipofectamine 2000 stock and the 10× oligomer solutions were mixed well, and incubated for 15 minutes at RT to allow complexation of the oligomer and lipid. The resulting mixture was 5×.
   d. After the 15 minute complexation, 4 volumes of full growth media was added to the oligomer/lipid complexes (solution was 1×).
   e. The media was aspirated from the cells, and 0.5 ml of the 1× oligomer/lipid complexes added to each well.
   f. The cells were incubated for 16–24 hours at 37° C. in a humidified $CO_2$ incubator.
   g. Cell pellets were harvested for RNA isolation and TaqMan analysis of downstream marker genes.

TaqMan Reactions

Quantitative RT-PCR analysis was performed on total RNA preps that had been treated with DNaseI or poly A selected RNA. The Dnase treatment may be performed using methods known in the art, though preferably using a Qiagen RNeasy kit to purify the RNA samples, wherein DNAse I treatment is performed on the column.

Briefly, a master mix of reagents was prepared according to the following table:

| Reagent | Per r'xn (in uL) |
|---|---|
| 10x Buffer | 2.5 |
| Dnase I (1 unit/ul @ 1 unit per ug sample) | 2 |
| DEPC $H_2O$ | 0.5 |
| RNA sample @ 0.1 ug/ul (2–3 ug total) | 20 |
| Total | 25 |

Dnase I Treatment

Next, 5 ul of master mix was aliquoted per well of a 96-well PCR reaction plate (PE part # N801-0560). RNA samples were adjusted to 0.1 ug/ul with DEPC treated $H_2O$ (if necessary), and 20 ul was added to the aliquoted master mix for a final reaction volume of 25 ul.

The wells were capped using strip well caps (PE part # N801-0935), placed in a plate, and briefly spun in a plate centrifuge (Beckman) to collect all volume in the bottom of the tubes. Generally, a short spin up to 500 rpm in a Sorvall RT is sufficient The plates were incubated at 37° C. for 30 mins. Then, an equal volume of 0.1 mM EDTA in 10 mM Tris was added to each well, and heat inactivated at 70° C. for 5 min. The plates were stored at −80° C. upon completion.

RT Reaction

A master mix of reagents was prepared according to the following table:

RT reaction

| Reagent | RT Per Rx'n (in ul) | No RT Per Rx'n (in ul) |
|---|---|---|
| 10x RT buffer | 5 | 2.5 |
| $MgCl_2$ | 11 | 5.5 |
| DNTP mixture | 10 | 5 |
| Random Hexamers | 2.5 | 1.25 |
| Rnase inhibitors | 1.25 | 0.625 |
| RT enzyme | 1.25 | — |
| Total RNA 500 ng (100 ng no RT) | 19.0 max | 10.125 max |
| DEPC $H_2O$ | — | — |
| Total | 50 uL | 25 uL |

Samples were adjusted to a concentration so that 500 ng of RNA was added to each RT rx'n (100 ng for the no RT). A maximum of 19 ul can be added to the RT rx'n mixture (10.125 ul for the no RT.) Any remaining volume up to the maximum values was filled with DEPC treated $H_2O$, so that the total reaction volume was 50 ul (RT) or 25 ul (no RT).

On a 96-well PCR reaction plate (PE part # N801-0560), 37.5 ul of master mix was aliquoted (22.5 ul of no RT master mix), and the RNA sample added for a total reaction volume of 50 ul (25 ul, no RT). Control samples were loaded into two or even three different wells in order to have enough template for generation of a standard curve.

The wells were capped using strip well caps (PE part # N801-0935), placed in a plate, and spin briefly in a plate centrifuge (Beckman) to collect all volume in the bottom of the tubes. Generally, a short spin up to 500 rpm in a Sorvall RT is sufficient.

For the RT-PCR reaction, the following thermal profile was used:

25° C. for 10 min
48° C. for 30 min
95° C. for 5 min
4° C. hold (for 1 hour)
Store plate @−20° C. or lower upon completion.

TaqMan Reaction (Template comes from RT Plate.)

A master mix was prepared according to the following table:

TaqMan reaction (per well)

| Reagent | Per Rx'n (in ul) |
|---|---|
| TaqMan Master Mix | 4.17 |
| 100 uM Probe (SEQ ID NO:33) | .025 |
| 100 uM Forward primer (SEQ ID NO:31) | .05 |
| 100 uM Reverse primer (SEQ ID NO:32) | .05 |
| Template | — |
| DEPC $H_2O$ | 18.21 |
| Total | 22.5 |

The primers used for the RT-PCR reaction is as follows: P21 primer and probes:

```
Forward Primer:
CTGGAGACTCTCAGGGTCGAA          (SEQ ID NO:31)

Reverse Primer:
GCGCTTCCAGGACTGCA              (SEQ ID NO:32)

TaqMan Probe:
ACAGATTTCTACCACTCCAAACGCCGG    (SEQ ID NO:33)
```

Using a Gilson P-10 repeat pipetter, 22.5 ul of master mix was aliquoted per well of a 96-well optical plate. Then, using P-10 pipetter, 2.5 ul of sample was added to individual wells. Generally, RT samples are run in triplicate with each primer/probe set used, and no RT samples are run once and only with one primer/probe set, often gapdh (or other internal control).

A standard curve is then constructed and loaded onto the plate. The curve has five points plus one no template control (NTC, =DEPC treated $H_2O$). The curve was made with a high point of 50 ng of sample (twice the amount of RNA in unknowns), and successive samples of 25, 10, 5, and 1 ng. The curve was made from a control sample(s) (see above).

The wells were capped using optical strip well caps (PE part # N801-0935), placed in a plate, and spun in a centrifuge to collect all volume in the bottom of the tubes. Generally, a short spin up to 500 rpm in a Sorvall RT is sufficient.

Plates were loaded onto a PE 5700 sequence detector making sure the plate is aligned properly with the notch in the upper right hand corner. The lid was tightened down and run using the 5700 and 5700 quantitation program and the SYBR probe using the following thermal profile:

50° C. for 2 min
95° C. for 10 min
and the following for 40 cycles:
95° C. for 15 sec
60° C. for 1 min
Change the reaction volume to 25 ul.

Once the reaction was complete, a manual threshold of around 0.1 was set to minimize the background signal.

Additional information relative to operation of the GeneAmp 5700 machine may be found in reference to the following manuals: "GeneAmp 5700 Sequence Detection System Operator Training CD"; and the "User's Manual for 5700 Sequence Detection System"; available from Perkin-Elmer and hereby incorporated by reference herein in their entirety.

References

Draetta, G Mammalian G1 cyclyns Curr Opin. Cell Biol. 6, 842–846 (1994).

Schafer, K A. The cell cycle: a review. Vet Pathol 1998 35, 461–478 (1998).

Bunz, F.; Dutriaux, A.; Lengauer, C.; Waldman, T.; Zhou, S.; Brown, J. P.; Sedivy, J. M.; Kinzler, K. W.; Vogelstein, B. Requirement for p53 and p21 to sustain G2 arrest after DNA damage. Science 282, 1497–1501 (1998).

Cheng, T.; Rodrigues, N.; Shen, H.; Yang, Y.; Dombkowski, D.; Sykes, M.; Scadden, D. T. Hematopoietic stem cell quiescence maintained by p21(cip1/waf1). Science 287, 1804–1808 (2000).

Example 7

Method of Assessing the Ability of HLRRBM1 to Modulate Apoptosis.

The role of the novel HLRRBM1 polypeptides in either promoting or inhibiting apoptosis could be determined by the generation of transfected cell lines with the HLRRBM1 polynucleotides of the present invention, either transient or stable, using methods known in the art and/or described herein, and any combination of commonly used assays for the detection of DNA fragmentation. One representative example being the TUNEL assay (Gavrieli, Y., Sherman, Y., Ben, Sasson, S A, J. Cell, Biol., 119(3):493–501, (1992); which is hereby incorporated herein by reference in its entirety) which involves end labeling broken ends of double-stranded DNA with biotin-conjugated dUTP using terminal transferase. Cells undergoing cell death can then be easily detected by staining with FITC-conjugated streptavidin and flow cytometric quantitation.

Alternatively, HLRRBM1 can be expressed by transforming a mammalian cell line such as COS7, HeLa or CHO with an eukaryotic expression vector encoding HLRRBM1. Eukaryotic expression vectors are commercially available, and the techniques to introduce them into cells are well known to those skilled in the art. The cells with and without the HLRRBM1 expression vector are incubated for 48–72 hours after transformation under conditions appropriate for the cell line to allow expression of HLRRBM1. Phase microscopy is subsequently used to compare the mitotic index of transformed versus control cells. An increase in the mitotic index where HLRRBM1 stimulates cell proliferation indicates apoptotic activity. Likewise, a decrease in cell numbers where HLRRBM1 stimulates apoptosis indicates apoptotic activity.

The invention encompasses other assay methods known in the art and/or described herein.

Example 8

Method of Assessing the Ability of HLRRBM1 to Modulate Cellular Adhesion.

The role of the novel HLRRBM1 polypeptides in promoting cell adhesion events could be determined by the generation of transfected cell lines with the HLRRBM1 polynucleotides of the present invention, either transient or stable, and then subjected such cells to a hydrodynamic assay that can evaluate the relative importance of various receptor/ligand interactions in cell-cell and cell-substrate adhesion. Dynamic adhesion assays can simulate the forces found in the bloodstream and may be used to estimate the strength of the bonds between cells and ligands. Once representative assay is described by Jones et al, 1994. The skilled artisan would appreciate that this assay could readily be adapted to address the potential for HLRRBM1 to modulate cellular adhesion.

The invention encompasses other assay methods known in the art and/or described herein.

Example 9

Method of Assessing the Physiological Function of the HLRRBM1 Polypeptide at the Cellular Level.

The physiological function of the HLRRBM1 polypeptide may be assessed by expressing the sequences encoding HLRRBM1 at physiologically elevated levels in mammalian cell culture systems. cDNA is subcloned into a mammalian expression vector containing a strong promoter that drives high levels of cDNA expression (examples are provided elsewhere herein). Vectors of choice include pCMV SPORT (Life Technologies) and pCR3.1 (Invitrogen, Carlsbad Calif.), both of which contain the cytomegalovirus promoter. 5–10, ug of recombinant vector are transiently transfected into a human cell line, preferably of endothelial or hematopoietic origin, using either liposome formulations or electroporation. 1–2 ug of an additional plasmid containing sequences encoding a marker protein are cotransfected. Expression of a marker protein provides a means to distinguish transfected cells from nontransfected cells and is a reliable predictor of cDNA expression from the recombinant vector. Marker proteins of choice include, e.g., Green Fluorescent Protein (GFP; Clontech), CD64, or a CD64-GFP fusion protein. Flow cytometry (FCM), an automated, laser optics-based technique, is used to identify transfected cells expressing GFP or CD64-GFP and to evaluate the apoptotic state of the cells and other cellular properties. FCM detects and quantifies the uptake of fluorescent molecules that diagnose events preceding or coincident with cell death. These events include changes in nuclear DNA content as measured by staining of DNA with propidium iodide; changes in cell size and granularity as measured by forward light scatter and 90 degree side light scatter; down-regulation of DNA synthesis as measured by decrease in bromodeoxyuridine uptake; alterations in expression of cell surface and intracellular proteins as measured by reactivity with specific antibodies; and alterations in plasma membrane composition as measured by the binding of fluorescein-conjugated Annexin V protein to the cell surface. Methods in flow cytometry are discussed in Ormerod, M. G. (1994) Flow Cytometry, Oxford, New York N.Y.

The influence of HLRRBM1 polypeptides on gene expression can be assessed using highly purified populations of cells transfected with sequences encoding HLRRBM1 and either CD64 or CD64-GFP. CD64 and CD64-GFP are expressed on the surface of transfected cells and bind to conserved regions of human immunoglobulin G (IgG). Transfected cells are efficiently separated from nontransfected cells using magnetic beads coated with either human IgG or antibody against CD64 (DYNAL, Lake Success N.Y.). mRNA can be purified from the cells using methods well known by those of skill in the art. Expression of mRNA encoding HLRRBM1 polypeptides and other genes of interest can be analyzed by northern analysis or microarray techniques.

Example 10

Method of Screening for Compounds that Interact with the HLRRBM1 Polypeptide.

The following assays are designed to identify compounds that bind to the HLRRBM1 polypeptide, bind to other cellular proteins that interact with the HLRRBM1 polypeptide, and to compounds that interfere with the interaction of the HLRRBM1 polypeptide with other cellular proteins.

Such compounds can include, but are not limited to, other cellular proteins. Specifically, such compounds can include, but are not limited to, peptides, such as, for example, soluble peptides, including, but not limited to Ig-tailed fusion peptides, comprising extracellular portions of HLRRBM1 polypeptide transmembrane receptors, and members of random peptide libraries (see, e.g., Lam, K. S. et al., 1991, Nature 354:82–84; Houghton, R. et al., 1991, Nature 354:84–86), made of D-and/or L-configuration amino acids, phosphopeptides (including, but not limited to, members of random or partially degenerate phosphopeptide libraries; see, e.g., Songyang, Z., et al., 1993, Cell 72:767–778), antibodies (including, but not limited to, polyclonal, monoclonal, humanized, anti-idiotypic, chimeric or single chain antibodies, and FAb, F(ab').sub.2 and FAb expression libary fragments, and epitope-binding fragments thereof), and small organic or inorganic molecules.

Compounds identified via assays such as those described herein can be useful, for example, in elaborating the biological function of the HLRRBM1 polypeptide, and for ameliorating symptoms of tumor progression, for example. In instances, for example, whereby a tumor progression state or disorder results from a lower overall level of HLRRBM1 expression, HLRRBM1 polypeptide, and/or HLRRBM1 polypeptide activity in a cell involved in the tumor progression state or disorder, compounds that interact with the HLRRBM1 polypeptide can include ones which accentuate or amplify the activity of the bound HLRRBM1 polypeptide. Such compounds would bring about an effective increase in the level of HLRRBM1 polypeptide activity, thus ameliorating symptoms of the tumor progression disorder or state. In instances whereby mutations within the HLRRBM1 polypeptide cause aberrant HLRRBM1 polypeptides to be made which have a deleterious effect that leads to tumor progression, compounds that bind HLRRBM1 polypeptide can be identified that inhibit the activity of the bound HLRRBM1 polypeptide. Assays for testing the effectiveness of such compounds are known in the art and discussed, elsewhere herein.

Example 11

Method of Screening, In Vitro, Compounds that Bind to the HLRRBM1 Polypeptide.

In vitro systems can be designed to identify compounds capable of binding the HLRRBM1 polypeptide of the invention. Compounds identified can be useful, for example, in modulating the activity of wild type and/or mutant HLRRBM1 polypeptide, preferably mutant HLRRBM1 polypeptide, can be useful in elaborating the biological function of the HLRRBM1 polypeptide, can be utilized in screens for identifying compounds that disrupt normal HLRRBM1 polypeptide interactions, or can in themselves disrupt such interactions.

The principle of the assays used to identify compounds that bind to the HLRRBM1 polypeptide involves preparing a reaction mixture of the HLRRBM1 polypeptide and the test compound under conditions and for a time sufficient to allow the two components to interact and bind, thus forming a complex which can be removed and/or detected in the reaction mixture. These assays can be conducted in a variety of ways. For example, one method to conduct such an assay would involve anchoring HLRRBM1 polypeptide or the test substance onto a solid phase and detecting HLRRBM1 polypeptide/test compound complexes anchored on the solid phase at the end of the reaction. In one embodiment of such a method, the HLRRBM1 polypeptide can be anchored onto a solid surface, and the test compound, which is not anchored, can be labeled, either directly or indirectly.

In practice, microtitre plates can conveniently be utilized as the solid phase. The anchored component can be immobilized by non-covalent or covalent attachments. Non-covalent attachment can be accomplished by simply coating the solid surface with a solution of the protein and drying. Alternatively, an immobilized antibody, preferably a monoclonal antibody, specific for the protein to be immobilized can be used to anchor the protein to the solid surface. The surfaces can be prepared in advance and stored.

In order to conduct the assay, the nonimmobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously immobilized component is pre-labeled, the detection of label immobilized on the surface indicates that complexes were formed. Where the previously nonimmobilized component is not pre-labeled, an indirect label can be used to detect complexes anchored on the surface; e.g., using a labeled antibody specific for the immobilized component (the antibody, in turn, can be directly labeled or indirectly labeled with a labeled anti-Ig antibody).

Alternatively, a reaction can be conducted in a liquid phase, the reaction products separated from unreacted components, and complexes detected; e.g., using an immobilized antibody specific for HLRRBM1 polypeptide or the test compound to anchor any complexes formed in solution, and a labeled antibody specific for the other component of the possible complex to detect anchored complexes.

Example 12

Method for Identifying a Putative Ligand for the HGCRBMY11 Polypeptide.

Ligand binding assays provide a direct method for ascertaining receptor pharmacology and are adaptable to a high throughput format. A panel of known leucine-rich repeat containing protein purified ligands may be radiolabeled to high specific activity (50–2000 Ci/mmol) for binding studies. A determination is then made that the process of radiolabeling does not diminish the activity of the ligand towards its receptor. Assay conditions for buffers, ions, pH and other modulators such as nucleotides are optimized to establish a workable signal to noise ratio for both membrane and whole cell receptor sources. For these assays, specific receptor binding is defined as total associated radioactivity minus the radioactivity measured in the presence of an excess of unlabeled competing ligand. Where possible, more than one competing ligand is used to define residual nonspecific binding.

A number of leucine-rich repeat containing protein ligands are known in the art and are encompassed by the present invention.

Alternatively, the HLRRBM1 polypeptide of the present invention may also be functionally screened against tissue extracts to identify natural ligands. Extracts that produce positive functional responses can be sequencially subfractionated until an activating ligand is isolated identified using methods well known in the art, some of which are described herein.

Example 13

Method of Identifying Compounds that Interfere with HLRRBM1 Polypeptide/Cellular Product Interaction.

The HLRRBM1 polypeptide of the invention can, in vivo, interact with one or more cellular or extracellular macromolecules, such as proteins. Such macromolecules include, but are not limited to, polypeptides, and those products identified via screening methods described, elsewhere herein. For the purposes of this discussion, such cellular and extracellular macromolecules are referred to herein as "binding partner(s)". For the purpose of the present invention, "binding partner" may also encompass polypeptides, small molecule compounds, polysaccarides, lipids, and any other molecule or molecule type referenced herein. Compounds that disrupt such interactions can be useful in regulating the activity of the HLRRBM1 polypeptide, especially mutant HLRRBM1 polypeptide. Such compounds can include, but are not limited to molecules such as antibodies, peptides, and the like described in elsewhere herein.

The basic principle of the assay systems used to identify compounds that interfere with the interaction between the HLRRBM1 polypeptide and its cellular or extracellular binding partner or partners involves preparing a reaction mixture containing the HLRRBM1 polypeptide, and the binding partner under conditions and for a time sufficient to allow the two products to interact and bind, thus forming a complex. In order to test a compound for inhibitory activity, the reaction mixture is prepared in the presence and absence of the test compound. The test compound can be initially included in the reaction mixture, or can be added at a time subsequent to the addition of HLRRBM1 polypeptide and its cellular or extracellular binding partner. Control reaction mixtures are incubated without the test compound or with a placebo. The formation of any complexes between the HLRRBM1 polypeptide and the cellular or extracellular binding partner is then detected. The formation of a complex in the control reaction, but not in the reaction mixture containing the test compound, indicates that the compound interferes with the interaction of the HLRRBM1 polypeptide and the interactive binding partner. Additionally, complex formation within reaction mixtures containing the test compound and normal HLRRBM1 polypeptide can also be compared to complex formation within reaction mixtures containing the test compound and mutant HLRRBM1 polypeptide. This comparison can be important in those cases wherein it is desirable to identify compounds that disrupt interactions of mutant but not normal HLRRBM1 polypeptide.

The assay for compounds that interfere with the interaction of the HLRRBM1 polypeptide and binding partners can be conducted in a heterogeneous or homogeneous format. Heterogeneous assays involve anchoring either the HLRRBM1 polypeptide or the binding partner onto a solid phase and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the HLRRBM1 polypeptide and the binding partners, e.g., by competition, can be identified by conducting the reaction in the presence of the test substance; i.e., by adding the test substance to the reaction mixture prior to or simultaneously with the HLRRBM1 polypeptide and interactive cellular or extracellular binding partner. Alternatively, test compounds that disrupt preformed complexes, e.g. compounds with higher binding constants that displace one of the components from the complex, can be tested by adding the test compound to the reaction mixture after complexes have been formed. The various formats are described briefly below.

In a heterogeneous assay system, either the HLRRBM1 polypeptide or the interactive cellular or extracellular binding partner, is anchored onto a solid surface, while the non-anchored species is labeled, either directly or indirectly. In practice, microtitre plates are conveniently utilized. The anchored species can be immobilized by non-covalent or covalent attachments. Non-covalent attachment can be accomplished simply by coating the solid surface with a solution of the HLRRBM1 polypeptide or binding partner and drying. Alternatively, an immobilized antibody specific for the species to be anchored can be used to anchor the species to the solid surface. The surfaces can be prepared in advance and stored.

In order to conduct the assay, the partner of the immobilized species is exposed to the coated surface with or without the test compound. After the reaction is complete, unreacted components are removed (e.g., by washing) and any complexes formed will remain immobilized on the solid surface. The detection of complexes anchored on the solid surface can be accomplished in a number of ways. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, can be directly labeled or indirectly labeled with a labeled anti-Ig antibody). Depending upon the order of addition of reaction components, test compounds which inhibit complex formation or which disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds which inhibit complex or which disrupt preformed complexes can be identified.

In an alternate embodiment of the invention, a homogeneous assay can be used. In this approach, a preformed complex of the HLRRBM1 polypeptide and the interactive cellular or extracellular binding partner product is prepared in which either the HLRRBM1 polypeptide or their binding partners are labeled, but the signal generated by the label is quenched due to complex formation (see, e.g., U.S. Pat. No.

4,109,496 by Rubenstein which utilizes this approach for immunoassays).

The addition of a test substance that competes with and displaces one of the species from the preformed complex will result in the generation of a signal above background. In this way, test substances which disrupt HLRRBM1 polypeptide—cellular or extracellular binding partner interaction can be identified.

In a particular embodiment, the HLRRBM1 polypeptide can be prepared for immobilization using recombinant DNA techniques known in the art. For example, the HLRRBM1 polypeptide coding region can be fused to a glutathione-S-transferase (GST) gene using a fusion vector such as pGEX-5X-1, in such a manner that its binding activity is maintained in the resulting fusion product. The interactive cellular or extracellular product can be purified and used to raise a monoclonal antibody, using methods routinely practiced in the art and described above. This antibody can be labeled with the radioactive isotope .sup.125 I, for example, by methods routinely practiced in the art. In a heterogeneous assay, e.g., the GST-HLRRBM1 polypeptide fusion product can be anchored to glutathione-agarose beads. The interactive cellular or extracellular binding partner product can then be added in the presence or absence of the test compound in a manner that allows interaction and binding to occur. At the end of the reaction period, unbound material can be washed away, and the labeled monoclonal antibody can be added to the system and allowed to bind to the complexed components. The interaction between the HLRRBM1 polypeptide and the interactive cellular or extracellular binding partner can be detected by measuring the amount of radioactivity that remains associated with the glutathione-agarose beads. A successful inhibition of the interaction by the test compound will result in a decrease in measured radioactivity.

Alternatively, the GST-HLRRBM1 polypeptide fusion product and the interactive cellular or extracellular binding partner product can be mixed together in liquid in the absence of the solid glutathione-agarose beads. The test compound can be added either during or after the binding partners are allowed to interact. This mixture can then be added to the glutathione-agarose beads and unbound material is washed away. Again the extent of inhibition of the binding partner interaction can be detected by adding the labeled antibody and measuring the radioactivity associated with the beads.

In another embodiment of the invention, these same techniques can be employed using peptide fragments that correspond to the binding domains of the HLRRBM1 polypeptide product and the interactive cellular or extracellular binding partner (in case where the binding partner is a product), in place of one or both of the full length products.

Any number of methods routinely practiced in the art can be used to identify and isolate the protein's binding site. These methods include, but are not limited to, mutagenesis of one of the genes encoding one of the products and screening for disruption of binding in a co-immunoprecipitation assay. Compensating mutations in the gene encoding the second species in the complex can be selected. Sequence analysis of the genes encoding the respective products will reveal the mutations that correspond to the region of the product involved in interactive binding. Alternatively, one product can be anchored to a solid surface using methods described in this Section above, and allowed to interact with and bind to its labeled binding partner, which has been treated with a proteolytic enzyme, such as trypsin. After washing, a short, labeled peptide comprising the binding domain can remain associated with the solid material, which can be isolated and identified by amino acid sequencing. Also, once the gene coding for the cellular or extracellular binding partner product is obtained, short gene segments can be engineered to express peptide fragments of the product, which can then be tested for binding activity and purified or synthesized.

Example 14

Isolation of a Specific Clone from the Deposited Sample.

The deposited material in the sample assigned the ATCC Deposit Number cited in Table I for any given cDNA clone also may contain one or more additional plasmids, each comprising a cDNA clone different from that given clone. Thus, deposits sharing the same ATCC Deposit Number contain at least a plasmid for each cDNA clone identified in Table I. Typically, each ATCC deposit sample cited in Table I comprises a mixture of approximately equal amounts (by weight) of about 1–10 plasmid DNAs, each containing a different cDNA clone and/or partial cDNA clone; but such a deposit sample may include plasmids for more or less than 2 cDNA clones.

Two approaches can be used to isolate a particular clone from the deposited sample of plasmid DNA(s) cited for that clone in Table I. First, a plasmid is directly isolated by screening the clones using a polynucleotide probe corresponding to SEQ ID NO:1.

Particularly, a specific polynucleotide with 30–40 nucleotides is synthesized using an Applied Biosystems DNA synthesizer according to the sequence reported. The oligonucleotide is labeled, for instance, with 32P-(-ATP using T4 polynucleotide kinase and purified according to routine methods. (E.g., Maniatis et al., Molecular Cloning: A Laboratory Manual, Cold Spring Harbor Press, Cold Spring, N.Y. (1982).) The plasmid mixture is transformed into a suitable host, as indicated above (such as XL-1 Blue (Stratagene)) using techniques known to those of skill in the art, such as those provided by the vector supplier or in related publications or patents cited above. The transformants are plated on 1.5% agar plates (containing the appropriate selection agent, e.g., ampicillin) to a density of about 150 transformants (colonies) per plate. These plates are screened using Nylon membranes according to routine methods for bacterial colony screening (e.g., Sambrook et al., Molecular Cloning: A Laboratory Manual, 2nd Edit., (1989), Cold Spring Harbor Laboratory Press, pages 1.93 to 1.104), or other techniques known to those of skill in the art.

Alternatively, two primers of 17–20 nucleotides derived from both ends of the SEQ ID NO:1 (i.e., within the region of SEQ ID NO:1 bounded by the 5' NT and the 3' NT of the clone defined in Table I) are synthesized and used to amplify the desired cDNA using the deposited cDNA plasmid as a template. The polymerase chain reaction is carried out under routine conditions, for instance, in 25 ul of reaction mixture with 0.5 ug of the above cDNA template. A convenient reaction mixture is 1.5–5 mM MgCl2, 0.01% (w/v) gelatin, 20 uM each of dATP, dCTP, dGTP, dTTP, 25 pmol of each primer and 0.25 Unit of Taq polymerase. Thirty five cycles of PCR (denaturation at 94 degree C. for 1 min; annealing at 55 degree C. for 1 min; elongation at 72 degree C. for 1 min) are performed with a Perkin-Elmer Cetus automated thermal cycler. The amplified product is analyzed by agarose gel electrophoresis and the DNA band with expected molecular weight is excised and purified. The PCR product is verified to be the selected sequence by subcloning and sequencing the DNA product.

The polynucleotide(s) of the present invention, the polynucleotide encoding the polypeptide of the present invention, or the polypeptide encoded by the deposited clone may represent partial, or incomplete versions of the complete coding region (i.e., full-length gene). Several methods are known in the art for the identification of the 5' or 3' non-coding and/or coding portions of a gene which may not be present in the deposited clone. The methods that follow are exemplary and should not be construed as limiting the scope of the invention. These methods include but are not limited to, filter probing, clone enrichment using specific probes, and protocols similar or identical to 5' and 3' "RACE" protocols that are well known in the art. For instance, a method similar to 5' RACE is available for generating the missing 5' end of a desired full-length transcript. (Fromont-Racine et al., Nucleic Acids Res. 21(7): 1683–1684 (1993)).

Briefly, a specific RNA oligonucleotide is ligated to the 5' ends of a population of RNA presumably containing full-length gene RNA transcripts. A primer set containing a primer specific to the ligated RNA oligonucleotide and a primer specific to a known sequence of the gene of interest is used to PCR amplify the 5' portion of the desired full-length gene. This amplified product may then be sequenced and used to generate the full-length gene.

This above method starts with total RNA isolated from the desired source, although poly-A+ RNA can be used. The RNA preparation can then be treated with phosphatase if necessary to eliminate 5' phosphate groups on degraded or damaged RNA that may interfere with the later RNA ligase step. The phosphatase should then be inactivated and the RNA treated with tobacco acid pyrophosphatase in order to remove the can structure present at the 5' ends of messenger RNAs. This reaction leaves a 5' phosphate group at the 5' end of the cap cleaved RNA which can then be ligated to an RNA oligonucleotide using T4 RNA ligase.

This modified RNA preparation is used as a template for first strand cDNA synthesis using a gene specific oligonucleotide. The first strand synthesis reaction is used as a template for PCR amplification of the desired 5' end using a primer specific to the ligated RNA oligonucleotide and a primer specific to the known sequence of the gene of interest. The resultant product is then sequenced and analyzed to confirm that the 5' end sequence belongs to the desired gene. Moreover, it may be advantageous to optimize the RACE protocol to increase the probability of isolating additional 5' or 3' coding or non-coding sequences. Various methods of optimizing a RACE protocol are known in the art, though a detailed description summarizing these methods can be found in B. C. Schaefer, Anal. Biochem., 227:255–273, (1995).

An alternative method for carrying out 5' or 3' RACE for the identification of coding or non-coding sequences is provided by Frohman, M. A., et al., Proc. Nat'l. Acad. Sci. USA, 85:8998–9002 (1988). Briefly, a cDNA clone missing either the 5' or 3' end can be reconstructed to include the absent base pairs extending to the translational start or stop codon, respectively. In some cases, cDNAs are missing the start of translation, therefor. The following briefly describes a modification of this original 5' RACE procedure. Poly A+ or total RNAs reverse transcribed with Superscript II (Gibco/BRL) and an antisense or I complementary primer specific to the cDNA sequence. The primer is removed from the reaction with a Microcon Concentrator (Amicon). The first-strand cDNA is then tailed with dATP and terminal deoxynucleotide transferase (Gibco/BRL). Thus, an anchor sequence is produced which is needed for PCR amplification. The second strand is synthesized from the dA-tail in PCR buffer, Taq DNA polymerase (Perkin-Elmer Cetus), an oligo-dT primer containing three adjacent restriction sites (XhoIJ SaiI and ClaI) at the 5' end and a primer containing just these restriction sites. This double-stranded cDNA is PCR amplified for 40 cycles with the same primers as well as a nested cDNA-specific antisense primer. The PCR products are size-separated on an ethidium bromide-agarose gel and the region of gel containing cDNA products the predicted size of missing protein-coding DNA is removed. cDNA is purified from the agarose with the Magic PCR Prep kit (Promega), restriction digested with XhoI or SalI, and ligated to a plasmid such as pBluescript SKII (Stratagene) at XhoI and EcoRV sites. This DNA is transformed into bacteria and the plasmid clones sequenced to identify the correct protein-coding inserts. Correct 5' ends are confirmed by comparing this sequence with the putatively identified homologue and overlap with the partial cDNA clone. Similar methods known in the art and/or commercial kits are used to amplify and recover 3' ends.

Several quality-controlled kits are commercially available for purchase. Similar reagents and methods to those above are supplied in kit form from Gibco/BRL for both 5' and 3' RACE for recovery of full length genes. A second kit is available from Clontech which is a modification of a related technique, SLIC (single-stranded ligation to single-stranded cDNA), developed by Dumas et al., Nucleic Acids Res., 19:5227–32(1991). The major differences in procedure are that the RNA is alkaline hydrolyzed after reverse transcription and RNA ligase is used to join a restriction site-containing anchor primer to the first-strand cDNA. This obviates the necessity for the dA-tailing reaction which results in a polyT stretch that is difficult to sequence past.

An alternative to generating 5' or 3' cDNA from RNA is to use cDNA library double-stranded DNA. An asymmetric PCR-amplified antisense cDNA strand is synthesized with an antisense cDNA-specific primer and a plasmid-anchored primer. These primers are removed and a symmetric PCR reaction is performed with a nested cDNA-specific antisense primer and the plasmid-anchored primer.

RNA Ligase Protocol for Generating the 5' or 3' End Sequences to Obtain Full Length Genes Once a gene of interest is identified, several methods are available for the identification of the 5' or 3' portions of the gene which may not be present in the original cDNA plasmid. These methods include, but are not limited to, filter probing, clone enrichment using specific probes and protocols similar and identical to 5' and 3'RACE. While the full-length gene may be present in the library and can be identified by probing, a useful method for generating the 5' or 3' end is to use the existing sequence information from the original cDNA to generate the missing information. A method similar to 5'RACE is available for generating the missing 5' end of a desired full-length gene. (This method was published by Fromont-Racine et al., Nucleic Acids Res., 21(7): 1683–1684 (1993)). Briefly, a specific RNA oligonucleotide is ligated to the 5' ends of a population of RNA presumably 30 containing full-length gene RNA transcript and a primer set containing a primer specific to the ligated RNA oligonucleotide and a primer specific to a known sequence of the gene of interest, is used to PCR amplify the 5' portion of the desired full length gene which may then be sequenced and used to generate the full length gene. This method starts with total RNA isolated from the desired source, poly A RNA may be used but is not a prerequisite for this procedure. The RNA preparation may then be treated with phosphatase if necessary to eliminate 5' phosphate groups on degraded or damaged RNA which may interfere with the later RNA ligase step. The phosphatase if used is then inactivated and the RNA is treated with tobacco acid pyrophosphatase in order to remove the cap structure present at the 5' ends of messenger RNAs. This reaction leaves a 5' phosphate group at the 5' end of the cap cleaved RNA which can then be ligated to an RNA oligonucleotide using T4 RNA ligase. This modified RNA preparation can then be used as a template for first strand cDNA synthesis using a gene specific oligonucleotide. The first strand synthesis reaction can then be used as a template for PCR amplification of the desired 5' end using a primer specific to the ligated RNA oligonucleotide and a primer specific to the known sequence of the apoptosis related of interest. The resultant product is then sequenced and analyzed to confirm that the 5' end sequence belongs to the relevant apoptosis related.

Example 15

Tissue Distribution of Polypeptide.

Tissue distribution of mRNA expression of polynucleotides of the present invention is determined using protocols for Northern blot analysis, described by, among others, Sambrook et al. For example, a cDNA probe produced by the method described in Example 11 is labeled with p32 using the rediprime™ DNA labeling system (Amersham Life Science), according to manufacturer's instructions. After labeling, the probe is purified using CHROMA SPIN0-100 column (Clontech Laboratories, Inc.) according to manufacturer's protocol number PT1200-1. The purified labeled probe is then used to examine various tissues for mRNA expression.

Tissue Northern blots containing the bound mRNA of various tissues are examined with the labeled probe using ExpressHybtm hybridization solution (Clonetech according to manufacturers protocol number PT1190-1. Northern blots can be produced using various protocols well known in the art (e.g., Sambrook et al). Following hybridization and washing, the blots are mounted and exposed to film at—70C. overnight, and the films developed according to standard procedures.

Example 16

Chromosomal Mapping of the Polynucleotides.

An oligonucleotide primer set is designed according to the sequence at the 5' end of SEQ ID NO:1. This primer preferably spans about 100 nucleotides. This primer set is then used in a polymerase chain reaction under the following set of conditions: 30 seconds, 95 degree C.; 1 minute, 56 degree C.; 1 minute, 70 degree C. This cycle is repeated 32 times followed by one 5 minute cycle at 70 degree C. Mammalian DNA, preferably human DNA, is used as template in addition to a somatic cell hybrid panel containing individual chromosomes or chromosome fragments (Bios, Inc). The reactions are analyzed on either 8% polyacrylamide gels or 3.5% agarose gels. Chromosome mapping is determined by the presence of an approximately 100 bp PCR fragment in the particular somatic cell hybrid.

Example 17

Bacterial Expression of a Polypeptide.

A polynucleotide encoding a polypeptide of the present invention is amplified using PCR oligonucleotide primers corresponding to the 5' and 3' ends of the DNA sequence, as outlined in Example 11, to synthesize insertion fragments. The primers used to amplify the cDNA insert should preferably contain restriction sites, such as BamHI and XbaI, at the 5' end of the primers in order to clone the amplified product into the expression vector. For example, BamHI and XbaI correspond to the restriction enzyme sites on the bacterial expression vector pQE-9. (Qiagen, Inc., Chatsworth, Calif.). This plasmid vector encodes antibiotic resistance (Ampr), a bacterial origin of replication (ori), an IPTG-regulatable promoter/operator (P/O), a ribosome binding site (RBS), a 6-histidine tag (6-His), and restriction enzyme cloning sites.

The pQE-9 vector is digested with BamHI and XbaI and the amplified fragment is ligated into the pQE-9 vector maintaining the reading frame initiated at the bacterial RBS. The ligation mixture is then used to transform the *E. coli* strain M15/rep4 (Qiagen, Inc.) which contains multiple copies of the plasmid pREP4, that expresses the lacI repressor and also confers kanamycin resistance (Kanr). Transformants are identified by their ability to grow on LB plates and ampicillin/kanamycin resistant colonies are selected. Plasmid DNA is isolated and confirmed by restriction analysis.

Clones containing the desired constructs are grown overnight (O/N) in liquid culture in LB media supplemented with both Amp (100 ug/ml) and Kan (25 ug/ml). The O/N culture is used to inoculate a large culture at a ratio of 1:100 to 1:250. The cells are grown to an optical density 600 (O.D.600) of between 0.4 and 0.6. IPTG (Isopropyl-B-D-thiogalacto pyranoside) is then added to a final concentration of 1 mM. IPTG induces by inactivating the lacI repressor, clearing the P/O leading to increased gene expression.

Cells are grown for an extra 3 to 4 hours. Cells are then harvested by centrifugation (20 mins at 6000×g). The cell pellet is solubilized in the chaotropic agent 6 Molar Guanidine HCl by stirring for 3–4 hours at 4 degree C. The cell debris is removed by centrifugation, and the supernatant containing the polypeptide is loaded onto a nickel-nitrilo-tri-acetic acid ("Ni-NTA") affinity resin column (available from QIAGEN, Inc., supra). Proteins with a 6× His tag bind to the Ni-NTA resin with high affinity and can be purified in a simple one-step procedure (for details see: The QIAexpressionist (1995) QIAGEN, Inc., supra).

Briefly, the supernatant is loaded onto the column in 6 M guanidine-HCl, pH 8, the column is first washed with 10 volumes of 6 M guanidine-HCl, pH 8, then washed with 10 volumes of 6 M guanidine-HCl pH 6, and finally the polypeptide is eluted with 6 M guanidine-HCl, pH 5.

The purified protein is then renatured by dialyzing it against phosphate-buffered saline (PBS) or 50 mM Na-acetate, pH 6 buffer plus 200 mM NaCl. Alternatively, the protein can be successfully refolded while immobilized on the Ni-NTA column. The recommended conditions are as follows: renature using a linear 6M–1M urea gradient in 500 mM NaCl, 20%, glycerol, 20 mM Tris/HCl pH 7.4, containing protease inhibitors. The renaturation should be performed over a period of 1.5 hours or more. After renaturation the proteins are eluted by the addition of 250 mM imidazole. Imidazole is removed by a final dialyzing step against PBS or 50 mM sodium acetate pH 6 buffer plus 200 mM NaCl. The purified protein is stored at 4 degree C. or frozen at −80 degree C.

Example 18

Purification of a Polypeptide from an Inclusion Body.

The following alternative method can be used to purify a polypeptide expressed in *E coli* when it is present in the form of inclusion bodies. Unless otherwise specified, all of the following steps are conducted at 4–10 degree C.

Upon completion of the production phase of the *E. coli* fermentation, the cell culture is cooled to 4–10 degree C. and the cells harvested by continuous centrifugation at 15,000 rpm (Heraeus Sepatech). On the basis of the expected yield of protein per unit weight of cell paste and the amount of purified protein required, an appropriate amount of cell paste, by weight, is suspended in a buffer solution containing 100 mM Tris, 50 mM EDTA, pH 7.4. The cells are dispersed to a homogeneous suspension using a high shear mixer.

The cells are then lysed by passing the solution through a microfluidizer (Microfluidics, Corp. or APV Gaulin, Inc.) twice at 4000–6000 psi. The homogenate is then mixed with NaCl solution to a final concentration of 0.5 M NaCl, followed by centrifugation at 7000×g for 15 min. The resultant pellet is washed again using 0.5M NaCl, 100 mM Tris, 50 mM EDTA, pH 7.4.

The resulting washed inclusion bodies are solubilized with 1.5 M guanidine hydrochloride (GuHCl) for 2–4 hours. After 7000×g centrifugation for 15 min., the pellet is discarded and the polypeptide containing supernatant is incubated at 4 degree C. overnight to allow further GuHCl extraction.

Following high speed centrifugation (30,000×g) to remove insoluble particles, the GuHCl solubilized protein is refolded by quickly mixing the GuHCl extract with 20 volumes of buffer containing 50 mM sodium, pH 4.5, 150 mM NaCl, 2 mM EDTA by vigorous stirring. The refolded diluted protein solution is kept at 4 degree C. without mixing for 12 hours prior to further purification steps.

To clarify the refolded polypeptide solution, a previously prepared tangential filtration unit equipped with 0.16 um membrane filter with appropriate surface area (e.g., Filtron), equilibrated with 40 mM sodium acetate, pH 6.0 is employed. The filtered sample is loaded onto a cation exchange resin (e.g., Poros HS-50, Perceptive Biosystems). The column is washed with 40 mM sodium acetate, pH 6.0 and eluted with 250 mM, 500 mM, 1000 mM, and 1500 mM NaCl in the same buffer, in a stepwise manner. The absorbance at 280 nm of the effluent is continuously monitored. Fractions are collected and further analyzed by SDS-PAGE.

Fractions containing the polypeptide are then pooled and mixed with 4 volumes of water. The diluted sample is then loaded onto a previously prepared set of tandem columns of strong anion (Poros HQ-50, Perceptive Biosystems) and weak anion (Poros CM-20, Perceptive Biosystems) exchange resins. The columns are equilibrated with 40 mM sodium acetate, pH 6.0. Both columns are washed with 40 mM sodium acetate, pH 6.0, 200 mM NaCl. The CM-20 column is then eluted using a 10 column volume linear gradient ranging from 0.2 M NaCl, 50 mM sodium acetate, pH 6.0 to 1.0 M NaCl, 50 mM sodium acetate, pH 6.5. Fractions are collected under constant A280 monitoring of the effluent. Fractions containing the polypeptide (determined, for instance, by 16% SDS-PAGE) are then pooled.

The resultant polypeptide should exhibit greater than 95% purity after the above refolding and purification steps. No major contaminant bands should be observed from Coomassie blue stained 16% SDS-PAGE gel when 5 ug of purified protein is loaded. The purified protein can also be tested for endotoxin/LPS contamination, and typically the LPS content is less than 0.1 ng/ml according to LAL assays.

Example 19

Cloning and Expression of a Polypeptide in a Baculovirus Expression System.

In this example, the plasmid shuttle vector pAc373 is used to insert a polynucleotide into a baculovirus to express a polypeptide. A typical baculovirus expression vector contains the strong polyhedrin promoter of the *Autographa californica* nuclear polyhedrosis virus (AcMNPV) followed by convenient restriction sites, which may include, for example BamHI, Xba I and Asp718. The polyadenylation site of the simian virus 40 ("SV40") is often used for efficient polyadenylation. For easy selection of recombinant virus, the plasmid contains the beta-galactosidase gene from *E. coli* under control of a weak *Drosophila* promoter in the same orientation, followed by the polyadenylation signal of the polyhedrin gene. The inserted genes are flanked on both sides by viral sequences for cell-mediated homologous recombination with wild-type viral DNA to generate a viable virus that express the cloned polynucleotide.

Many other baculovirus vectors can be used in place of the vector above, such as pVL941 and pAcIM1, as one skilled in the art would readily appreciate, as long as the construct provides appropriately located signals for transcription, translation, secretion and the like, including a signal peptide and an in-frame AUG as required. Such vectors are described, for instance, in Luckow et al., Virology 170:31–39 (1989).

A polynucleotide encoding a polypeptide of the present invention is amplified using PCR oligonucleotide primers corresponding to the 5' and 3' ends of the DNA sequence, as outlined in Example 11, to synthesize insertion fragments. The primers used to amplify the cDNA insert should preferably contain restriction sites at the 5' end of the primers in order to clone the amplified product into the expression vector. Specifically, the cDNA sequence contained in the deposited clone, including the AUG initiation codon and the naturally associated leader sequence identified elsewhere herein (if applicable), is amplified using the PCR protocol described in Example 11. If the naturally occurring signal sequence is used to produce the protein, the vector used does not need a second signal peptide. Alternatively, the vector can be modified to include a baculovirus leader sequence, using the standard methods described in Summers et al., "A Manual of Methods for Baculovirus Vectors and Insect Cell Culture Procedures," Texas Agricultural Experimental Station Bulletin No. 1555 (1987).

The amplified fragment is isolated from a 1% agarose gel using a commercially available kit ("Geneclean," BIO 101 Inc., La Jolla, Calif.). The fragment then is digested with appropriate restriction enzymes and again purified on a 1% agarose gel.

The plasmid is digested with the corresponding restriction enzymes and optionally, can be dephosphorylated using calf intestinal phosphatase, using routine procedures known in the art. The DNA is then isolated from a 1% agarose gel using a commercially available kit ("Geneclean" BIO 101 Inc., La Jolla, Calif.).

The fragment and the dephosphorylated plasmid are ligated together with T4 DNA ligase. *E. coli* HB101 or other suitable *E. coli* hosts such as XL-1 Blue (Stratagene Cloning Systems, La Jolla, Calif.) cells are transformed with the ligation mixture and spread on culture plates. Bacteria containing the plasmid are identified by digesting DNA from individual colonies and analyzing the digestion product by gel electrophoresis. The sequence of the cloned fragment is confirmed by DNA sequencing.

Five ug of a plasmid containing the polynucleotide is co-transformed with 1.0 ug of a commercially available linearized baculovirus DNA ("BaculoGoldtm baculovirus DNA", Pharmingen, San Diego, Calif.), using the lipofection method described by Felgner et al., Proc. Natl. Acad.

Sci. USA 84:7413–7417 (1987). One ug of BaculoGoldtm virus DNA and 5 ug of the plasmid are mixed in a sterile well of a microtiter plate containing 50 ul of serum-free Grace's medium (Life Technologies Inc., Gaithersburg, Md.). Afterwards, 10 ul Lipofectin plus 90 ul Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is then incubated for 5 hours at 27 degrees C. The transfection solution is then removed from the plate and 1 ml of Grace's insect medium supplemented with 10% fetal calf serum is added. Cultivation is then continued at 27 degrees C. for four days.

After four days the supernatant is collected and a plaque assay is performed, as described by Summers and Smith, supra. An agarose gel with "Blue Gal" (Life Technologies Inc., Gaithersburg) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9–10.) After appropriate incubation, blue stained plaques are picked with the tip of a micropipettor (e.g., Eppendorf). The agar containing the recombinant viruses is then resuspended in a microcentrifuge tube containing 200 ul of Grace's medium and the suspension containing the recombinant baculovirus is used to infect Sf9 cells seeded in 35 mm dishes. Four days later the supernatants of these culture dishes are harvested and then they are stored at 4 degree C.

To verify the expression of the polypeptide, Sf9 cells are grown in Grace's medium supplemented with 10% heat-inactivated FBS. The cells are infected with the recombinant baculovirus containing the polynucleotide at a multiplicity of infection ("MOI") of about 2. If radiolabeled proteins are desired, 6 hours later the medium is removed and is replaced with SF900 II medium minus methionine and cysteine (available from Life Technologies Inc., Rockville, Md.). After 42 hours, 5 uCi of 35S-methionine and 5 uCi 35S-cysteine (available from Amersham) are added. The cells are further incubated for 16 hours and then are harvested by centrifugation. The proteins in the supernatant as well as the intracellular proteins are analyzed by SDS-PAGE followed by autoradiography (if radiolabeled).

Microsequencing of the amino acid sequence of the amino terminus of purified protein may be used to determine the amino terminal sequence of the produced protein.

Example 20

Expression of a Polypeptide in Mammalian Cells.

The polypeptide of the present invention can be expressed in a mammalian cell. A typical mammalian expression vector contains a promoter element, which mediates the initiation of transcription of mRNA, a protein coding sequence, and signals required for the termination of transcription and polyadenylation of the transcript. Additional elements include enhancers, Kozak sequences and intervening sequences flanked by donor and acceptor sites for RNA splicing. Highly efficient transcription is achieved with the early and late promoters from SV40, the long terminal repeats (LTRs) from Retroviruses, e.g., RSV, HTLVI, HIVI and the early promoter of the cytomegalovirus (CMV). However, cellular elements can also be used (e.g., the human actin promoter).

Suitable expression vectors for use in practicing the present invention include, for example, vectors such as pSVL and pMSG (Pharmacia, Uppsala, Sweden), pRSVcat (ATCC 37152), pSV2dhfr (ATCC 37146), pBC12MI (ATCC 67109), pCMVSport 2.0, and pCMVSport 3.0. Mammalian host cells that could be used include, human Hela, 293, H9 and Jurkat cell, mouse NIH3T3 and C127 cells, Cos 1, Cos 7 and CV1, quail QC1–3 cells, mouse L cells and Chinese hamster ovary (CHO) cells.

Alternatively, the polypeptide can be expressed in stable cell lines containing the polynucleotide integrated into a chromosome. The co-transformation with a selectable marker such as dhfr, gpt, neomycin, hygromycin allows the identification and isolation of the transformed cells.

The transformed gene can also be amplified to express large amounts of the encoded protein. The DHFR (dihydrofolate reductase) marker is useful in developing cell lines that carry several hundred or even several thousand copies of the gene of interest. (See, e.g., Alt, F. W., et al., J. Biol. Chem. 253:1357–1370 (1978); Hamlin, J. L. and Ma, C., Biochem. et Biophys. Acta, 1097:107–143 (1990); Page, M. J. and Sydenham, M. A., Biotechnology 9:64–68 (1991).) Another useful selection marker is the enzyme glutamine synthase (GS) (Murphy et al., Biochem J. 227:277–279 (1991); Bebbington et al., Bio/Technology 10:169–175 (1992). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of proteins.

A polynucleotide of the present invention is amplified according to the protocol outlined in herein. If the naturally occurring signal sequence is used to produce the protein, the vector does not need a second signal peptide. Alternatively, if the naturally occurring signal sequence is not used, the vector can be modified to include a heterologous signal sequence. (See, e.g., WO 96/34891.) The amplified fragment is isolated from a 1% agarose gel using a commercially available kit ("Geneclean," BIO 101 Inc., La Jolla, Calif.). The fragment then is digested with appropriate restriction enzymes and again purified on a 1% agarose gel.

The amplified fragment is then digested with the same restriction enzyme and purified on a 1% agarose gel. The isolated fragment and the dephosphorylated vector are then ligated with T4 DNA ligase. *E. coli* HB101 or XL-1 Blue cells are then transformed and bacteria are identified that contain the fragment inserted into plasmid pC6 using, for instance, restriction enzyme analysis.

Chinese hamster ovary cells lacking an active DHFR gene is used for transformation. Five μg of an expression plasmid is cotransformed with 0.5 ug of the plasmid pSVneo using lipofectin (Felgner et al., supra). The plasmid pSV2-neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of methotrexate plus 1 mg/ml G418. After about 10–14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 uM, 2 uM, 5 uM, 10 mM, 20 mM). The same procedure is repeated until clones are obtained which grow at a concentration of 100–200 uM. Expression of the desired gene product is analyzed, for instance, by SDS-PAGE and Western blot or by reversed phase HPLC analysis.

Example 21

Protein Fusions.

The polypeptides of the present invention are preferably fused to other proteins. These fusion proteins can be used for a variety of applications. For example, fusion of the present polypeptides to His-tag, HA-tag, protein A, IgG domains, and maltose binding protein facilitates purification. (See Example described herein; see also EP A 394,827; Traunecker, et al., Nature 331:84–86 (1988).) Similarly, fusion to IgG-1, IgG-3, and albumin increases the half-life time in vivo. Nuclear localization signals fused to the polypeptides of the present invention can target the protein to a specific subcellular localization, while covalent heterodimer or homodimers can increase or decrease the activity of a fusion protein. Fusion proteins can also create chimeric molecules having more than one function. Finally, fusion proteins can increase solubility and/or stability of the fused protein compared to the non-fused protein. All of the types of fusion proteins described above can be made by modifying the following protocol, which outlines the fusion of a polypeptide to an IgG molecule.

Briefly, the human Fc portion of the IgG molecule can be PCR amplified, using primers that span the 5' and 3' ends of the sequence described below. These primers also should have convenient restriction enzyme sites that will facilitate cloning into an expression vector, preferably a mammalian expression vector. Note that the polynucleotide is cloned without a stop codon, otherwise a fusion protein will not be produced.

The naturally occurring signal sequence may be used to produce the protein (if applicable). Alternatively, if the naturally occurring signal sequence is not used, the vector can be modified to include a heterologous signal sequence. (See, e.g., WO 96/34891 and/or U.S. Pat. No. 6,066,781, supra.)

Human IgG Fc region:

```
                                         (SEQ ID NO:17)
GGGATCCGGAGCCCAAATCTTCTGACAAAACTCACACATGCCCACCGTGC

CCAGCACCTGAATTCGAGGGTGCACCGTCAGTCTTCCTCTTCCCCCCAAA

ACCCAAGGACACCCTCATGATCTCCCGGACTCCTGAGGTCACATGCGTGG

TGGTGGACGTAAGCCACGAAGACCCTGAGGTCAAGTTCAACTGGTACGTG

GACGGCGTGGAGGTGCATAATGCCAAGACAAAGCCGCGGGAGGAGCAGTA

CAACAGCACGTACCGTGTGGTCAGCGTCCTCACCGTCCTGCACCAGGACT

GGCTGAATGGCAAGGAGTACAAGTGCAAGGTCTCCAACAAAGCCCTCCCA

ACCCCCATCGAGAAAACCATCTCCAAAGCCAAAGGGCAGCCCCGAGAACC

ACAGGTGTACACCCTGCCCCCATCCCGGGATGAGCTGACCAAGAACCAGG

TCAGCCTGACCTGCCTGGTCAAAGGCTTCTATCCAAGCGACATCGCCGTG

GAGTGGGAGAGCAATGGGCAGCCGGAGAACAACTACAAGACCACGCCTCC

CGTGCTGGACTCCGACGGCTCCTTCTTCCTCTACAGCAAGCTCACCGTGG
```

-continued

```
ACAAGAGCAGGTGGCAGCAGGGGAACGTCTTCTCATGCTCCGTGATGCAT

GAGGCTCTGCACAACCACTACACGCAGAAGAGCCTCTCCCTGTCTCCGGG

TAAATGAGTGCGACGGCCGCGACTCTAGAGGAT
```

Example 22

Regulation of Protein Expression Via Controlled Aggregation in the Endoplasmic Reticulum.

As described more particularly herein, proteins regulate diverse cellular processes in higher organisms, ranging from rapid metabolic changes to growth and differentiation. Increased production of specific proteins could be used to prevent certain diseases and/or disease states. Thus, the ability to modulate the expression of specific proteins in an organism would provide significant benefits.

Numerous methods have been developed to date for introducing foreign genes, either under the control of an inducible, constitutively active, or endogenous promoter, into organisms. Of particular interest are the inducible promoters (see, M. Gossen, et al., Proc. Natl. Acad. Sci. USA., 89:5547 (1992); Y. Wang, et al., Proc. Natl. Acad. Sci. USA, 91:8180 (1994), D. No., et al., Proc. Natl. Acad. Sci. USA, 93:3346 (1996); and V. M. Rivera, et al., Nature Med, 2:1028 (1996); in addition to additional examples disclosed elsewhere herein). In one example, the gene for erthropoietin (Epo) was transferred into mice and primates under the control of a small molecule inducer for expression (e.g., tetracycline or rapamycin) (see, D. Bohl, et al., Blood, 92:1512, (1998); K. G. Rendahl, et al., Nat. Biotech, 16:757, (1998); V. M. Rivera, et al., Proc. Natl. Acad. Sci. USA, 96:8657 (1999); and X. Ye et al., Science, 283:88 (1999). Although such systems enable efficient induction of the gene of interest in the organism upon addition of the inducing agent (i.e., tetracycline, rapamycin, etc,.), the levels of expression tend to peak at 24 hours and trail off to background levels after 4 to 14 days. Thus, controlled transient expression is virtually impossible using these systems, though such control would be desirable.

A new alternative method of controlling gene expression levels of a protein from a transgene (i.e., includes stable and transient transformants) has recently been elucidated (V. M. Rivera., et al., Science, 287:826–830, (2000)). This method does not control gene expression at the level of the mRNA like the aforementioned systems. Rather, the system controls the level of protein in an active secreted form. In the absence of the inducing agent, the protein aggregates in the ER and is not secreted. However, addition of the inducing agent results in dis-aggregation of the protein and the subsequent secretion from the ER. Such a system affords low basal secretion, rapid, high level secretion in the presence of the inducing agent, and rapid cessation of secretion upon removal of the inducing agent. In fact, protein secretion reached a maximum level within 30 minutes of induction, and a rapid cessation of secretion within 1 hour of removing the inducing agent. The method is also applicable for controlling the level of production for membrane proteins.

Detailed methods are presented in V. M. Rivera., et al., Science, 287:826–830, (2000)), briefly:

Fusion protein constructs are created using polynucleotide sequences of the present invention with one or more copies (preferably at least 2, 3, 4, or more) of a conditional aggregation domain (CAD) a domain that interacts with itself in a ligand-reversible manner (i.e., in the presence of an inducing agent) using molecular biology methods known in the art and discussed elsewhere herein. The CAD domain may be the mutant domain isolated from the human FKBP12 ($Phe^{36}$ to Met) protein (as disclosed in V. M. Rivera., et al., Science, 287:826–830, (2000), or alternatively other proteins having domains with similar ligand-reversible, self-aggregation properties. As a principle of design the fusion protein vector would contain a furin cleavage sequence operably linked between the polynucleotides of the present invention and the CAD domains. Such a cleavage site would enable the proteolytic cleavage of the CAD domains from the polypeptide of the present invention subsequent to secretion from the ER and upon entry into the trans-Golgi (J. B. Denault, et al., FEBS Lett., 379:113, (1996)). Alternatively, the skilled artisan would recognize that any proteolytic cleavage sequence could be substituted for the furin sequence provided the substituted sequence is cleavable either endogenously (e.g., the furin sequence) or exogenously (e.g., post secretion, post purification, post production, etc.). The preferred sequence of each feature of the fusion protein construct, from the 5' to 3' direction with each feature being operably linked to the other, would be a promoter, signal sequence, "X" number of (CAD)x domains, the furin sequence (or other proteolytic sequence), and the coding sequence of the polypeptide of the present invention. The artisan would appreciate that the promotor and signal sequence, independent from the other, could be either the endogenous promotor or signal sequence of a polypeptide of the present invention, or alternatively, could be a heterologous signal sequence and promotor.

The specific methods described herein for controlling protein secretion levels through controlled ER aggregation are not meant to be limiting are would be generally applicable to any of the polynucleotides and polypeptides of the present invention, including variants, homologues, orthologs, and fragments therein.

Example 23

Alteration of Protein Glycosylation Sites to Enhance Characteristics of Polypeptides of the Invention.

Many eukaryotic cell surface and proteins are post-translationally processed to incorporate N-linked and O-linked carbohydrates (Kornfeld and Kornfeld (1985) Annu. Rev. Biochem. 54:631–64; Rademacher et al., (1988) Annu. Rev. Biochem. 57:785–838). Protein glycosylation is thought to serve a variety of functions including: augmentation of protein folding, inhibition of protein aggregation, regulation of intracellular trafficking to organelles, increasing resistance to proteolysis, modulation of protein antigenicity, and mediation of intercellular adhesion (Fieldler and Simons (1995) Cell, 81:309–312; Helenius (1994) Mol. Biol. Of the Cell 5:253–265; Olden et al., (1978) Cell, 13:461–473; Caton et al., (1982) Cell, 37:417–427; Alexander and Elder (1984), Science, 226:1328–1330; and Flack et al., (1994), J. Biol. Chem., 269:14015–14020). In higher organisms, the nature and extent of glycosylation can markedly affect the circulating half-life and bio-availability of proteins by mechanisms involving receptor mediated uptake and clearance (Ashwell and Morrell, (1974), Adv. Enzymol., 41:99–128; Ashwell and Harford (1982), Ann. Rev. Biochem., 51:531–54). Receptor systems have been identified that are thought to play a major role in the clearance of serum proteins through recognition of various carbohydrate structures on the glycoproteins (Stockert (1995), Physiol. Rev., 75:591–609; Kery et al., (1992), Arch. Biochem. Biophys., 298:49–55). Thus, production strategies resulting in incomplete attachment of terminal sialic acid residues might provide a means of shortening the bioavailability and half-life of glycoproteins. Conversely, expression strategies resulting in saturation of terminal sialic acid attachment sites might lengthen protein bioavailability and half-life.

In the development of recombinant glycoproteins for use as pharmaceutical products, for example, it has been speculated that the pharmacodynamics of recombinant proteins can be modulated by the addition or deletion of glycosylation sites from a glycoproteins primary structure (Berman and Lasky (1985a) Trends in Biotechnol., 3:51–53). However, studies have reported that the deletion of N-linked glycosylation sites often impairs intracellular transport and results in the intracellular accumulation of glycosylation site variants (Machamer and Rose (1988), J. Biol Chem., 263:5955–5960; Gallagher et al., (1992), J. Virology., 66:7136–7145; Collier et al., (1993), Biochem., 32:7818–7823; Claffey et al., (1995) Biochemica et Biophysica Acta, 1246:1–9; Dube et al., (1988), J. Biol. Chem. 263:17516–17521). While glycosylation site variants of proteins can be expressed intracellularly, it has proved difficult to recover useful quantities from growth conditioned cell culture medium.

Moreover, it is unclear to what extent a glycosylation site in one species will be recognized by another species glycosylation machinery. Due to the importance of glycosylation in protein metabolism, particularly the secretion and/or expression of the protein, whether a glycosylation signal is recognized may profoundly determine a proteins ability to be expressed, either endogenously or recombinately, in another organism (i.e., expressing a human protein in *E.coli*, yeast, or viral organisms; or an *E.coli*, yeast, or viral protein in human, etc.). Thus, it may be desirable to add, delete, or modify a glycosylation site, and possibly add a glycosylation site of one species to a protein of another species to improve the proteins functional, bioprocess purification, and/or structural characteristics (e.g., a polypeptide of the present invention).

A number of methods may be employed to identify the location of glycosylation sites within a protein. One preferred method is to run the translated protein sequence through the PROSITE computer program (Swiss Institute of Bioinformatics). Once identified, the sites could be systematically deleted, or impaired, at the level of the DNA using mutagenesis methodology known in the art and available to the skilled artisan, Preferably using PCR-directed mutagenesis (See Maniatis, Molecular Cloning: A Laboratory Manual, Cold Spring Harbor Press, Cold Spring, N.Y. (1982)). Similarly, glycosylation sites could be added, or modified at the level of the DNA using similar methods, preferably PCR methods (See, Maniatis, supra). The results of modifying the glycosylation sites for a particular protein (e.g., solubility, secretion potential, activity, aggregation, proteolytic resistance, etc.) could then be analyzed using methods know in the art.

The skilled artisan would acknowledge the existence of other computer algorithms capable of predicting the location of glycosylation sites within a protein. For example, the Motif computer program (Genetics Computer Group suite of programs) provides this function, as well.

Example 24

Method of Enhancing the Biological Activity/Functional Characteristics of Invention through Molecular Evolution.

Although many of the most biologically active proteins known are highly effective for their specified function in an organism, they often possess characteristics that make them undesirable for transgenic, therapeutic, and/or industrial applications. Among these traits, a short physiological half-life is the most prominent problem, and is present either at the level of the protein, or the level of the proteins mRNA. The ability to extend the half-life, for example, would be particularly important for a proteins use in gene therapy, transgenic animal production, the bioprocess production and purification of the protein, and use of the protein as a chemical modulator among others. Therefore, there is a need to identify novel variants of isolated proteins possessing characteristics which enhance their application as a therapeutic for treating diseases of animal origin, in addition to the proteins applicability to common industrial and pharmaceutical applications.

Thus, one aspect of the present invention relates to the ability to enhance specific characteristics of invention through directed molecular evolution. Such an enhancement may, in a non-limiting example, benefit the inventions utility as an essential component in a kit, the inventions physical attributes such as its solubility, structure, or codon optimization, the inventions specific biological activity, including any associated enzymatic activity, the proteins enzyme kinetics, the proteins Ki, Kcat, Km, Vmax, Kd, protein-protein activity, protein-DNA binding activity, antagonist/inhibitory activity (including direct or indirect interaction), agonist activity (including direct or indirect interaction), the proteins antigenicity (e.g., where it would be desirable to either increase or decrease the antigenic potential of the protein), the immunogenicity of the protein, the ability of the protein to form dimers, trimers, or multimers with either itself or other proteins, the antigenic efficacy of the invention, including its subsequent use a preventative treatment for disease or disease states, or as an effector for targeting diseased genes. Moreover, the ability to enhance specific characteristics of a protein may also be applicable to changing the characterized activity of an enzyme to an activity completely unrelated to its initially characterized activity. Other desirable enhancements of the invention would be specific to each individual protein, and would thus be well known in the art and contemplated by the present invention.

For example, an engineered leucine-rich repeat protein may be constitutively active upon binding of its cognate ligand. Alternatively, an engineered leucine-rich repeat protein may be constitutively active in the absence of ligand binding. In yet another example, an engineered leucine-rich repeat protein may be capable of being activated with less than all of the regulatory factors and/or conditions typically required for leucine-rich repeat protein activation (e.g., ligand binding, phosphorylation, conformational changes, etc.). Such leucine-rich repeat proteins would be useful in screens to identify leucine-rich repeat protein modulators, among other uses described herein.

Directed evolution is comprised of several steps. The first step is to establish a library of variants for the gene or protein of interest. The most important step is to then select for those variants that entail the activity you wish to identify. The design of the screen is essential since your screen should be selective enough to eliminate non-useful variants, but not so stringent as to eliminate all variants. The last step is then to repeat the above steps using the best variant from the previous screen. Each successive cycle, can then be tailored as necessary, such as increasing the stringency of the screen, for example.

Over the years, there have been a number of methods developed to introduce mutations into macromolecules. Some of these methods include, random mutagenesis, "error-prone" PCR, chemical mutagenesis, site-directed mutagenesis, and other methods well known in the art (for a comprehensive listing of current mutagenesis methods, see Maniatis, Molecular Cloning: A Laboratory Manual, Cold Spring Harbor Press, Cold Spring, N.Y. (1982)). Typically, such methods have been used, for example, as tools for identifying the core functional region(s) of a protein or the function of specific domains of a protein (if a multi-domain protein). However, such methods have more recently been applied to the identification of macromolecule variants with specific or enhanced characteristics.

Random mutagenesis has been the most widely recognized method to date. Typically, this has been carried out either through the use of "error-prone" PCR (as described in Moore, J., et al, Nature Biotechnology 14:458, (1996), or through the application of randomized synthetic oligonucleotides corresponding to specific regions of interest (as described by Derbyshire, K. M. et al, Gene, 46:145–152, (1986), and Hill, D E, et al, Methods Enzymol., 55:559–568, (1987). Both approaches have limits to the level of mutagenesis that can be obtained. However, either approach enables the investigator to effectively control the rate of mutagenesis. This is particularly important considering the fact that mutations beneficial to the activity of the enzyme are fairly rare. In fact, using too high a level of mutagenesis may counter or inhibit the desired benefit of a useful mutation.

While both of the aforementioned methods are effective for creating randomized pools of macromolecule variants, a third method, termed "DNA Shuffling", or "sexual PCR" (WPC, Stemmer, PNAS, 91:10747, (1994)) has recently been elucidated. DNA shuffling has also been referred to as "directed molecular evolution", "exon-shuffling", "directed enzyme evolution", "in vitro evolution", and "artificial evolution". Such reference terms are known in the art and are encompassed by the invention. This new, preferred, method apparently overcomes the limitations of the previous methods in that it not only propagates positive traits, but simultaneously eliminates negative traits in the resulting progeny.

DNA shuffling accomplishes this task by combining the principal of in vitro recombination, along with the method of "error-prone" PCR. In effect, you begin with a randomly digested pool of small fragments of your gene, created by Dnase I digestion, and then introduce said random fragments into an "error-prone" PCR assembly reaction. During the PCR reaction, the randomly sized DNA fragments not only hybridize to their cognate strand, but also may hybridize to other DNA fragments corresponding to different regions of the polynucleotide of interest—regions not typically accessible via hybridization of the entire polynucleotide. Moreover, since the PCR assembly reaction utilizes "error-prone" PCR reaction conditions, random mutations are introduced during the DNA synthesis step of the PCR reaction for all of the fragments—further diversifying the potential hybridization sites during the annealing step of the reaction.

A variety of reaction conditions could be utilized to carry-out the DNA shuffling reaction. However, specific reaction conditions for DNA shuffling are provided, for example, in PNAS, 91:10747, (1994). Briefly:

Prepare the DNA substrate to be subjected to the DNA shuffling reaction. Preparation may be in the form of simply purifying the DNA from contaminating cellular material, chemicals, buffers, oligonucleotide primers, deoxynucleotides, RNAs, etc., and may entail the use of DNA purification kits as those provided by Qiagen, Inc., or by the Promega, Corp., for example.

Once the DNA substrate has been purified, it would be subjected to Dnase I digestion. About 2–4 ug of the DNA substrate(s) would be digested with 0.0015 units of Dnase I (Sigma) per ul in 100 ul of 50 mM Tris-HCL, pH 7.4/1 mM MgCl2 for 10–20 min. at room temperature. The resulting fragments of 10–50 bp could then be purified by running them through a 2% low-melting point agarose gel by electrophoresis onto DE81 ion-exchange paper (Whatmann) or could be purified using Microcon concentrators (Amicon) of the appropriate molecular weight cutoff, or could use oligonucleotide purification columns (Qiagen), in addition to other methods known in the art. If using DE81 ion-exchange paper, the 10–50 bp fragments could be eluted from said paper using 1M NaCl, followed by ethanol precipitation.

The resulting purified fragments would then be subjected to a PCR assembly reaction by re-suspension in a PCR mixture containing: 2 mM of each dNTP, 2.2 mM MgCl2, 50 mM KCl, 10 mM Tris•HCL, pH 9.0, and 0.1% Triton X-100, at a final fragment concentration of 10–30 ng/ul. No primers are added at this point. Taq DNA polymerase (Promega) would be used at 2.5 units per 100 ul of reaction mixture. A PCR program of 94 C for 60 s; 94 C for 30 s, 50–55 C for 30 s, and 72 C for 30 s using 30–45 cycles, followed by 72 C for Smin using an MJ Research (Cambridge, Mass.) PTC-150 thermocycler. After the assembly reaction is completed, a 1:40 dilution of the resulting primerless product would then be introduced into a PCR mixture (using the same buffer mixture used for the assembly reaction) containing 0.8 um of each primer and subjecting this mixture to 15 cycles of PCR (using 94 C for 30 s, 50 C for 30 s, and 72 C for 30 s). The referred primers would be primers corresponding to the nucleic acid sequences of the polynucleotide(s) utilized in the shuffling reaction. Said primers could consist of modified nucleic acid base pairs using methods known in the art and referred to else where herein, or could contain additional sequences (i.e., for adding restriction sites, mutating specific base-pairs, etc.).

The resulting shuffled, assembled, and amplified product can be purified using methods well known in the art (e.g., Qiagen PCR purification kits) and then subsequently cloned using appropriate restriction enzymes.

Although a number of variations of DNA shuffling have been published to date, such variations would be obvious to the skilled artisan and are encompassed by the invention. The DNA shuffling method can also be tailored to the desired level of mutagenesis using the methods described by Zhao, et al. (Nucl Acid Res., 25(6):1307–1308, (1997).

As described above, once the randomized pool has been created, it can then be subjected to a specific screen to identify the variant possessing the desired characteristic(s). Once the variant has been identified, DNA corresponding to the variant could then be used as the DNA substrate for initiating another round of DNA shuffling. This cycle of shuffling, selecting the optimized variant of interest, and then re-shuffling, can be repeated until the ultimate variant is obtained. Examples of model screens applied to identify variants created using DNA shuffling technology may be found in the following publications: J. C., Moore, et al., J. Mol. Biol., 272:336–347, (1997), F. R., Cross, et al., Mol. Cell. Biol., 18:2923–2931, (1998), and A. Crameri., et al., Nat. Biotech., 15:436–438, (1997).

DNA shuffling has several advantages. First, it makes use of beneficial mutations. When combined with screening, DNA shuffling allows the discovery of the best mutational combinations and does not assume that the best combination contains all the mutations in a population. Secondly, recombination occurs simultaneously with point mutagenesis. An effect of forcing DNA polymerase to synthesize full-length genes from the small fragment DNA pool is a background mutagenesis rate. In combination with a stringent selection method, enzymatic activity has been evolved up to 16000 fold increase over the wild-type form of the enzyme. In essence, the background mutagenesis yielded the genetic variability on which recombination acted to enhance the activity.

A third feature of recombination is that it can be used to remove deleterious mutations. As discussed above, during the process of the randomization, for every one beneficial mutation, there may be at least one or more neutral or inhibitory mutations. Such mutations can be removed by including in the assembly reaction an excess of the wild-type random-size fragments, in addition to the random-size fragments of the selected mutant from the previous selection. During the next selection, some of the most active variants of the polynucleotide/polypeptide/enzyme, should have lost the inhibitory mutations.

Finally, recombination enables parallel processing. This represents a significant advantage since there are likely multiple characteristics that would make a protein more desirable (e.g. solubility, activity, etc.). Since it is increasingly difficult to screen for more than one desirable trait at a time, other methods of molecular evolution tend to be inhibitory. However, using recombination, it would be possible to combine the randomized fragments of the best representative variants for the various traits, and then select for multiple properties at once.

DNA shuffling can also be applied to the polynucleotides and polypeptides of the present invention to decrease their immunogenicity in a specified host. For example, a particular variant of the present invention may be created and isolated using DNA shuffling technology. Such a variant may have all of the desired characteristics, though may be highly immunogenic in a host due to its novel intrinsic structure. Specifically, the desired characteristic may cause the polypeptide to have a non-native structure which could no longer be recognized as a "self" molecule, but rather as a "foreign", and thus activate a host immune response directed against the novel variant. Such a limitation can be overcome, for example, by including a copy of the gene sequence for a xenobiotic ortholog of the native protein in with the gene sequence of the novel variant gene in one or more cycles of DNA shuffling. The molar ratio of the ortholog and novel variant DNAs could be varied accordingly. Ideally, the resulting hybrid variant identified would contain at least some of the coding sequence which enabled the xenobiotic protein to evade the host immune system, and additionally, the coding sequence of the original novel variant that provided the desired characterstics.

Likewise, the invention encompasses the application of DNA shuffling technology to the evolution of polynucleotides and polypeptides of the invention, wherein one or more cycles of DNA shuffling include, in addition to the gene template DNA, oligonucleotides coding for known allelic sequences, optimized codon sequences, known variant sequences, known polynucleotide polymorphism sequences, known ortholog sequences, known homologue sequences, additional homologous sequences, additional non-homologous sequences, sequences from another species, and any number and combination of the above.

In addition to the described methods above, there are a number of related methods that may also be applicable, or desirable in certain cases. Representative among these are the methods discussed in PCT applications WO 98/31700, and WO 98/32845, which are hereby incorporated by reference. Furthermore, related methods can also be applied to the polynucleotide sequences of the present invention in order to evolve invention for creating ideal variants for use in gene therapy, protein engineering, evolution of whole cells containing the variant, or in the evolution of entire enzyme pathways containing polynucleotides of the invention as described in PCT applications WO 98/13485, WO 98/13487, WO 98/27230, WO 98/31837, and Crameri, A., et al., Nat. Biotech., 15:436–438, (1997), respectively.

Additional methods of applying "DNA Shuffling" technology to the polynucleotides and polypeptides of the present invention, including their proposed applications, may be found in U.S. Pat. No. 5,605,793; PCT Application No. WO 95/22625; PCT Application No. WO 97/20078; PCT Application No. WO 97/35966; and PCT Application No. WO 98/42832; PCT Application No. WO 00/09727 specifically provides methods for applying DNA shuffling to the identification of herbicide selective crops which could be applied to the polynucleotides and polypeptides of the present invention; additionally, PCT Application No. WO 00/12680 provides methods and compositions for generating, modifying, adapting, and optimizing polynucleotide sequences that confer detectable phenotypic properties on plant species; each of the above are hereby incorporated in their entirety herein for all purposes.

Example 25

Method of Determining Alterations in a Gene Corresponding to a Polynucleotide.

RNA isolated from entire families or individual patients presenting with a phenotype of interest (such as a disease) is be isolated. cDNA is then generated from these RNA samples using protocols known in the art. (See, Sambrook.) The cDNA is then used as a template for PCR, employing primers surrounding regions of interest in SEQ ID NO:1. Suggested PCR conditions consist of 35 cycles at 95 degrees C. for 30 seconds; 60–120 seconds at 52–58 degrees C.; and 60–120 seconds at 70 degrees C., using buffer solutions described in Sidransky et al., Science 252:706 (1991).

PCR products are then sequenced using primers labeled at their 5' end with T4 polynucleotide kinase, employing SequiTherm Polymerase. (Epicentre Technologies). The intron-exon borders of selected exons is also determined and genomic PCR products analyzed to confirm the results. PCR products harboring suspected mutations is then cloned and sequenced to validate the results of the direct sequencing.

PCR products is cloned into T-tailed vectors as described in Holton et al., Nucleic Acids Research, 19:1156 (1991) and sequenced with T7 polymerase (United States Biochemical). Affected individuals are identified by mutations not present in unaffected individuals.

Genomic rearrangements are also observed as a method of determining alterations in a gene corresponding to a polynucleotide. Genomic clones isolated according to Example 2 are nick-translated with digoxigenindeoxy-uridine 5'-triphosphate (Boehringer Manheim), and FISH performed as described in Johnson et al., Methods Cell Biol. 35:73–99 (1991). Hybridization with the labeled probe is carried out using a vast excess of human cot-1 DNA for specific hybridization to the corresponding genomic locus.

Chromosomes are counterstained with 4,6-diamino-2-phenylidole and propidium iodide, producing a combination of C- and R-bands. Aligned images for precise mapping are obtained using a triple-band filter set (Chroma Technology, Brattleboro, Vt.) in combination with a cooled charge-coupled device camera (Photometrics, Tucson, Ariz.) and variable excitation wavelength filters. (Johnson et al., Genet. Anal. Tech. Appl., 8:75 (1991).) Image collection, analysis and chromosomal fractional length measurements are performed using the ISee Graphical Program System. (Inovision Corporation Durham, N.C.) Chromosome alterations of the genomic region hybridized by the probe are identified as insertions, deletions, and translocations. These alterations are used as a diagnostic marker for an associated disease.

Example 26

Method of Detecting Abnormal Levels of a Polypeptide in a Biological Sample.

A polypeptide of the present invention can be detected in a biological sample, and if an increased or decreased level of the polypeptide is detected, this polypeptide is a marker for a particular phenotype. Methods of detection are numerous, and thus, it is understood that one skilled in the art can modify the following assay to fit their particular needs.

For example, antibody-sandwich ELISAs are used to detect polypeptides in a sample, preferably a biological sample. Wells of a microtiter plate are coated with specific antibodies, at a final concentration of 0.2 to 10 ug/ml. The antibodies are either monoclonal or polyclonal and are produced by the method described elsewhere herein. The wells are blocked so that non-specific binding of the polypeptide to the well is reduced.

The coated wells are then incubated for >2 hours at RT with a sample containing the polypeptide. Preferably, serial dilutions of the sample should be used to validate results. The plates are then washed three times with deionized or distilled water to remove unbounded polypeptide.

Next, 50 ul of specific antibody-alkaline phosphatase conjugate, at a concentration of 25–400 ng, is added and incubated for 2 hours at room temperature. The plates are again washed three times with deionized or distilled water to remove unbounded conjugate.

Add 75 ul of 4-methylumbelliferyl phosphate (MUP) or p-nitrophenyl phosphate (NPP) substrate solution to each well and incubate 1 hour at room temperature. Measure the reaction by a microtiter plate reader. Prepare a standard curve, using serial dilutions of a control sample, and plot polypeptide concentration on the X-axis (log scale) and fluorescence or absorbance of the Y-axis (linear scale). Interpolate the concentration of the polypeptide in the sample using the standard curve.

Example 27

Formulation.

The invention also provides methods of treatment and/or prevention diseases, disorders, and/or conditions (such as, for example, any one or more of the diseases or disorders disclosed herein) by administration to a subject of an effective amount of a Therapeutic. By therapeutic is meant a polynucleotides or polypeptides of the invention (including fragments and variants), agonists or antagonists thereof, and/or antibodies thereto, in combination with a pharmaceutically acceptable carrier type (e.g., a sterile carrier).

The Therapeutic will be formulated and dosed in a fashion consistent with good medical practice, taking into account the clinical condition of the individual patient (especially the side effects of treatment with the Therapeutic alone), the site of delivery, the method of administration, the scheduling of administration, and other factors known to practitioners. The "effective amount" for purposes herein is thus determined by such considerations.

As a general proposition, the total pharmaceutically effective amount of the Therapeutic administered parenterally per dose will be in the range of about 1 ug/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the Therapeutic is typically administered at a dose rate of about 1 ug/kg/hour to about 50 ug/kg/hour, either by 1–4 injections per day or by continuous subcutaneous infusions, for example, using a mini-pump. An intravenous bag solution may also be employed. The length of treatment needed to observe changes and the interval following treatment for responses to occur appears to vary depending on the desired effect.

Therapeutics can be administered orally, rectally, parenterally, intracisternally, intravaginally, intraperitoneally, topically (as by powders, ointments, gels, drops or transdermal patch), bucally, or as an oral or nasal spray. "Pharmaceutically acceptable carrier" refers to a non-toxic solid, semisolid or liquid filler, diluent, encapsulating material or formulation auxiliary of any. The term "parenteral" as used herein refers to modes of administration which include intravenous, intramuscular, intraperitoneal, intrasternal, subcutaneous and intraarticular injection and infusion.

Therapeutics of the invention are also suitably administered by sustained-release systems. Suitable examples of sustained-release Therapeutics are administered orally, rectally, parenterally, intracisternally, intravaginally, intraperitoneally, topically (as by powders, ointments, gels, drops or transdermal patch), bucally, or as an oral or nasal spray. "Pharmaceutically acceptable carrier" refers to a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

Therapeutics of the invention may also be suitably administered by sustained-release systems. Suitable examples of sustained-release Therapeutics include suitable polymeric materials (such as, for example, semi-permeable polymer matrices in the form of shaped articles, e.g., films, or microcapsules), suitable hydrophobic materials (for example as an emulsion in an acceptable oil) or ion exchange resins, and sparingly soluble derivatives (such as, for example, a sparingly soluble salt).

Sustained-release matrices include polylactides (U.S. Pat. No. 3,773,919, EP 58,481), copolymers of L-glutamic acid and gamma-ethyl-L-glutamate (Sidman et al., Biopolymers 22:547–556 (1983)), poly (2-hydroxyethyl methacrylate) (Langer et al., J. Biomed. Mater. Res. 15:167–277 (1981), and Langer, Chem. Tech. 12:98–105 (1982)), ethylene vinyl acetate (Langer et al., Id.) or poly-D-(−)-3-hydroxybutyric acid (EP 133,988).

Sustained-release Therapeutics also include liposomally entrapped Therapeutics of the invention (see, generally, Langer, Science 249:1527–1533 (1990); Treat et al., in Liposomes in the Therapy of Infectious Disease and Cancer, Lopez-Berestein and Fidler (eds.), Liss, New York, pp. 317–327 and 353–365 (1989)). Liposomes containing the Therapeutic are prepared by methods known per se: DE 3,218,121; Epstein et al., Proc. Natl. Acad. Sci. (USA) 82:3688–3692 (1985); Hwang et al., Proc. Natl. Acad. Sci.(USA) 77:4030–4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimal Therapeutic.

In yet an additional embodiment, the Therapeutics of the invention are delivered by way of a pump (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)).

Other controlled release systems are discussed in the review by Langer (Science 249:1527–1533 (1990)).

For parenteral administration, in one embodiment, the Therapeutic is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to the Therapeutic.

Generally, the formulations are prepared by contacting the Therapeutic uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium; and/or nonionic surfactants such as polysorbates, poloxamers, or PEG.

The Therapeutic will typically be formulated in such vehicles at a concentration of about 0.1 mg/ml to 100 mg/ml, preferably 1–10 mg/ml, at a pH of about 3 to 8. It will be understood that the use of certain of the foregoing excipients, carriers, or stabilizers will result in the formation of polypeptide salts.

Any pharmaceutical used for therapeutic administration can be sterile. Sterility is readily accomplished by filtration through sterile filtration membranes (e.g., 0.2 micron membranes). Therapeutics generally are placed into a container having a sterile access port, for example, an intravenous solution bag or vial having a stopper pierceable by a hypodermic injection needle.

Therapeutics ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous Therapeutic solution, and the resulting mixture is lyophilized. The infusion solution is prepared by reconstituting the lyophilized Therapeutic using bacteriostatic Water-for-Injection.

The invention also provides a pharmaceutical pack or kit comprising one or more containers filled with one or more of the ingredients of the Therapeutics of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the Therapeutics may be employed in conjunction with other therapeutic compounds.

The Therapeutics of the invention may be administered alone or in combination with adjuvants. Adjuvants that may be administered with the Therapeutics of the invention include, but are not limited to, alum, alum plus deoxycholate (ImmunoAg), MTP-PE (Biocine Corp.), QS21 (Genentech, Inc.), BCG, and MPL. In a specific embodiment, Therapeutics of the invention are administered in combination with alum. In another specific embodiment, Therapeutics of the invention are administered in combination with QS-21. Further adjuvants that may be administered with the Therapeutics of the invention include, but are not limited to, Monophosphoryl lipid immunomodulator, AdjuVax 100a, QS-21, QS-18, CRL1005, Aluminum salts, MF-59, and Virosomal adjuvant technology. Vaccines that may be administered with the Therapeutics of the invention include, but are not limited to, vaccines directed toward protection against MMR (measles, mumps, rubella), polio, varicella, tetanus/diptheria, hepatitis A, hepatitis B, haemophilus influenzae B, whooping cough, pneumonia, influenza, Lyme's Disease, rotavirus, cholera, yellow fever, Japanese encephalitis, poliomyelitis, rabies, typhoid fever, and pertussis. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

The Therapeutics of the invention may be administered alone or in combination with other therapeutic agents. Therapeutic agents that may be administered in combination with the Therapeutics of the invention, include but not limited to, other members of the TNF family, chemotherapeutic agents, antibiotics, steroidal and non-steroidal anti-inflammatories, conventional immunotherapeutic agents, cytokines and/or growth factors. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

In one embodiment, the Therapeutics of the invention are administered in combination with members of the TNF family. TNF, TNF-related or TNF-like molecules that may be administered with the Therapeutics of the invention include, but are not limited to, soluble forms of TNF-alpha, lymphotoxin-alpha (LT-alpha, also known as TNF-beta), LT-beta (found in complex heterotrimer LT-alpha2-beta), OPGL, FasL, CD27L, CD30L, CD40L, 4-1BBL, DcR3, OX40L, TNF-gamma (International Publication No. WO 96/14328), AIM-I (International Publication No. WO 97/33899), endokine-alpha (International Publication No. WO 98/07880), TR6 (International Publication No. WO 98/30694), OPG, and neutrokine-alpha (International Publication No. WO 98/18921, OX40, and nerve growth factor (NGF), and soluble forms of Fas, CD30, CD27, CD40 and 4-IBB, TR2 (International Publication No. WO 96/34095), DR3 (International Publication No. WO 97/33904), DR4 (International Publication No. WO 98/32856), TR5 (International Publication No. WO 98/30693), TR6 (International Publication No. WO 98/30694), TR7 (International Publication No. WO 98/41629), TRANK, TR9 (International Publication No. WO 98/56892), TR10 (International Publication No. WO 98/54202), 312C2 (International Publication No. WO 98/06842), and TR12, and soluble forms CD154, CD70, and CD153.

In certain embodiments, Therapeutics of the invention are administered in combination with antiretroviral agents, nucleoside reverse transcriptase inhibitors, non-nucleoside reverse transcriptase inhibitors, and/or protease inhibitors. Nucleoside reverse transcriptase inhibitors that may be administered in combination with the Therapeutics of the invention, include, but are not limited to, RETROVIR ((zidovudine/AZT), VIDEX((didanosine/ddI), HIVID ((zalcitabine/ddC), ZERIT((stavudine/d4T), EPIVIR ((lamivudine/3TC), and COMBIVIR((zidovudine/lamivudine). Non-nucleoside reverse transcriptase inhibitors that may be administered in combination with the Therapeutics of the invention, include, but are not limited to, VIRAMUNE((nevirapine), RESCRIPTOR((delavirdine), and SUSTIVA((efavirenz). Protease inhibitors that may be administered in combination with the Therapeutics of the invention, include, but are not limited to, CRIXIVAN ((indinavir), NORVIR((ritonavir), INVIRASE((saquinavir), and VIRACEPT((nelfinavir). In a specific embodiment, antiretroviral agents, nucleoside reverse transcriptase inhibitors, non-nucleoside reverse transcriptase inhibitors, and/or protease inhibitors may be used in any combination with Therapeutics of the invention to treat AIDS and/or to prevent or treat HIV infection.

In other embodiments, Therapeutics of the invention may be administered in combination with anti-opportunistic infection agents. Anti-opportunistic agents that may be administered in combination with the Therapeutics of the invention, include, but are not limited to, TRIMETHOPRIM-SULFAMETHOXAZOLE(, DAPSONE(, PENTAMIDINE(, ATOVAQUONE(, ISONIAZID(, RIFAMPIN(, PYRAZINAMIDE(, ETHAMBUTOL(, RIFABUTIN(, CLARITHROMYCIN(, AZITHROMYCIN(, GANCICLOVIR(, FOSCARNET(, CIDOFOVIR(, FLUCONAZOLE(, ITRACONAZOLE(, KETOCONAZOLE(, ACYCLOVIR(, FAMCICOLVIR(, PYRIMETHAMINE(, LEUCOVORIN(, NEUPOGEN ((filgrastim/G-CSF), and LEUKINE((sargramostim/GM-CSF). In a specific embodiment, Therapeutics of the invention are used in any combination with TRIMETHOPRIM-SULFAMETHOXAZOLE(, DAPSONE(, PENTAMIDINE(, and/or ATOVAQUONE( to prophylactically treat or prevent an opportunistic Pneumocystis carinii pneumonia infection. In another specific embodiment, Therapeutics of the invention are used in any combination with ISONIAZID(, RIFAMPIN(, PYRAZINAMIDE(, and/or ETHAMBUTOL( to prophylactically treat or prevent an opportunistic Mycobacterium avium complex infection. In another specific embodiment, Therapeutics of the invention are used in any combination with RIFABUTIN(, CLARITHROMYCIN(, and/or AZITHROMYCIN( to prophylactically treat or prevent an opportunistic Mycobacterium tuberculosis infection. In another specific embodiment, Therapeutics of the invention are used in any combination with GANCICLOVIR(, FOSCARNET(, and/or CIDOFOVIR( to prophylactically treat or prevent an opportunistic cytomegalovirus infection. In another specific embodiment, Therapeutics of the invention are used in any combination with FLUCONAZOLE(, ITRACONAZOLE(, and/or KETOCONAZOLE( to prophylactically treat or prevent an opportunistic fungal infection. In another specific embodiment, Therapeutics of the invention are used in any combination with ACYCLOVIR( and/or FAMCICOLVIR( to prophylactically treat or prevent an opportunistic herpes simplex virus type I and/or type II infection. In another specific embodiment, Therapeutics of the invention are used in any combination with PYRIMETHAMINE( and/or LEUCOVORIN( to prophylactically treat or prevent an opportunistic Toxoplasma gondii infection. In another specific embodiment, Therapeutics of the invention are used in any combination with LEUCOVORIN( and/or NEUPOGEN( to prophylactically treat or prevent an opportunistic bacterial infection.

In a further embodiment, the Therapeutics of the invention are administered in combination with an antiviral agent. Antiviral agents that may be administered with the Therapeutics of the invention include, but are not limited to, acyclovir, ribavirin, amantadine, and remantidine.

In a further embodiment, the Therapeutics of the invention are administered in combination with an antibiotic agent. Antibiotic agents that may be administered with the Therapeutics of the invention include, but are not limited to, amoxicillin, beta-lactamases, aminoglycosides, beta-lactam (glycopeptide), beta-lactamases, Clindamycin, chloramphenicol, cephalosporins, ciprofloxacin, ciprofloxacin, erythromycin, fluoroquinolones, macrolides, metronidazole, penicillins, quinolones, rifampin, streptomycin, sulfonamide, tetracyclines, trimethoprim, trimethoprim-sulfamthoxazole, and vancomycin.

Conventional nonspecific immunosuppressive agents, that may be administered in combination with the Therapeutics of the invention include, but are not limited to, steroids, cyclosporine, cyclosporine analogs, cyclophosphamide methylprednisone, prednisone, azathioprine, FK-506, 15-deoxyspergualin, and other immunosuppressive agents that act by suppressing the function of responding T cells.

In specific embodiments, Therapeutics of the invention are administered in combination with immunosuppressants. Immunosuppressants preparations that may be administered with the Therapeutics of the invention include, but are not limited to, ORTHOCLONE((OKT3), SANDIMMUNE(/NEORAL(/SANGDYA((cyclosporin), PROGRAF ((tacrolimus), CELLCEPT((mycophenolate), Azathioprine, glucorticosteroids, and RAPAMUNE((sirolimus). In a specific embodiment, immunosuppressants may be used to prevent rejection of organ or bone marrow transplantation.

In an additional embodiment, Therapeutics of the invention are administered alone or in combination with one or more intravenous immune globulin preparations. Intravenous immune globulin preparations that may be administered with the Therapeutics of the invention include, but not limited to, GAMMAR(, IVEEGAM(, SANDOGLOBULIN(, GAMMAGARD S/D(, and GAMIMUNE(. In a specific embodiment, Therapeutics of the invention are administered in combination with intravenous immune globulin preparations in transplantation therapy (e.g., bone marrow transplant).

In an additional embodiment, the Therapeutics of the invention are administered alone or in combination with an anti-inflammatory agent. Anti-inflammatory agents that may be administered with the Therapeutics of the invention include, but are not limited to, glucocorticoids and the nonsteroidal anti-inflammatories, aminoarylcarboxylic acid derivatives, arylacetic acid derivatives, arylbutyric acid derivatives, arylcarboxylic acids, arylpropionic acid derivatives, pyrazoles, pyrazolones, salicylic acid derivatives, thiazinecarboxamides, c-acetamidocaproic acid, S-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole, and tenidap.

In another embodiment, compositions of the invention are administered in combination with a chemotherapeutic agent. Chemotherapeutic agents that may be administered with the Therapeutics of the invention include, but are not limited to, antibiotic derivatives (e.g., doxorubicin, bleomycin, daunorubicin, and dactinomycin); antiestrogens (e.g., tamoxifen); antimetabolites (e.g., fluorouracil, 5-FU, methotrexate, floxuridine, interferon alpha-2b, glutamic acid, plicamycin, mercaptopurine, and 6-thioguanine); cytotoxic agents (e.g., carmustine, BCNU, lomustine, CCNU, cytosine arabinoside, cyclophosphamide, estramustine, hydroxyurea, procarbazine, mitomycin, busulfan, cis-platin, and vincristine sulfate); hormones (e.g., medroxyprogesterone, estramustine phosphate sodium, ethinyl estradiol, estradiol, megestrol acetate, methyltestosterone, diethylstilbestrol diphosphate, chlorotrianisene, and testolactone); nitrogen mustard derivatives (e.g., mephalen, chorambucil, mechlorethamine (nitrogen mustard) and thiotepa); steroids and combinations (e.g., bethamethasone sodium phosphate); and others (e.g., dicarbazine, asparaginase, mitotane, vincristine sulfate, vinblastine sulfate, and etoposide).

In a specific embodiment, Therapeutics of the invention are administered in combination with CHOP (cyclophosphamide, doxorubicin, vincristine, and prednisone) or any combination of the components of CHOP. In another embodiment, Therapeutics of the invention are administered in combination with Rituximab. In a further embodiment, Therapeutics of the invention are administered with Rituxmab and CHOP, or Rituxmab and any combination of the components of CHOP.

In an additional embodiment, the Therapeutics of the invention are administered in combination with cytokines. Cytokines that may be administered with the Therapeutics of the invention include, but are not limited to, IL2, IL3, IL4, IL5, IL6, IL7, IL10, IL12, IL13, IL15, anti-CD40, CD40L, IFN-gamma and TNF-alpha. In another embodiment, Therapeutics of the invention may be administered with any interleukin, including, but not limited to, IL-1alpha, IL-1beta, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, and IL-21.

In an additional embodiment, the Therapeutics of the invention are administered in combination with angiogenic proteins. Angiogenic proteins that may be administered with the Therapeutics of the invention include, but are not limited to, Glioma Derived Growth Factor (GDGF), as disclosed in European Patent Number EP-399816; Platelet Derived Growth Factor-A (PDGF-A), as disclosed in European Patent Number EP-682110; Platelet Derived Growth Factor-B (PDGF-B), as disclosed in European Patent Number EP-282317; Placental Growth Factor (PIGF), as disclosed in International Publication Number WO 92/06194; Placental Growth Factor-2 (PlGF-2), as disclosed in Hauser et al., Growth Factors, 4:259–268 (1993); Vascular Endothelial Growth Factor (VEGF), as disclosed in International Publication Number WO 90/13649; Vascular Endothelial Growth Factor-A (VEGF-A), as disclosed in European Patent Number EP-506477; Vascular Endothelial Growth Factor-2 (VEGF-2), as disclosed in International Publication Number WO 96/39515; Vascular Endothelial Growth Factor B (VEGF-3); Vascular Endothelial Growth Factor B-186 (VEGF-B186), as disclosed in International Publication Number WO 96/26736; Vascular Endothelial Growth Factor-D (VEGF-D), as disclosed in International Publication Number WO 98/02543; Vascular Endothelial Growth Factor-D (VEGF-D), as disclosed in International Publication Number WO 98/07832; and Vascular Endothelial Growth Factor-E (VEGF-E), as disclosed in German Patent Number DE19639601. The above mentioned references are incorporated herein by reference herein.

In an additional embodiment, the Therapeutics of the invention are administered in combination with hematopoietic growth factors. Hematopoietic growth factors that may be administered with the Therapeutics of the invention include, but are not limited to, LEUKINE((SARGRAMOSTIM( ) and NEUPOGEN((FILGRASTIM( ).

In an additional embodiment, the Therapeutics of the invention are administered in combination with Fibroblast Growth Factors. Fibroblast Growth Factors that may be administered with the Therapeutics of the invention include, but are not limited to, FGF-1, FGF-2, FGF-3, FGF-4, FGF-5, FGF-6, FGF-7, FGF-8, FGF-9, FGF-10, FGF-11, FGF-12, FGF-13, FGF-14, and FGF-15.

In a specific embodiment, formulations of the present invention may further comprise antagonists of P-glycoprotein (also referred to as the multiresistance protein, or PGP), including antagonists of its encoding polynucleotides (e.g., antisense oligonucleotides, ribozymes, zinc-finger proteins, etc.). P-glycoprotein is well known for decreasing the efficacy of various drug administrations due to its ability to export intracellular levels of absorbed drug to the cell exterior. While this activity has been particularly pronounced in cancer cells in response to the administration of chemotherapy regimens, a variety of other cell types and the administration of other drug classes have been noted (e.g., T-cells and anti-HIV drugs). In fact, certain mutations in the PGP gene significantly reduces PGP function, making it less able to force drugs out of cells. People who have two versions of the mutated gene—one inherited from each parent—have more than four times less PGP than those with two normal versions of the gene. People may also have one normal gene and one mutated one. Certain ethnic populations have increased incidence of such PGP mutations. Among individuals from Ghana, Kenya, the Sudan, as well as African Americans, frequency of the normal gene ranged from 73% to 84%. In contrast, the frequency was 34% to 59% among British whites, Portuguese, Southwest Asian, Chinese, Filipino and Saudi populations. As a result, certain ethnic populations may require increased administration of PGP antagonist in the formulation of the present invention to arrive at the an efficacious dose of the therapeutic (e.g., those from African descent). Conversely, certain ethnic populations, particularly those having increased frequency of the mutated PGP (e.g., of Caucasian descent, or non-African descent) may require less pharmaceutical compositions in the formulation due to an effective increase in efficacy of such compositions as a result of the increased effective absorption (e.g., less PGP activity) of said composition.

Moreover, in another specific embodiment, formulations of the present invention may further comprise antagonists of OATP2 (also referred to as the multiresistance protein, or MRP2), including antagonists of its encoding polynucleotides (e.g., antisense oligonucleotides, ribozymes, zinc-finger proteins, etc.). The invention also further comprises any additional antagonists known to inhibit proteins thought to be attributable to a multidrug resistant phenotype in proliferating cells.

In additional embodiments, the Therapeutics of the invention are administered in combination with other therapeutic or prophylactic regimens, such as, for example, radiation therapy.

Example 28

Method of Treating Decreased Levels of the Polypeptide.

The present invention relates to a method for treating an individual in need of an increased level of a polypeptide of the invention in the body comprising administering to such an individual a composition comprising a therapeutically effective amount of an agonist of the invention (including polypeptides of the invention). Moreover, it will be appreciated that conditions caused by a decrease in the standard or normal expression level of a secreted protein in an individual can be treated by administering the polypeptide of the present invention, preferably in the secreted form. Thus, the invention also provides a method of treatment of an individual in need of an increased level of the polypeptide comprising administering to such an individual a Therapeutic comprising an amount of the polypeptide to increase the activity level of the polypeptide in such an individual.

For example, a patient with decreased levels of a polypeptide receives a daily dose 0.1–100 ug/kg of the polypeptide for six consecutive days. Preferably, the polypeptide is in the secreted form. The exact details of the dosing scheme, based on administration and formulation, are provided herein.

Example 29

Method of Treating Increased Levels of the Polypeptide.

The present invention also relates to a method of treating an individual in need of a decreased level of a polypeptide of the invention in the body comprising administering to such an individual a composition comprising a therapeutically effective amount of an antagonist of the invention (including polypeptides and antibodies of the invention).

In one example, antisense technology is used to inhibit production of a polypeptide of the present invention. This technology is one example of a method of decreasing levels of a polypeptide, preferably a secreted form, due to a variety of etiologies, such as cancer. For example, a patient diagnosed with abnormally increased levels of a polypeptide is administered intravenously antisense polynucleotides at 0.5, 1.0, 1.5, 2.0 and 3.0 mg/kg day for 21 days. This treatment is repeated after a 7-day rest period if the treatment was well tolerated. The formulation of the antisense polynucleotide is provided herein.

Example 30

Method of Treatment Using Gene Therapy-Ex Vivo.

One method of gene therapy transplants fibroblasts, which are capable of expressing a polypeptide, onto a patient. Generally, fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin) is added. The flasks are then incubated at 37 degree C. for approximately one week.

At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al., DNA, 7:219–25 (1988)), flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention can be amplified using PCR primers which correspond to the 5' and 3' end sequences respectively as set forth in Example 11 using primers and having appropriate restriction sites and initiation/stop codons, if necessary. Preferably, the 5' primer contains an EcoRI site and the 3' primer includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is then used to transform bacteria HB101, which are then plated onto agar containing kanamycin for the purpose of confirming that the vector has the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his. Once the fibroblasts have been efficiently infected, the fibroblasts are analyzed to determine whether protein is produced.

The engineered fibroblasts are then transplanted onto the host, either alone or after having been grown to confluence on cytodex 3 microcarrier beads.

Example 31

Gene Therapy Using Endogenous Genes Corresponding to Polynucleotides of the Invention.

Another method of gene therapy according to the present invention involves operably associating the endogenous polynucleotide sequence of the invention with a promoter via homologous recombination as described, for example, in U.S. Pat. No. 5,641,670, issued Jun. 24, 1997; International Publication NO: WO 96/29411, published Sep. 26, 1996; International Publication NO: WO 94/12650, published Aug. 4, 1994; Koller et al., Proc. Natl. Acad. Sci. USA, 86:8932–8935 (1989); and Zijlstra et al., Nature, 342:435–438 (1989). This method involves the activation of a gene which is present in the target cells, but which is not expressed in the cells, or is expressed at a lower level than desired.

Polynucleotide constructs are made which contain a promoter and targeting sequences, which are homologous to the 5' non-coding sequence of endogenous polynucleotide sequence, flanking the promoter. The targeting sequence will be sufficiently near the 5' end of the polynucleotide sequence so the promoter will be operably linked to the endogenous sequence upon homologous recombination. The promoter and the targeting sequences can be amplified using PCR. Preferably, the amplified promoter contains distinct restriction enzyme sites on the 5' and 3' ends. Preferably, the 3' end of the first targeting sequence contains the same restriction enzyme site as the 5' end of the amplified promoter and the 5' end of the second targeting sequence contains the same restriction site as the 3' end of the amplified promoter.

The amplified promoter and the amplified targeting sequences are digested with the appropriate restriction enzymes and subsequently treated with calf intestinal phosphatase. The digested promoter and digested targeting sequences are added together in the presence of T4 DNA ligase. The resulting mixture is maintained under conditions appropriate for ligation of the two fragments. The construct is size fractionated on an agarose gel then purified by phenol extraction and ethanol precipitation.

In this Example, the polynucleotide constructs are administered as naked polynucleotides via electroporation. However, the polynucleotide constructs may also be administered with transfection-facilitating agents, such as liposomes, viral sequences, viral particles, precipitating agents, etc. Such methods of delivery are known in the art.

Once the cells are transfected, homologous recombination will take place which results in the promoter being operably linked to the endogenous polynucleotide sequence. This results in the expression of polynucleotide corresponding to the polynucleotide in the cell. Expression may be detected by immunological staining, or any other method known in the art.

Fibroblasts are obtained from a subject by skin biopsy. The resulting tissue is placed in DMEM+10% fetal calf serum. Exponentially growing or early stationary phase fibroblasts are trypsinized and rinsed from the plastic surface with nutrient medium. An aliquot of the cell suspension is removed for counting, and the remaining cells are subjected to centrifugation. The supernatant is aspirated and the pellet is resuspended in 5 ml of electroporation buffer (20 mM HEPES pH 7.3, 137 mM NaCl, 5 mM KCl, 0.7 mM Na2 HPO4, 6 mM dextrose). The cells are recentrifuged, the supernatant aspirated, and the cells resuspended in electroporation buffer containing 1 mg/ml acetylated bovine serum albumin. The final cell suspension contains approximately 3×106 cells/ml. Electroporation should be performed immediately following resuspension.

Plasmid DNA is prepared according to standard techniques. For example, to construct a plasmid for targeting to the locus corresponding to the polynucleotide of the invention, plasmid pUC18 (MBI Fermentas, Amherst, N.Y.) is digested with HindIII. The CMV promoter is amplified by PCR with an XbaI site on the 5'end and a BamHI site on the 3'end. Two non-coding sequences are amplified via PCR: one non-coding sequence (fragment 1) is amplified with a HindIII site at the 5'9237 end and an Xba site at the 3'end; the other non-coding sequence (fragment 2) is amplified with a BamHI site at the 5'end and a HindIII site at the 3'end. The CMV promoter and the fragments (1 and 2) are digested with the appropriate enzymes (CMV promoter—XbaI and BamHI; fragment 1—XbaI; fragment 2—BamHI) and ligated together. The resulting ligation product is digested with HindIII, and ligated with the HindIII-digested pUC18 plasmid.

Plasmid DNA is added to a sterile cuvette with a 0.4 cm electrode gap (Bio-Rad). The final DNA concentration is generally at least 120 μg/ml. 0.5 ml of the cell suspension (containing approximately 1.5×106 cells) is then added to the cuvette, and the cell suspension and DNA solutions are gently mixed. Electroporation is performed with a Gene-Pulser apparatus (Bio-Rad). Capacitance and voltage are set at 960 μF and 250–300 V, respectively. As voltage increases, cell survival decreases, but the percentage of surviving cells that stably incorporate the introduced DNA into their genome increases dramatically. Given these parameters, a pulse time of approximately 14–20 mSec should be observed.

Electroporated cells are maintained at room temperature for approximately 5 min, and the contents of the cuvette are then gently removed with a sterile transfer pipette. The cells are added directly to 10 ml of prewarmed nutrient media (DMEM with 15% calf serum) in a 10 cm dish and incubated at 37 degree C. The following day, the media is aspirated and replaced with 10 ml of fresh media and incubated for a further 16–24 hours.

The engineered fibroblasts are then injected into the host, either alone or after having been grown to confluence on cytodex 3 microcarrier beads. The fibroblasts now produce the protein product. The fibroblasts can then be introduced into a patient as described above.

Example 32

Method of Treatment Using Gene Therapy—In Vivo.

Another aspect of the present invention is using in vivo gene therapy methods to treat disorders, diseases and conditions. The gene therapy method relates to the introduction of naked nucleic acid (DNA, RNA, and antisense DNA or RNA) sequences into an animal to increase or decrease the expression of the polypeptide. The polynucleotide of the present invention may be operatively linked to a promoter or any other genetic elements necessary for the expression of the polypeptide by the target tissue. Such gene therapy and delivery techniques and methods are known in the art, see, for example, WO90/11092, WO98/11779; U.S. Pat. Nos. 5,693,622, 5,705,151, 5,580,859; Tabata et al., Cardiovasc. Res. 35(3):470–479 (1997); Chao et al., Pharmacol. Res. 35(6):517–522 (1997); Wolff, Neuromuscul. Disord. 7(5): 314–318 (1997); Schwartz et al., Gene Ther. 3(5):405–411 (1996); Tsurumi et al., Circulation 94(12):3281–3290 (1996) (incorporated herein by reference).

The polynucleotide constructs may be delivered by any method that delivers injectable materials to the cells of an animals, such as, injection into the interstitial space of tissues (heart, muscle, skin, lung, liver, intestine and the like). The polynucleotide constructs can be delivered in a pharmaceutically acceptable liquid or aqueous carrier.

The term "naked" polynucleotide, DNA or RNA, refers to sequences that are free from any delivery vehicle that acts to assist, promote, or facilitate entry into the cell, including viral sequences, viral particles, liposome formulations, lipofectin or precipitating agents and the like. However, the polynucleotides of the present invention may also be delivered in liposome formulations (such as those taught in Felgner P. L. et al. (1995) Ann. NY Acad. Sci. 772:126–139 and Abdallah B. et al. (1995) Biol. Cell 85(1):1–7) which can be prepared by methods well known to those skilled in the art.

The polynucleotide vector constructs used in the gene therapy method are preferably constructs that will not integrate into the host genome nor will they contain sequences that allow for replication. Any strong promoter known to those skilled in the art can be used for driving the expression of DNA. Unlike other gene therapies techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The polynucleotide construct can be delivered to the interstitial space of tissues within the an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the naked polynucleotide injection, an effective dosage amount of DNA or RNA will be in the range of from about 0.05 g/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration. The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked polynucleotide constructs can be delivered to arteries during angioplasty by the catheter used in the procedure.

The dose response effects of injected polynucleotide in muscle in vivo is determined as follows. Suitable template DNA for production of mRNA coding for polypeptide of the present invention is prepared in accordance with a standard recombinant DNA methodology. The template DNA, which may be either circular or linear, is either used as naked DNA or complexed with liposomes. The quadriceps muscles of mice are then injected with various amounts of the template DNA.

Five to six week old female and male Balb/C mice are anesthetized by intraperitoneal injection with 0.3 ml of 2.5% Avertin. A 1.5 cm incision is made on the anterior thigh, and the quadriceps muscle is directly visualized. The template DNA is injected in 0.1 ml of carrier in a 1 cc syringe through a 27 gauge needle over one minute, approximately 0.5 cm from the distal insertion site of the muscle into the knee and about 0.2 cm deep. A suture is placed over the injection site for future localization, and the skin is closed with stainless steel clips.

After an appropriate incubation time (e.g., 7 days) muscle extracts are prepared by excising the entire quadriceps. Every fifth 15 um cross-section of the individual quadriceps muscles is histochemically stained for protein expression. A time course for protein expression may be done in a similar fashion except that quadriceps from different mice are harvested at different times. Persistence of DNA in muscle following injection may be determined by Southern blot analysis after preparing total cellular DNA and HIRT supernatants from injected and control mice. The results of the above experimentation in mice can be use to extrapolate proper dosages and other treatment parameters in humans and other animals using naked DNA.

Example 33

Transgenic Animals.

The polypeptides of the invention can also be expressed in transgenic animals. Animals of any species, including, but not limited to, mice, rats, rabbits, hamsters, guinea pigs, pigs, micro-pigs, goats, sheep, cows and non-human primates, e.g., baboons, monkeys, and chimpanzees may be used to generate transgenic animals. In a specific embodiment, techniques described herein or otherwise known in the art, are used to express polypeptides of the invention in humans, as part of a gene therapy protocol.

Any technique known in the art may be used to introduce the transgene (i.e., polynucleotides of the invention) into animals to produce the founder lines of transgenic animals. Such techniques include, but are not limited to, pronuclear microinjection (Paterson et al., Appl. Microbiol. Biotechnol. 40:691–698 (1994); Carver et al., Biotechnology (NY) 11:1263–1270 (1993); Wright et al., Biotechnology (NY) 9:830–834 (1991); and Hoppe et al., U.S. Pat. No. 4,873,191 (1989)); retrovirus mediated gene transfer into germ lines (Van der Putten et al., Proc. Natl. Acad. Sci., USA 82:6148–6152 (1985)), blastocysts or embryos; gene targeting in embryonic stem cells (Thompson et al., Cell 56:313–321 (1989)); electroporation of cells or embryos (Lo, 1983, Mol Cell. Biol. 3:1803–1814 (1983)); introduction of the polynucleotides of the invention using a gene gun (see, e.g., Ulmer et al., Science 259:1745 (1993); introducing nucleic acid constructs into embryonic pleuripotent stem cells and transferring the stem cells back into the blastocyst; and sperm-mediated gene transfer (Lavitrano et al., Cell 57:717–723 (1989); etc. For a review of such techniques, see Gordon, "Transgenic Animals," Intl. Rev. Cytol. 115:171–229 (1989), which is incorporated by reference herein in its entirety.

Any technique known in the art may be used to produce transgenic clones containing polynucleotides of the invention, for example, nuclear transfer into enucleated oocytes of nuclei from cultured embryonic, fetal, or adult cells induced to quiescence (Campell et al., Nature 380:64–66 (1996); Wilmut et al., Nature 385:810–813 (1997)).

The present invention provides for transgenic animals that carry the transgene in all their cells, as well as animals which carry the transgene in some, but not all their cells, i.e., mosaic animals or chimeric. The transgene may be integrated as a single transgene or as multiple copies such as in concatamers, e.g., head-to-head tandems or head-to-tail tandems. The transgene may also be selectively introduced into and activated in a particular cell type by following, for example, the teaching of Lasko et al. (Lasko et al., Proc. Natl. Acad. Sci. USA 89:6232–6236 (1992)). The regulatory sequences required for such a cell-type specific activation will depend upon the particular cell type of interest, and will be apparent to those of skill in the art. When it is desired that the polynucleotide transgene be integrated into the chromosomal site of the endogenous gene, gene targeting is preferred. Briefly, when such a technique is to be utilized, vectors containing some nucleotide sequences homologous to the endogenous gene are designed for the purpose of integrating, via homologous recombination with chromosomal sequences, into and disrupting the function of the nucleotide sequence of the endogenous gene. The transgene may also be selectively introduced into a particular cell type, thus inactivating the endogenous gene in only that cell type, by following, for example, the teaching of Gu et al. (Gu et al., Science 265:103–106 (1994)). The regulatory sequences required for such a cell-type specific inactivation will depend upon the particular cell type of interest, and will be apparent to those of skill in the art.

Once transgenic animals have been generated, the expression of the recombinant gene may be assayed utilizing standard techniques. Initial screening may be accomplished by Southern blot analysis or PCR techniques to analyze animal tissues to verify that integration of the transgene has taken place. The level of mRNA expression of the transgene in the tissues of the transgenic animals may also be assessed using techniques which include, but are not limited to, Northern blot analysis of tissue samples obtained from the animal, in situ hybridization analysis, and reverse transcriptase-PCR(RT-PCR). Samples of transgenic gene-expressing tissue may also be evaluated immunocytochemically or immunohistochemically using antibodies specific for the transgene product.

Once the founder animals are produced, they may be bred, inbred, outbred, or crossbred to produce colonies of the particular animal. Examples of such breeding strategies include, but are not limited to: outbreeding of founder animals with more than one integration site in order to establish separate lines; inbreeding of separate lines in order to produce compound transgenics that express the transgene at higher levels because of the effects of additive expression of each transgene; crossing of heterozygous transgenic animals to produce animals homozygous for a given integration site in order to both augment expression and eliminate the need for screening of animals by DNA analysis; crossing of separate homozygous lines to produce compound heterozygous or homozygous lines; and breeding to place the transgene on a distinct background that is appropriate for an experimental model of interest.

Transgenic animals of the invention have uses which include, but are not limited to, animal model systems useful in elaborating the biological function of polypeptides of the present invention, studying diseases, disorders, and/or conditions associated with aberrant expression, and in screening for compounds effective in ameliorating such diseases, disorders, and/or conditions.

Example 34

Knock-Out Animals.

Endogenous gene expression can also be reduced by inactivating or "knocking out" the gene and/or its promoter using targeted homologous recombination. (E.g., see Smithies et al., Nature 317:230–234 (1985); Thomas & Capecchi, Cell 51:503–512 (1987); Thompson et al., Cell 5:313–321 (1989); each of which is incorporated by reference herein in its entirety). For example, a mutant, non-functional polynucleotide of the invention (or a completely unrelated DNA sequence) flanked by DNA homologous to the endogenous polynucleotide sequence (either the coding regions or regulatory regions of the gene) can be used, with or without a selectable marker and/or a negative selectable marker, to transfect cells that express polypeptides of the invention in vivo. In another embodiment, techniques known in the art are used to generate knockouts in cells that contain, but do not express the gene of interest. Insertion of the DNA construct, via targeted homologous recombination, results in inactivation of the targeted gene. Such approaches are particularly suited in research and agricultural fields where modifications to embryonic stem cells can be used to generate animal offspring with an inactive targeted gene (e.g., see Thomas & Capecchi 1987 and Thompson 1989, supra). However this approach can be routinely adapted for use in humans provided the recombinant DNA constructs are directly administered or targeted to the required site in vivo using appropriate viral vectors that will be apparent to those of skill in the art.

In further embodiments of the invention, cells that are genetically engineered to express the polypeptides of the invention, or alternatively, that are genetically engineered not to express the polypeptides of the invention (e.g., knockouts) are administered to a patient in vivo. Such cells may be obtained from the patient (i.e., animal, including human) or an MHC compatible donor and can include, but are not limited to fibroblasts, bone marrow cells, blood cells (e.g., lymphocytes), adipocytes, muscle cells, endothelial cells etc. The cells are genetically engineered in vitro using recombinant DNA techniques to introduce the coding sequence of polypeptides of the invention into the cells, or alternatively, to disrupt the coding sequence and/or endogenous regulatory sequence associated with the polypeptides of the invention, e.g., by transduction (using viral vectors, and preferably vectors that integrate the transgene into the cell genome) or transfection procedures, including, but not limited to, the use of plasmids, cosmids, YACs, naked DNA, electroporation, liposomes, etc. The coding sequence of the polypeptides of the invention can be placed under the control of a strong constitutive or inducible promoter or promoter/enhancer to achieve expression, and preferably secretion, of the polypeptides of the invention. The engineered cells which express and preferably secrete the polypeptides of the invention can be introduced into the patient systemically, e.g., in the circulation, or intraperitoneally.

Alternatively, the cells can be incorporated into a matrix and implanted in the body, e.g., genetically engineered fibroblasts can be implanted as part of a skin graft; genetically engineered endothelial cells can be implanted as part of a lymphatic or vascular graft. (See, for example, Anderson et al. U.S. Pat. No. 5,399,349; and Mulligan & Wilson, U.S. Pat. No. 5,460,959 each of which is incorporated by reference herein in its entirety).

When the cells to be administered are non-autologous or non-MHC compatible cells, they can be administered using well known techniques which prevent the development of a host immune response against the introduced cells. For example, the cells may be introduced in an encapsulated form which, while allowing for an exchange of components with the immediate extracellular environment, does not allow the introduced cells to be recognized by the host immune system.

Transgenic and "knock-out" animals of the invention have uses which include, but are not limited to, animal model systems useful in elaborating the biological function of polypeptides of the present invention, studying diseases, disorders, and/or conditions associated with aberrant expression, and in screening for compounds effective in ameliorating such diseases, disorders, and/or conditions.

Example 35

Method of Isolating Antibody Fragments Directed Against HLRRBM1 from a Library of scFvs.

Naturally occurring V-genes isolated from human PBLs are constructed into a library of antibody fragments which contain reactivities against HLRRBM1 to which the donor may or may not have been exposed (see e.g., U.S. Pat. No. 5,885,793 incorporated herein by reference in its entirety).

Rescue of the Library. A library of scFvs is constructed from the RNA of human PBLs as described in PCT publication WO 92/01047. To rescue phage displaying antibody fragments, approximately 109 *E. coli* harboring the phagemid are used to inoculate 50 ml of 2×TY containing 1% glucose and 100 μg/ml of ampicillin (2×TY-AMP-GLU) and grown to an O.D. of 0.8 with shaking. Five ml of this culture is used to inoculate 50 ml of 2×TY-AMP-GLU, 2×108 TU of delta gene 3 helper (M13 delta gene III, see PCT publication WO 92/01047) are added and the culture incubated at 37° C. for 45 minutes without shaking and then at 37° C. for 45 minutes with shaking. The culture is centrifuged at 4000 r.p.m. for 10 min. and the pellet resuspended in 2 liters of 2×TY containing 100 μg/ml ampicillin and 50 ug/ml kanamycin and grown overnight. Phage are prepared as described in PCT publication WO 92/01047.

M13 delta gene III is prepared as follows: M13 delta gene III helper phage does not encode gene III protein, hence the phage(mid) displaying antibody fragments have a greater avidity of binding to antigen. Infectious M13 delta gene III particles are made by growing the helper phage in cells harboring a pUC19 derivative supplying the wild type gene III protein during phage morphogenesis. The culture is incubated for 1 hour at 37° C. without shaking and then for a further hour at 37° C. with shaking. Cells are spun down (IEC-Centra 8,400 r.p.m. for 10 min), resuspended in 300 ml 2×TY broth containing 100 μg ampicillin/ml and 25 μg kanamycin/ml (2×TY-AMP-KAN) and grown overnight, shaking at 37° C. Phage particles are purified and concentrated from the culture medium by two PEG-precipitations (Sambrook et al., 1990), resuspended in 2 ml PBS and passed through a 0.45 μm filter (Minisart NML; Sartorius) to give a final concentration of approximately 1013 transducing units/ml (ampicillin-resistant clones).

Panning of the Library. Immunotubes (Nunc) are coated overnight in PBS with 4 ml of either 100 μg/ml or 10 μg/ml of a polypeptide of the present invention. Tubes are blocked with 2% Marvel-PBS for 2 hours at 37° C. and then washed 3 times in PBS. Approximately 1013 TU of phage is applied to the tube and incubated for 30 minutes at room temperature tumbling on an over and under turntable and then left to stand for another 1.5 hours. Tubes are washed 10 times with PBS 0.1% Tween-20 and 10 times with PBS. Phage are eluted by adding 1 ml of 100 mM triethylamine and rotating 15 minutes on an under and over turntable after which the solution is immediately neutralized with 0.5 ml of 1.0M Tris-HCl, pH 7.4. Phage are then used to infect 10 ml of mid-log *E. coli* TG1 by incubating eluted phage with bacteria for 30 minutes at 37° C. The *E. coli* are then plated on TYE plates containing 1% glucose and 100 μg/ml ampicillin. The resulting bacterial library is then rescued with delta gene 3 helper phage as described above to prepare phage for a subsequent round of selection. This process is then repeated for a total of 4 rounds of affinity purification with tube-washing increased to 20 times with PBS, 0.1% Tween-20 and 20 times with PBS for rounds 3 and 4.

Characterization of Binders. Eluted phage from the 3rd and 4th rounds of selection are used to infect *E. coli* HB 2151 and soluble scFv is produced (Marks, et al., 1991) from single colonies for assay. ELISAs are performed with microtitre plates coated with either 10 pg/ml of the polypeptide of the present invention in 50 mM bicarbonate pH 9.6. Clones positive in ELISA are further characterized by PCR fingerprinting (see, e.g., PCT publication WO 92/01047) and then by sequencing. These ELISA positive clones may also be further characterized by techniques known in the art, such as, for example, epitope mapping, binding affinity, receptor signal transduction, ability to block or competitively inhibit antibody/antigen binding, and competitive agonistic or antagonistic activity.

Moreover, in another preferred method, the antibodies directed against the polypeptides of the present invention may be produced in plants. Specific methods are disclosed in U.S. Pat. Nos. 5,959,177, and 6,080,560, which are hereby incorporated in their entirety herein. The methods not only describe methods of expressing antibodies, but also the means of assembling foreign multimeric proteins in plants (i.e., antibodies, etc,), and the subsequent secretion of such antibodies from the plant.

Example 36

Assays Detecting Stimulation or Inhibition of B Cell Proliferation and Differentiation.

Generation of functional humoral immune responses requires both soluble and cognate signaling between B-lineage cells and their microenvironment. Signals may impart a positive stimulus that allows a B-lineage cell to continue its programmed development, or a negative stimulus that instructs the cell to arrest its current developmental pathway. To date, numerous stimulatory and inhibitory signals have been found to influence B cell responsiveness including IL-2, IL-4, IL-5, IL-6, IL-7, IL10, IL-13, IL-14 and IL-15. Interestingly, these signals are by themselves weak effectors but can, in combination with various co-stimulatory proteins, induce activation, proliferation, differentiation, homing, tolerance and death among B cell populations.

One of the best studied classes of B-cell co-stimulatory proteins is the TNF-superfamily. Within this family CD40, CD27, and CD30 along with their respective ligands CD154, CD70, and CD153 have been found to regulate a variety of immune responses. Assays which allow for the detection and/or observation of the proliferation and differentiation of these B-cell populations and their precursors are valuable tools in determining the effects various proteins may have on these B-cell populations in terms of proliferation and differentiation. Listed below are two assays designed to allow for the detection of the differentiation, proliferation, or inhibition of B-cell populations and their precursors.

In Vitro Assay-Purified polypeptides of the invention, or truncated forms thereof, is assessed for its ability to induce activation, proliferation, differentiation or inhibition and/or death in B-cell populations and their precursors. The activity of the polypeptides of the invention on purified human tonsillar B cells, measured qualitatively over the dose range from 0.1 to 10,000 ng/mL, is assessed in a standard B-lymphocyte co-stimulation assay in which purified tonsillar B cells are cultured in the presence of either formalin-fixed Staphylococcus aureus Cowan I (SAC) or immobilized anti-human IgM antibody as the priming agent. Second signals such as IL-2 and IL-15 synergize with SAC and IgM crosslinking to elicit B cell proliferation as measured by tritiated-thymidine incorporation. Novel synergizing agents can be readily identified using this assay. The assay involves isolating human tonsillar B cells by magnetic bead (MACS) depletion of CD3-positive cells. The resulting cell population is greater than 95% B cells as assessed by expression of CD45R(B220).

Various dilutions of each sample are placed into individual wells of a 96-well plate to which are added 105 B-cells suspended in culture medium (RPMI 1640 containing 10% FBS, 5×10-5M 2ME, 100U/ml penicillin, 10 ug/ml streptomycin, and 10-5 dilution of SAC) in a total volume of 150 ul. Proliferation or inhibition is quantitated by a 20 h pulse (1 uCi/well) with 3H-thymidine (6.7 Ci/mM) beginning 72 h post factor addition. The positive and negative controls are IL2 and medium respectively.

In Vivo Assay-BALB/c mice are injected (i.p.) twice per day with buffer only, or 2 mg/Kg of a polypeptide of the invention, or truncated forms thereof. Mice receive this treatment for 4 consecutive days, at which time they are sacrificed and various tissues and serum collected for analyses. Comparison of H&E sections from normal spleens and spleens treated with polypeptides of the invention identify the results of the activity of the polypeptides on spleen cells, such as the diffusion of peri-arterial lymphatic sheaths, and/or significant increases in the nucleated cellularity of the red pulp regions, which may indicate the activation of the differentiation and proliferation of B-cell populations. Immunohistochemical studies using a B cell marker, anti-CD45R(B220), are used to determine whether any physiological changes to splenic cells, such as splenic disorganization, are due to increased B-cell representation within loosely defined B-cell zones that infiltrate established T-cell regions.

Flow cytometric analyses of the spleens from mice treated with polypeptide is used to indicate whether the polypeptide specifically increases the proportion of ThB+, CD45R (B220)dull B cells over that which is observed in control mice.

Likewise, a predicted consequence of increased mature B-cell representation in vivo is a relative increase in serum Ig titers. Accordingly, serum IgM and IgA levels are compared between buffer and polypeptide-treated mice.

One skilled in the art could easily modify the exemplified studies to test the activity of polynucleotides of the invention (e.g., gene therapy), agonists, and/or antagonists of polynucleotides or polypeptides of the invention.

Example 37

T Cell Proliferation Assay.

A CD3-induced proliferation assay is performed on PBMCs and is measured by the uptake of 3H-thymidine. The assay is performed as follows. Ninety-six well plates are coated with 100 (1/well of mAb to CD3 (HIT3a, Pharmingen) or isotype-matched control mAb (B33.1) overnight at 4 degrees C. (1 (g/ml in 0.05M bicarbonate buffer, pH 9.5), then washed three times with PBS. PBMC are isolated by F/H gradient centrifugation from human peripheral blood and added to quadruplicate wells (5×104/well) of mAb coated plates in RPMI containing 10% FCS and P/S in the presence of varying concentrations of polypeptides of the invention (total volume 200 ul). Relevant protein buffer and medium alone are controls. After 48 hr. culture at 37 degrees C., plates are spun for 2 min. at 1000 rpm and 100 (1 of supernatant is removed and stored −20 degrees C. for measurement of IL-2 (or other cytokines) if effect on proliferation is observed. Wells are supplemented with 100 ul of medium containing 0.5 uCi of 3H-thymidine and cultured at 37 degrees C. for 18–24 hr. Wells are harvested and incorporation of 3H-thymidine used as a measure of proliferation. Anti-CD3 alone is the positive control for proliferation. IL-2 (100 U/ml) is also used as a control which enhances proliferation. Control antibody which does not induce proliferation of T cells is used as the negative controls for the effects of polypeptides of the invention.

One skilled in the art could easily modify the exemplified studies to test the activity of polynucleotides of the invention (e.g., gene therapy), agonists, and/or antagonists of polynucleotides or polypeptides of the invention.

Example 38

Effect of Polypeptides of the Invention on the Expression of MHC Class II, Costimulatory and Adhesion Molecules and Cell Differentiation of Monocytes and Monocyte-Derived Human Dendritic Cells.

Dendritic cells are generated by the expansion of proliferating precursors found in the peripheral blood: adherent PBMC or elutriated monocytic fractions are cultured for 7–10 days with GM-CSF (50 ng/ml) and IL-4 (20 ng/ml). These dendritic cells have the characteristic phenotype of immature cells (expression of CD1, CD80, CD86, CD40 and MHC class II antigens). Treatment with activating factors, such as TNF-(, causes a rapid change in surface phenotype (increased expression of MHC class I and II, costimulatory and adhesion molecules, downregulation of FC(RII, upregulation of CD83). These changes correlate with increased antigen-presenting capacity and with functional maturation of the dendritic cells.

FACS analysis of surface antigens is performed as follows. Cells are treated 1–3 days with increasing concentrations of polypeptides of the invention or LPS (positive control), washed with PBS containing 1% BSA and 0.02 mM sodium azide, and then incubated with 1:20 dilution of appropriate FITC- or PE-labeled monoclonal antibodies for 30 minutes at 4 degrees C. After an additional wash, the labeled cells are analyzed by flow cytometry on a FACScan (Becton Dickinson).

Effect on the production of cytokines. Cytokines generated by dendritic cells, in particular IL-12, are important in the initiation of T-cell dependent immune responses. IL-12 strongly influences the development of Th1 helper T-cell immune response, and induces cytotoxic T and NK cell function. An ELISA is used to measure the IL-12 release as follows. Dendritic cells (106/ml) are treated with increasing concentrations of polypeptides of the invention for 24 hours. LPS (100 ng/ml) is added to the cell culture as positive control. Supernatants from the cell cultures are then collected and analyzed for IL-12 content using commercial ELISA kit(e.g., R & D Systems (Minneapolis, Minn.)). The standard protocols provided with the kits are used.

Effect on the expression of MHC Class II, costimulatory and adhesion molecules. Three major families of cell surface antigens can be identified on monocytes: adhesion molecules, molecules involved in antigen presentation, and Fe receptor. Modulation of the expression of MHC class II antigens and other costimulatory molecules, such as B7 and ICAM-1, may result in changes in the antigen presenting capacity of monocytes and ability to induce T cell activation. Increase expression of Fc receptors may correlate with improved monocyte cytotoxic activity, cytokine release and phagocytosis.

FACS analysis is used to examine the surface antigens as follows. Monocytes are treated 1–5 days with increasing concentrations of polypeptides of the invention or LPS (positive control), washed with PBS containing 1% BSA and 0.02 mM sodium azide, and then incubated with 1:20 dilution of appropriate FITC- or PE-labeled monoclonal antibodies for 30 minutes at 4 degrees C. After an additional wash, the labeled cells are analyzed by flow cytometry on a FACScan (Becton Dickinson).

Monocyte activation and/or increased survival. Assays for molecules that activate (or alternatively, inactivate) monocytes and/or increase monocyte survival (or alternatively, decrease monocyte survival) are known in the art and may routinely be applied to determine whether a molecule of the invention functions as an inhibitor or activator of monocytes. Polypeptides, agonists, or antagonists of the invention can be screened using the three assays described below. For each of these assays, Peripheral blood mononuclear cells (PBMC) are purified from single donor leukopacks (American Red Cross, Baltimore, Md.) by centrifugation through a Histopaque gradient (Sigma). Monocytes are isolated from PBMC by counterflow centrifugal elutriation.

Monocyte Survival Assay. Human peripheral blood monocytes progressively lose viability when cultured in absence of serum or other stimuli. Their death results from internally regulated process (apoptosis). Addition to the culture of activating factors, such as TNF-alpha dramatically improves cell survival and prevents DNA fragmentation. Propidium iodide (PI) staining is used to measure apoptosis as follows. Monocytes are cultured for 48 hours in polypropylene tubes in serum-free medium (positive control), in the presence of 100 ng/ml TNF-alpha (negative control), and in the presence of varying concentrations of the compound to be tested. Cells are suspended at a concentration of 2×106/ml in PBS containing PI at a final concentration of 5 (g/ml, and then incubated at room temperature for 5 minutes before FACScan analysis. PI uptake has been demonstrated to correlate with DNA fragmentation in this experimental paradigm.

Effect on cytokine release. An important function of monocytes/macrophages is their regulatory activity on other cellular populations of the immune system through the release of cytokines after stimulation. An ELISA to measure cytokine release is performed as follows. Human monocytes are incubated at a density of 5×105 cells/ml with increasing concentrations of the a polypeptide of the invention and under the same conditions, but in the absence of the polypeptide. For IL-12 production, the cells are primed overnight with IFN (100 U/ml) in presence of a polypeptide of the invention. LPS (10 ng/ml) is then added. Conditioned media are collected after 24 h and kept frozen until use. Measurement of TNF-alpha, IL-10, MCP-1 and IL-8 is then performed using a commercially available ELISA kit(e.g., R & D Systems (Minneapolis, Minn.)) and applying the standard protocols provided with the kit.

Oxidative burst. Purified monocytes are plated in 96-w plate at 2–1×105 cell/well. Increasing concentrations of polypeptides of the invention are added to the wells in a total volume of 0.2 ml culture medium (RPMI 1640+10% FCS, glutamine and antibiotics). After 3 days incubation, the plates are centrifuged and the medium is removed from the wells. To the macrophage monolayers, 0.2 ml per well of phenol red solution (140 mM NaCl, 10 mM potassium phosphate buffer pH 7.0, 5.5 mM dextrose, 0.56 mM phenol red and 19 U/ml of HRPO) is added, together with the stimulant (200 nM PMA). The plates are incubated at 37(C for 2 hours and the reaction is stopped by adding 20 μl 1N NaOH per well. The absorbance is read at 610 nm. To calculate the amount of H2O2 produced by the macrophages, a standard curve of a H2O2 solution of known molarity is performed for each experiment.

One skilled in the art could easily modify the exemplified studies to test the activity of polynucleotides of the invention (e.g., gene therapy), agonists, and/or antagonists of polynucleotides or polypeptides of the invention.

Example 39

Suppression of TNF Alpha-Induced Adhesion Molecule Expression by a Polypeptide of the Invention.

The recruitment of lymphocytes to areas of inflammation and angiogenesis involves specific receptor-ligand interactions between cell surface adhesion molecules (CAMs) on lymphocytes and the vascular endothelium. The adhesion process, in both normal and pathological settings, follows a multi-step cascade that involves intercellular adhesion molecule-1 (ICAM-1), vascular cell adhesion molecule-1 (VCAM-1), and endothelial leukocyte adhesion molecule-1 (E-selectin) expression on endothelial cells (EC). The expression of these molecules and others on the vascular endothelium determines the efficiency with which leukocytes may adhere to the local vasculature and extravasate into the local tissue during the development of an inflammatory response. The local concentration of cytokines and growth factor participate in the modulation of the expression of these CAMs.

Tumor necrosis factor alpha (TNF-a), a potent proinflammatory cytokine, is a stimulator of all three CAMs on endothelial cells and may be involved in a wide variety of inflammatory responses, often resulting in a pathological outcome.

The potential of a polypeptide of the invention to mediate a suppression of TNF-a induced CAM expression can be examined. A modified ELISA assay which uses ECs as a solid phase absorbent is employed to measure the amount of CAM expression on TNF-a treated ECs when co-stimulated with a member of the FGF family of proteins.

To perform the experiment, human umbilical vein endothelial cell (HUVEC) cultures are obtained from pooled cord harvests and maintained in growth medium (EGM-2; Clonetics, San Diego, Calif.) supplemented with 10% FCS and 1% penicillin/streptomycin in a 37 degree C. humidified incubator containing 5% CO2. HUVECs are seeded in 96-well plates at concentrations of 1×104 cells/well in EGM medium at 37 degree C. for 18–24 hrs or until confluent. The monolayers are subsequently washed 3 times with a serum-free solution of RPMI-1640 supplemented with 100 U/ml penicillin and 100 mg/ml streptomycin, and treated with a given cytokine and/or growth factor(s) for 24 h at 37 degree C. Following incubation, the cells are then evaluated for CAM expression.

Human Umbilical Vein Endothelial cells (HUVECS) are grown in a standard 96 well plate to confluence. Growth medium is removed from the cells and replaced with 90 ul of 199 Medium (10% FBS). Samples for testing and positive or negative controls are added to the plate in triplicate (in 10 ul volumes). Plates are incubated at 37 degree C. for either 5 h (selectin and integrin expression) or 24 h (integrin expression only). Plates are aspirated to remove medium and 100 μl of 0.1% paraformaldehyde-PBS(with Ca++ and Mg++) is added to each well. Plates are held at 4° C. for 30 min.

Fixative is then removed from the wells and wells are washed 1× with PBS(+Ca,Mg)+0.5% BSA and drained. Do not allow the wells to dry. Add 10 μl of diluted primary antibody to the test and control wells. Anti-ICAM-1-Biotin, Anti-VCAM-1-Biotin and Anti-E-selectin-Biotin are used at a concentration of 10 μg/ml (1:10 dilution of 0.1 mg/ml stock antibody). Cells are incubated at 37° C. for 30 min. in a humidified environment. Wells are washed ×3 with PBS (+Ca,Mg)+0.5% BSA.

Then add 20 μl of diluted ExtrAvidin-Alkaline Phosphatase (1:5,000 dilution) to each well and incubated at 37° C. for 30 min. Wells are washed ×3 with PBS(+Ca,Mg)+0.5% BSA. 1 tablet of p-Nitrophenol Phosphate pNPP is dissolved in 5 ml of glycine buffer (pH 10.4). 100 μl of pNPP substrate in glycine buffer is added to each test well. Standard wells in triplicate are prepared from the working dilution of the ExtrAvidin-Alkaline Phosphatase in glycine buffer: 1:5,000 (100)>10-0.5>10-1>10-1.5. 5 μl of each dilution is added to triplicate wells and the resulting AP content in each well is 5.50 ng, 1.74 ng, 0.55 ng, 0.18 ng. 100 μl of pNNP reagent must then be added to each of the standard wells. The plate must be incubated at 37° C. for 4 h. A volume of 50 μl of 3M NaOH is added to all wells. The results are quantified on a plate reader at 405 nm. The background subtraction option is used on blank wells filled with glycine buffer only. The template is set up to indicate the concentration of AP-conjugate in each standard well [5.50 ng; 1.74 ng; 0.55 ng; 0.18 ng]. Results are indicated as amount of bound AP-conjugate in each sample.

Example 40

Method of Creating N- and C-terminal Deletion Mutants Corresponding to the HLRRBM1 Polypeptide of the Present Invention.

As described elsewhere herein, the present invention encompasses the creation of N- and C-terminal deletion mutants, in addition to any combination of N- and C-terminal deletions thereof, corresponding to the HLRRBM1 polypeptide of the present invention. A number of methods are available to one skilled in the art for creating such mutants. Such methods may include a combination of PCR amplification and gene cloning methodology. Although one of skill in the art of molecular biology, through the use of the teachings provided or referenced herein, and/or otherwise known in the art as standard methods, could readily create each deletion mutant of the present invention, exemplary methods are described below.

Briefly, using the isolated cDNA clone encoding the full-length HLRRBM1 polypeptide sequence (as described in Example 14, for example), appropriate primers of about 15–25 nucleotides derived from the desired 5' and 3' positions of SEQ ID NO:1 may be designed to PCR amplify, and subsequently clone, the intended N- and/or C-terminal deletion mutant. Such primers could comprise, for example, an inititation and stop codon for the 5' and 3' primer, respectively. Such primers may also comprise restriction sites to facilitate cloning of the deletion mutant post amplification. Moreover, the primers may comprise additional sequences, such as, for example, flag-tag sequences, kozac sequences, or other sequences discussed and/or referenced herein.

For example, in the case of the Y121 to R449 N-terminal deletion mutant, the following primers could be used to amplify a cDNA fragment corresponding to this deletion mutant:

```
5' Primer 5'-GCAGCA GCGGCCGC TACAAGTATTTCCACAATGCAGAGC-3'  (SEQ ID NO:19)
                   NotI

3' Primer 5'-GCAGCA GTCGAC CCTCAGGTTCTGAAGTTTGCAGTTG-3'    (SEQ ID NO:20)
                 SalI
```

For example, in the case of the M1 to M182 C-terminal deletion mutant, the following primers could be used to amplify a cDNA fragment corresponding to this deletion mutant:

```
5' Primer 5'-GCAGCA GCGGCCGC ATGAACCAGAGTGCCACGGAATGC-3'   (SEQ ID NO:21)
                   NotI

3' Primer 5'-GCAGCA GTCGAC CATGTACACTGCAGTGGTGGTCCTG-3'    (SEQ ID NO:22)
                 SalI
```

Representative PCR amplification conditions are provided below, although the skilled artisan would appreciate that other conditions may be required for efficient amplification. A 100 ul PCR reaction mixture may be prepared using 10 ng of the template DNA (cDNA clone of HLRRBM1), 200 uM 4 dNTPs, 1 uM primers, 0.25U Taq DNA polymerase (PE), and standard Taq DNA polymerase buffer. Typical PCR cycling condition are as follows:

| | |
|---|---|
| 20–25 cycles: | 45 sec, 93 degrees |
| | 2 min, 50 degrees |
| | 2 min, 72 degrees |
| 1 cycle: | 10 min, 72 degrees |

After the final extension step of PCR, 5U Klenow Fragment may be added and incubated for 15 min at 30 degrees.

Upon digestion of the fragment with the NotI and SalI restriction enzymes, the fragment could be cloned into an appropriate expression and/or cloning vector which has been similarly digested (e.g., pSport1, among others). The skilled artisan would appreciate that other plasmids could be equally substituted, and may be desirable in certain circumstances. The digested fragment and vector are then ligated using a DNA ligase, and then used to transform competent *E.coli* cells using methods provided herein and/or otherwise known in the art.

The 5' primer sequence for amplifying any additional N-terminal deletion mutants may be determined by reference to the following formula:

(S+(X*3)) to ((S+(X*3))+25), wherein 'S' is equal to the nucleotide position of the initiating start codon of the HLRRBM1 gene (SEQ ID NO:1), and 'X' is equal to the most N-terminal amino acid of the intended N-terminal deletion mutant. The first term will provide the start 5' nucleotide position of the 5' primer, while the second term will provide the end 3' nucleotide position of the 5' primer corresponding to sense strand of SEQ ID NO:1. Once the corresponding nucleotide positions of the primer are determined, the final nucleotide sequence may be created by the addition of applicable restriction site sequences to the 5' end of the sequence, for example. As referenced herein, the addition of other sequences to the 5' primer may be desired in certain circumstances (e.g., kozac sequences, etc.).

The 3' primer sequence for amplifying any additional N-terminal deletion mutants may be determined by reference to the following formula:

(S+(X*3)) to ((S+(X*3))−25), wherein 'S' is equal to the nucleotide position of the initiating start codon of the HLRRBM1 gene (SEQ ID NO:1), and 'X' is equal to the most C-terminal amino acid of the intended N-terminal deletion mutant. The first term will provide the start 5' nucleotide position of the 3' primer, while the second term will provide the end 3' nucleotide position of the 3' primer corresponding to the anti-sense strand of SEQ ID NO:1. Once the corresponding nucleotide positions of the primer are determined, the final nucleotide sequence may be created by the addition of applicable restriction site sequences to the 5' end of the sequence, for example. As referenced herein, the addition of other sequences to the 3' primer may be desired in certain circumstances (e.g., stop codon sequences, etc.). The skilled artisan would appreciate that modifications of the above nucleotide positions may be necessary for optimizing PCR amplification.

The same general formulas provided above may be used in identifying the 5' and 3' primer sequences for amplifying any C-terminal deletion mutant of the present invention. Moreover, the same general formulas provided above may be used in identifying the 5' and 3' primer sequences for amplifying any combination of N-terminal and C-terminal deletion mutant of the present invention. The skilled artisan would appreciate that modifications of the above nucleotide positions may be necessary for optimizing PCR amplification.

One skilled in the art could easily modify the exemplified studies to test the activity of polynucleotides of the invention (e.g., gene therapy), agonists, and/or antagonists of polynucleotides or polypeptides of the invention.

It will be clear that the invention may be practiced otherwise than as particularly described in the foregoing description and examples. Numerous modifications and variations of the present invention are possible in light of the above teachings and, therefore, are within the scope of the appended claims.

The entire disclosure of each document cited (including patents, patent applications, journal articles, abstracts, laboratory manuals, books, or other disclosures) in the Background of the Invention, Detailed Description, and Examples is hereby incorporated herein by reference. Further, the hard copy of the sequence listing submitted herewith and the corresponding computer readable form are both incorporated herein by reference in their entireties.

What is claimed is:

1. An isolated nucleic acid molecule comprising a polynucleotide sequence selected from the group consisting of:

(a) an isolated polynucleotide encoding a polypeptide comprising amino acids 1 to 449 of SEQ ID NO:2; and (b) an isolated polynucleotide encoding a polypeptide comprising amino acids 2 to 449 of SEQ ID NO:2.

2. The isolated nucleic acid molecule of claim 1, wherein said polynucleotide is (a).

3. The isolated nucleic acid molecule of claim 2, wherein said polynucleotide comprises nucleotides 1320 to 2666 of SEQ ID NO:1.

4. The isolated nucleic acid molecule of claim 1, wherein said polynucleotide is (b).

5. The isolated nucleic acid molecule of claim 4, wherein said polynucleotide comprises nucleotides 1323 to 2666 of SEQ ID NO:1.

6. A recombinant vector comprising the isolated nucleic acid molecule of claim 1.

7. A recombinant host cell comprising vector sequences of claim 6.

8. A method of making an isolated polype tide comprising:

(a) culturing the recombinant host cell of claim 7 under conditions such that said polypeptide is expressed; and (b) recovering said polypeptide.

9. The isolated polynucleotide of claim 1 wherein said nucleic acid sequence further comprises a heterologous nucleic acid sequence.

10. The isolated polynucleotide of claim 9 wherein said heterologous nucleic acid sequence encodes a heterologous polypeptide.

11. The isolated polynucleotide of claim 10 wherein said heterologous polypeptide is the Fc domain of immunoglobulin.

12. An isolated nucleic acid molecule comp sing a polynucleotide having a nucleotide sequence that is at least 80.0% identical to nucleotides 1323 to 2666 of SEQ ID NO:1, wherein percent identity is calculated using a CLUSTALW global sequence alignment, and wherein said polynucleotide encodes a polypeptide that decreases the level of p21 protein transcription in a cell in which said polypeptide is expressed.

13. The isolated polynucleotide of claim 12 wherein said nucleic acid sequence further comprises a heterologous nucleic acid sequence.

14. The isolated polynucleotide of cliam 13 wherein said heterologous nucleic acid sequence encodes a heterologous polypeptide.

15. The isolated polynucleotide of claim 14 wherein said heterologous polypeptide is the Fe domain of immunoglobulin.

16. The isolated nucleic acid molecule of claim 12 wherein said polynucleotide encodes a polypeptide having a polypeptide sequence that is t least 80.0% identical to the polypeptide sequence provided in SEQ ID NO:2, wherein percent identity is calculated using a CLUSTALW global sequence alignment; and wherein said polypetide decreases the level of p21 protein transcription in a cell in which said polypeptide is expressed.

17. An isolated polynucleotide encoding the polypeptide of SEQ ID NO:2 as encoded by the cDNA clone contained in ATCC Deposit No: PTA-2676.

18. An isolated polynucleotide encoding a polypeptide comprising at least 255 contiguous amino acids of SEQ ID NO:2, wherein said polypeptide decreases the level of p21 protein transcription in a cell in which said polypeptide is expressed.

19. The isolated nucleic acid molecule of claim 18, wherein said polynucleotide comprises at least 765 contiguous nucleotides of SEQ ID NO:1.

20. An isolated polynucleotide which represents the complimentary sequence of a member of the group consisting of (a), and (b) of claim 1.

* * * * *

UNITED STATES PATENT AND TRADEMARK OFFICE

CERTIFICATE OF CORRECTION

PATENT NO. : 6,949,363 B2
APPLICATION NO. : 10/183770
DATED : September 27, 2005
INVENTOR(S) : David K. Bol et al.

It is certified that error appears in the above-identified patent and that said Letters Patent is hereby corrected as shown below:

Column 22:

Line 61, "As descussed elsewhere herein, the Drosophia Toll" should read

--As discussed elsewhere herein, the Drosophia Toll--

Column 243:

Line 58, "7. A recombinant host cell comprising vector sequences of claim 6." should read: --7. An isolated recombinant host cell comprising the vector sequence of claim 6.--

Column 243:

Line 60, "8. A method of making an isolated polype tide comprising:" should read:

--8. A method of making an isolated polypeptide comprising:--

Column 244:

Line 47, "12. An isolated nucleic acid molecule comp sing a poly-" should read:

--12. An isolated nucleic acid molecule comprising a poly- --

Column 245:

Line 1, "polypeptide sequence that is t least 80.0% identical to the" should read --polypeptide sequence that is at least 80.0% identical to the--

Column 245:

Line 8, "of SEQ ID NO:2 as encoded by the cDNA clone contained" should read

--of SEQ ID NO:2 as encoded by the cDNA clone BMLRR2 contained--

UNITED STATES PATENT AND TRADEMARK OFFICE

CERTIFICATE OF CORRECTION

PATENT NO. : 6,949,363 B2
APPLICATION NO. : 10/183770
DATED : September 27, 2005
INVENTOR(S) : David K. Bol et al.

It is certified that error appears in the above-identified patent and that said Letters Patent is hereby corrected as shown below:

Column 246:

Line 10, Add new claim

--21. The isolated nucleic acid molecule of claim 1, wherein said polynucleotide encodes a leucine-rich repeat protein.--

Signed and Sealed this

Ninth Day of January, 2007

JON W. DUDAS
*Director of the United States Patent and Trademark Office*

UNITED STATES PATENT AND TRADEMARK OFFICE
Certificate

Patent No. 6,949,363 B2

Patented: September 27, 2005

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: John N. Feder, Belle Mead, NJ (US); Chandra S. Ramanathan, Wallingford, CT (US); Gabriel A. Mintier, Hightstown, NJ (US); and David K. Bol, Gaithersburg, MD (US).

Signed and Sealed this Thirtieth Day of January 2007.

BRENDA BRUMBACK
*Supervisory Patent Examiner*
Art Unit 1647